(12) United States Patent
Eckhardt et al.

(10) Patent No.: US 10,695,334 B2
(45) Date of Patent: Jun. 30, 2020

(54) HETEROAROMATIC CARBOXAMIDE DERIVATIVES AS PLASMA KALLIKREIN INHIBITORS

(71) Applicant: Boehringer Ingelheim International GmbH, Ingelheim am Rhein (DE)

(72) Inventors: Matthias Eckhardt, Biberach an der Riss (DE); Andreas Gollner, Vienna (AT); Elke Langkopf, Biberach an der Riss (DE); Holger Wagner, Mettenberg (DE); Dieter Wiedenmayer, Bieberach an der Riss (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 0 days.

(21) Appl. No.: 16/540,091

(22) Filed: Aug. 14, 2019

(65) Prior Publication Data

US 2020/0054617 A1 Feb. 20, 2020

(30) Foreign Application Priority Data

Aug. 16, 2018 (EP) .................................. 18189330

(51) Int. Cl.

| | |
|---|---|
| *A61K 31/4439* | (2006.01) |
| *A61K 31/5386* | (2006.01) |
| *A61K 31/506* | (2006.01) |
| *C07D 401/14* | (2006.01) |
| *C07D 409/14* | (2006.01) |
| *C07D 403/14* | (2006.01) |
| *C07D 491/107* | (2006.01) |
| *C07D 471/08* | (2006.01) |
| *C07D 498/08* | (2006.01) |
| *C07D 487/08* | (2006.01) |
| *C07D 487/04* | (2006.01) |
| *A61K 31/519* | (2006.01) |

(52) U.S. Cl.
CPC ........ *A61K 31/4439* (2013.01); *A61K 31/506* (2013.01); *A61K 31/519* (2013.01); *A61K 31/5386* (2013.01); *C07D 401/14* (2013.01); *C07D 403/14* (2013.01); *C07D 409/14* (2013.01); *C07D 471/08* (2013.01); *C07D 487/04* (2013.01); *C07D 487/08* (2013.01); *C07D 491/107* (2013.01); *C07D 498/08* (2013.01)

(58) Field of Classification Search
CPC .............. A61K 31/4439; A61K 31/506; A61K 31/519; A61K 31/5386; C07D 401/14; C07D 403/14; C07D 409/14; C07D 471/08; C07D 487/04; C07D 487/08; C07D 491/107; C07D 498/08
USPC .................................................. 514/210.16
See application file for complete search history.

(56) References Cited

FOREIGN PATENT DOCUMENTS

| | | |
|---|---|---|
| JP | 2005089362 A | 4/2005 |
| WO | 2009097141 A1 | 8/2009 |
| WO | 2013111107 A1 | 8/2013 |
| WO | 2013111108 A1 | 8/2013 |
| WO | 2014188211 A1 | 11/2014 |
| WO | 2017072020 A1 | 5/2017 |
| WO | 2017072021 A1 | 5/2017 |
| WO | 2018011628 A1 | 1/2018 |

OTHER PUBLICATIONS

Japtap, Heck Reaction, Catalysts, 2017.
Hashiguchi, Asymmetric Transfer Hrydogenation of Aromatic Ketones Catalyzed by Chiral Ruthenium (II) Complexes, J. Am. Chem. Soc, 1995, vol. 117, p. 7562-7563.
Li, Enantioselective, Organocataltyic Reduction of Ketones using Bifunctional Thiorea-Amine Catalysts, Organic Letters, 2010, vol. 12, p. 1756-1759.
Kim, Asymmetric Reductions involving Borohydrides, Organic Research and Development, 2006, vol. 10, p. 949-958.
Nakamura, Recent Developments in asymmetric reduction of ketones with biocatalysts, Tetrahedron: Asymmetry, 2003, vol. 14, p. 2659-2681.
Yoshimura, Recent topics in catalytic asymmetric hydrogenation of ketones, Tetrahedron Letters, 2014, vol. 55, p. 3635-3640.
Biagetti, Synthesis and structure-activity relationship of N-(3-azabicyclo[3.1.0]hex-6-ylmethyl)-5-(2-pyridinyl)-1,3-thiazol-2-amines derivatives as NPY Y5 antagonists, Bioorganic & Medicinal Chem Letters, 2010, vol. 20, p. 4741-4744.
International Search Report for PCT/EP2016/075221 dated Jan. 18, 2017.
Written Opinion for PCT/EP2016/075221 dated Jan. 18, 2017.
Keener, Plasma Kallikrein and Diabetic Macular Edema, Curr. Diab. Rep. 2010.

(Continued)

*Primary Examiner* — Kristin A Vajda
(74) *Attorney, Agent, or Firm* — David L. Kershner

(57) ABSTRACT

Heteroaromatic carboxamides of formula (I),

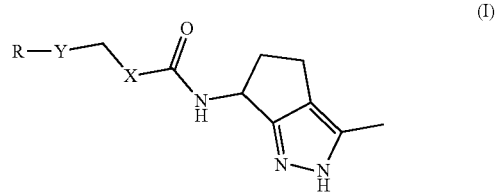

wherein Y, R, and X are as defined herein, and pharmaceutically acceptable salts thereof. The compounds of formula (I) can be used in methods for the treatment of diseases which can be influenced by inhibition of plasma kallikrein.

25 Claims, No Drawings

(56) References Cited

OTHER PUBLICATIONS

International Search Report for PCT/EP2016/075222 dated Oct. 25, 2016.
Written Opinion for PCT/EP2016/075222 dated Oct. 26, 2016.
International Search Report and Written Opinion for PCT/EP2018059633 dated Jul. 6, 2018.
International Search Report and Written Opinion for PCT/EP2019/071855 dated Sep. 1, 2019.
Database Pub Chem, NCBI, No. 8248531, 2014.

HETEROAROMATIC CARBOXAMIDE DERIVATIVES AS PLASMA KALLIKREIN INHIBITORS

FIELD OF THE INVENTION

This invention relates to novel heteroaromatic carboxamide derivatives, and pharmaceutically acceptable salts thereof, that are plasma kallikrein inhibitors. In addition, the invention relates to intermediates of the synthesis of said compounds, to pharmaceutical compositions and combinations comprising said compounds and to their use in methods for the treatment of diseases which can be influenced by the inhibition of plasma kallikrein. Particularly, the pharmaceutical compositions of the invention are suitable for the prophylaxis and/or therapy of diabetic complications, ocular diseases and edema-associated diseases, in particular diabetic macular edema, age-related macular degeneration, choroidal neovascularization and hereditary angioedema.

BACKGROUND OF THE INVENTION

Plasma kallikrein (PKK) is a trypsin-like serine protease secreted by hepatocytes in the liver as an inactive plasma prekallikrein that circulates in plasma either as a free zymogen or as a heterodimer complex bound to high molecular weight kininogen which is activated to give the active PKK that can liberate kinins from kininogens in addition to processing other substrates. Kinins are potent mediators of inflammation that act through G protein-coupled receptors such as bradykinin receptors.

PKK is thought to play a role in a number of inflammatory disorders and may have numerous implications in disorders such as hereditary angioedema (HAE), retinopathy or diabetic retinopathy, proliferative and non-proliferative retinopathy, diabetic macular edema (DME), clinically significant macular edema (CSME), cystoid macular edema (CME), CME following cataract extraction, CME induced by cryotherapy, CME induced by uveitis, endophthalmitis, CME following vascular occlusion (e.g. central retina vein occlusion, branch retinal vein occlusion, or hemiretinal vein occlusion), retinal edema, complications related to cataract surgery in diabetic retinopathy, hypertensive retinopathy, retinal trauma, dry and wet age-related macular degeneration (AMD), polypoidal choroidal vasculopathy (PCV), choroidal neovascularization (CNV; e.g. non-exudative choroidal neovascularization), posterior vitreous detachment (PVD), ischemic reperfusion injuries, e.g. in all kind of contexts associated with tissue and/or organ transplantation, surgically-induced brain injury, focal cerebral ischemia, global cerebral ischemia, glioma-associated edema, spinal cord injury, pain, ischemia, focal brain ischemia, neurological and cognitive deficits, deep vein thrombosis, stroke, myocardial infarction, acquired angioedema, drug-related (ACE-inhibitors) edema, high altitude cerebral edema, cytotoxic cerebral edema, osmotic cerebral edema, obstructive hydrocephalus, radiation induced edema, lymph edema, traumatic brain injury, hemorrhagic stroke (e.g., cerebral stroke or subarachnoid stroke), intracerebral hemorrhage, hemorrhagic transformation of ischemic stroke, cerebral trauma associated with injury or surgery, brain aneurysm, arterio-venous malformation, reduction of blood losses during surgical procedures (e.g. cardiothoracic surgery, such as cardiopulmonary bypass or coronary artery bypass grafting), blood coagulation disorders such as thrombosis, itch, disorders with an inflammation component (such as multiple sclerosis), epilepsy, encephalitis, Alzheimer's disease, excessive daytime sleepiness, essential hypertension, increased blood pressure associated with diabetes or hyperlipidemia, renal insufficiency, chronic kidney disease, heart failure, microalbuminuria, albuminuria, proteinuria, disorders associated with increased vascular permeability (e.g. increased retinal vascular permeability, increased leg, feet, ankle vascular permeability), cerebral hemorrhage, deep vein thrombosis, coagulation from post fibrinolytic treatments, angina, angioedema, sepsis, arthritis (e.g. rheumatoid arthritis, osteoarthritis, infection arthritis), lupus, gout, psoriasis, inflammatory bowel, diabetes, diabetic complications, complications arising from metabolic syndrome, infectious diseases, astrocyte-activation related diseases (e.g. Alzheimer's disease or multiple sclerosis), Parkinson's disease, amyotrophic lateral sclerosis, Creutzfeld-Jacob disease, stroke, epilepsy and trauma (e.g. brain trauma), allergic edema e.g. airflow obstruction in chronic allergic sinusitis or perennial rhinitis; airflow obstruction in acute asthma; serositis associated with systemic lupus erythematosus (SLE), acute respiratory distress syndrome (ARDS) and other diseases.

PKK inhibitors are considered to be useful in the treatment of a wide range of disorders, particularly in the treatment of edema formation in diseases, e.g. edema formation related to ischemic reperfusion injuries, retinopathy or edema-associated diseases, such as hereditary angioedema, macular edema and brain edema. PKK inhibitors are considered to be especially useful in the treatment of retinopathy, e.g. retinopathy associated with diabetes and/or hypertension, and in the treatment of macular edema, e.g. macular edema associated with diabetes and/or hypertension.

PKK inhibitors suitable for therapeutic use should bind potently and with high selectivity to PKK. They should be well absorbed from the gastrointestinal tract, be sufficiently metabolically stable and possess favorable pharmacokinetic properties. They should be non-toxic and demonstrate few side-effects.

The compounds of the invention are PKK inhibitors and are therefore potentially useful in the treatment of disorders mentioned hereinbefore, particularly should have utility as a treatment to reduce retinal vascular permeability associated with diabetic retinopathy and diabetic macular edema retinopathy or edema-associated diseases.

Other complications of diabetes such as cerebral haemorrhage, nephropathy, cardiomyopathy and neuropathy, all of which have associations with PKK may also be considered as targets for a PKK inhibitor.

Low molecular weight PKK inhibitors are known in the art, for example, the compounds disclosed in WO 2013/111108, WO 2013/111107, WO 2014/188211, WO 2017/072020, and WO 2017/072021.

SUMMARY OF THE INVENTION

In a first aspect, the present invention relates to a compound of formula (I)

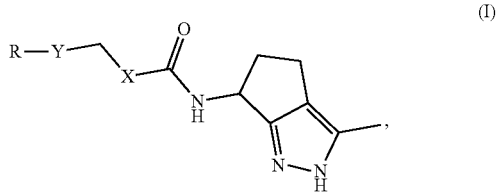

wherein
Y is selected from the group Y-G1 consisting of

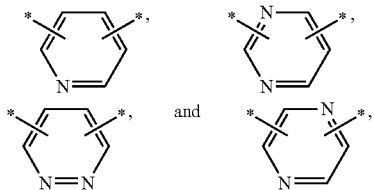

each of which is substituted with 1 or 2 independent substituents $R^1$;

R is selected from the group R-G1 consisting of
saturated 4- to 7-membered monocyclic and saturated 6- to 12-membered bicyclic ring systems containing 1 to 3 N atoms as ring members and optionally 1 to 2 ring members selected from the group consisting of C=O, O, S, S=O, and $SO_2$,
provided that the ring systems do not contain any heteroatom-heteroatom bonds between ring members,
wherein said ring systems are attached to Y in formula (I) via an N atom, and
wherein said ring systems are optionally substituted with 1 to 6 F, optionally substituted with 1 substituent $R^2$, and optionally substituted with 1 or 2 $CH_3$ groups.

X is selected from the group X-G1 consisting of
5-membered heteroaryls, containing 1 to 4 N atoms or containing 1 O or S atom or containing 1 to 3 N atoms and 1 O or S atom, and 9-membered heteroaryls, consisting of a 5-membered ring fused to a 6-membered ring and containing 1 to 5 N atoms,
wherein said heteroaryls are attached to the carbonyl group in formula (I) via a C atom of the 5-membered ring and to the $CH_2$ group in formula (I) via a non-adjacent C or N atom of the 5-membered ring, and wherein said heteroaryls are optionally substituted with 1 substituent $R^3$;

$R^1$ is selected from the group $R^1$-G1 consisting of
H, $C_{1-4}$-alkyl optionally substituted with 1 to 5 F, cyclopropyl optionally substituted with 1 F or 1 $CH_3$ group, CN, OH, O—$C_{1-3}$-alkyl optionally substituted with 1 to 5 F, $C_{1-3}$-alkyl optionally substituted with 1 substituent selected from the group consisting of CN, OH, and O—$CH_3$;

$R^2$ is selected from the group $R^2$-G1 consisting of
Cl, $C_{1-4}$-alkyl optionally substituted with 1 to 5 F, $C_{3-4}$-cycloalkyl, $C_{1-3}$-alkylene-OH, $C_{1-3}$-alkylene-O—$C_{1-4}$-alkyl, CN, COOH, $NH_2$, NH—$C_{1-3}$-alkyl, N($C_{1-3}$-alkyl)$_2$, OH, O—$C_{1-4}$-alkyl optionally substituted with 1 to 5 F, phenyl, 5-membered heteroaryls containing 1 —NH—, —N<, —O— or —S— ring member and optionally additionally 1 or 2 =N— ring members, and 6-membered heteroaryls containing 1 or 2 =N— ring members;
wherein said phenyl and 5- and 6-membered heteroaryls are optionally substituted at 1 or 2 carbon atoms independently of each other with F, Cl, $CH_3$, $CF_3$, CN, OH, and/or O—$CH_3$, and
wherein N—H groups present within these rings are optionally replaced by N—$C_{1-3}$-alkyl;

$R^3$ is selected from the group $R^3$-G1 consisting of
F, Cl, Br, CN, COOH, $C_{1-3}$-alkyl optionally substituted with 1 to 5 F, $C_{3-5}$-cycloalkyl, $C_{1-3}$-alkylene-OH, $C_{1-3}$-alkylene-O—$C_{1-4}$-alkyl, O—$C_{1-4}$-alkyl optionally substituted with 1 to 5 F, 5-membered heteroaryls containing 1 —NH—, —O— or —S— ring member and optionally additionally 1 or 2 =N— ring members, and 6-membered heteroaryls containing 1 or 2 =N— ring members;
wherein said 5- and 6-membered heteroaryls are optionally substituted at 1 or 2 carbon atoms independently of each other with F, Cl, $CH_3$, $CF_3$, CN, OH, and/or O—$CH_3$, and
wherein N—H groups present within these rings are optionally replaced by N—$C_{1-3}$-alkyl;

wherein in any definition mentioned hereinbefore and if not specified otherwise, any alkyl group or sub-group may be straight-chained or branched,
the isoforms, tautomers, stereoisomers, metabolites, prodrugs, solvates, hydrates, cocrystals and the salts thereof, particularly the pharmaceutically acceptable cocrystals and salts thereof, or the combinations thereof.

In a second aspect, the present invention relates to a pharmaceutical composition comprising one or more compounds of formula (I), as defined hereinbefore or hereinafter, and/or their tautomers or pharmaceutically acceptable salts thereof, optionally together with one or more inert carriers and/or diluents.

In a third aspect, the present invention relates to a pharmaceutical composition comprising one or more compounds of formula (I), as defined hereinbefore or hereinafter, and/or their tautomers or pharmaceutically acceptable salts thereof, and one or more additional therapeutic agents, optionally together with one or more inert carriers and/or diluents.

In a fourth aspect, the present invention relates to a compound of formula (I), as defined hereinbefore or hereinafter, and/or its tautomers or a pharmaceutically acceptable salt thereof for use as a medicament.

In a fifth aspect, the present invention relates to a method for the treatment of diseases or conditions which can be influenced by the inhibition of plasma kallikrein in a patient in need thereof, the method being characterized in that one or more compounds of formula (I), as defined hereinbefore or hereinafter, and/or their tautomers or pharmaceutically acceptable salts thereof are administered to the patient.

Also, the present invention relates to the use of one or more compounds of formula (I), as defined hereinbefore or hereinafter, in the manufacture of a medicament for the treatment of diseases or conditions which can be influenced by the inhibition of plasma kallikrein.

Also, the present invention relates to a compound of formula (I), as defined hereinbefore or hereinafter, and/or its tautomers or a pharmaceutically acceptable salt thereof for use in a method for the treatment of diseases or conditions which can be influenced by the inhibition of plasma kallikrein, in a patient in need thereof.

In a sixth aspect, the present invention relates to one or more compounds selected from the group consisting of (XVI)

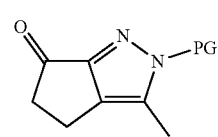

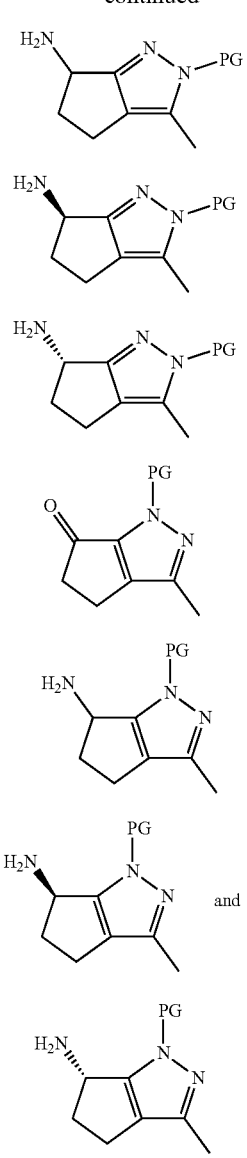

wherein PG is H or a protective group, e.g. selected from the group consisting of $C_{1-4}$-alkyl optionally substituted with 1 to 5 F or Cl and optionally substituted with 1 group selected from $Si(CH_3)_3$, CN, $SO_2$—$C_{1-4}$-alkyl, or $SO_2$-phenyl;

$CH_2$-phenyl optionally substituted with 1 or 2 $OCH_3$;

$CH_2$—$N(C_{1-4}$-alkyl$)_2$, $CH_2$-pyrrolidin-1-yl, $CH_2$—NHCO—$C_{1-4}$-alkyl, $CH_2$—$N(CH_3)CO$—$C_{1-4}$-alkyl;

$CH_2$—O—$C_{1-4}$-alkyl optionally substituted with 1 $CH_3$, 1 $Si(CH_3)_3$, or 3 Cl;

$CH_2$—O—$CH_2$-phenyl optionally substituted with 1 or 2 $OCH_3$; tetrahydropyran-2-yl, tetrahydrofuran-2-yl;

CO—$C_{1-4}$-alkyl optionally substituted with 1 to 5 F or Cl; CO—$N(C_{1-4}$-alkyl$)_2$, CO-pyrrolidin-1-yl;

CO—O—$C_{1-4}$-alkyl optionally substituted with 1 $Si(CH_3)_3$ or 3 Cl;

COO—$CH_2$-phenyl optionally substituted with 1 or 2 $OCH_3$;

$SO_2(C_{1-4}$-alkyl) optionally substituted with 1 to 5 F or 1 to 3 Cl;

$SO_2$-phenyl optionally substituted with 1 or 2 groups selected from Cl, Br, $CH_3$, $NO_2$, and $OC_{1-4}$-alkyl; $SO_2$—$N(C_{1-4}$-alkyl$)_2$, $SO_2$-pyrrolidin-1-yl;

phenyl substituted with 1 or 2 groups selected from Cl, Br, $NO_2$, $OC_{1-3}$-alkyl, and $SO_2C_{1-3}$-alkyl;

or a salt thereof, which are valuable intermediates in the synthesis of compounds of formula (I).

Further aspects of the present invention will become apparent to the person skilled in the art directly from the foregoing and following description and the examples.

General Terms and Definitions

Terms not specifically defined herein should be given the meanings that would be given to them by one of skill in the art in light of the disclosure and the context. As used in the specification, however, unless specified to the contrary, the following terms have the meaning indicated and the following conventions are adhered to.

The terms "compound(s) according to this invention", "compound(s) of formula (I)", "compound(s) of the invention" and the like denote the compounds of formula (I) according to the present invention including their tautomers, stereoisomers and mixtures thereof and the salts thereof, in particular the pharmaceutically acceptable salts thereof, and the solvates, hydrates and cocrystals of such compounds, in particular the pharmaceutically acceptable cocrystals thereof, including the solvates, hydrates and cocrystals of such tautomers, stereoisomers and salts thereof.

Also, unless specifically indicated, throughout the specification and the appended claims, a given chemical formula or name shall encompass tautomers and all stereo, optical and geometrical isomers (e.g. enantiomers, diastereomers, E/Z isomers etc. . . . ) and racemates thereof as well as mixtures in different proportions of the separate enantiomers, mixtures of diastereomers, or mixtures of any of the foregoing forms where such isomers and enantiomers exist, as well as salts, including pharmaceutically acceptable salts thereof, and solvates thereof, such as for instance hydrates, including solvates of the free compounds or solvates of a salt of the compound, and cocrystals thereof, including pharmaceutically acceptable cocrystals thereof and cocrystals of the free compounds or of a salt thereof.

The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, and commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

For example, such salts include salts from benzenesulfonic acid, benzoic acid, citric acid, ethanesulfonic acid, fumaric acid, gentisic acid, hydrobromic acid, hydrochloric acid, maleic acid, malic acid, malonic acid, mandelic acid, methanesulfonic acid, 4-methyl-benzenesulfonic acid, phosphoric acid, salicylic acid, succinic acid, sulfuric acid and tartaric acid.

The pharmaceutically acceptable salts of the present invention can be synthesized from the parent compound which contains a basic or acidic moiety by conventional chemical methods. Generally, such salts can be prepared by reacting the free acid or base forms of these compounds with a sufficient amount of the appropriate base or acid in water or in an organic diluent like ether, EtOAc, EtOH, isopropanol, or ACN, or a mixture thereof.

Salts of other acids than those mentioned above which for example are useful for purifying or isolating the compounds of the present invention (e.g. trifluoro acetate salts) also comprise a part of the invention.

As used herein, "pharmaceutically acceptable cocrystals" refer to derivatives of the disclosed compounds wherein the parent compound is modified by making a cocrystal thereof with the help of one or more coformers. Also, cocrystals of solvates and/or salts of the disclosed compounds are encompassed.

For example, coformers include hydrogen bond donors, such as carboxylic acids, and hydrogen bond acceptors, such as amines and amides.

The pharmaceutically acceptable cocrystals of the present invention can be synthesized from the parent compound by methods known to the one skilled in the art, including solid-based methods, such as solid state grinding, melt extrusion and melt crystallization, and liquid-based methods, such as solution crystallization, solvent evaporation, cooling crystallization, supercritical fluid assisted crystallization, ultrasound assisted crystallization, spray drying, liquid assisted grinding and planetary milling.

In case a compound of the present invention is depicted in form of a chemical name and as a formula in case of any discrepancy the formula shall prevail.

In the groups, radicals, or moieties defined below, the number of carbon atoms is often specified preceding the group, for example, $C_{1-6}$-alkyl means an alkyl group or radical having 1 to 6 carbon atoms.

An asterisk may be used in sub-formulas to indicate the bond which is connected to the core molecule as defined. In the case of more than one attachment point, i.e. more than one asterisk, in a sub-formula, the asterisks may be further specified by a bracketed designation of the connected part of the core molecule.

The numeration of the atoms of a substituent starts with the atom which is closest to the core or to the group to which the substituent is attached.

For example, the term "3-carboxypropyl-group" represents the following substituent:

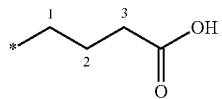

wherein the carboxy group is attached to the third carbon atom of the propyl group. The terms "1-methylpropyl-", "2,2-dimethylpropyl-" or "cyclopropylmethyl-" group represent the following groups:

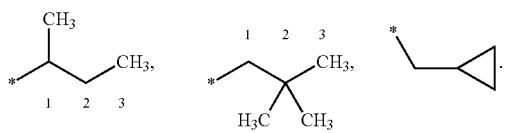

The term "substituted" as used herein, means that any one or more hydrogens on the designated atom, radical or moiety is replaced with a selection from the indicated group, provided that the atom's normal valence is not exceeded, and that the substitution results in an acceptably stable compound.

In a definition of a group, the term "wherein each X, Y and Z group is optionally substituted with" and the like denotes that each group X, each group Y and each group Z either each as a separate group or each as part of a composed group may be substituted as defined. For example a definition "$R^{ex}$ denotes H, $C_{1-3}$-alkyl, $C_{3-6}$-cycloalkyl, $C_{3-6}$-cycloalkyl-$C_{1-3}$-alkyl or $C_{1-3}$-alkyl-O—, wherein each alkyl group is optionally substituted with one or more $L^{ex}$." or the like means that in each of the beforementioned groups which comprise the term alkyl, i.e. in each of the groups $C_{1-3}$-alkyl, $C_{3-6}$-cycloalkyl-$C_{1-3}$-alkyl and $C_{1-3}$-alkyl-O—, the alkyl moiety may be substituted with $L^{ex}$ as defined.

The term "$C_{1-n}$-alkyl", wherein n is an integer from 1 to n, either alone or in combination with another radical denotes an acyclic, saturated, branched or linear hydrocarbon radical with 1 to n C atoms. For example the term $C_{1-5}$-alkyl embraces the radicals $H_3C$—, $H_3C$—$CH_2$—, $H_3C$—$CH_2$—$CH_2$—, $H_3C$—$CH(CH_3)$—, $H_3C$—$CH_2$—$CH_2$—$CH_2$—, $H_3C$—$CH_2$—$CH(CH_3)$—, $H_3C$—$CH(CH_3)$—$CH_2$—, $H_3C$—$C(CH_3)_2$—, $H_3C$—$CH_2$—$CH_2$—$CH_2$—$CH_2$—, $H_3C$—$CH_2$—$CH_2$—$CH(CH_3)$—, $H_3C$—$CH_2$—$CH(CH_3)$—$CH_2$—, $H_3C$—$CH(CH_3)$—$CH_2$—$CH_2$—, $H_3C$—$CH_2$—$C(CH_3)_2$—, $H_3C$—$C(CH_3)_2$—$CH_2$—, $H_3C$—$CH(CH_3)$—$CH(CH_3)$— and $H_3C$—$CH_2$—$CH(CH_2CH_3)$—.

The term "$C_{1-n}$-alkylene" wherein n is an integer selected from 2, 3, 4, 5 or 6, preferably 4 or 6, either alone or in combination with another radical, denotes an acyclic, straight or branched chain divalent alkyl radical containing from 1 to n carbon atoms. For example the term $C_{1-4}$-alkylene includes —$CH_2$—, —$CH_2$—$CH_2$—, —$CH(CH_3)$—, —$CH_2$—$CH_2$—$CH_2$—, —$C(CH_3)_2$—, —$CH(CH_2CH_3)$—, —$CH(CH_3)$—$CH_2$—, —$CH_2$—$CH(CH_3)$—, —$CH_2$—$CH_2$—$CH_2$—$CH_2$—, —$CH_2$—$CH_2$—$CH(CH_3)$—, —$CH(CH_3)$—$CH_2$—$CH_2$—, —$CH_2$—$CH(CH_3)$—$CH_2$—, —$CH_2$—$C(CH_3)_2$—, —$C(CH_3)_2$—$CH_2$—, —$CH(CH_3)$—$CH(CH_3)$—, —$CH_2$—$CH(CH_2CH_3)$—, —$CH(CH_2CH_3)$—$CH_2$—, —$CH(CH_2CH_2CH_3)$—, —$CH(CH(CH_3))_2$— and —$C(CH_3)(CH_2CH_3)$—.

The term "$C_{3-n}$-cycloalkyl", wherein n is an integer 3 to n, either alone or in combination with another radical denotes a cyclic, saturated, unbranched hydrocarbon radical with 3 to n C atoms. The cyclic group may be mono-, bi-, tri- or spirocyclic, most preferably monocyclic. Examples of such cycloalkyl groups include cyclopropyl, cyclobutyl, cyclo-pentyl, cyclohexyl, cycloheptyl, cyclooctyl, cyclononyl, cyclododecyl, bicyclo[3.2.1.]octyl, spiro[4.5] decyl, norpinyl, norbonyl, norcaryl, adamantyl, etc.

The term "aryl" as used herein, either alone or in combination with another radical, denotes a carbocyclic aromatic monocyclic group containing 6 carbon atoms which is optionally further fused to a second five- or six-membered, carbocyclic group which is optionally aromatic, saturated or unsaturated. The term "aryl" includes, but is not limited to, phenyl, indanyl, indenyl, naphthyl, anthracenyl, phenanthrenyl, tetrahydronaphthyl and dihydronaphthyl.

The term "heteroaryl" means a mono- or polycyclic aromatic ring system containing one or more heteroatoms selected from N, O or $S(O)_r$, wherein r=0, 1 or 2, consisting of 5 to 14 ring atoms wherein at least one of the heteroatoms is part of an aromatic ring. The term "heteroaryl" is intended to include all the possible isomeric forms.

Thus, the term "heteroaryl" includes the following exemplary structures; they are not depicted as radicals as each form is optionally attached through a covalent bond to any atom so long as appropriate valences are maintained:

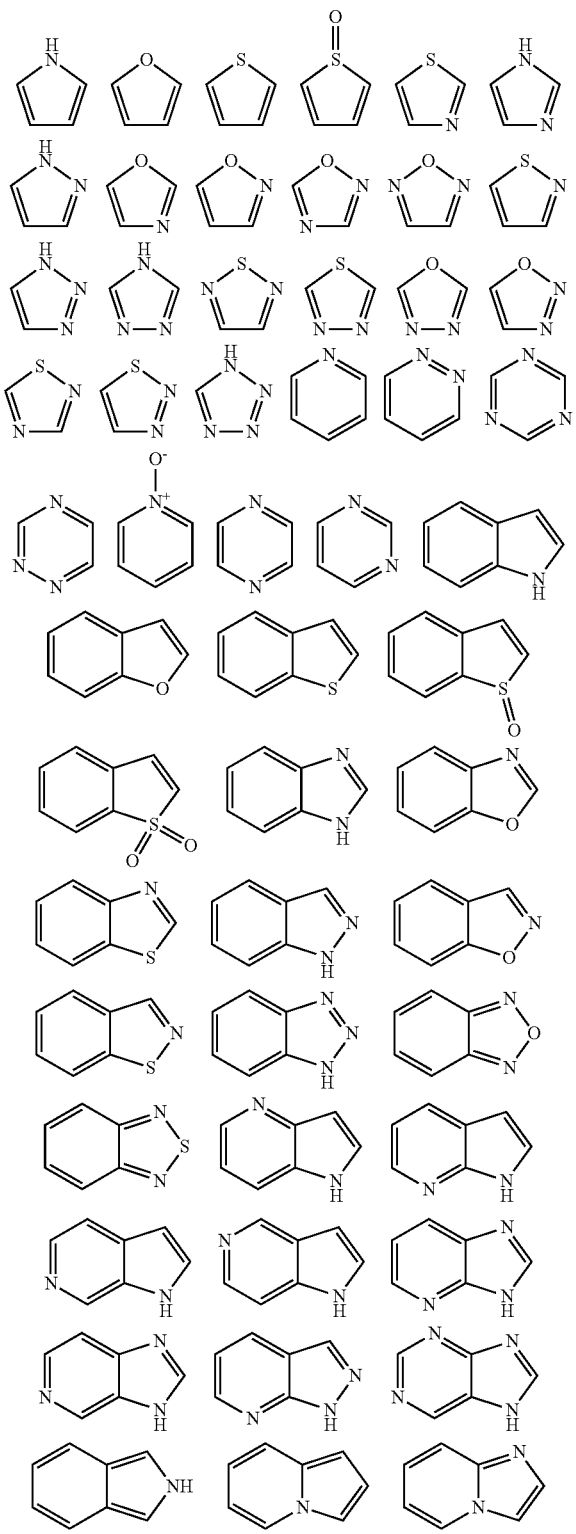

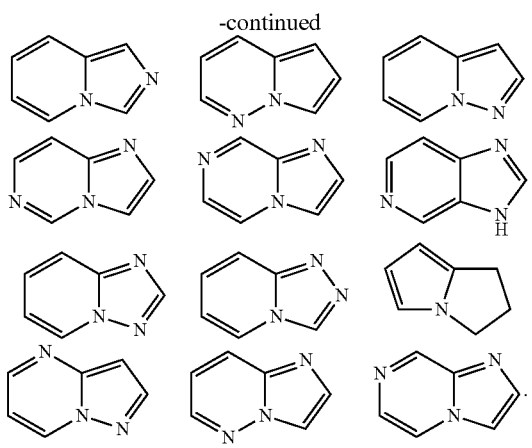

The term "bicyclic ring systems" means groups consisting of 2 joined cyclic substructures including spirocyclic, fused, and bridged ring systems.

The term halogen generally denotes fluorine, chlorine, bromine and iodine.

Many of the terms given above may be used repeatedly in the definition of a formula or group and in each case have one of the meanings given above, independently of one another.

The terms "treatment" and "treating" as used herein embrace both therapeutic, i.e. curative and/or palliative, and preventive, i.e. prophylactic, treatment.

Therapeutic treatment refers to the treatment of patients having already developed one or more of said conditions in manifest, acute or chronic form. Therapeutic treatment may be symptomatic treatment in order to relieve the symptoms of the specific indication or causal treatment in order to reverse or partially reverse the conditions of the indication or to stop or slow down progression of the disease.

Preventive treatment ("prevention") refers to the treatment of patients at risk of developing one or more of said conditions, prior to the clinical onset of the disease in order to reduce said risk.

The terms "treatment" and "treating" include the administration of one or more active compounds in order to prevent or delay the onset of the symptoms or complications and to prevent or delay the development of the disease, condition or disorder and/or in order to eliminate or control the disease, condition or disorder as well as to alleviate the symptoms or complications associated with the disease, condition or disorder.

When this invention refers to patients requiring treatment, it relates primarily to treatment in mammals, in particular humans.

The term "therapeutically effective amount" means an amount of a compound of the present invention that (i) treats or prevents the particular disease or condition, (ii) attenuates, ameliorates, or eliminates one or more symptoms of the particular disease or condition, or (iii) prevents or delays the onset of one or more symptoms of the particular disease or condition described herein.

DETAILED DESCRIPTION OF THE INVENTION

The present invention discloses novel heteroaromatic carboxamide derivatives, which are effective plasma kallikrein (PKK) inhibitors and possess suitable pharmacological and pharmacokinetic properties to use them as medicaments for the treatment of diseases and/or conditions that may be influenced by PKK inhibition, including but not limited to diabetic complications, ocular diseases and edema-associated diseases, in particular diabetic macular edema, age-related macular degeneration, choroidal neovascularization and hereditary angioedema.

The compounds of the present invention may provide several advantages, such as enhanced potency, high metabolic and/or chemical stability, high selectivity, safety and tolerability, enhanced solubility, enhanced permeability, desirable plasma protein binding, enhanced bioavailability, improved pharmacokinetic profiles, and the possibility to form stable salts.

Compounds of the Invention

In a first aspect of the present invention, it is found that compounds of formula (I)

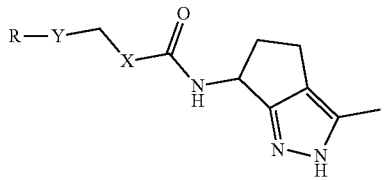
(I)

wherein Y, R, and X are defined as hereinbefore and hereinafter, are potent inhibitors of PKK and exhibit favorable properties with regard to selectivity, safety and tolerability, metabolic and/or chemical stability, pharmacokinetic and physicochemical characteristics, solubility, permeability, plasma protein binding, bioavailability and/or the possibility to form stable salts. In particular, they provide an advantageous combination of high potency on human PKK and significant selectivity, e.g. vs. various serine proteases, such as human tissue kallikrein 1 (TK1). Also, advantageous safety features, such as low potential of mutagenicity and low propensity for mechanism based inhibition of cytochrom P450 3A4, are exhibited.

Therefore, the compounds of formula (I), as defined hereinbefore or hereinafter, or pharmaceutically acceptable salts thereof are expected to be useful in the treatment of diseases and/or conditions which can be influenced by PKK inhibition.

Thus, according to one aspect of the present invention, a compound of formula (I)

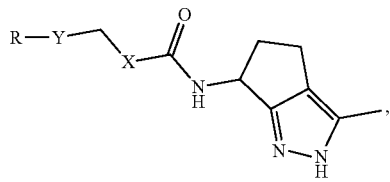
(I)

wherein Y, R, and X are defined as hereinbefore or hereinafter, is provided
as well as the isoforms, tautomers, stereoisomers, metabolites, prodrugs, solvates, hydrates, cocrystals, and the salts thereof, particularly the pharmaceutically acceptable cocrystals and salts thereof.

Unless otherwise stated, the groups, residues and substituents, particularly Y, R, X, $R^1$, $R^2$, and $R^3$ are defined as hereinbefore and hereinafter. Some preferred meanings of the substituents Y, R, X, $R^1$, $R^2$, and $R^3$ as well as of the stereochemistry of the compounds of formula (I) will be given hereinafter as embodiments of the invention. Any and each of these definitions and embodiments may be combined with one another.

According to one embodiment, Y is selected from the group Y-G1 consisting of

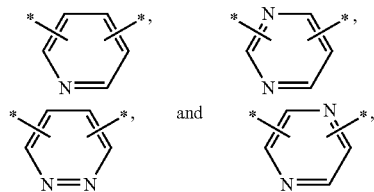

each of which is substituted with 1 or 2 independent substituents $R^1$.

According to another embodiment, Y is selected from the group Y-G2 consisting of

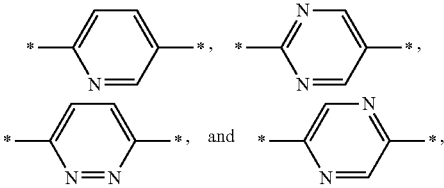

each of which is substituted with 1 or 2 independent substituents $R^1$ and wherein the bonds with asterisk indicate the sites of attachment of R and the $CH_2$ group of formula (I).

According to another embodiment, Y is selected from the group Y-G3 consisting of

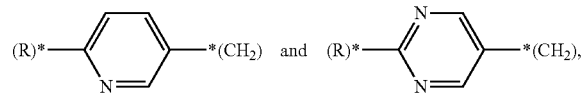

each of which is substituted with 1 substituent $R^1$ and wherein the bonds with asterisk and brackets indicate the sites of attachment of R and the $CH_2$ group of formula (I).

According to another embodiment, Y is selected from the group Y-G4 consisting of

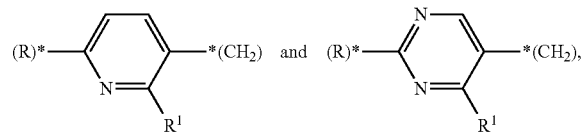

wherein the bonds with asterisk and brackets indicate the sites of attachment of R and the $CH_2$ group of formula (I).

According to another embodiment, Y is selected from the group Y-G5 consisting of

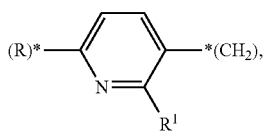

wherein the bonds with asterisk and brackets indicate the sites of attachment of R and the CH₂ group of formula (I).

According to another embodiment, Y is selected from the group Y-G6 consisting of

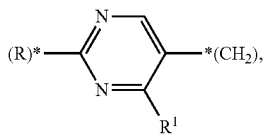

wherein the bonds with asterisk and brackets indicate the sites of attachment of R and the CH₂ group of formula (I).

R:

According to one embodiment, R is selected from the group R-G1 consisting of saturated 4- to 7-membered monocyclic and saturated 6- to 12-membered bicyclic ring systems containing 1 to 3 N atoms as ring members and optionally 1 to 2 ring members selected from the group consisting of C=O, O, S, S=O, and SO₂, provided that the ring systems do not contain any heteroatom-heteroatom bonds between ring members, wherein said ring systems are attached to Y in formula (I) via an N atom, and wherein said ring systems are optionally substituted with 1 to 6 F, optionally substituted with 1 substituent R², and optionally substituted with 1 or 2 CH₃ groups.

According to another embodiment, R is selected from the group R-G2 consisting of saturated 4- to 7-membered monocyclic and saturated 6- to 12-membered bicyclic ring systems containing 1 to 2 N atoms as ring members and optionally 1 ring member selected from the group consisting of C=O and O, provided that the ring systems do not contain any heteroatom-heteroatom bonds between ring members, wherein said ring systems are attached to Y in formula (I) via an N atom, and wherein said ring systems are optionally substituted with 1 to 4 F, optionally substituted with 1 substituent R², and optionally substituted with 1 or 2 CH₃ groups.

According to another embodiment, R is selected from the group R-G3 consisting of azetidin-1-yl, 5-aza-spiro[2.3]hexan-5-yl, 2-aza-spiro[3.3]heptan-2-yl, 6-oxa-2-aza-spiro[3.4]octan-2-yl, 5-oxa-2-aza-spiro[3.4]octan-2-yl, 7-oxa-2-aza-spiro[3.5]nonan-2-yl, pyrrolidin-1-yl, 2-aza-bicyclo[2.1.1]hexan-2-yl, 3-aza-bicyclo[3.1.0]hexan-3-yl, 5-aza-spiro[2.4]heptan-5-yl, 6-aza-spiro[3.4]octan-6-yl, 3-aza-bicyclo[3.2.0]heptan-3-yl, 2-oxa-7-aza-spiro[4.4]nonan-7-yl, octahydro-cyclopenta[c]pyrrol-1-yl, hexahydro-pyrrolo[3,4-c]pyrrol-1-on-5-yl, hexahydro-furo[3,4-c]pyrrol-5-yl, piperidin-1-yl, 3-aza-bicyclo[4.1.0]heptan-3-yl, 3-aza-bicyclo[3.1.1]heptan-3-yl, 6-oxa-3-aza-bicyclo[3.1.1]heptan-3-yl, 3-oxa-7-aza-bicyclo[3.3.1]nonan-7-yl, azepan-1-yl, and 4-aza-bicyclo[5.1.0]octan-4-yl, each of which is optionally substituted with 1 or 2 F, optionally substituted with 1 substituent R², and optionally substituted with 1 or 2 CH₃ groups.

According to another embodiment, R is selected from the group R-G4 consisting of azetidin-1-yl, 5-aza-spiro[2.3]hexan-5-yl, 2-aza-spiro[3.3]heptan-2-yl, pyrrolidin-1-yl, 3-aza-bicyclo[3.1.0]hexan-3-yl, 5-aza-spiro[2.4]heptan-5-yl, 6-aza-spiro[3.4]octan-6-yl, 3-aza-bicyclo[3.2.0]heptan-3-yl, octahydro-cyclopenta[c]pyrrol-1-yl, 3-aza-bicyclo[4.1.0]heptan-3-yl, 3-aza-bicyclo[3.1.1]heptan-3-yl, and azepan-1-yl, each of which is optionally substituted with 1 or 2 F, optionally substituted with 1 substituent R², and optionally substituted with 1 or 2 CH₃ groups.

According to another embodiment, R is selected from the group R-G5 consisting of 6-oxa-2-aza-spiro[3.4]octan-2-yl, 5-oxa-2-aza-spiro[3.4]octan-2-yl, 7-oxa-2-aza-spiro[3.5]nonan-2-yl, 2-aza-bicyclo[2.1.1]hexan-2-yl, 2-oxa-7-aza-spiro[4.4]nonan-7-yl, hexahydro-pyrrolo[3,4-c]pyrrol-1-on-5-yl, hexahydro-furo[3,4-c]pyrrol-5-yl, piperidin-1-yl, 6-oxa-3-aza-bicyclo[3.1.1]heptan-3-yl, 3-oxa-7-aza-bicyclo[3.3.1]nonan-7-yl, and 4-aza-bicyclo[5.1.0]octan-4-yl, each of which is optionally substituted with 1 or 2 F, optionally substituted with 1 substituent R², and optionally substituted with 1 or 2 CH₃ groups.

According to another embodiment, R is selected from the group R-G6 consisting of

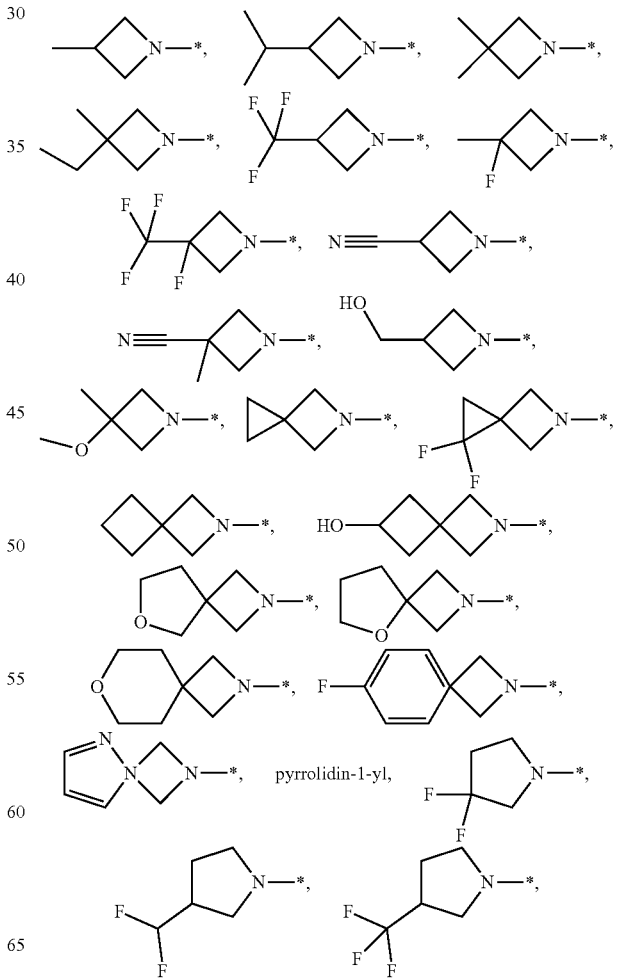

-continued
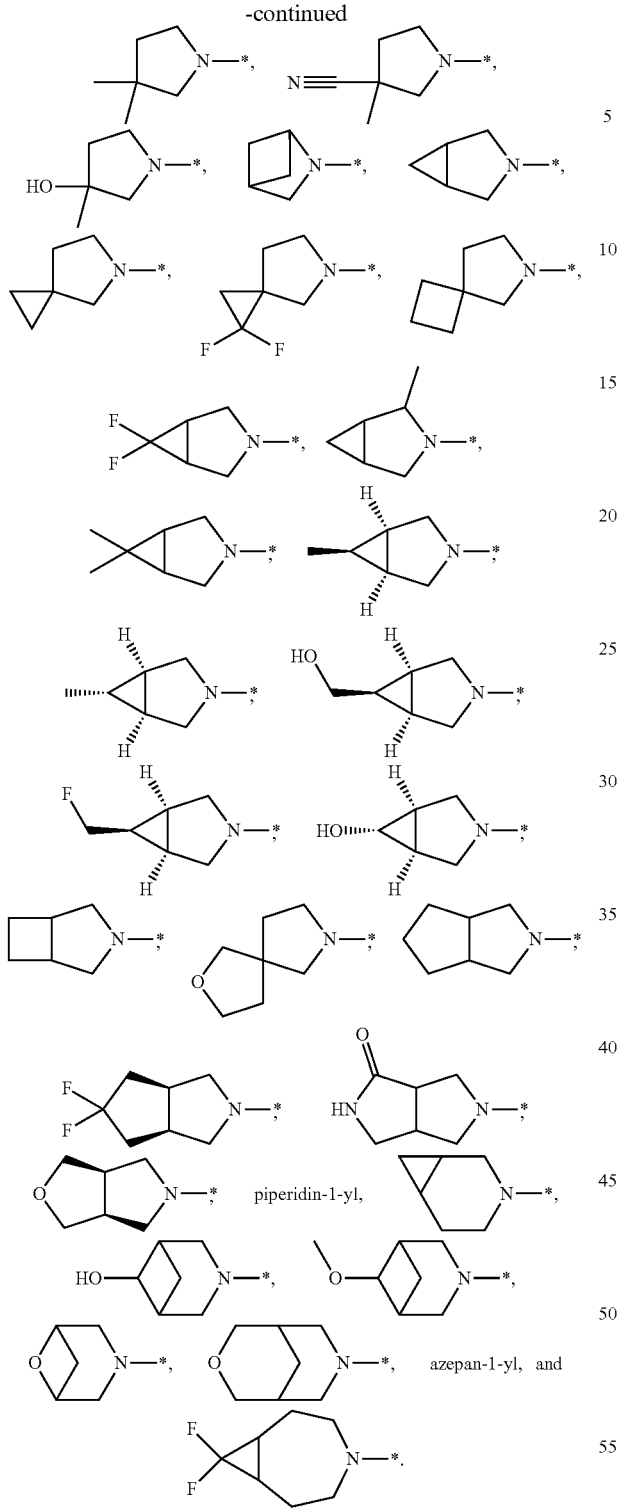
According to another embodiment, R is selected from the group R-G7 consisting of
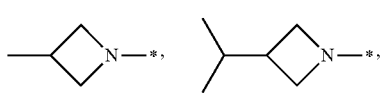
-continued
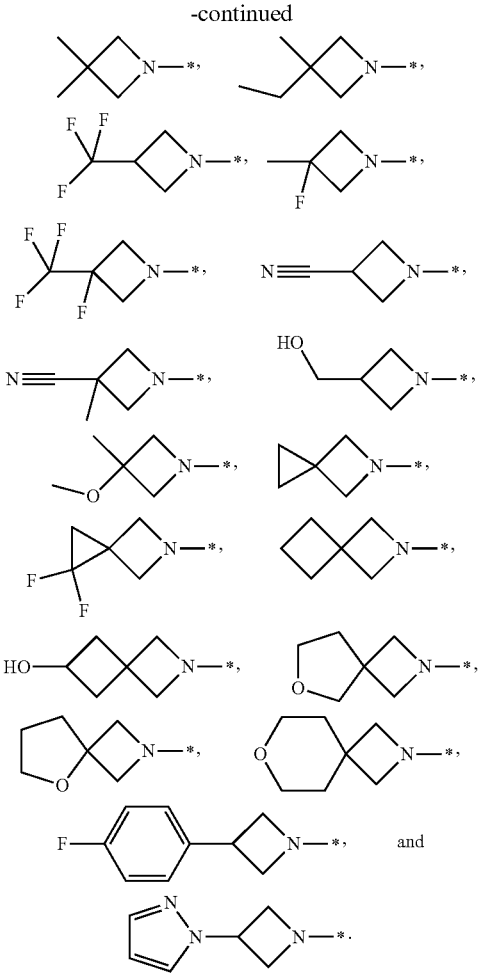
According to another embodiment, R is selected from the group R-G8 consisting of
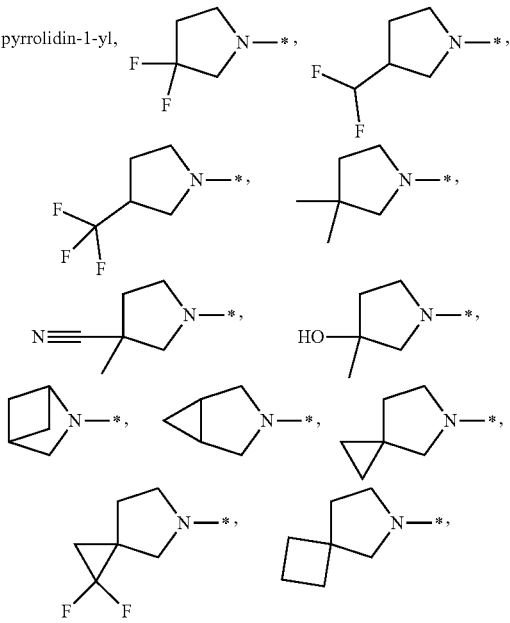

-continued

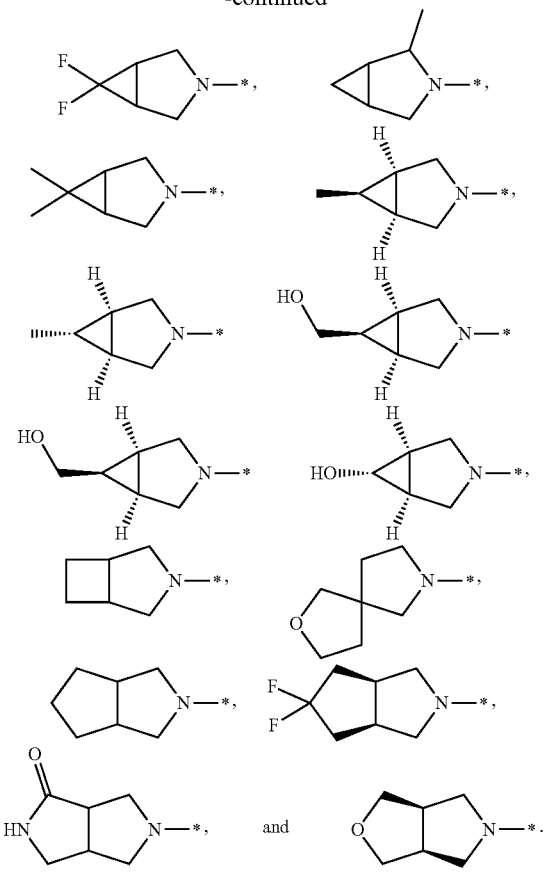

According to another embodiment, R is selected from the group R-G9 consisting of piperidin-1-yl,

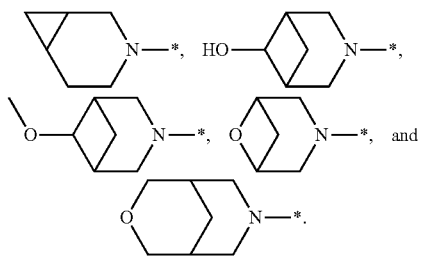

According to another embodiment, R is selected from the group R-G10 consisting of azepan-1-yl and

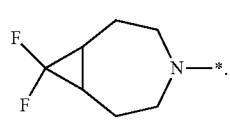

X:

According to one embodiment, X is selected from the group R-G10 consisting of 5-membered heteroaryls, containing 1 to 4 N atoms or containing 1 O or S atom or containing 1 to 3 N atoms and 1 O or S atom, and 9-membered heteroaryls, consisting of a 5-membered ring fused to a 6-membered ring and containing 1 to 5 N atoms, wherein said heteroaryls are attached to the carbonyl group in formula (I) via a C atom of the 5-membered ring and to the $CH_2$ group in formula (I) via a non-adjacent C or N atom of the 5-membered ring, and wherein said heteroaryls are optionally substituted with 1 substituent $R^3$.

According to another embodiment, X is selected from the group X-G2 consisting of 5-membered heteroaryls, containing 1 to 4 N atoms or 1 S atom, and 9-membered heteroaryls, consisting of a 5-membered ring fused to a 6-membered ring and containing 1 to 3 N atoms, wherein said heteroaryls are attached to the carbonyl group in formula (I) via a C atom of the 5-membered ring and to the $CH_2$ group in formula (I) via a non-adjacent C or N atom of the 5-membered ring, and wherein said heteroaryls are optionally substituted with 1 substituent $R^3$.

According to another embodiment, X is selected from the group X-G3 consisting of

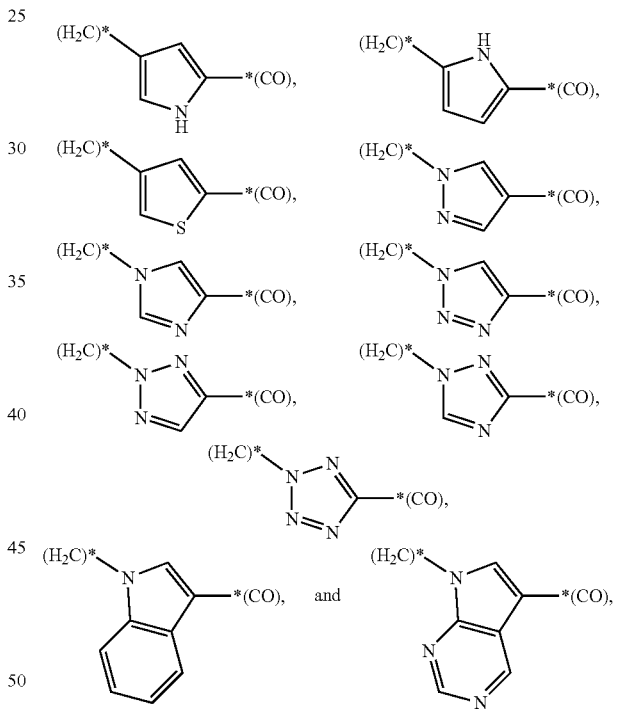

each of which is optionally substituted with 1 substituent $R^3$ and wherein the bonds with asterisk and brackets indicate the sites of attachment of the groups C=O and $CH_2$ of formula (I).

According to another embodiment, X is selected from the group X-G4 consisting of

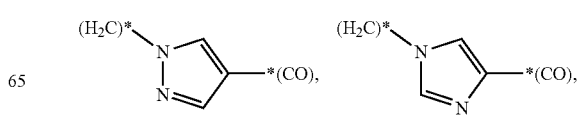

each of which is optionally substituted with 1 substituent R³ and wherein the bonds with asterisk and brackets indicate the sites of attachment of the groups C=O and CH₂ of formula (I).

According to another embodiment, X is selected from the group X-G5 consisting of each of which is optionally substituted with 1 substituent R³ and wherein the bonds with asterisk and brackets indicate the sites of attachment of the groups C=O and CH₂ of formula (I).

According to another embodiment, X is selected from the group X-G6 consisting of each of which is optionally substituted with 1 substituent R³ and wherein the bonds with asterisk and brackets indicate the sites of attachment of the groups C=O and CH₂ of formula (I).

According to another embodiment, X is selected from the group X-G7 consisting of each of which is optionally substituted with 1 substituent R³ and wherein the bonds with asterisk and brackets indicate the sites of attachment of the groups C=O and CH₂ of formula (I).

According to another embodiment, X is selected from the group X-G8 consisting of each of which is optionally substituted with 1 substituent R³ and wherein the bonds with asterisk and brackets indicate the sites of attachment of the groups C=O and CH₂ of formula (I).

According to another embodiment, X is selected from the group X-G9 consisting of wherein the bonds with asterisk and brackets indicate the sites of attachment of the groups C=O and CH₂ of formula (I).

R¹:

According to one embodiment, R¹ is selected from the group R¹-G1 consisting of

H, $C_{1-4}$-alkyl optionally substituted with 1 to 5 F, cyclopropyl optionally substituted with 1 F or 1 $CH_3$ group, CN, OH, O—$C_{1-3}$-alkyl optionally substituted with 1 to 5 F, $C_{1-3}$-alkyl optionally substituted with 1 substituent selected from the group consisting of CN, OH, and O—$CH_3$.

According to another embodiment, R¹ is selected from the group R¹-G2 consisting of H, $CH_3$, ON, $CF_3$, and $CH_2CH_3$.

According to another embodiment, R¹ is selected from the group R¹-G3 consisting of H, $CH_3$, and ON.

According to another embodiment, R¹ is selected from the group R¹-G4 consisting of H.

According to another embodiment, R¹ is selected from the group R¹-G5 consisting of $CH_3$.

According to another embodiment, R¹ is selected from the group R¹-G6 consisting of CN.

R²:

According to one embodiment, R² is selected from the group R²-G1 consisting of Cl, $C_{1-4}$-alkyl optionally substituted with 1 to 5 F, $C_{3-4}$-cycloalkyl, $C_{1-3}$-alkylene-OH, $C_{1-3}$-alkylene-O—$C_{1-4}$-alkyl, CN, COOH, $NH_2$, NH—$C_{1-3}$-alkyl, $N(C_{1-3}$-alkyl$)_2$, OH, O—$C_{1-4}$-alkyl optionally substituted with 1 to 5 F, phenyl, 5-membered heteroaryls containing 1 —NH—, —N<, —O— or —S— ring member and optionally additionally 1 or 2 =N— ring members, and 6-membered heteroaryls containing 1 or 2 =N— ring members;
  wherein said phenyl and 5- and 6-membered heteroaryls are optionally substituted at 1 or 2 carbon atoms independently of each other with F, Cl, $CH_3$, $CF_3$, CN, OH, and/or O—$CH_3$, and
  wherein N—H groups present within these rings are optionally replaced by N—$C_{1-3}$-alkyl.

According to another embodiment, R² is selected from the group R²-G2 consisting of
Cl, $C_{1-3}$-alkyl optionally substituted with 1 to 3 F, $CH_2OH$, $CH_2OCH_3$, CN, OH, O—$CH_3$, phenyl, 5-membered heteroaryls containing 1 —N<ring member and optionally additionally 1 or 2 =N— ring members, and 6-membered heteroaryls containing 1 or 2 =N— ring members;
  wherein said phenyl and 5- and 6-membered heteroaryls are optionally substituted at 1 carbon atom with F or $CH_3$.

According to another embodiment, $R^2$ is selected from the group $R^2$-G3 consisting of
  $CH_3$, $CH_2CH_3$, $CH(CH_3)_2$, $CH_2F$, $CHF_2$, $CF_3$, $CH_2OH$, CN, OH, O—$CH_3$, 4-fluorophenyl and pyrazolyl.

According to another embodiment, $R^2$ is selected from the group $R^2$-G4 consisting of
  $CF_3$, $CH_2OH$, CN, OH, and O—$CH_3$.

According to another embodiment, $R^2$ is selected from the group $R^2$-G5 consisting of
  $CH_3$, $CH_2CH_3$, $CH(CH_3)_2$, $CH_2F$, $CHF_2$, $CF_3$ and CN.

According to another embodiment, $R^2$ is selected from the group $R^2$-G6 consisting of
  $CH_2OH$ and OH.

According to another embodiment, $R^2$ is selected from the group $R^2$-G7 consisting of
  O—$CH_3$, 4-fluorophenyl and pyrazolyl.

$R^3$:
According to one embodiment, $R^3$ is selected from the group $R^3$-G1 consisting of
  F, Cl, Br, CN, COOH, $C_{1-4}$-alkyl optionally substituted with 1 to 5 F, $C_{3-5}$-cycloalkyl, $C_{1-3}$-alkylene-OH, $C_{1-3}$-alkylene-O—$C_{1-4}$-alkyl, O—$C_{1-4}$-alkyl optionally substituted with 1 to 5 F, 5-membered heteroaryls containing 1 —NH—, —O— or —S— ring member and optionally additionally 1 or 2 =N— ring members, and 6-membered heteroaryls containing 1 or 2 =N— ring members;
  wherein said 5- and 6-membered heteroaryls are optionally substituted at 1 or 2 carbon atoms independently of each other with F, Cl, $CH_3$, $CF_3$, CN, OH, and/or O—$CH_3$, and
  wherein N—H groups present within these rings are optionally replaced by N—$C_{1-3}$-alkyl.

According to another embodiment, $R^3$ is selected from the group $R^3$-G2 consisting of F, Cl, CN, COOH, $C_{1-2}$-alkyl optionally substituted with 1 to 3 F, $C_{3-4}$-cycloalkyl, $C_{1-3}$-alkylene-OH, $C_{1-3}$-alkylene-O—$CH_3$, O—$C_{1-2}$-alkyl optionally substituted with 1 to 3 F, and 5-membered heteroaryls containing 1 —NH—, —N($CH_3$)—, —O— or —S— ring member and optionally additionally 1 or 2 =N— ring members;
  wherein said 5-membered heteroaryls are optionally substituted at 1 or 2 carbon atoms independently of each other with F, $CH_3$, $CF_3$, CN, OH, and/or O—$CH_3$.

According to another embodiment, $R^3$ is selected from the group $R^3$-G3 consisting of
  F, Cl, CN, COOH, $C_{1-2}$-alkyl optionally substituted with 1 to 3 F, $C_{3-4}$-cycloalkyl, $C_{1-3}$-alkylene-OH, $C_{1-3}$-alkylene-O—$CH_3$, O—$CH_3$ optionally substituted with 1 to 3 F, and 5-membered heteroaryls containing 1 —NH— or —N($CH_3$)— ring member and optionally additionally 1 or 2 =N— ring members.

According to another embodiment, $R^3$ is selected from the group $R^3$-G4 consisting of
  Cl, CN, COOH, $CH_3$ optionally substituted with 1 to 3 F, cyclopropyl, $C(CH_3)_2OH$, $CH_2OCH_3$, $OCH_3$, and N-methyl-pyrazolyl.

According to another embodiment, $R^3$ is selected from the group $R^3$-G5 consisting of
  Cl, CN, $CH_3$, $CHF_2$, $CF_3$, and cyclopropyl.

According to another embodiment, $R^3$ is selected from the group $R^3$-G6 consisting of
  COOH and $C(CH_3)_2OH$.

According to another embodiment, $R^3$ is selected from the group $R^3$-G7 consisting of
  $CH_2OCH_3$, $OCH_3$, and N-methyl-pyrazolyl.

Stereochemistry:
According to one embodiment, the stereochemistry of the compound of formula (I) is according to formula (I.1)

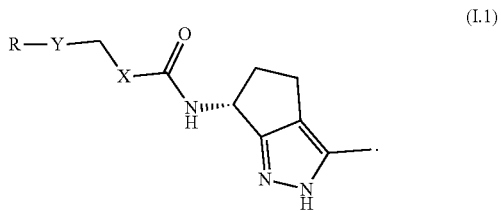

(I.1)

According to another embodiment, the stereochemistry of the compound of formula (I) is according to formula (I.2)

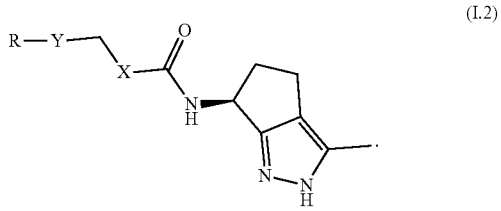

(I.2)

Further preferred subgeneric embodiments of the compounds of formula (I) are set forth as embodiments (I-a) to (I-r) in the following Table 1, wherein the above-mentioned substituent definitions are used. For example, the entry -G1 in column $R^1$ and row (I-a) means that in embodiment (I-a) substituent $R^1$ is selected from the definition designated $R^1$-G1. The same applies analogously to the other variables incorporated in the general formulas.

TABLE 1

| Embodiment | Substituents | | | | | |
|---|---|---|---|---|---|---|
| | Y | R | X | $R^1$ | $R^2$ | $R^3$ |
| (I-a) | Y-G1 | R-G1 | X-G1 | $R^1$-G1 | $R^2$-G1 | $R^3$-G1 |
| (I-b) | Y-G2 | R-G2 | X-G1 | $R^1$-G1 | $R^2$-G2 | $R^3$-G2 |
| (I-c) | Y-G2 | R-G2 | X-G2 | $R^1$-G2 | $R^2$-G2 | $R^3$-G2 |
| (I-d) | Y-G2 | R-G2 | X-G2 | $R^1$-G2 | $R^2$-G3 | $R^3$-G3 |
| (I-e) | Y-G3 | R-G2 | X-G2 | $R^1$-G2 | $R^2$-G3 | $R^3$-G3 |
| (I-f) | Y-G3 | R-G3 | X-G2 | $R^1$-G2 | $R^2$-G2 | $R^3$-G3 |
| (I-g) | Y-G3 | R-G3 | X-G2 | $R^1$-G2 | $R^2$-G3 | $R^3$-G3 |
| (I-h) | Y-G3 | R-G4 | X-G3 | $R^1$-G2 | $R^2$-G3 | $R^3$-G3 |
| (I-i) | Y-G3 | R-G5 | X-G3 | $R^1$-G2 | $R^2$-G3 | $R^3$-G3 |
| (I-j) | Y-G4 | R-G5 | X-G3 | $R^1$-G3 | $R^2$-G3 | $R^3$-G4 |
| (I-k) | Y-G4 | R-G6 | X-G3 | $R^1$-G3 | — | $R^3$-G4 |
| (I-l) | Y-G4 | R-G7 | X-G4 | $R^1$-G3 | — | $R^3$-G7 |
| (I-m) | Y-G4 | R-G7 | X-G6 | $R^1$-G3 | — | $R^3$-G5 |
| (I-n) | Y-G4 | R-G7 | X-G7 | $R^1$-G3 | — | $R^3$-G7 |
| (I-o) | Y-G4 | R-G8 | X-G4 | $R^1$-G3 | — | $R^3$-G5 |
| (I-p) | Y-G4 | R-G8 | X-G6 | $R^1$-G3 | — | $R^3$-G7 |
| (I-q) | Y-G4 | R-G8 | X-G7 | $R^1$-G3 | — | $R^3$-G7 |
| (I-r) | Y-G4 | R-G6 | X-G9 | $R^1$-G3 | — | — |

Particularly preferred are those subgeneric embodiments (I.1-a) to (I.1-r) which, in respect of the definitions of Y, R, X, $R^1$, $R^2$, and $R^3$ correspond to the subgeneric embodiments (I-a) to (I-r) of Table 1, but wherein the stereochemistry of the compounds is according to formula (I.1).

According to another preferred embodiment, the stereochemistry of the compounds of the present invention is according to formula (I.1) wherein Y is selected from the group Y-G5.

According to another preferred embodiment, the stereochemistry of the compounds of the present invention is according to formula (I.1) wherein Y is selected from the group Y-G6.

Particularly preferred compounds, including their tautomers, the salts thereof, or any solvates, hydrates or cocrystals thereof, are those described in the section Examples and Experimental Data.

Preparation

The compounds according to the invention and their intermediates may be obtained using methods of synthesis which are known to the one skilled in the art and described in the literature of organic synthesis for example using methods described in "Comprehensive Organic Transformations", $2^{nd}$ Edition, Richard C. Larock, John Wiley & Sons, 2010, and "March's Advanced Organic Chemistry", $7^{th}$ Edition, Michael B. Smith, John Wiley & Sons, 2013. Preferably the compounds are obtained analogously to the methods of preparation explained more fully hereinafter, in particular as described in the experimental section. In some cases the sequence adopted in carrying out the reaction schemes may be varied. Variants of these reactions that are known to the skilled man but are not described in detail here may also be used. The general processes for preparing the compounds according to the invention will become apparent to the skilled man on studying the schemes that follow. Starting compounds are commercially available or may be prepared by methods that are described in the literature or herein, or may be prepared in an analogous or similar manner. Before the reaction is carried out, any corresponding functional groups in the starting compounds may be protected using conventional protecting groups. These protecting groups may be cleaved again at a suitable stage within the reaction sequence using methods familiar to the skilled man and described in the literature for example in "Protecting Groups", $3^{rd}$ Edition, Philip J. Kocienski, Thieme, 2005, and "Protective Groups in Organic Synthesis", $4^{th}$ Edition, Peter G. M. Wuts, Theodora W. Greene, John Wiley & Sons, 2006.

Scheme 1:

Compounds of formula (I') can be prepared by reaction of a suitable acid of formula (II) (either as free acid or carboxylate with a suitable metal cation such as $Li^+$, $Na^+$, $K^+$ etc.) and a suitable amine of formula (III) (either as free amine or a salt such as hydrochloride, hydrobromide, etc.) in a suitable solvent (e.g., DCM, THF, 1,4-dioxane, DMF, N,N-dimethylacetamide, and 1-methyl-2-pyrrolidinone) in the presence of a suitable coupling agent (e.g., O-(7-azabenzotriazol-1-yl)-N,N,N',N'-tetramethyluronium-hexafluorophosphate (HATU), O-(benzotriazol-1-yl)-N,N,N',N'-tetramethyluronium tetrafluoroborate (TBTU), (benzotriazol-1-yloxy)tripyrrolidinophosphonium hexafluorophosphate (PyBOP), carbodiimide reagents, etc.) and a base (e.g., triethylamine, N,N-diisopropyl-ethylamine, pyridine, etc.) to form an amide bond; Y, R, and X in Scheme 1 have the meanings as defined hereinbefore. Alternatively, the carboxylic acid is transformed into a carboxylic chloride (using, e.g., oxalyl choride or thionyl chloride in DCM) and coupled as such with amine (III) in the presence of a suited base (e.g., triethylamine, N,N-diisopropyl-ethylamine, pyridine, etc.). In case amine (III) is employed with a protective group on the pyrazole ring (PG is not H) this group is cleaved off afterwards by applying standard procedures reported in the literature of organic chemistry. 2-Trimethylsilylethyloxymethyl and tert-butyl ester are preferably cleaved under acidic conditions with, e.g., TFA or hydrochloric acid in a solvent such as DCM, 1,4-dioxane, isopropanol, or EtOAC. 2-Trimethylsilylethyloxymethyl may also be removed by using a fluoride source (e.g., $^{11}Bu_4NF$) in a suited solvent such as THF. A benzyloxymethyl group can be removed by using hydrogen in the presence of a transition metal such as palladium on carbon. Benzyloxymethyl groups bearing electron donating groups such as methoxy on the phenyl ring may also be removed under oxidative conditions (e.g., with ceric ammonium nitrate (CAN) or 2,3-dichloro-5,6-dicyanoquinone (DDQ)) or acidic conditions (e.g., with TFA or hydrochloric acid).

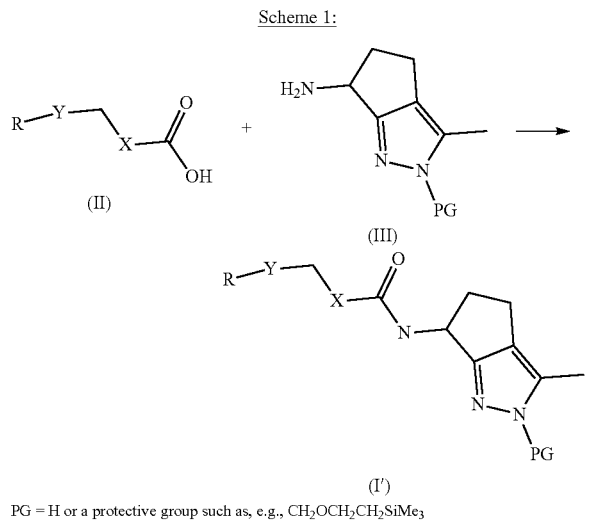

Scheme 1:

PG = H or a protective group such as, e.g., $CH_2OCH_2CH_2SiMe_3$

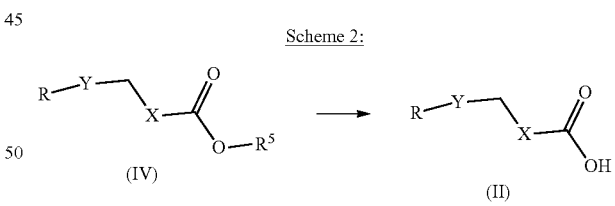

Scheme 2:

Scheme 2:

Acids of formula (II), wherein Y, R, and X have the meanings as defined hereinbefore, are preferably prepared from the corresponding ester (IV) through hydrolysis or hydrogenolysis depending on the nature of $R^5$. Lower alkyl group esters such as ethyl or methyl esters are preferably cleaved by hydrolysis with a hydroxide salt such as NaOH, LiOH, or KOH in a mixture of water and a suitable miscible solvent (e.g., THF, MeOH, EtOH, 1,4-dioxane, or mixtures of these) at ambient or elevated temperature. The acid may be isolated either as a salt with the metal cation or as free acid. tert-Butyl ester is preferably cleaved by treatment with an acid (e.g., hydrochloric acid or TFA) in a suitable solvent (e.g., DCM, 1,4-dioxane, MeOH, EtOH, THF, water, or mixtures of these). A benzyl ester is preferably cleaved by hydrogenolysis with a suitable catalyst (e.g., palladium on carbon) in a suitable solvent (e.g., EtOH, MeOH, THF, DCM, or EtOAC) under an atmosphere of hydrogen (preferably 1 to 5 bar).

Scheme 3

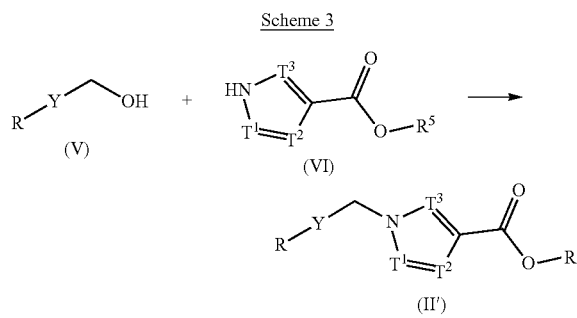

$T^1$ and $T^2$ are independently of each other N, C-H, or C-$R^3$; or
$T^1$ and $T^2$ form together an annulated benzo, pyrido, or pyrimido ring, which is optionally monosubstituted with $R^3$
$T^3$ = CH, N;
$R^5$ = $C_{1-4}$-alkyl or benzyl Scheme 3:

Some of the compounds (II') can be prepared by reaction of an alcohol (V) with an ester (VI) employing the conditions of the Mitsunobu reaction (e.g., triphenylphosphine or tri-n-butylphosphine combined with, e.g., diethyl azodicarboxylate (DEAD), diisopropyl azodicarboxylate (DIAD), or di-tert-butyl azodicarboxylate (DBAD) in a solvent such as THF, 1,4-dioxane, toluene etc.); Y, R, and $R^3$ in Scheme 3 have the meanings as defined hereinbefore. Alcohol (V) may bear the desired residue R on the heteroaromatic ring Y or a leaving group instead to introduce R later on. Alternatively, some of the compounds (II') can be obtained by reacting alcohol (V) and ester (VI) in the presence of a Lewis acid or Brønsted acid (e.g., 4-toluenesulfonic acid) in a suited solvent (e.g., ACN) at elevated temperature (20 to 120° C.).

Scheme 4

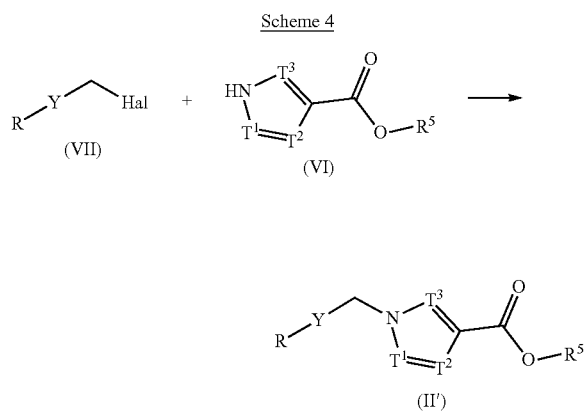

$T^1$ and $T^2$ are independently of each other N, C-H, or C-$R^3$; or
$T^1$ and $T^2$ form together an annulated benzo, pyrido, or pyrimido ring, which is optionally monosubstituted with $R^3$
$T^3$ = CH, N;
$R^5$ = $C_{1-4}$-alkyl or benzyl
Hal = leaving group such as Cl, Br, I, OSO$_2$CH$_3$ Scheme 4:

Some of the compounds (II') can also be prepared by reaction of compound (VII), bearing a leaving group at the heteroarylmethyl position such as Cl, Br, or mesyloxy (methanesulfonyloxy), with ester (VI) in the presence of a suitable base (e.g., sodium hydride, cesium carbonate, potassium carbonate) in a suitable solvent (e.g., THF, DMF); Y, R, and $R^3$ in Scheme 4 have the meanings as defined hereinbefore. Compound (VII) may bear the desired residue R on the heteroaromatic ring Y or a leaving group instead to introduce R later on.

Scheme 5

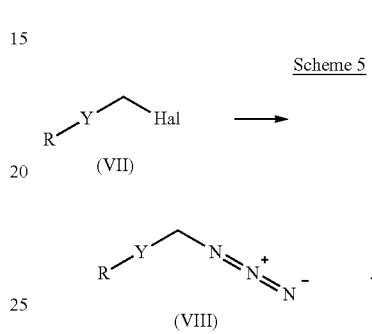

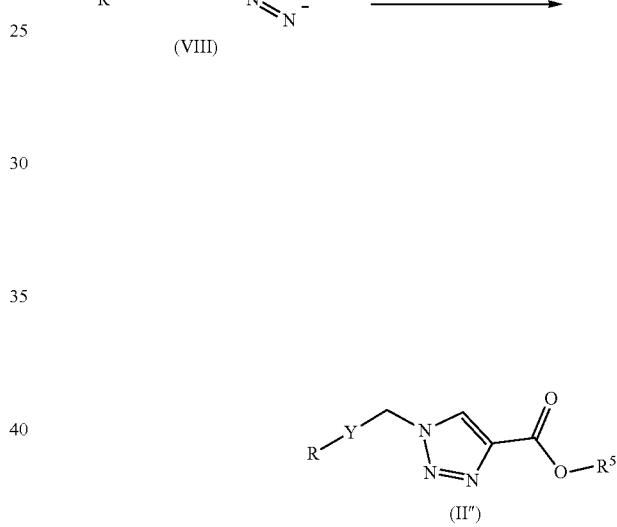

$R^5$ = $C_{1-4}$-alkyl or benzyl
Hal = leaving group such as OH, Cl, Br, I, OSO$_2$CH$_3$ Scheme 5:

Some esters of formula (II"), wherein Y and R have the meanings defined hereinbefore, can be prepared by the treatment of a corresponding alkyl halide (bromide or chloride) or sulfonate (e.g., mesylate) of formula (VII) with sodium azide in DMF or another suitable solvent to give an intermediate of formula (VIII) which is then reacted with a suitable propiolic acid ester under copper mediated catalytic conditions (e.g., ethyl propiolate or tert-butyl propiolate with catalytic copper sulfate and sodium ascorbate in water/tert-butanol) to give compound (II"). Alternatively, azide (VIII) can be obtained from an alcohol of formula (V) (Hal is OH) by treatment with diphenylphosphoryl azide in the presence of a suitable base such as DBU in a suitable solvent (e.g., THF or DMF). Compound (VII) may bear the desired residue R on the heteroaromatic ring Y or a leaving group instead to introduce R later on.

Scheme 6

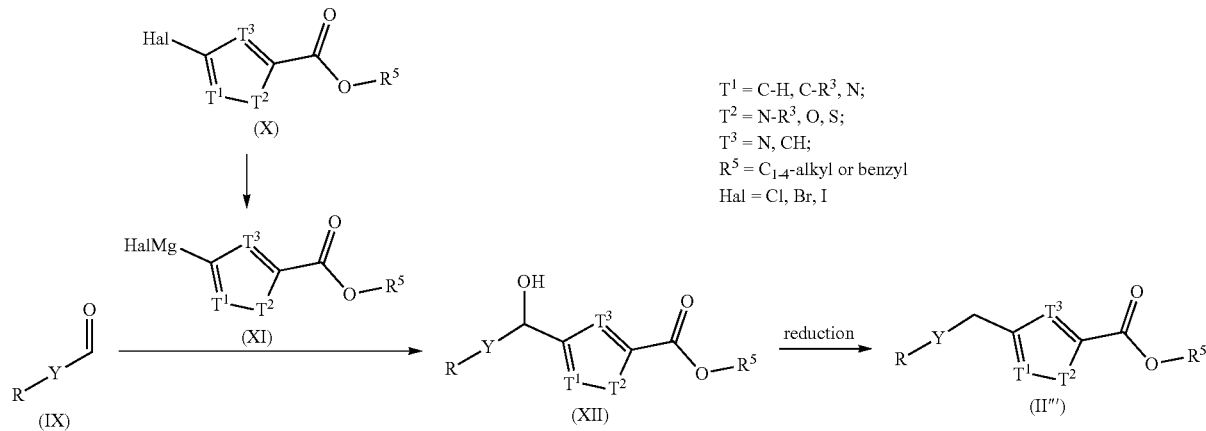

Scheme 6:
Esters of formula (II'''), wherein Y, R, and $R^3$ have the meanings defined hereinbefore, can be prepared from alcohols (XII) by displacement of the hydroxyl group with hydrogen employing methods reported in the literature (with, e.g., triethylsilane and TFA or borontrifluoride etherate in DCM, or hydrogen in the presence of palladium on carbon in a solvent such as THF or EtOH). Alcohols (XII) may be prepared by adding magnesium halide (XI) to aldehyde (IX), that, in turn, can be obtained from its corresponding alcohol by oxidation (e.g., Dess-Martin oxidation or Swern oxidation) in an inert solvent (e.g., THF or diethyl ether) at low to ambient temperature. Magnesium halide (XI) may be obtained after a halogen metal exchange reaction from the corresponding bromide or iodide of (X) using isopropyl magnesium chloride optionally combined with lithium chloride in THF at low temperature. Alternatively, magnesium metal is inserted into the carbon halogen bond to provide magnesium halide (XI). Compounds (IX) and (XII) may bear the desired residue R on the heteroaromatic ring Y or a leaving group instead to introduce R later on.

Scheme 7:
Compounds of formula (II''''), wherein Y, R, and $R^3$ have the meanings defined hereinbefore, can be prepared in an analogous fashion to the compounds delineated in Scheme 6 using the isomeric magnesium halide

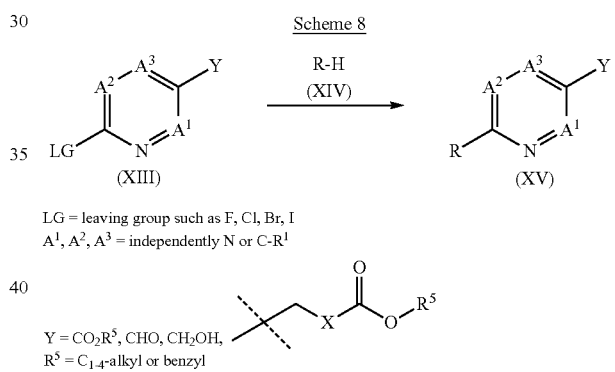

Scheme 7

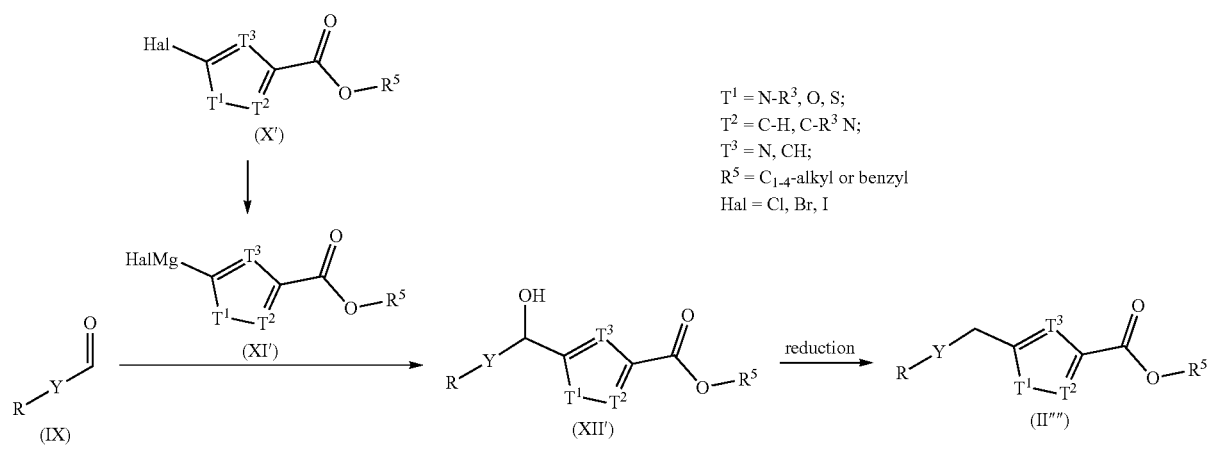

Scheme 8:

Intermediates of formula (XV) can be prepared from heteroaromatic compound (XIII) and amine (XIV) via either a nucleophilic substitution reaction on the heteroaromatic ring or a transition metal catalyzed coupling reaction; X and R in Scheme 8 have the meanings defined hereinbefore. The nucleophilic substitution of a leaving group on the heteroaromatic ring in (XIII) with the N in compound (XIV) can be conducted in the presence of a suitable base (e.g., sodium hydride, cesium carbonate, potassium carbonate, N,N-diisopropyl-ethylamine) in a suitable solvent (e.g., THF, 1,4-dioxane, DMF, DMSO) at ambient or elevated temperature. A transition metal catalyzed coupling reaction is preferably carried out in analogy to procedures reported in the literature of organic chemistry referred to as Ullmann or Buchwald/Hartwig coupling reaction using suitable palladium or copper salts or complexes thereof, optionally combined with additional ligands, in the presence of a base and in a suited solvent.

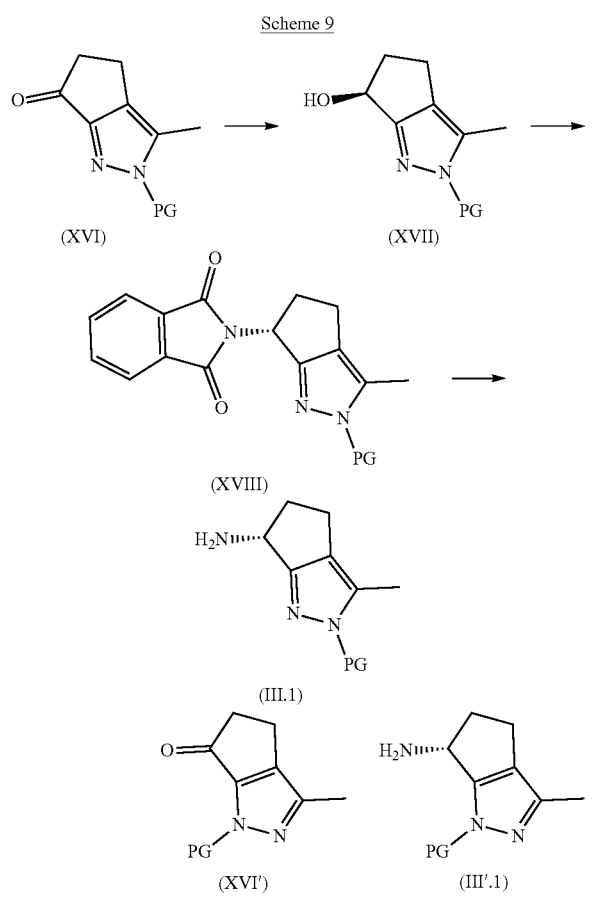

PG = protective group, see Scheme 10,
e.g., CH$_2$OCH$_2$CH$_2$SiMe$_3$

Scheme 9:

Enantiopure amines of formulae (III.1) and (III'.1) can be prepared from ketone (XVI) and (XVI'), respectively, as delineated in Scheme 9. Ketones of formula (XVI) can be enantioselectively reduced under various conditions reported in the literature of organic chemistry (e.g., J. Am. Chem. Soc. 1995, 117, 7562-3; Org. Lett. 2010, 12, 1756-9; Org. Proc. Res. Dev. 2006, 10, 949-958; Tetrahedron: Asymmetry 2003, 14, 2659-2681; Tetrahedron Lett. 2014, 55, 3635-40; and references quoted therein) to give an enantiopure or enantioenriched alcohol of formula (XVII) or (XVII') (not shown), the compound derived from ketone (XVI'). The alcohol can then be reacted with a sufficiently acidic N—H containing molecule such as phthalimide or (tert-Bu-OCO)$_2$NH in a Mitsunobu or Mitsunobu-type reaction (using, e.g., triphenylphosphine or tri-n-butylphosphine combined with dimethyl azodicarboxylate, DEAD, DIAD, di-(4-chlorobenzyl) azodicarboxylate, dibenzyl azodicarboxylate, DBAD, azodicarboxylic acid bis-(dimethylamide), azodicarboxylic acid dipiperidide, or azodicarboxylic acid dimorpholide in a suitable solvent (e.g., THF, 1,4-dioxane, EtOAC, benzene, toluene, etc.)) leading to introduction of a N residue with inversion of the configuration of the stereocenter (→(XVIII)). Alternatively, a phosphoryl azide (e.g., diphenylphosphoryl azide) can be employed to replace the OH in (XVII) under inversion of the configuration of the adjacent carbon atom with an azide. The amino group can be liberated from the phthalimide group by treatment with, e.g., hydrazine, hydroxylamine, methylamine, n-butylamine, or ethanolamine in a suitable solvent (e.g., EtOH, MeOH, ACN, THF, dioxane, DMSO, N,N-dimethylacetamide, water, or mixtures of these) with heating if necessary to give an intermediate of formula (III.1). tert-Bu-O—CO is preferably removed under acidic conditions (using, e.g., TFA or hydrochloric acid) to give amine (III.1). An azide can be reduced to the amine (III.1) with, e.g., hydrogen in the presence of a transition metal (e.g., Pd on carbon, Raney-Ni, PtO$_2$, etc.) or a phosphine (e.g., triphenylphosphine). The racemate (III) is obtained upon reduction of compound (XVI) with an achiral reducing agent such as sodium borohydride and following the further route described above.

Alternatively, compound (III.1) can be obtained from ketone (XVI) via a 3-step synthesis sequence employing enantiopure tert-butanesulfinamide in the presence of a titanium alcoholate (e.g., Ti(OEt)$_4$ or Ti (O$^i$Pr)$_4$) in a solvent (e.g., THF, DCM, toluene, or neat) at ambient or elevated temperature to generate the corresponding enantiopure tert-butylsulfinylated imine which can be diastereoselectively reduced to the corresponding tert-butylsulfinylated amine using a hydride (e.g., lithium or sodium borohydride, L-selectride, diisobutylaluminum hydride, etc.) in a suited solvent (e.g., THF, toluene, MeOH, etc., depending on the hydride source used). tert-Butylsulfinyl group can be cleaved off using an acid (e.g., TFA or hydrochloric acid) in a suitable solvent (e.g., toluene, DCM, dioxane, alcohol, water, etc.) at ambient or elevated temperature.

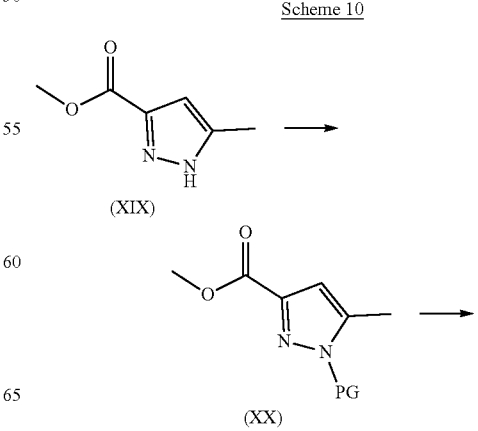

-continued

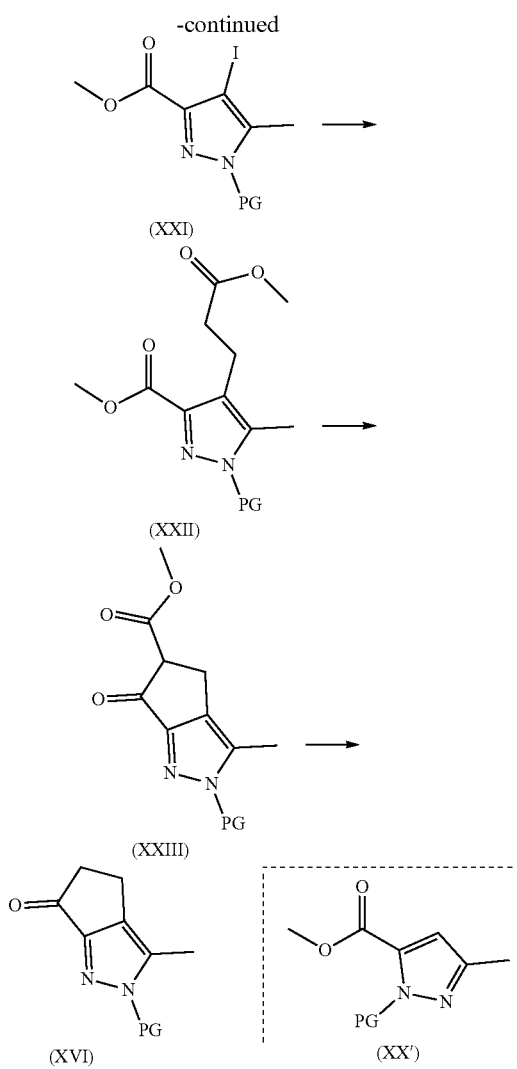

PG = protective group, e.g.,
C$_{1-4}$-alkyl optionally substituted with 1 to 5 F or Cl and optionally substituted with 1 group selected from Si(CH$_3$)$_3$, CN, SO$_2$-C$_{1-4}$-alkyl, or SO$_2$-phenyl;
CH$_2$-phenyl optionally substituted with 1 or 2 OCH$_3$;
CH$_2$-N(C$_{1-4}$-alkyl)$_2$, CH$_2$-pyrrolidin-1-yl, CH$_2$-NHCO-C$_{1-4}$-alkyl,
CH$_2$-N(CH$_3$)CO-C$_{1-4}$-alkyl;
CH$_2$-O-C$_{1-4}$-alkyl optionally substituted with 1 CH$_3$, 1 Si(CH$_3$)$_3$, or 3 Cl;
CH$_2$-O-CH$_2$-phenyl optionally substituted with 1 or 2 OCH$_3$, tetrahydropyran-2-yl, tetrahydrofuran-2-yl;
CO-C$_{1-4}$-alkyl optionally substituted with 1 to 5 F or Cl;
CO-N(C$_{1-4}$-alkyl)$_2$, CO-pyrrolidin-1-yl;
CO-O-C$_{1-4}$-alkyl optionally substituted with 1 Si(CH$_3$)$_3$ or 3 Cl;
CO-O-CH$_2$-phenyl optionally substituted with 1 or 2 OCH$_3$;
SO$_2$(C$_{1-4}$-alkyl) optionally substituted with 1 to 5 F or 1 to 3 Cl;
SO$_2$-phenyl optionally substituted with 1 or 2 groups selected from Cl, Br, CH$_3$,NO$_2$, and OC$_{1-4}$-alkyl;
SO$_2$-N(C$_{1-4}$-alkyl)$_2$, SO$_2$-pyrrolidin-1-yl;
phenyl substituted with 1 or 2 groups selected from Cl, Br, NO$_2$, OC$_{1-4}$-alkyl, and SO$_2$C$_{1-4}$-alkyl;
wherein in each of said protective groups each C$_{1-4}$-alkyl is independent from one another and e.g. selected from the group consisting of methyl, ethyl, iso-propyl and tert-butyl.

Scheme 10:
Compounds (XVI) can be obtained from reported ester (XIX) (or the corresponding higher alkyl esters, e.g., ethyl, propyl, isopropyl, or tert-butyl ester) in a sequence consisting of 5 or 6 reaction steps. Compound (XIX) can be derivatized on one of its N atoms with a broad range of protecting groups that are reported in the literature of organic chemistry. For instance, compound (XIX) can be transformed into compound (XX) by treatment with a base (e.g., a hydride such as sodium hydride, a hydroxide such as sodium hydroxide, a carbonate such as sodium or potassium carbonate, an alcoholate such as lithium methoxide or potassium tert-butylate, an organic amine such as triethylamine, Hinig's base, DABCO, DBN, or DBU, a phosphazene such as P$_2$Et phosphazene, an amide such as lithium diisopropylamide or lithium hexamethyldisilazide) in a suited solvent (e.g., benzene, toluene, DCM, THF, dioxane, EtOAc, ACN, DMF, N,N-dimethylacetamide, N-methylpyrrolidinone, etc., depending on the nature of the base used) and concurrent or subsequent reaction with an electrophile (a protective group bearing a leaving group such as chloride, bromide, iodide, alkyl- or arylsulfonyloxy, alkyloxy, acyloxy, etc.) of a suited protective group (e.g., 2-trimethylsilylethyloxymethyl chloride for introducing 2-trimethylsilylethyloxymethyl as protective group). Compound (XX) can be chlorinated, brominated, or iodinated employing a suited electrophilic source of the corresponding halogen (e.g., N-chlorosuccinimide for Cl, N-bromosuccinimide or Br$_2$ for Br, N-iodosuccinimide, I$_2$, or ICl for I, optionally in the presence of additives such as silver salts or acids) in a suited solvent (e.g., DCM, dichloroethane, dioxane, ACN, DMF, etc.). For instance, iodine can be introduced using N-iodosuccinimide and TFA in ACN to furnish compound (XXI). Compound (XXII) can then be prepared from the corresponding halide (e.g., iodide (XXI)) employing a 1- or 2-step synthesis route encompassing a Heck coupling reaction (broadly covered in the literature of organic chemistry, e.g., in Catalysts 2017, 7, 267 and references quoted therein) with either acrolein dialkyl acetal (e.g., acrolein dimethyl acetal) or an acrylic acid ester (e.g., acrylic methyl ester); using the latter coupling partner requires an additional step to reduce the olefinic bond formed that can be conducted with hydrogen in the presence of a transition metal catalyst (e.g., Pd such as palladium on carbon, Ni such as Raney-Ni, Pt such as platinum oxide, Rh such as rhodium on carbon, etc.) in a suited solvent (e.g., DCM, dioxane, THF, EtOAc, alcohol such as MeOH, water, etc.). Ketoester (XXIII) can be produced upon treatment of compound (XXII) with a base (e.g., a hydride such as sodium hydride, an alcoholate such as lithium methoxide or potassium tert-butylate, an organic amine such as DBU, a phosphazene such as P$_2$Et phosphazene, an amide such as lithium diisopropylamide, lithium, sodium or potassium hexamethyldisilazide, etc.) in a suited solvent (e.g., benzene, toluene, dioxane, THF, alcohol, etc., depending on the base used) at low to increased temperature (−78° C. to 100° C., depending on the base and solvent employed). Hydrolysis of the ester group in compound (XXIII) followed by decarboxylation can be achieved by stirring the compound in a solvent (e.g., dioxane, THF, ACN, DMF, N,N-dimethylacetamide, DMSO, alcohol, water, etc., or mixtures of these), optionally in the presence of a base (e.g., sodium hydroxide), a halide salt such as lithium iodide or chloride, or an acid (e.g., hydrochloric acid) at 0 to 140° C. to give ketone (XVI). The entire sequence may be analogously applied to the isomerically protected compound (XX') to give the ketone (XVI') and does not necessarily rely on the use of a protective group and thus might be carried out without one (PG=H).

The compounds of formula (I) may be resolved into their enantiomers and/or diastereomers as mentioned below. Thus, for example, cis/trans mixtures may be resolved into their cis and trans isomers and racemic compounds may be separated into their enantiomers.

The cis/trans mixtures may be resolved, for example, by chromatography into the cis and trans isomers thereof. The compounds of formula (I) which occur as racemates may be separated by methods known per se into their optical antipodes and diastereomeric mixtures of compounds of general formula (I) may be resolved into their diastereomers by taking advantage of their different physico-chemical properties using methods known per se, e.g. chromatography and/or fractional crystallization; if the compounds obtained thereafter are racemates, they may be resolved into the enantiomers as mentioned below.

The racemates are preferably resolved by column chromatography on chiral phases or by crystallization from an optically active solvent or by reacting with an optically active substance which forms salts or derivatives such as esters or amides with the racemic compound. Salts may be formed with enantiomerically pure acids for basic compounds and with enantiomerically pure bases for acidic compounds. Diastereomeric derivatives are formed with enantiomerically pure auxiliary compounds, e.g. acids, their activated derivatives, or alcohols. Separation of the diastereomeric mixture of salts or derivatives thus obtained may be achieved by taking advantage of their different physico-chemical properties, e.g. differences in solubility; the free antipodes may be released from the pure diastereomeric salts or derivatives by the action of suitable agents. Optically active acids commonly used for such a purpose as well as optically active alcohols applicable as auxiliary residues are known to those skilled in the art.

As mentioned above, the compounds of formula (I) may be converted into salts, particularly for pharmaceutical use into the pharmaceutically acceptable salts. As used herein, "pharmaceutically acceptable salts" refer to derivatives of the disclosed compounds wherein the parent compound is modified by making acid or base salts thereof.

The compounds according to the invention are advantageously also obtainable using the methods described in the examples that follow, which may also be combined for this purpose with methods known to the skilled man from the literature.

Thus, according to another aspect of the present invention, processes for the synthesis of compounds of formula (I) are provided.

According to another aspect of the present invention, intermediates of the synthesis of compounds of formula (I) are provided.

According to one embodiment, the invention relates to intermediates as depicted and described in Schemes 9 and/or 10.

According to another embodiment, the invention relates to one or more of the following intermediates

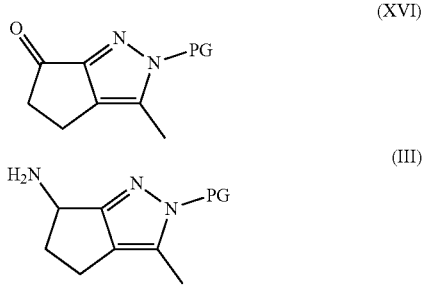

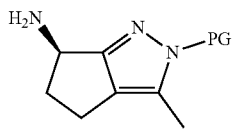

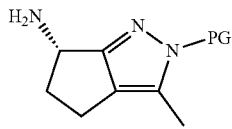

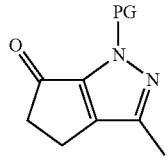

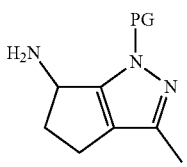

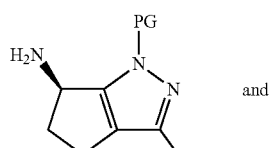

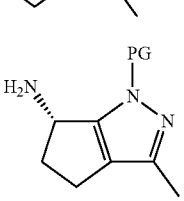

wherein PG is defined as hereinbefore or hereinafter.

Pharmacological Activity

The activity of the compounds of the invention may be demonstrated using the following assay:

Biological Methods

The ability of compounds of formula (I) to inhibit plasma kallikrein (PKK), Factor XIIa (FXIIa), Factor XIa (FXIa), Factor Xa (FXa), Factor IIa (alpha-thrombin; FIIa), plasmin, trypsin, tissue kallikrein 1 (TK1), Factor VIIa (FVIIa), or FVIIa complexed with Tissue Factor, phospholipids and $CaCl_2$ (FVIIa/TF/PL/$CaCl_2$) was determined using the following biochemical assays in assay buffer (100 mM Tris, 150 mM NaCL, adjusted to a pH of 7.8 with HCl, and containing 0.1% (w/v) BSA and 0.05% (v/v) Tween20) in the presence of 1% (v/v) DMSO: EVALUATION OF THE INHIBITION OF PKK USING AN ENDPOINT ASSAY Human PKK (0.01 U/mL; Enzyme Research Laboratories) or rat PKK (0.625 nM; produced in-house) was incubated for 1 h at room temperature with 0.10 µM fluorogenic substrate H-Pro-Phe-Arg-AMC (11295 from Bachem) and various concentrations of the test compound in assay buffer. Subsequently, PPACK II (Calbiochem) was added as a stop solution to achieve a final concentration of 1 µM and fluorescence was measured using an Envision Reader (PerkinElmer) with the wavelength excitation setting of 355 nm and the wavelength emission setting of 460 nm.

$IC_{50}$ values for compounds according to the invention are shown in the following table. The number of the compound corresponds to the number of the Example in the experimental section.

| Example | $IC_{50}$ (nM) |
|---|---|
| 1 | 2 |
| 2 | 32 |
| 3 | 0.8 |
| 4 | 9 |
| 5 | 0.6 |
| 6 | 0.7 |
| 7 | 1 |
| 8 | 4 |
| 9 | 7 |
| 10 | 26 |
| 11 | 1 |
| 12 | 1 |
| 13 | 0.5 |
| 14 | 0.5 |
| 15 | 0.8 |
| 16 | 0.9 |
| 17 | 0.9 |
| 18 | 0.9 |
| 19 | 1 |
| 20 | 1 |
| 21 | 1 |
| 22 | 2 |
| 23 | 2 |
| 24 | 2 |
| 25 | 3 |
| 26 | 3 |
| 27 | 3 |
| 28 | 4 |
| 29 | 7 |
| 30 | 8 |
| 31 | 10 |
| 32 | 2 |
| 33 | 3 |
| 34 | 11 |
| 35 | 2 |
| 36 | 4 |
| 37 | 7 |
| 38 | 26 |
| 39 | 9 |
| 40 | 137 |
| 41 | 13 |
| 42 | 6 |
| 43 | 23 |
| 44 | 20 |
| 45 | 4 |
| 46 | 4 |
| 47 | 0.9 |
| 48 | 5 |
| 49 | 42 |
| 50 | 8 |
| 51 | 25 |
| 52 | 4 |
| 53 | 9 |
| 54 | 2 |
| 55 | 15 |
| 56 | 56 |
| 57 | 37 |
| 58 | 20 |
| 59 | 17 |
| 60 | 7 |
| 61 | 5 |
| 62 | 7 |
| 63 | 85 |
| 64 | 32 |
| 65 | 10 |
| 66 | 51 |
| 67 | 2 |
| 68 | 4 |
| 69 | 17 |
| 70 | 13 |
| 71 | 2 |
| 72 | 36 |
| 73 | 17 |
| 74 | 38 |
| 75 | 19 |
| 76 | 572 |
| 77 | 5 |
| 78 | 9 |
| 79 | 4 |
| 80 | 9 |
| 81 | 161 |
| 82 | 2 |
| 83 | 41 |
| 84 | 2 |
| 85 | 4 |
| 86 | 0.4 |
| 87 | 2 |
| 88 | 1 |
| 89 | 0.6 |
| 90 | 0.8 |
| 91 | 3 |
| 92 | 1 |
| 93 | 4 |
| 94 | 2 |
| 95 | 4 |
| 96 | 2 |
| 97 | 2 |
| 98 | 5 |
| 99 | 1 |
| 100 | 0.4 |
| 101 | 2 |
| 102 | 1 |
| 103 | 2 |
| 104 | 3 |
| 105 | 1 |
| 106 | 0.9 |
| 107 | 7 |
| 108 | 1 |
| 109 | 3 |

Evaluation of the Inhibition of PKK in Kaolin Activated Human PPP

Platelet poor plasma (PPP) obtained from human whole-blood, anticoagulated with Na-Citrat, was incubated with various concentrations of the test compound together with either 25, 75, 250, or 750 µg/mL kaolin in assay buffer for 20 min at 37° C. such that for each kaolin dose used a concentration response was obtained for the test compound. Afterwards 0.25 mM fluorogenic substrate H-Pro-Phe-Arg-AMC (11295 from Bachem) was added to the mixture and measurements were performed in a kinetic interval every 2nd minute for 12 min using a Spectramax M5 (Molecular Devices) with the following settings of the wavelength excitation of 350 nm and wavelength emission of 450 nm. pIC50 and pIC90 values were obtained from 4 x/y-plots (x=log M,Compound; y=delta rfu/min) fitted with GraphPad prism 7.0 (Equation: log(agonist) vs. response—Find ECanything; the four concentration response curves obtained for the test compound, each obtained using a different kaolin dose, were fitted using a global fitting procedure yielding shared pIC50 or pIC90 values).

$IC_{90}$ values for compounds according to the invention are shown in the following table. The number of the compound corresponds to the number of the Example in the experimental section.

| Example | $IC_{90}$ (nM) |
|---|---|
| 1 | 705 |
| 3 | 679 |
| 5 | 241 |
| 6 | 291 |

-continued

| Example | IC$_{90}$ (nM) |
|---|---|
| 7 | 342 |
| 8 | 1820 |
| 9 | 3480 |
| 11 | 598 |
| 12 | 3090 |
| 35 | 2010 |
| 36 | 4670 |
| 37 | 4980 |
| 46 | 2840 |
| 47 | 445 |
| 52 | 5120 |
| 54 | 944 |
| 67 | 545 |
| 71 | 708 |
| 77 | 1110 |
| 87 | 1170 |
| 96 | 781 |
| 97 | 302 |
| 98 | 3140 |
| 99 | 388 |
| 100 | 303 |
| 101 | 727 |
| 102 | 5480 |
| 103 | 416 |
| 104 | 444 |
| 105 | 586 |
| 108 | 776 |

Evaluation of the Inhibition of PKK ($K_i$)

Human PKK (1.78 nM or 0.025 U/mL; Enzyme Research Laboratories) was incubated at 24° C. with 0.25 mM fluorogenic substrate H-Pro-Phe-Arg-AMC (11295 from Bachem) and various concentrations of the test compound in assay buffer. Measurements were performed in a kinetic interval every $2^{nd}$ minute for 16 min using a Spectramax M5 (Molecular Devices) with the following settings of the wavelength excitation of 350 nm and wavelength emission of 450 nm. $K_i$ values for compounds according to the invention are shown in the following table. The number of the compound corresponds to the number of the Example in the experimental section.

| Example | $K_i$ (nM) |
|---|---|
| 1 | 1 |
| 3 | 0.5 |
| 5 | 0.3 |
| 6 | 0.5 |
| 7 | 0.7 |
| 8 | 3 |
| 9 | 5 |
| 11 | 0.4 |
| 12 | 2 |
| 13 | 0.1 |
| 14 | 0.1 |
| 15 | 0.1 |
| 16 | 0.1 |
| 17 | 0.1 |
| 18 | 0.1 |
| 19 | 0.3 |
| 20 | 0.2 |
| 21 | 0.1 |
| 22 | 0.1 |
| 23 | 0.3 |
| 35 | 0.9 |
| 36 | 1 |
| 37 | 2 |
| 46 | 1 |
| 47 | 0.4 |
| 52 | 1 |
| 54 | 1 |
| 67 | 1 |
| 71 | 1 |
| 77 | 4 |
| 87 | 1 |
| 96 | 1 |
| 97 | 1 |
| 98 | 6 |
| 99 | 1 |
| 100 | 0.8 |
| 101 | 2 |
| 102 | 4 |
| 103 | 3 |
| 104 | 3 |
| 105 | 1 |
| 108 | 6 |

Evaluation of the Inhibition of FXIIa ($K_i$)

Human FXIIa (47.5 nM or 1.1 U/mL; Enzyme Research Laboratories) was incubated at 24° C. with 0.5 mM chromogenic Substrate S2302 (Chromogenix) and various concentrations of the test compound in assay buffer. Measurements were performed in a kinetic interval every $2^{nd}$ minute for 16 min using a Spectramax M5 (Molecular Devices) measuring the optical absorbance at 405 nm.

Evaluation of the Inhibition of FXIa ($K_i$)

Human FXIa (0.5 nM or 0.016 U/mL; Enzyme Research Laboratories) was incubated at 24° C. with 0.25 mM fluorogenic substrate Boc-Glu(OBzl)-Ala-Arg-AMC.HCl (11575 from Bachem) and various concentrations of the test compound in assay buffer. Measurements were performed in a kinetic interval every $2^{nd}$ minute for 16 min using a Spectramax M5 (Molecular Devices) with the following settings of the wavelength excitation of 350 nm and wavelength emission of 450 nm.

Evaluation of the Inhibition of FXa ($K_i$) Human FXa (0.86 nM or 0.01 U/mL; Enzyme Research Laboratories) was incubated at 24° C. with 0.5 mM chromogenic Substrate S2765 (Chromogenix) and various concentrations of the test compound in assay buffer. Measurements were performed in a kinetic interval every $2^{nd}$ minute for 16 min using a Spectramax M5 (Molecular Devices) measuring the optical absorbance at 405 nm.

Evaluation of the Inhibition of FIIa ($K_i$)

Human FIIa (44.6 nM or 5 U/mL; Enzyme Research Laboratories) was incubated at 24° C. with 0.5 mM chromogenic Substrate S2238 (Chromogenix) and various concentrations of the test compound in assay buffer. Measurements were performed in a kinetic interval every $2^{nd}$ minute for 16 min using a Spectramax M5 (Molecular Devices) measuring the optical absorbance at 405 nm.

Evaluation of the Inhibition of Plasmin ($K_i$)

Human plasmin (64.1 nM or 0.0275 U/mL; Enzyme Research Laboratories) was incubated at 24° C. with 0.3 mM chromogenic Substrate S2251 (Chromogenix) and various concentrations of the test compound in assay buffer. Measurements were performed in a kinetic interval every $2^{nd}$ minute for 16 min using a Spectramax M5 (Molecular Devices) measuring the optical absorbance at 405 nm.

Evaluation of the Inhibition of Trypsin ($K_i$)

Human trypsin (4.54 nM or 250 U/mL; Calbiochem) was incubated at 24° C. with 0.5 mM chromogenic Substrate S2222 (Chromogenix) and various concentrations of the test compound in assay buffer. Measurements were performed in a kinetic interval every $2^{nd}$ minute for 16 min using a Spectramax M5 (Molecular Devices) measuring the optical absorbance at 405 nm.

Evaluation of the Inhibition of Tk1 ($K_i$)

Prior to the assay, human TK1 (R&D Systems) was activated by incubation with human trypsin (Calbiochem) in a 1:10,000 ratio for 15 min at 37° C. For assaying TK1 inhibitory activity, activated TK1 (31.25 nM or 1 U/mL) was incubated at 24° C. with 0.1 mM fluorogenic substrate H-Pro-Phe-Arg-AMC (11295 from Bachem) and various concentrations of the test compound in assay buffer. Measurements were performed in a kinetic interval every $2^{nd}$ minute for 16 min using a Spectramax M5 (Molecular Devices) with the following settings of the wavelength excitation of 350 nm and wavelength emission of 450 nm.

$K_i$ values for compounds according to the invention are shown in the following table. The number of the compound corresponds to the number of the Example in the experimental section.

| Example | IC$_{50}$ (nM) |
|---|---|
| 1 | >10000 |
| 3 | >10000 |
| 5 | >10000 |
| 6 | >10000 |
| 7 | >10000 |
| 8 | >10000 |
| 9 | >10000 |
| 11 | >10000 |
| 12 | >10000 |
| 13 | >10000 |
| 14 | >10000 |
| 15 | >10000 |
| 16 | >10000 |
| 17 | >10000 |
| 18 | >10000 |
| 19 | >10000 |
| 20 | >10000 |
| 21 | >10000 |
| 22 | >10000 |
| 23 | >10000 |
| 25 | >10000 |
| 33 | >10000 |
| 35 | >10000 |
| 36 | >10000 |
| 37 | >10000 |
| 45 | >10000 |
| 46 | >10000 |
| 47 | >10000 |
| 48 | >10000 |
| 52 | >10000 |
| 54 | >10000 |
| 71 | >10000 |
| 77 | >10000 |
| 79 | >10000 |
| 82 | >10000 |
| 84 | >10000 |
| 86 | >10000 |
| 87 | >10000 |
| 88 | >10000 |
| 89 | >10000 |
| 90 | >10000 |
| 92 | >10000 |
| 93 | >10000 |
| 94 | >10000 |
| 96 | >10000 |
| 97 | >10000 |
| 98 | >10000 |
| 99 | >10000 |
| 100 | >10000 |
| 101 | >10000 |
| 102 | >10000 |
| 103 | >10000 |
| 104 | >10000 |
| 105 | >10000 |
| 108 | >10000 |
| 109 | >10000 |

Evaluation of the Inhibition of FVIIa ($K_i$)

Human FVIIa (0.86 nM or 0.01 U/mL; Enzyme Research Laboratories) was incubated at 24° C. with 1.5 mM chromogenic Pefachrome® FVIIa (Loxo) and various concentrations of the test compound in assay buffer. Measurements were performed in a kinetic interval every $2^{nd}$ minute for 16 min using a Spectramax M5 (Molecular Devices) measuring the optical absorbance at 405 nm.

Evaluation of the Inhibition of FVIIa/TF/PL/CaCl$_2$ ($K_i$)

Human FVIIa (300 nM or 585 U/mL; Enzyme Research Laboratories) together with 10 mM CaCl$_2$*2H$_2$O and 13.3% (v/v) Dade®Innovin® (Siemens; OQUMI94E0002(5534), which contains recombinant human tissue factor synthetic phospholipids (thromboplastin), was incubated at 24° C. with 1.5 mM chromogenic Pefachrome® FVIIa (Loxo) and various concentrations of the test compound in assay buffer. Measurements were performed in a kinetic interval every $2^{nd}$ minute for 16 min using a Spectramax M5 (Molecular Devices) measuring the optical absorbance at 405 nm.

Calculation of pIC$_{50}$ AND pK$_i$ Values

The average V$_{max}$ values for the time interval from 2 to 12 min after initiation of the assay (expressed as either delta OD/min for assays using a chromogenic substrate or delta RFU/min for assays using a fluorigenic substrate, respectively) were plotted versus the Log of the concentration in molar of the evaluated inhibitor compound. The pIC$_{50}$ values were then fitted using a four-parametric fitting procedure using using GraphPad Prism (version 6; GraphPad Software, Inc.). Respective K$_i$ values were obtained by correction of the IC$_{50}$ values for the respective K$_M$ value of the used substrate (see Table A for the obtained K$_M$ values of the used substrates) using the following formula:

$$K_i = \frac{IC_{50}}{1 + \frac{[Substrate, mM]}{K_M}}$$

Where the IC$_{50}$ is in molar and the K$_M$ value in mM.

TABLE A

K$_M$ values obtained for the substrates used in the enzymatic assays.

| Enzyme | Substrate | K$_M$ (mM) |
|---|---|---|
| PKK | I1295 | 0.16 |
| FXIIa | S2302 | 0.20 |
| FXIa | I1575 | 0.29 |
| FXa | S2765 | 1.31 |
| FIIa | S2238 | 1.25 |
| Plasmin | S2251 | 1.45 |
| Trypsin | S2222 | 2.03 |
| TK1 | I1295 | 0.07 |
| FVIIa | Pefachrome ® FVIIa | 0.42 |
| FVIIa/TF/PL/CaCl$_2$ | Pefachrome ® FVIIa | 3.92 |

Evaluation of Permeability

Caco-2 cells (1-2×10$^5$ cells/1 cm$^2$ area) are seeded on filter inserts (Costar transwell polycarbonate or PET filters, 0.4 µm pore size) and cultured (DMEM) for 10 to 25 days.

Compounds are dissolved in appropriate solvent (like DMSO, 1-20 mM stock solutions). Stock solutions are diluted with HTP-4 buffer (128.13 mM NaCl, 5.36 mM KCl, 1 mM MgSO$_4$, 1.8 mM CaCl$_2$, 4.17 mM NaHCO$_3$, 1.19 mM Na$_2$HPO$_4$×7H$_2$O, 0.41 mM NaH$_2$PO$_4$×H$_2$O, 15 mM HEPES, 20 mM glucose, pH 7.2) to prepare the transport solutions (0.1-300 µM compound, final DMSO<=0.5%). The transport solution (TL) is applied to the apical or basolateral donor side for measuring A-B or B-A permeability (3 filter replicates), respectively. The receiver side contains HTP-4 buffer supplemented with 2% BSA. Samples are collected at the start and end of experiment from the donor and at various time intervals for up to 2 hours also from the receiver side for concentration measurement by HPLC-MS/MS or scintillation counting. Sampled receiver volumes are replaced with fresh receiver solution.

Evaluation of Metabolic Stability in Human or Rat Liver Microsomes

The metabolic degradation of the test compound is assayed at 37° C. with pooled human or rat liver microsomes. The final incubation volume of 100 μl per time point contains TRIS buffer pH 7.6 at RT (0.1 M), magnesium chloride (5 mM), microsomal protein (1 mg/mL) and the test compound at a final concentration of 1 μM.

Following a short preincubation period at 37° C., the reactions were initiated by addition of beta-nicotinamide adenine dinucleotide phosphate, reduced form (NADPH, 1 mM) and terminated by transferring an aliquot into solvent after different time points. Additionally, the NADPH-independent degradation was monitored in incubations without NADPH, terminated at the last time point. The quenched incubations are pelleted by centrifugation (10000 g, 5 min). An aliquot of the supernatant is assayed by LC-MS/MS for the amount of parent compound. The half-life (t1/2 INVITRO) is determined by the slope of the semilogarithmic plot of the concentration-time profile.

Evaluation of Metabolic Stability in Human or Rat Hepatocytes

The metabolic degradation of the test compound is assayed in a hepatocyte suspension. Hepatocytes (typically cryopreserved) are incubated in an appropriate buffer system (e.g. Dulbecco's modified eagle medium plus 3.5 μg glucagon/500 mL, 2.5 mg insulin/500 mL and 3.75 mg/500 mL hydrocortison) containing 5% species serum.

Following a (typically) 30 min preincubation in an incubator (37° C., 10% $CO_2$) 5 μL of test compound solution (80 μM; from 2 mM in DMSO stock solution diluted 1:25 with medium) are added into 395 μL hepatocyte suspension (cell density in the range 0.25-5 Mio cells/mL, typically 1 Mio cells/mL; final concentration of test compound 1 μM, final DMSO concentration 0.05%).

The cells are incubated for six hours (incubator, orbital shaker) and samples (25 μL) are taken at 0, 0.5, 1, 2, 4 and 6 h. Samples are transferred into ACN and pelleted by centrifugation (5 min). The supernatant is transferred to a new 96-deepwell plate, evaporated under nitrogen and resuspended.

Decline of parent compound is analyzed by HPLC-MS/MS CLint is calculated as follows CL_INTRINSIC=Dose/AUC=(C0/CD)/(AUD+clast/k)×1000/60. C0: initial concentration in the incubation [μM], CD: cell density of vital cells [10e6 cells/mL], AUD: area under the data [μM×h], clast: concentration of last data point [μM], k: slope of the regression line for parent decline [h−1].

Evaluation of Plasma Protein Binding

This equilibrium dialysis (ED) technique is used to determine the approximate in vitro fractional binding of test compounds to plasma proteins. Dianorm Teflon dialysis cells (micro 0.2) are used. Each cell consists of a donor and an acceptor chamber, separated by an ultrathin semipermeable membrane with a 5 kDa molecular weight cutoff. Stock solutions for each test compound are prepared in DMSO at 1 mM and diluted to a final concentration of 1.0 μM. The subsequent dialysis solutions are prepared in pooled human or rat plasma (with NaEDTA) from male and female donors. Aliquots of 200 μL dialysis buffer (100 mM potassium phosphate, pH 7.4) are dispensed into the buffer chamber. Aliquots of 200 μL test compound dialysis solution are dispensed into the plasma chambers. Incubation is carried out for 2 hours under rotation at 37° C.

At the end of the dialysis period, the dialysate is transferred into reaction tubes. The tubes for the buffer fraction contain 0.2 mL ACN/water (80/20). Aliquots of 25 μL of the plasma dialysate are transferred into deep well plates and mixed with 25 μL ACN/water (80/20), 25 μL buffer, 25 μL calibration solution and 25 μL Internal Standard solution. Protein precipitation is done by adding 200 μL ACN.

Aliquots of 50 μL of the buffer dialysate are transferred into deep well plates and mixed with 25 μL blank plasma, 25 μL Internal Standard solution and 200 μL ACN.

Samples are measured on HPLC-MS/MS-Systems and evaluated with Analyst-Software.

Percent bound is calculated with the formula: % bound=(plasma concentration−buffer concentration/plasma concentration)×100

Evaluation of Solubility

The aqueous solubility of the test compound is determined by comparing the amount dissolved in buffer to the amount in an ACN/water (1/1) solution. Starting from a 10 mM DMSO stock solution aliquots are diluted with acetonitril/water (1/1) or buffer resp. After 24 h of shaking, the solutions are filtrated and analyzed by LC-UV. The amount dissolved in buffer is compared to the amount in the ACN solution.

Solubility will usually be measured from 0.001 to 0.125 mg/mL at a DMSO concentration of 2.5%. If more than 90% of the compound is dissolved in buffer, the value is marked with ">".

Evaluation of Pharmacokinetic Characteristics in Rodents

The test compound is administered either intravenously to fed rats or orally to fasted rats. Blood samples are taken at several time points post application of the test compound, anticoagulated and centrifuged.

The concentration of analytes—the administered compound and/or metabolites—are quantified in the plasma samples. PK parameters are calculated using non compartment methods. AUC and Cmax are normalized to a dose of 1 μmol/kg.

Methods of Treatment

In another aspect of the present invention, it is found that compounds of formula (I) or pharmaceutically acceptable salts thereof may be useful for the treatment of diseases or conditions mediated by unwanted PKK activity in a mammal.

Diseases and conditions mediated by unwanted PKK activity embrace diabetic complications, diabetic retinopathy, proliferative and non-proliferative retinopathy, diabetic macular edema (DME), clinically significant macular edema (CSME), cystoid macular edema (CME), CME following cataract extraction, CME induced by cryotherapy, CME induced by uveitis, endophthalmitis, CM E following vascular occlusion (e.g. central retinal vein occlusion, branch retinal vein occlusion, or hemiretinal vein occlusion), retinal edema, complications related to cataract surgery in diabetic retinopathy, hypertensive retinopathy, retinal trauma, dry and wet age-related macular degeneration (AMD), polypoidal choroidal vasculopathy (PCV), choroidal neovascularization (CNV; e.g. non-exudative choroidal neovascularization), hereditary angioedema, acute respiratory distress syndrome (ARDS), hemorrhage and edema after stroke, vascular dementia, Alzheimers' disease, fibrotic disease, colitis, arthritis and renal injury.

Thus, the compounds and pharmaceutical compositions of the present invention are particularly suitable for treating ocular diseases including diabetic retinopathy, proliferative and non-proliferative retinopathy, diabetic macular edema (DME), retinal vein occlusion, age-related macular degeneration (AMD), polypoidal choroidal vasculopathy (PCV) and choroidal neovascularization (CNV; e.g. non-exudative choroidal neovascularization).

In addition, the compounds and pharmaceutical compositions according to the invention are particularly suitable for the treatment of edema, such as hereditary angioedema.

In particular, the compounds and pharmaceutical compositions according to the invention are suitable for the treatment of diabetic retinopathy, proliferative and non-proliferative retinopathy, diabetic macular edema (DME), age-related macular degeneration (AMD), polypoidal choroidal vasculopathy (PCV), choroidal neovascularization (CNV) and hereditary angioedema.

The compounds and pharmaceutical compositions according to the invention are most particularly suitable for treating diabetic macular edema (DME), wet age-related macular degeneration (AMD), non-exudative choroidal neovascularization (CNV) and hereditary angioedema.

For instance, they are particularly suitable for the prevention of diabetic macular edema (DME), wet age-related macular degeneration (AMD) and hereditary angioedema as well as for the prevention of the conversion from non-exudative choroidal neovascularization (neCNV) to exudative choroidal neovascularization (eCNV).

The dose range of the compounds of formula (I) applicable per day is usually from 0.01 to 10 mg per kg body weight. The actual therapeutically effective amount or therapeutic dosage will of course depend on factors known by those skilled in the art such as age and weight of the patient, route of administration and severity of disease. In any case the compound or composition will be administered at dosages and in a manner which allows a therapeutically effective amount to be delivered based upon patient's unique condition.

The compounds, compositions, including any combinations with one or more additional therapeutic agents, according to the invention may be administered by oral, intravitreal, transdermal, inhalative, parenteral or sublingual route. Of the possible methods of administration, oral or intravitreal administration is preferred. In case of intravitreal injection the preferred dose should not exceed 5 mg per eye.

Thus, in a further aspect the invention provides new compounds of formula (I) and their tautomers, including pharmaceutically acceptable salts thereof, which inhibit plasma kallikrein and possess suitable pharmacological and pharmacokinetic properties for use in therapy, i.e. for use as medicaments.

In a further aspect the invention provides new compounds of formula (I) and their tautomers, including pharmaceutically acceptable salts thereof, for use in a method for the treatment of a disease or condition which can be influenced in a beneficial way by inhibition of plasma kallikrein.

In a further aspect the invention provides new compounds of formula (I) and their tautomers, or pharmaceutically acceptable salts thereof, for the treatment of ophthalmic indications such as diabetic retinopathy, proliferative and non-proliferative retinopathy, diabetic macular edema (DME), age-related macular degeneration (AMD), polypoidal choroidal vasculopathy (PCV) and choroidal neovascularization (CNV) as well as of edema-associated diseases such as hereditary angioedema.

In another aspect, the present invention provides the use of a compound of formula (I) and/or its tautomers, or pharmaceutically acceptable salts thereof, in the manufacture of a medicament for use in the treatment of a disease or condition in which inhibition of plasma kallikrein is beneficial.

In a further aspect, the present invention provides the use of a compound of formula (I) and/or its tautomers, or pharmaceutically acceptable salts thereof, in the manufacture of a medicament for use in the treatment of ophthalmic indications such as diabetic retinopathy, proliferative and non-proliferative retinopathy, diabetic macular edema (DME), age-related macular degeneration (AMD), polypoidal choroidal vasculopathy (PCV) and choroidal neovascularization (CNV) and of edema-associated diseases such as hereditary angioedema.

Accordingly, the present invention relates to compounds of formula (I) as a medicament.

Furthermore, the present invention relates to the use of a compound of formula (I) in a method for the treatment of diseases or conditions which are mediated by unwanted plasma kallikrein activity in a patient, preferably in a human.

Furthermore, the present invention relates to the use of a compound of formula (I) in a method for the treatment of ophthalmic indications such as diabetic retinopathy, proliferative and non-proliferative retinopathy, diabetic macular edema (DME), age-related macular degeneration (AMD), polypoidal choroidal vasculopathy (PCV) and choroidal neovascularization (CNV) and of edema-associated diseases such as hereditary angioedema.

In yet another aspect the present invention relates to a method for the treatment of a disease or condition which can be influenced by the inhibition of plasma kallikrein in a mammal that includes the step of administering to a patient, preferably a human, in need of such treatment a therapeutically effective amount of a compound or a pharmaceutical composition of the present invention.

In a further aspect the invention provides a method for the treatment of a disease or condition which can be influenced in a beneficial way by inhibition of plasma kallikrein, in a subject comprising administering a therapeutically effective amount of a compound of formula (I) and/or its tautomers, or a pharmaceutically acceptable salt thereof, to a patient in need thereof.

In a further aspect the invention provides a method for the treatment of ophthalmic indications such as diabetic retinopathy, proliferative and non-proliferative retinopathy, diabetic macular edema (DME), age-related macular degeneration (AMD), polypoidal choroidal vasculopathy (PCV) and choroidal neovascularization (CNV) and of edema-associated diseases such as hereditary angioedema in a patient, comprising administering a therapeutically effective amount of a compound of formula (I), or a pharmaceutically acceptable salt, thereof to a patient in need thereof.

According to another aspect of the invention, there is provided a method for the treatment of diabetic complications, particularly of retinal vascular permeability associated with diabetic retinopathy and diabetic macular edema, in a patient in need thereof characterized in that a therapeutically effective amount of a compound of formula (I) and/or its tautomers or a pharmaceutically acceptable salt thereof is administered to the patient.

Pharmaceutical Compositions

In another aspect of the present invention, it is described that a compound of the invention or a pharmaceutically acceptable salt thereof may be used as active ingredients in pharmaceutical compositions.

Suitable preparations for administering the compounds of the invention, optionally in combination with one or more further therapeutic agents, will be apparent to those with ordinary skill in the art and include for example tablets, pills, capsules, suppositories, lozenges, troches, solutions, syrups, elixirs, sachets, injectables, inhalatives and powders etc. Oral formulations, particularly solid forms such as e.g. tablets or capsules are preferred. For intravitreal injection, solutions are preferred. The content of the pharmaceutically active compound(s) is advantageously in the range from 0.1 to 90 wt.-%, for example from 1 to 70 wt.-% of the composition as a whole.

Suitable tablets may be obtained, for example, by mixing one or more compounds according to formula (I) with known excipients, for example inert diluents, carriers, disintegrants, adjuvants, surfactants, binders and/or lubricants. The tablets may also consist of several layers. The particular excipients, carriers and/or diluents that are suitable for the desired preparations will be familiar to the skilled man on the basis of his specialist knowledge. The preferred ones are those that are suitable for the particular formulation and method of administration that are desired. The preparations or formulations according to the invention may be prepared using methods known per se that are familiar to the skilled man, such as for example by mixing or combining at least one compound of formula (I) according to the invention, or a pharmaceutically acceptable salt of such a compound, and one or more excipients, carriers and/or diluents.

Thus, according to another aspect of the present invention, pharmaceutical compositions comprising one or more compounds of formula (I) and/or their tautomers, or pharmaceutically acceptable salts thereof, optionally together with one or more inert carriers and/or diluents are provided.

Also, a pharmaceutical composition is provided that comprises one or more of the above-mentioned compounds, or pharmaceutically acceptable salts thereof, optionally together with one or more inert carriers and/or diluents for use in a method for the treatment of diseases or conditions which can be influenced by the inhibition of plasma kallikrein.

In particular, the invention provides a pharmaceutical composition according to the invention for use in a method of treatment of ophthalmic indications such as diabetic retinopathy, proliferative and non-proliferative retinopathy, diabetic macular edema (DME), age-related macular degeneration (AMD), polypoidal choroidal vasculopathy (PCV) and choroidal neovascularization (CNV) and of edema-associated diseases such as hereditary angioedema.

Furthermore, the present invention relates to the use of a pharmaceutical composition according to this invention for the treatment of diseases or conditions which are mediated by unwanted plasma kallikrein activity in a patient, preferably in a human.

Also, the present invention relates to the use of a pharmaceutical composition according to this invention for the treatment of diseases or conditions which can be influenced by the inhibition of plasma kallikrein in a patient, preferably in a human.

According to another embodiment, a pharmaceutical composition comprising one or more compounds of formula (I) and/or their tautomers, or pharmaceutically acceptable salts thereof, and one or more additional therapeutic agents, optionally together with one or more inert carriers and/or diluents is provided. Preferably, this composition comprises one compound of formula (I) and/or its tautomers or a pharmaceutically acceptable salt thereof and one or more additional therapeutic agents.

Combination Therapy

The compounds of the invention may further be combined with one or more, preferably one additional therapeutic agent. According to one embodiment the additional therapeutic agent is selected from the group of therapeutic agents useful in the treatment of diseases or conditions described hereinbefore, in particular associated with metabolic diseases or conditions such as for example diabetes mellitus, obesity, diabetic complications, hypertension, hyperlipidemia, or therapeutic agents useful for the treatment of ocular diseases. Additional therapeutic agents which are suitable for such combinations include in particular those which for example potentiate the therapeutic effect of one or more active substances with respect to one of the indications mentioned and/or which allow the dosage of one or more active substances to be reduced.

Therefore a compound of the invention may be combined with one or more additional therapeutic agents selected from the group consisting of antidiabetic agents, agents for the treatment of overweight and/or obesity, agents for the treatment of high blood pressure, heart failure and/or atherosclerosis and agents for the treatment of ocular diseases.

Antidiabetic agents are for example metformin, sulphonylureas, nateglinide, repaglinide, thiazolidinediones, PPAR-(alpha, gamma or alpha/gamma) agonists or modulators, alpha-glucosidase inhibitors, DPPIV inhibitors, SGLT2-inhibitors, insulin and insulin analogues, GLP-1 and GLP-1 analogues or amylin and amylin analogues, cycloset, 11β-HSD inhibitors. Other suitable combination partners are inhibitors of protein tyrosinephosphatase 1, substances that affect deregulated glucose production in the liver, such as e.g. inhibitors of glucose-6-phosphatase, or fructose-1,6-bisphosphatase, glycogen phosphorylase, glucagon receptor antagonists and inhibitors of phosphoenol pyruvate carboxykinase, glycogen synthase kinase or pyruvate dehydrokinase, alpha2-antagonists, CCR-2 antagonists or glucokinase activators. One or more lipid lowering agents are also suitable as combination partners, such as for example HMG-CoA-reductase inhibitors, fibrates, nicotinic acid and the derivatives thereof, PPAR-(alpha, gamma or alpha/gamma) agonists or modulators, PPAR-delta agonists, ACAT inhibitors or cholesterol absorption inhibitors such as, bile acid-binding substances such as, inhibitors of ileac bile acid transport, MTP inhibitors, or HDL-raising compounds such as CETP inhibitors or ABC1 regulators.

Therapeutic agents for the treatment of overweight and/or obesity are for example antagonists of the cannabinoid1 receptor, MCH-1 receptor antagonists, MC4 receptor agonists, NPY5 or NPY2 antagonists, β3-agonists, leptin or leptin mimetics, agonists of the 5HT2c receptor.

Therapeutic agents for the treatment of high blood pressure, chronic heart failure and/or atherosclerosis are for example A-II antagonists or ACE inhibitors, ECE inhibitors, diuretics, β-blockers, Ca-antagonists, centrally acting antihypertensives, antagonists of the alpha-2-adrenergic receptor, inhibitors of neutral endopeptidase, thrombocyte aggregation inhibitors and others or combinations thereof are suitable. Angiotensin II receptor antagonists are preferably used for the treatment or prevention of high blood pressure and complications of diabetes, often combined with a diuretic such as hydrochlorothiazide.

Therapeutic agents for the treatment of ocular diseases may include for example intravitreally administered corticosteroids, intravitreally administered anti-VEGF therapy, anti-Ang2 inhibitors, dual anti-VEGF/anti-Ang2 inhibitors, anti PDGF, dual anti-VEGF/anti-PDGF, VAP-1 (AOC3)

inhibitors, Complement inhibitors (e.g. Complement factors 3, 5, B, and D inhibitors), Bradykinin receptor 1 antagonists, CCR-2 antagonists.

Additional treatments for ocular diseases may include laser coagulation therapy.

The dosage for the combination partners mentioned above is usually 1/5 of the lowest dose normally recommended up to 1/1 of the normally recommended dose.

Preferably, compounds of the present invention and/or pharmaceutical compositions comprising a compound of the present invention optionally in combination with one or more additional therapeutic agents are administered in conjunction with exercise and/or a diet.

Therefore, in another aspect, this invention relates to the use of a compound according to the invention in combination with one or more additional therapeutic agents described hereinbefore and hereinafter for the treatment of diseases or conditions which may be affected or which are mediated by unwanted plasma kallikrein activity, in particular diseases or conditions as described hereinbefore and hereinafter.

In a further aspect this invention relates to a method for treating a disease or condition which can be influenced by the inhibition of plasma kallikrein in a patient that includes the step of administering to the patient in need of such treatment a therapeutically effective amount of a compound of formula (I) and/or its tautomers or a pharmaceutically acceptable salt thereof in combination with a therapeutically effective amount of one or more additional therapeutic agents.

In a further aspect this invention relates to the use of a compound of formula (I) and/or its tautomers or a pharmaceutically acceptable salt thereof in combination with one or more additional therapeutic agents for the treatment of diseases or conditions which can be influenced by the inhibition of plasma kallikrein in a patient in need thereof.

In yet another aspect the present invention relates a method for the treatment of a disease or condition mediated by unwanted plasma kallikrein activity in a patient that includes the step of administering to the patient, preferably a human, in need of such treatment a therapeutically effective amount of a compound of the present invention in combination with a therapeutically effective amount of one or more additional therapeutic agents described in hereinbefore and hereinafter.

The use of the compound according to the invention in combination with the additional therapeutic agent may take place simultaneously or at staggered times.

The compound according to the invention and the one or more additional therapeutic agents may both be present together in one formulation, for example a tablet or capsule, or separately in two identical or different formulations, for example as a so-called kit-of-parts.

Consequently, in another aspect, this invention relates to a pharmaceutical composition which comprises a compound according to the invention and one or more additional therapeutic agents described hereinbefore and hereinafter, optionally together with one or more inert carriers and/or diluents.

Other features and advantages of the present invention will become apparent from the following more detailed Examples which illustrate, by way of example, the principles of the invention.

Examples and Experimental Data

The following examples are for the purpose of illustration of the invention only and are not intended in any way to limit the scope of the present invention.

Abbreviations

Ac acetyl
ACN acetonitrile
AMC 7-amino-4-methylcoumarin
Boc tert-butyloxycarbonyl
BSA bovine serum albumin
Bzl benzyl
CAN ceric ammonium nitrate
CI chemical ionization
d day(s)
DABCO 1,4-diazabicyclo[2.2.2]octane
DAD diode array detector
DBAD di-tert-butyl azodicarboxylate
DBU 1,8-diazabicyclo[5.4.0]undec-7-ene
DBN 1,5-diazabicyclo[4.3.0]non-5-ene
DCM dichloromethane
DDQ 2,3-dichloro-5,6-dicyanoquinone
DEAD diethyl azodicarboxylate
DIAD diisopropyl azodicarboxylate
DIPEA N,N-diisopropylethylamine
DMEM Dulbecco's modified eagle medium
DMF N,N-dimethylformamide
DMSO dimethyl sulfoxide
EDTA ethylenediaminetetraacetate
EI electron ionization
ESI electrospray ionization (in MS)
EtOAc ethyl acetate
EtOH ethanol
h hour(s)
HATU O-(7-azabenzotriazol-1-yl)-N,N,N',N'-tetramethyluronium-hexafluorophosphate
HPLC high performance liquid chromatography
HPLC-MS coupled high performance liquid chromatography-mass spectrometry
LC liquid chromatography
LC-MS coupled liquid chromatography—mass spectrometry
LG leaving group
M molar (mol/L)
MeOH methanol
min minute(s)
MS mass spectrometry
NADPH nicotinamide adenine dinucleotide phosphate
NMR nuclear magnetic resonance
PET polyethylene terephthalate
PyBop (benzotriazol-1-yloxy)tripyrrolidinophosphonium hexafluorophosphate
$R_f$ retardation factor
RFU relative fluorescence units
RP reverse phase
rt room temperature
$t_R$ retention time (in HPLC/LC)
SFC supercritical fluid chromatography
TBTU O-(benzotriazol-1-yl)-N,N,N',N'-tetramethyluronium tetrafluoroborate
TFA trifluoroacetic acid
THF tetrahydrofuran
TLC thin-layer chromatography
UV ultraviolet The terms "ambient temperature" and "room temperature" are used interchangeably and designate a temperature of about 20° C., e.g. 15 to 25° C.

As a rule, $^1$H-NMR and/or mass spectra have been obtained for the compounds prepared.

Unless otherwise specified, compounds containing chiral centers have the stereochemistry depicted. The assignment of stereochemistry has been made either by use of a chiral starting material of known stereochemistry, by stereoselective synthesis of known stereochemistry or by biological activity.

Method: 1
Device: Agilent 1200 with DA- and MS-Detector
Column: Sunfire C18, 3 × 30 mm, 2.5 μm
Column Supplier: Waters

| Gradient/ Solvent Time [min] | % Solvent [H$_2$O, 0.1% TFA] | % Solvent [ACN] | Flow [mL/min] | Temperature [° C.] |
|---|---|---|---|---|
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

Method: 2
Device: Agilent 1200 with DA- and MS-Detector
Column: XBridge C18, 3 × 30 mm, 2.5 μm
Column Supplier: Waters

| Gradient/ Solvent Time [min] | % Solvent [H$_2$O, 0.1% NH3] | % Solvent [ACN] | Flow [mL/min] | Temperature [° C.] |
|---|---|---|---|---|
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

Method: 3
Device: Agilent 1200 with DA- and MS-Detector
Column: XBridge C18, 3 × 30 mm, 2.5 μm
Column Supplier: Waters

| Gradient/ Solvent Time [min] | % Solvent [H$_2$O, 0.1% TFA] | % Solvent [ACN] | Flow [mL/min] | Temperature [° C.] |
|---|---|---|---|---|
| 0.00 | 97 | 3 | 2.2 | 60 |
| 0.20 | 97 | 3 | 2.2 | 60 |
| 1.20 | 0 | 100 | 2.2 | 60 |
| 1.25 | 0 | 100 | 3 | 60 |
| 1.40 | 0 | 100 | 3 | 60 |

Method: 4
Device: Waters Acquity with DA- and MS-Detector
Column: Sunfire C18, 2.1 × 30 mm, 2.5 μm
Column Supplier: Waters

| Gradient/ Solvent Time [min] | % Solvent [H$_2$O, 0.1% TFA] | % Solvent [ACN] | Flow [mL/min] | Temperature [° C.] |
|---|---|---|---|---|
| 0.00 | 99 | 1 | 1.5 | 60 |
| 0.02 | 99 | 1 | 1.5 | 60 |
| 1.00 | 0 | 100 | 1.5 | 60 |
| 1.10 | 0 | 100 | 1.5 | 60 |

Method: 5
Device: Waters Acquity, QDa Detector
Column: Sunfire C18, 3 × 30 mm, 2.5 μm
Column Supplier: Waters

| Gradient/ Solvent Time [min] | % Solvent [H$_2$O, 0.1% TFA] | % Solvent [ACN 0.08% TFA] | Flow [mL/min] | Temperature [° C.] |
|---|---|---|---|---|
| 0.00 | 95 | 5 | 1.5 | 60 |
| 1.30 | 0 | 100 | 1.5 | 60 |
| 1.50 | 0 | 100 | 1.5 | 60 |
| 1.60 | 95 | 5 | 1.5 | 60 |

Method: 6
Device: Waters Acquity, QDa Detector
Column: XBridge C18, 3 × 30 mm, 2.5 μm
Column Supplier: Waters

| Gradient/ Solvent Time [min] | % Solvent [H$_2$O, 0.1% NH3] | % Solvent [ACN] | Flow [mL/min] | Temperature [° C.] |
|---|---|---|---|---|
| 0.00 | 95 | 5 | 1.5 | 60 |
| 1.30 | 0 | 100 | 1.5 | 60 |
| 1.50 | 0 | 100 | 1.5 | 60 |
| 1.60 | 95 | 5 | 1.5 | 60 |

Method: 7
Device: Waters Acquity, QDa Detector
Column: XBridge C18, 3 × 30 mm, 2.5 μm
Column Supplier: Waters

| Gradient/ Solvent Time [min] | % Solvent [H$_2$O, 0.1% NH3] | % Solvent [ACN] | Flow [mL/min] | Temperature [° C.] |
|---|---|---|---|---|
| 0.00 | 95 | 5 | 1.5 | 60 |
| 1.30 | 0 | 100 | 1.5 | 60 |
| 1.50 | 0 | 100 | 1.5 | 60 |
| 1.60 | 95 | 5 | 1.5 | 60 |

Method: 8
Device: Waters Acquity, QDa Detector
Column: Sunfire C18, 3 × 30 mm, 2.5 μm
Column Supplier: Waters

| Gradient/ Solvent Time [min] | % Solvent [H$_2$O, 0.1% TFA] | % Solvent [ACN 0.08% TFA] | Flow [mL/min] | Temperature [° C.] |
|---|---|---|---|---|
| 0.00 | 95 | 5 | 1.5 | 60 |
| 1.30 | 0 | 100 | 1.5 | 60 |

-continued

| | | Method: 8 | | |
| --- | --- | --- | --- | --- |
| | | Device: Waters Acquity, QDa Detector | | |
| | | Column: Sunfire C18, 3 × 30 mm, 2.5 µm | | |
| | | Column Supplier: Waters | | |
| Gradient/ Solvent Time [min] | % Solvent [H₂O, 0.1% TFA] | % Solvent [ACN 0.08% TFA] | Flow [mL/min] | Temperature [° C.] |
| 1.50 | 0 | 100 | 1.5 | 60 |
| 1.60 | 95 | 5 | 1.5 | 60 |

Synthesis of Intermediates

Intermediate 1

3-Methyl-2-{[2-(trimethylsilyl)ethoxy]methyl}-2H,4H,5H,6H-cyclopenta[c]pyrazol-6-one

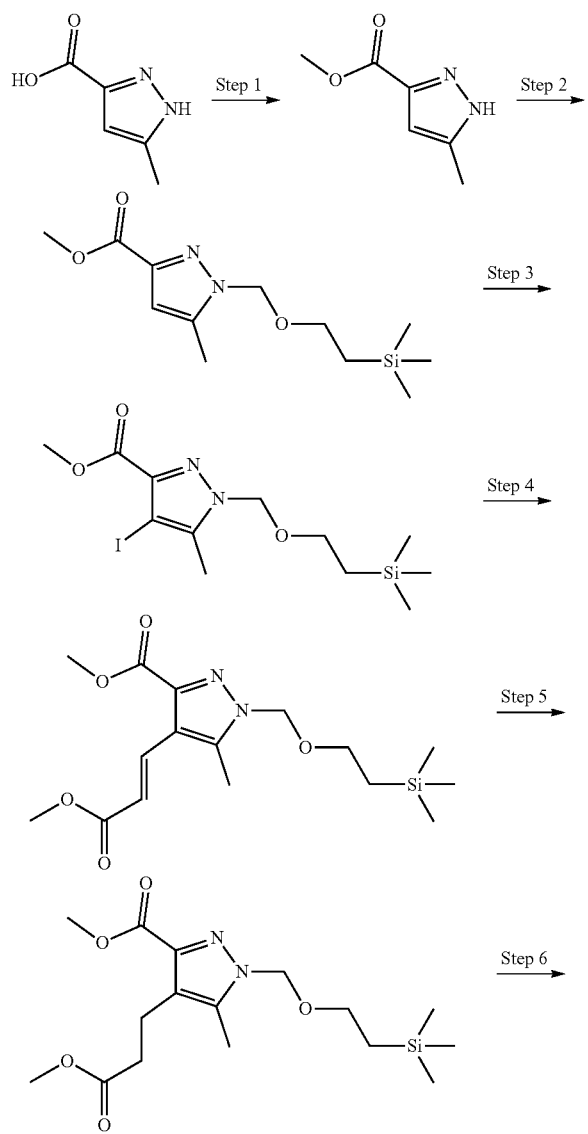

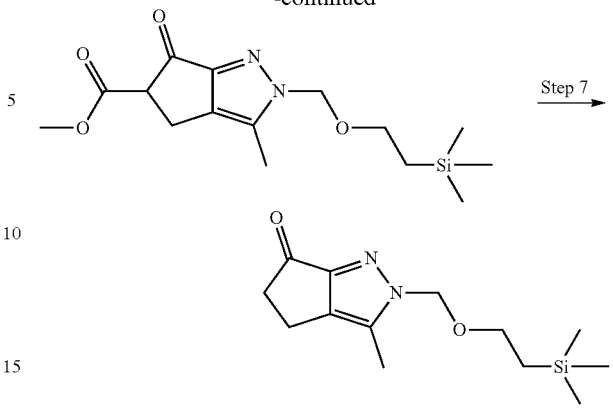

Step 1: Methyl 5-methyl-1H-pyrazole-3-carboxylate

To a solution of 5-methyl-1H-pyrazole-3-carboxylic acid (45 g) in MeOH (450 mL) is added dropwise thionylchloride (58 mL). After addition the mixture is stirred for 16 h at room temperature. The mixture is concentrated in vacuo. The residue is dissolved in EtOAC, washed successively with saturated aqueous $NaHCO_3$ and brine. After drying ($MgSO_4$) the mixture is concentrated in vacuo to give the title compound.

LC (Method 1): $t_R$=0.64 min; Mass spectrum (ESI⁺): m/z=141 [M+H]⁺.

Step 2: Methyl 5-methyl-1-{[2-(trimethylsilyl)ethoxy]methyl}-1H-pyrazole-3-carboxylate Sodium hydride (60% in mineral oil, 16.8 g) is added portionwise to DMF (470 mL). The mixture is stirred for 10 min, cooled to 0° C. and treated dropwise with a solution of methyl 5-methyl-1H-pyrazole-3-carboxylate (46.9 g) in DMF (470 mL). After stirring for 20 min [2-(chloromethoxy)ethyl]trimethylsilane (SEM-Cl, 77.7 mL) is added dropwise. The mixture is stirred for 2 h, diluted with EtOAC and washed successively water and brine. After drying ($MgSO_4$) the mixture is concentrated in vacuo and the residue is chromatographed over silica gel with petrole ether/EtOAC 2:1. The solvents are evaporated in vacuo to give the title compound, which is used directly in the next step.

Step 3: Methyl 4-iodo-5-methyl-1-{[2-(trimethylsilyl)ethoxy]methyl}-1H-pyrazole-3-carboxylate To a solution of methyl 5-methyl-1-{[2-(trimethylsilyl)ethoxy]methyl}-1H-pyrazole-3-carboxylate (94.4 g) in ACN (1.4 L) is added TFA (2.7 mL) and N-iodosuccinimide (94.2 g). The mixture is stirred for 48 h, diluted with EtOAC and washed successively with water, saturated aqueous $Na_2S_2O_3$ and brine. After drying ($MgSO_4$) the mixture is concentrated in vacuo and the residue is chromatographed over silica gel with petrole ether/EtOAC 2:1. The solvents are evaporated in vacuo to give the title compound, which contains approximately 15% of the regioisomeric methyl 4-iodo-3-methyl-1-{[2-(trimethylsilyl)ethoxy]methyl}-1H-pyrazole-5-carboxylate.

LC (Method 1): $t_R$=1.17 min; Mass spectrum (ESI⁺): m/z=397 [M+H]⁺.

Step 4: Methyl 4-[(1E)-3-methoxy-3-oxoprop-1-en-1-yl]-5-methyl}-1-{[2-(trimethylsilyl)ethoxy]methyl}-1H-pyrazole-3-carboxylate Methyl 4-iodo-5-methyl-1-{[2-(trimethylsilyl)ethoxy]methyl}-1H-pyrazole-3-carboxylate (44 g), methylacrylate (15 mL) and N-methyldicyclohexylamin (35 mL) are dissolved in dimethylyacetamide (430 mL) and water (110 mL). The mixture is purged for 10 min with argon. Dichlorobis(tri-o-tolylphosphine)palladium(II) (PdCl$_2$[P(o-Tol)$_3$]$_2$, 2.6 g) is added and the mixture is stirred for 2 h at 85° C. Then the mixture is diluted with EtOAC and washed successively with 1 M aqueous H$_3$PO$_4$ and brine. After drying (MgSO$_4$) the mixture is concentrated in vacuo and the residue is chromatographed on silica gel (petrole ether/EtOAC 95:5→50:50) to give the title compound.

LC (Method 1): $t_R$=1.13 min; Mass spectrum (ESI$^+$): m/z=355 [M+H]$^+$.

Step 5: Methyl 4-(3-methoxy-3-oxopropyl)-5-methyl-1-{[2-(trimethylsilyl)ethoxy]methyl}-1H-pyrazole-3-carboxylate A mixture of methyl 4-[(1E)-3-methoxy-3-oxoprop-1-en-1-yl]-5-methyl-1-{[2-(trimethylsilyl)ethoxy]methyl}-1H-pyrazole-3-carboxylate (38.6 g) and 10% palladium on carbon (5.8 g) in EtOAC (580 mL) is shaken under hydrogen atmosphere (3 bar) at room temperature for 3 h. The mixture is filtered, and the filtrate is concentrated to give the title compound.

LC (Method 1): $t_R$=1.10 min; Mass spectrum (ESI$^+$): m/z=357 [M+H]$^+$.

Step 6: Methyl 3-methyl-6-oxo-2-{[2-(trimethylsilyl)ethoxy]methyl}-2H,4H,5H,6H-cyclopenta[c]pyrazole-5-carboxylate A solution of methyl 4-(3-methoxy-3-oxopropyl)-5-methyl-1-{[2-(trimethylsilyl)ethoxy]methyl}-1H-pyrazole-3-carboxylate (37.8 g) in THF is cooled to 0° C., treated with NaN(Si(CH$_3$)$_3$)$_2$ (40% in THF; 105 mL) and stirred for 15 min. The mixture is poured under ice-cooling and vigorous stirring into 1 M aqueous H$_3$PO$_4$. The organic phase is separated, washed with brine and dried (MgSO$_4$). The solvents are evaporated in vacuo to give the title compound.

LC (Method 1): $t_R$=1.06 min; Mass spectrum (ESI$^+$): m/z=325 [M+H]$^+$.

Step 7: 3-Methyl-2-{[2-(trimethylsilyl)ethoxy]methyl}-2H,4H,5H,6H-cyclopenta[c]pyrazol-6-one A solution of methyl 3-methyl-6-oxo-2-{[2-(trimethylsilyl)ethoxy]methyl}-2H,4H,5H,6H-cyclopenta[c]pyrazole-5-carboxylate (34.9 g) in 1,4-dioxane (350 mL) and water (9 mL) is heated under reflux for 12 h. The solvents are evaporated in vacuo and the residue is chromatographed on silica gel (petrole ether/EtOAC 80:20→40:60) to give the title compound.

LC (Method 1): $t_R$=1.05 min; Mass spectrum (ESI$^+$): m/z=267 [M+H]$^+$.

Intermediate 2

3-Methyl-2-{[2-(trimethylsilyl)ethoxy]methyl}-2H,4H,5H,6H-cyclopenta[c]pyrazol-6-amine

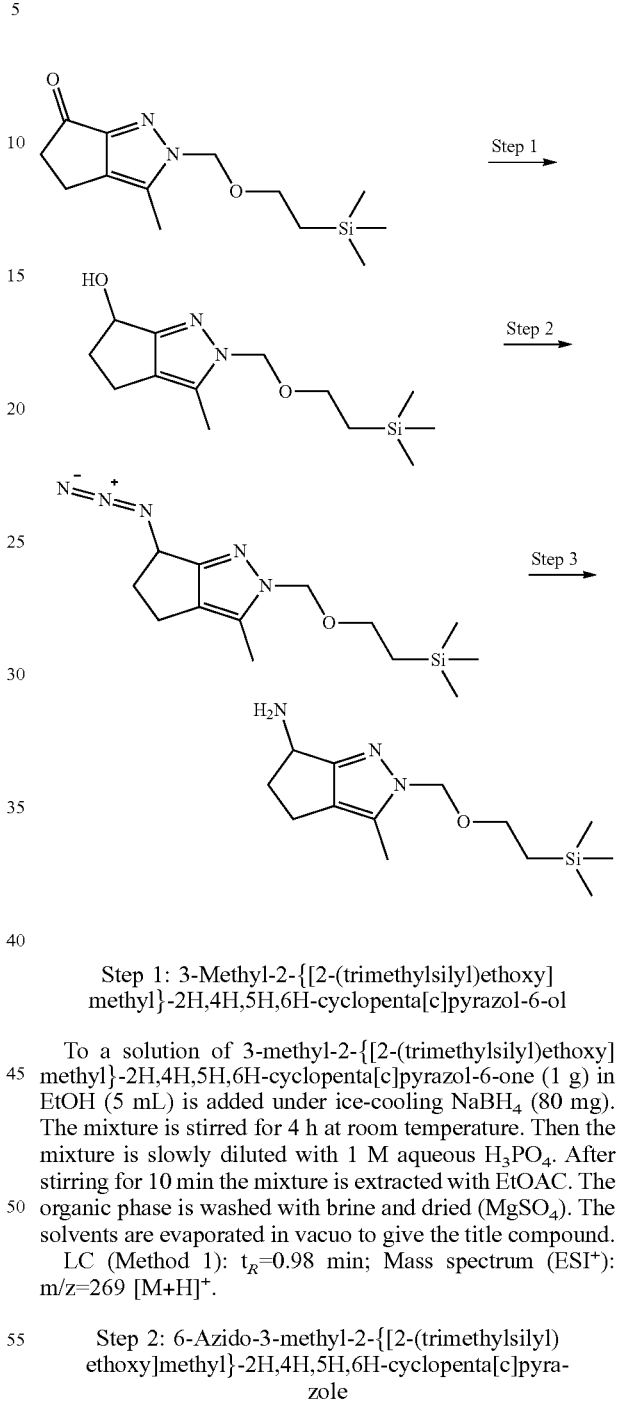

Step 1: 3-Methyl-2-{[2-(trimethylsilyl)ethoxy]methyl}-2H,4H,5H,6H-cyclopenta[c]pyrazol-6-ol To a solution of 3-methyl-2-{[2-(trimethylsilyl)ethoxy]methyl}-2H,4H,5H,6H-cyclopenta[c]pyrazol-6-one (1 g) in EtOH (5 mL) is added under ice-cooling NaBH$_4$ (80 mg). The mixture is stirred for 4 h at room temperature. Then the mixture is slowly diluted with 1 M aqueous H$_3$PO$_4$. After stirring for 10 min the mixture is extracted with EtOAC. The organic phase is washed with brine and dried (MgSO$_4$). The solvents are evaporated in vacuo to give the title compound.

LC (Method 1): $t_R$=0.98 min; Mass spectrum (ESI$^+$): m/z=269 [M+H]$^+$.

Step 2: 6-Azido-3-methyl-2-{[2-(trimethylsilyl)ethoxy]methyl}-2H,4H,5H,6H-cyclopenta[c]pyrazole Under argon DBU (2 mL) is added to a solution of 3-methyl-2-{[2-(trimethylsilyl)ethoxy]methyl}-2H,4H,5H,6H-cyclopenta[c]pyrazol-6-ol (950 mg) in toluene (20 mL). The mixture is cooled to 0° C. and diphenylphosphorylazide (2 mL) is added dropwise over 1 hour. The mixture is stirred for 12 h while warming to room temperature. Then the mixture is washed with water, dried (MgSO$_4$) and concentrated in vacuo. The residue is chromatographed on Al$_2$O$_3$ (DCM) to give the title compound.

LC (Method 1): $t_R$=1.15 min; Mass spectrum (ESI⁺): m/z=294 [M+H]⁺.

Step 3: 3-Methyl-2-{[2-(trimethylsilyl)ethoxy]methyl}-2H,4H,5H,6H-cyclopenta[c]pyrazol-6-amine A mixture of 6-azido-3-methyl-2-{[2-(trimethylsilyl)ethoxy]methyl}-2H,4H,5H,6H-cyclopenta[c]pyrazole (770 mg), 10% palladium on carbon (140 mg) in EtOH (10 mL) is shaken under hydrogen atmosphere (3 bar) at room temperature for 12 h. The mixture is filtered, and the filtrate is concentrated to give the title compound.

LC (Method 1): $t_R$=0.81 min; Mass spectrum (ESI⁺): m/z=268 [M+H]⁺.

Intermediate 3

3-Methyl-1H,4H,5H,6H-cyclopenta[c]pyrazol-6-amine dihydrochloride

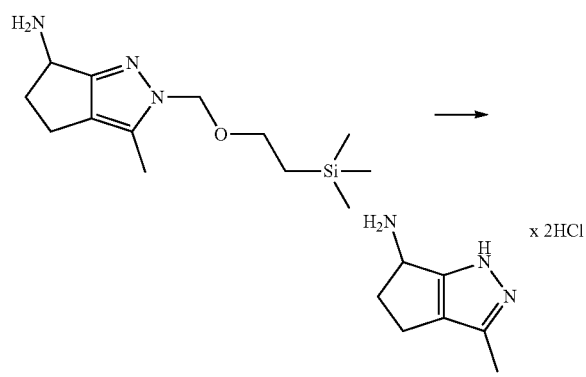

A solution of 3-methyl-2-{[2-(trimethylsilyl)ethoxy]methyl}-2H,4H,5H,6H-cyclopenta[c]pyrazol-6-amine (25 mg) in 4 N HCl in 1,4-dioxane (1 mL) is stirred for 48 h at room temperature. The solvents are evaporated in vacuo to give the title compound.

LC (Method 2): $t_R$=0.57 min; Mass spectrum (ESI): m/z=138 [M+H]⁺.

Intermediate 4

(6R)-3-Methyl-2-{[2-(trimethylsilyl)ethoxy]methyl}-2H,4H,5H,6H-cyclopenta[c]pyrazol-6-amine

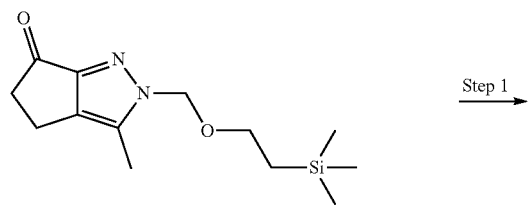

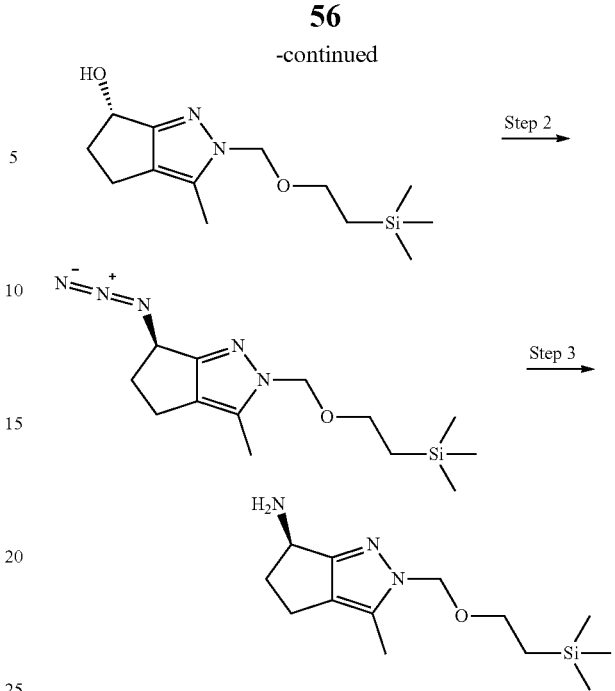

Step 1: (6S)-3-Methyl-2-{[2-(trimethylsilyl)ethoxy]methyl}-2H,4H,5H,6H-cyclopenta[c]pyrazol-6-ol To a solution of triethylamine (27 mL) in DCM (260 mL) is added at 0° C. formic acid (11 mL). The mixture is warmed to room temperature and 3-methyl-2-{[2-(trimethylsilyl)ethoxy]methyl}-2H,4H,5H,6H-cyclopenta[c]pyrazol-6-one (26 g) is added. After purging for 10 min with argon [N-[(1S,2S)-2-(amino-κN)-1,2-diphenylethyl]-4-methylbenzenesulfonamidato-κN]chloro[(1,2,3,4,5,6-η)-1,3,5-trimethylbenzene]-ruthenium (RuCl[(S,S)-TsDPEN](me-sitylene); 0.5 g) is added and the mixture is stirred for 48 h at room temperature. Then the mixture is treated with 1 M aqueous NaHCO₃ under vigorous stirring. The phases are separated and the aqueous phase is extracted with DCM. The combined organic phases are washed with water and brine. After drying (MgSO₄), the solvents are evaporated in vacuo and the residue is chromatographed on silica gel (DCM/MeOH 98:2→90:10) to give the title compound with an enantiomeric excess (ee) of 84%.

LC (Method 1): $t_R$=0.99 min; Mass spectrum (ESI⁺): m/z=269 [M+H]⁺.

Step 2: (6R)-6-Azido-3-methyl-2-{[2-(trimethylsilyl)ethoxy]methyl}-2H,4H,5H,6H-cyclopenta[c]pyrazole Under argon DBU (16 mL) is added to a solution of (6S)-3-methyl-2-{[2-(trimethylsilyl)ethoxy]methyl}-2H,4H,5H,6H-cyclopenta[c]pyrazol-6-ol (25.5 g) in toluene (250 mL). The mixture is cooled to 0° C. and diphenylphosphorylazide (22 mL) is added dropwise over 1 h. The mixture is stirred for 12 h while warming to room temperature. Then MeOH (25 mL) is added and the mixture is stirred for 1 h. The mixture is washed twice with water, dried (MgSO₄) and concentrated in vacuo. The residue is chromatographed on Al₂O₃(DCM) to give the title compound.

LC (Method 1): $t_R$=1.15 min; Mass spectrum (ESI⁺): m/z=294 [M+H]⁺.

Step 3: (6R)-3-Methyl-2-{[2-(trimethylsilyl)ethoxy]methyl}-2H,4H,5H,6H-cyclopenta[c]pyrazol-6-amine A mixture of (6R)-6-azido-3-methyl-2-{[2-(trimethylsilyl)ethoxy]methyl}-2H,4H,5H,6H-cyclopenta[c]pyrazole (19.7 g) and 10% palladium on carbon (3 g) in EtOH (200 mL) is shaken under hydrogen atmosphere (3 bar) at room temperature for 12 h. The mixture is filtered, and the filtrate is concentrated to give the title compound.

LC (Method 1): $t_R$=0.80 min; Mass spectrum (ESI$^+$): m/z=268 [M+H]$^+$.

Intermediate 5

3-Methyl-1H,4H,5H,6H-cyclopenta[c]pyrazol-6-amine

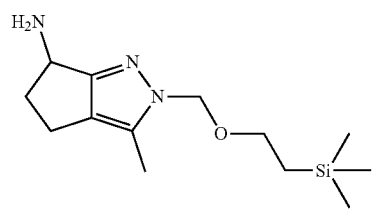

A solution of 3-methyl-2-{[2-(trimethylsilyl)ethoxy]methyl}-2H,4H,5H,6H-cyclopenta[c]pyrazol-6-amine (225 mg) in DCM (2 mL) is cooled to 0° C., treated with TFA (970 μL) and stirred for 12 h while warming to room temperature. The solvents are evaporated in vacuo and the residue is dissolved in DCM and MeOH. 1 M KOH in EtOH is added until pH of 10 is reached. The solvents are evaporated in vacuo and the residue is chromatographed on Al$_2$O$_3$(DCM/MeOH/(1 M NH$_3$ in MeOH) 97:1:2→80:18:2) to give the title compound.

LC (Method 1): $t_R$=0.18 min; Mass spectrum (ESI$^+$): m/z=121 [M-NH$_3$+H].

Intermediate 6

(6S)-3-Methyl-1H,4H,5H,6H-cyclopenta[c]pyrazol-6-amine

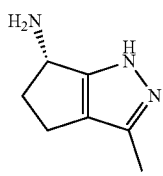

The title compound is obtained from the racemic mixture upon SFC separation on chiral phase (column: Chiralpak IC, 5 μm, 250 mm×20 mm; eluent: scCO$_2$/(20 mM NH$_3$ in MeOH) 80:20, 40° C., 200 bar, 60 mL/min); $t_R$=5.9 min

Intermediate 7

(6R)-3-Methyl-1H,4H,5H,6H-cyclopenta[c]pyrazol-6-amine

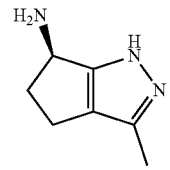

The title compound is obtained from the racemic mixture upon SFC separation on chiral phase (column: Chiralpak IC, 5 μm, 250 mm×20 mm; eluent: scCO$_2$/(20 mM NH$_3$ in MeOH) 80:20, 40° C., 200 bar, 60 mL/min); $t_R$=5.2 min

Intermediate 8

1-[(6-{3-Azabicyclo[3.1.0]hexan-3-yl}-2-methylpyridin-3-yl)methyl]-1H-pyrazole-4-carboxylic acid

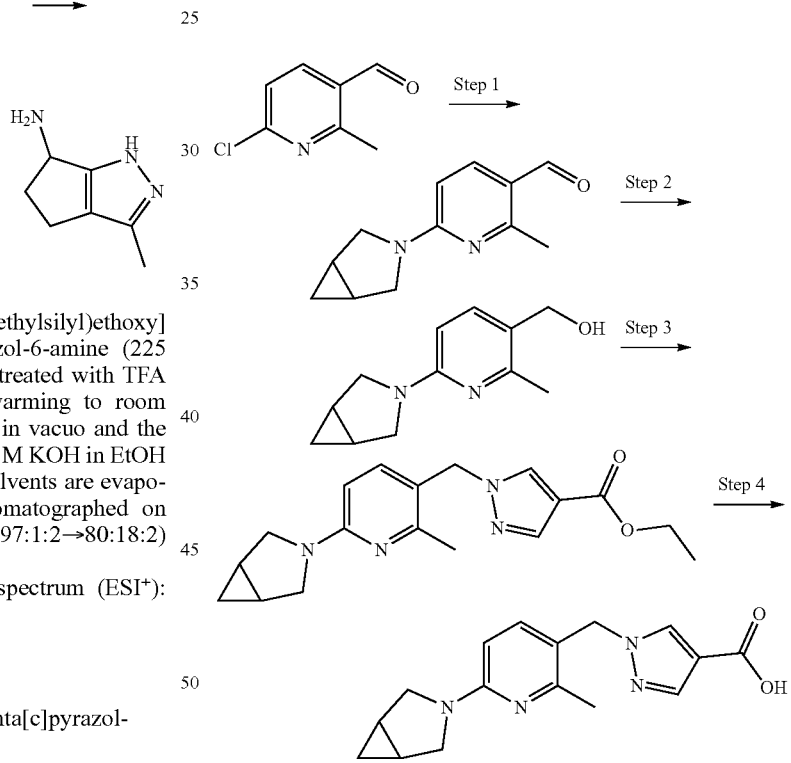

Step 1: 6-{3-Azabicyclo[3.1.0]hexan-3-yl}-2-methylpyridine-3-carbaldehyde

6-Chloro-2-methylpyridine-3-carbaldehyde (15 g), 3-azabicyclo[3.1.0]hexane hydrochloride (14 g) and KHCO$_3$ (22.5 g) are suspended in DMSO (70 mL) and heated to 60° C. for 12 h. The mixture is cooled, partitioned between water and DCM and the phases are separated. The aqueous phase is extracted three times with DCM and the combined organic phases are washed with brine. After drying (MgSO$_4$) the solvents are evaporated in vacuo to give the title compound.

LC (Method 1): $t_R$=0.59 min; Mass spectrum (ESI⁺): m/z=203 [M+H]⁺.

Step 2: (6-{3-Azabicyclo[3.1.0]hexan-3-yl}-2-methylpyridin-3-yl)methanol

To a solution of 6-{3-azabicyclo[3.1.0]hexan-3-yl}-2-methylpyridine-3-carbaldehyde (19.5 g) in EtOH (300 mL) is added under ice-cooling NaBH₄ (4 g). The mixture is stirred for 2 h at room temperature. After cooling to 0° C. the mixture is slowly treated with 4 M aqueous HCl (72 mL) and stirred for 15 min. Then the mixture is basified by addition of 4 M aqueous NaOH. EtOH is distilled off in vacuo. The residue is extracted with DCM. The organic phase is washed with brine and dried (MgSO₄). The solvents are evaporated in vacuo to give the title compound.

LC (Method 1): $t_R$=0.55 min; Mass spectrum (ESI⁺): m/z=205 [M+H]⁺.

Step 3: Ethyl 1-[(6-{3-azabicyclo[3.1.0]hexan-3-yl}-2-methylpyridin-3-yl)methyl]-1H-pyrazole-4-carboxylate (6-{3-Azabicyclo[3.1.0]hexan-3-yl}-2-methylpyridin-3-yl)methanol (19.2 g) is dissolved in THF (150 mL) and cooled to 0° C. Ethyl 1H-pyrazole-4-carboxylate (14.5 g) and tributyl phosphine (30 mL) are added. Di-tert.-butyl-azodicarboxylate (26 g) is slowly added portionwise and the mixture is stirred for 45 min. Saturated aqueous NaHCO₃ is added, the mixture is vigorously stirred for 10 min and then extracted with EtOAC. The organic phase is washed with brine, dried (MgSO₄) and concentrated in vacuo. The residue is chromatographed on silica gel (petrole ether/EtOAC 80:20→50:50) to give the title compound.

LC (Method 1): $t_R$=0.73 min; Mass spectrum (ESI⁺): m/z=327 [M+H]⁺.

Step 4: 1-[(6-{3-Azabicyclo[3.1.0]hexan-3-yl}-2-methylpyridin-3-yl)methyl]-1H-pyrazole-4-carboxylic acid A mixture of ethyl 1-[(6-{3-azabicyclo[3.1.0]hexan-3-yl}-2-methylpyridin-3-yl)methyl]-1H-pyrazole-4-carboxylate (15.5 g), 1 M KOH in EtOH (100 mL) and THF (250 mL) is stirred at 50° C. for 48 h. After cooling to room temperature acetic acid (5.5 mL) is added and the solvents are evaporated in vacuo. The residue is partitioned between water and DCM/isopropanol 9:1. The organic phase is washed with brine and dried (MgSO₄). The solvents are evaporated in vacuo and the residue is crystallized from ACN to give the title compound.

LC (Method 1): $t_R$=0.60 min; Mass spectrum (ESI⁺): m/z=299 [M+H]⁺.

Intermediate 9

1-[(6-{6,6-Difluoro-3-azabicyclo[3.1.0]hexan-3-yl}-2-methylpyridin-3-yl)methyl]-1H-pyrazole-4-carboxylic acid

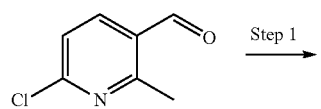

Step 1

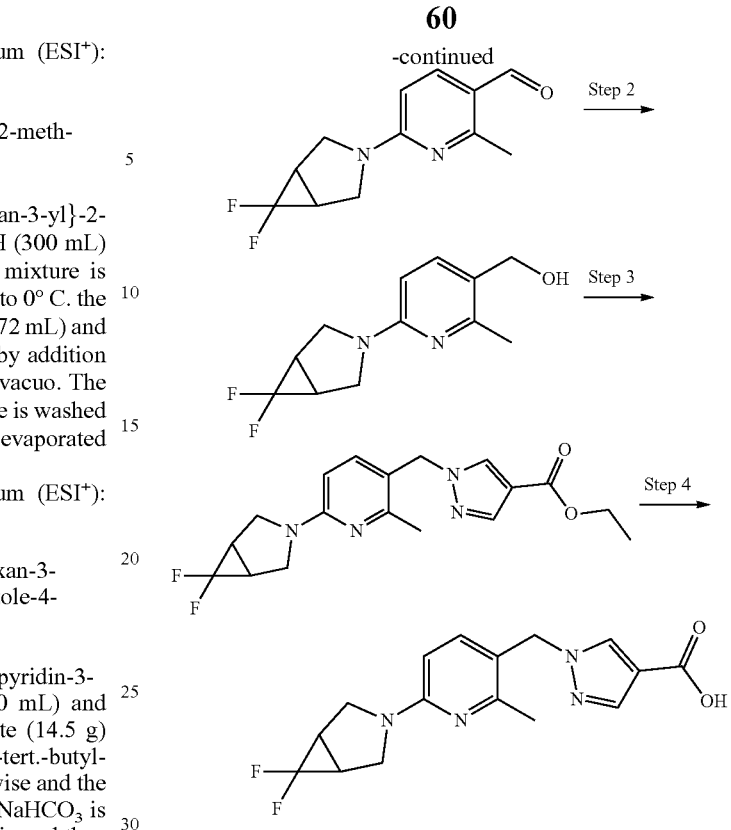

Step 1: 6-{6,6-Difluoro-3-azabicyclo[3.1.0]hexan-3-yl}-2-methylpyridine-3-carbaldehyde 6-Chloro-2-methylpyridine-3-carbaldehyde (19.6 g), 6,6-difluoro-3-azabicyclo[3.1.0]hexane hydrochloride (19.6 g) and KHCO₃ (58 g) are suspended in DMSO (70 mL) and heated to 75° C. for 48 h. The mixture is cooled, partitioned between water and EtOAC and the phases are separated. The organic phase is washed with brine. After drying (MgSO₄) the solvents are evaporated in vacuo to give the title compound.

LC (Method 1): $t_R$=0.66 min; Mass spectrum (ESI⁺): m/z=239 [M+H]⁺.

Step 2: (6-{6,6-Difluoro-3-azabicyclo[3.1.0]hexan-3-yl}-2-methylpyridin-3-yl)methanol To a solution 6-{6,6-difluoro-3-azabicyclo[3.1.0]hexan-3-yl}-2-methylpyridine-3-carbaldehyde (41.6 g) in EtOH (600 mL) is added under ice-cooling NaBH₄ (9 g). The mixture is stirred for 12 h at room temperature. After cooling to 000 the mixture is slowly treated with 4 M aqueous HCl (150 mL) and stirred for 15 min. Then the mixture is basified by addition of 4 M aqueous NaOH. EtOH is distilled off in vacuo. The residue is extracted with DCM. The organic phase is washed with brine and dried (MgSO₄). The solvents are evaporated in vacuo and the residue is triturated from diisopropylether to give the title compound.

LC (Method 1): $t_R$=0.54 min; Mass spectrum (ESI⁺): m/z=241 [M+H]⁺.

Step 3: Ethyl 1-[(6-{6,6-difluoro-azabicyclo[3.1.0]hexan-3-yl}-2-methylpyridin-3-yl)methyl]-1H-pyrazole-4-carboxylate (6-{6,6-Difluoro-3-azabicyclo[3.1.0]hexan-3-yl}-2-methylpyridin-3-yl)methanol (24.4 g) is dissolved in THF (500 mL) and cooled to 0° C. Ethyl 1H-pyrazole-4-carboxylate (15.3 g) and tributyl phosphine (28 mL) are added. Di-tert.-butyl-azodicarboxylate (24.6 g) is slowly added portionwise and the mixture is stirred for 45 min. Saturated aqueous NaHCO₃ is added, the mixture is vigorously stirred for 10 min and then extracted with EtOAC. The organic phase is washed with brine, dried (MgSO₄) and concentrated in vacuo. The residue is chromatographed on silica gel (cyclohexane/EtOAC 50:50→20:80) to give the title compound.

LC (Method 1): $t_R$=0.75 min; Mass spectrum (ESI⁺): m/z=363 [M+H]⁺.

Step 4: 1-[(6-{6,6-Difluoro-3-azabicyclo[3.1.0] hexan-3-yl}-2-methylpyridin-3-yl)methyl]-1H-pyrazole-4-carboxylic acid A mixture of ethyl 1-[(6-{6,6-difluoro-3-azabicyclo [3.1.0]hexan-3-yl}-2-methylpyridin-3-yl)methyl]-1H-pyrazole-4-carboxylate (24.5 g), 4 M aqueous NaOH (30 mL) and EtOH (220 mL) is stirred at 60° C. for 4 h. After cooling to room temperature 4 M aqueous HCl (30 mL) is added and the solvents are evaporated in vacuo. The residue is taken up in water. The precipitate is isolated by filtration to give the title compound.

LC (Method 1): $t_R$=0.61 min; Mass spectrum (ESI⁺): m/z=335 [M+H]⁺.

Intermediate 10

1-[(6-{6,6-Difluoro-3-azabicyclo[3.1.0]hexan-3-yl}-2-methylpyridin-3-yl)methyl]-N-[(6R)-3-methyl-2-{[2-(trimethylsilyl)ethoxy]methyl}-2H,4H,5H,6H-cyclopenta[c]pyrazol-6-yl]-1H-pyrazole-4-carboxamide

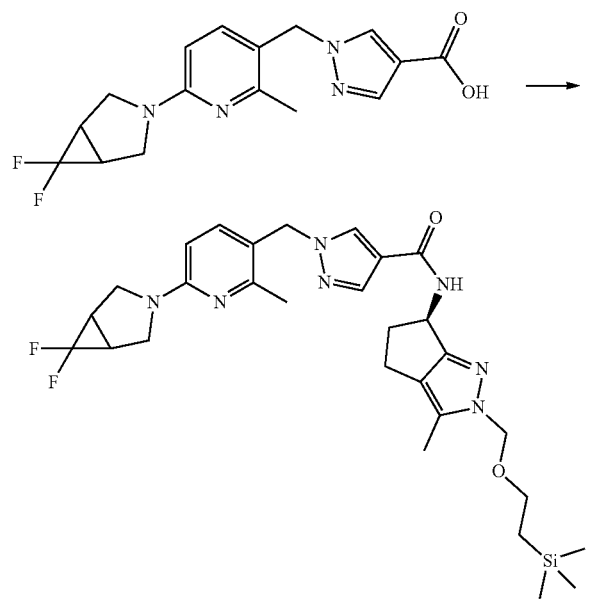

To a solution of 1-[(6-{6,6-difluoro-3-azabicyclo[3.1.0] hexan-3-yl}-2-methylpyridin-3-yl)methyl]-1H-pyrazole-4-carboxylic acid (1 g) in DMF (10 mL) is added DIPEA (700 µL) and O-(7-azabenzotriazol-1-yl)-N,N,N',N'-tetramethyl-uronium-hexafluorophosphat (HATU, 1.3 g) and the mixture is stirred for 5 min. (6R)-3-Methyl-2-{[2-(trimethylsilyl) ethoxy]methyl}-2H,4H,5H,6H-cyclopenta[c]pyrazol-6-amine (750 mg) is added and the mixture is stirred for 1 h. The mixture is partitioned between water and EtOAC. The organic phase is washed with brine and dried (MgSO₄). The solvents are evaporated in vacuo to give the title compound.

LC (Method 1): $t_R$=0.93 min; Mass spectrum (ESI⁺): m/z=584 [M+H]⁺.

Intermediate 11

4-[(6-{3-Azabicyclo[3.1.0]hexan-3-yl}-2-methyl-pyridin-3-yl)methyl]thiophene-2-carboxylic acid

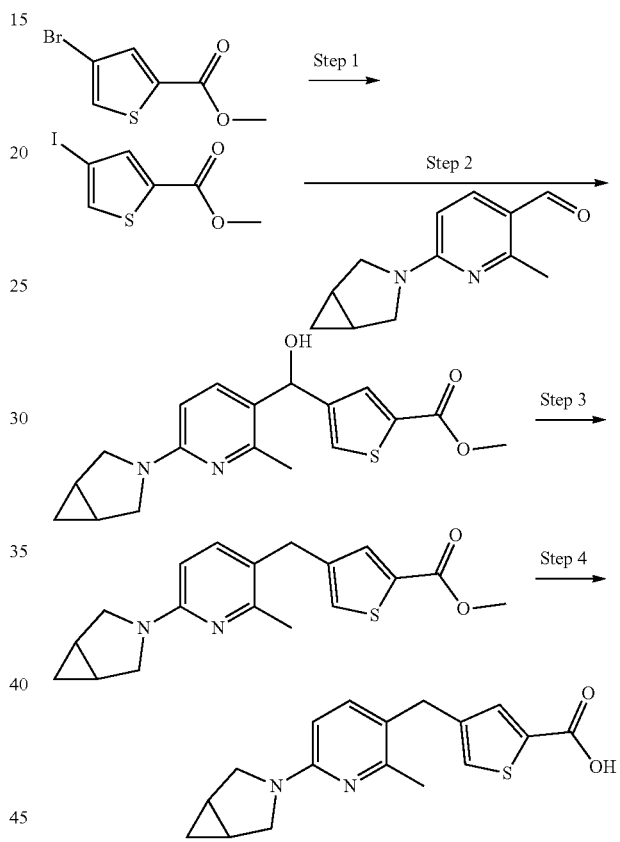

Step 1: Methyl 4-iodothiophene-2-carboxylate

In a microwave vial under argon methyl 4-bromothiophene-2-carboxylate (1 g), copper-I-iodide (43 mg), (1R, 2R)—N,N'-dimethyl-cyclohexane-1,2-diamine (64 mg) and sodium iodide (1.4 g) are suspended in 1,4-dioxane (5 mL) and heated to 120° C. for 2 h. The mixture is cooled, partitioned between water and EtOAC and the phases are separated. The aqueous phase is extracted with EtOAC and the combined organic phases are washed with brine. After drying (MgSO₄) the solvents are evaporated in vacuo. The residue is chromatographed on silica gel (cyclohexane/ EtOAC 100:0→95:5) to give the title compound.

LC (Method 1): $t_R$=1.02 min.

Step 2: Methyl 4-[(6-{3-azabicyclo[3.1.0]hexan-3-yl}-2-methylpyridin-3-yl)(hydroxy)methyl]thiophene-2-carboxylate To a solution of methyl 4-iodothiophene-2-carboxylate (940 mg) in THF (15 mL) is added dropwise at −80° C.

isopropylmagnesuim chloride-lithium chloride complex (iPrMgClxLiCl, 2.8 mL of a 1.3 M solution in THF). The mixture is stirred for 1 h and then treated dropwise with a solution of 6-{3-azabicyclo[3.1.0]hexan-3-yl}-2-methylpyridine-3-carbaldehyde (730 mg) in THF (4.5 mL). After stirring for 1.5 h, the reaction is quenched by addition of 10% aqueous NH$_4$Cl. The phases are separated and the aqueous phase is extracted with EtOAC. The combined organic phases are dried (MgSO$_4$) and concentrated in vacuo. The residue is chromatographed on silica gel (cyclohexane/EtOAC 85:15→30:70) to give the title compound.

LC (Method 1): $t_R$=0.75 min; Mass spectrum (ESI$^+$): m/z=345 [M+H]$^+$.

Step 3: Methyl 4-[(6-{3-azabicyclo[3.1.0]hexan-3-yl}-2-methylpyridin-3-yl)methyl]thiophene-2-carboxylate Methyl 4-[(6-{3-azabicyclo[3.1.0]hexan-3-yl}-2-methylpyridin-3-yl)(hydroxy)methyl]thiophene-2-carboxylate (1.15 g) is dissolved in 1,2-dichloroethane (15 mL) and cooled to 0° C. Triethylsilane (2.1 mL) and TFA (900 µL) are added and the mixture is stirred for 4 h, while warming room temperature. Then the mixture is stirred for 12 h at 50° C. After cooling to room temperature triethylsilane (1 mL) and TFA (350 µL) are added and the mixture is stirred for 4 h at 50° C. The mixture is cooled to room temperature and carefully partitioned between saturated aqueous NaHCO$_3$ and DCM. The phases are separated and the aqueous phase is extracted with DCM. The combined organic phases are dried (MgSO$_4$) and concentrated in vacuo. The residue is chromatographed on silica gel (petrole ether/EtOAC 100:0→75:25) to give the title compound.

LC (Method 1): $t_R$=0.79 min; Mass spectrum (ESI$^+$): m/z=329 [M+H]$^+$.

Step 4: 4-[(6-{3-Azabicyclo[3.1.0]hexan-3-yl}-2-methylpyridin-3-yl)methyl]thiophene-2-carboxylic acid A mixture of methyl 4-[(6-{3-azabicyclo[3.1.0]hexan-3-yl}-2-methylpyridin-3-yl)methyl]thiophene-2-carboxylate (515 mg), 4 M aqueous NaOH (784 µL), THF (5 mL) and MeOH (5 mL) is stirred at 50° C. for 2.5 h. After cooling to room temperature EtOAC is added. The organic solvents are evaporated in vacuo and the residue is treated with 4 M aqueous HCl (800 µL). The aqueous phase is twice extracted with EtOAC. The combined organic phases are dried (MgSO$_4$) and concentrated in vacuo to give the title compound.

LC (Method 1): $t_R$=0.71 min; Mass spectrum (ESI$^+$): m/z=315 [M+H]$^+$.

Intermediate 12

4-[(6-{3-Azabicyclo[3.1.0]hexan-3-yl}-2-methylpyridin-3-yl)methyl]-1-{[2-(trimethylsilyl)ethoxy]methyl}-1H-pyrrole-2-carboxylic acid

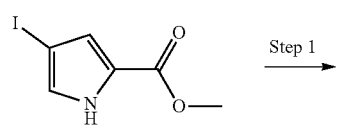

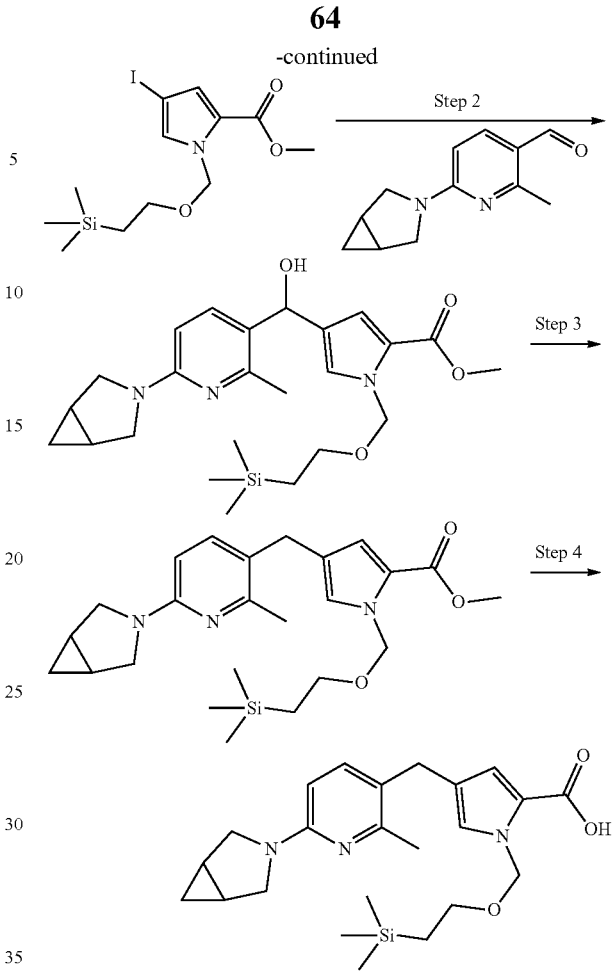

Step 1: Methyl 4-iodo-1-{[2-(trimethylsilyl)ethoxy]methyl}-1H-pyrrole-2-carboxylate Under argon methyl 4-iodo-1H-pyrrole-2-carboxylate (1 g) is dissolved in DMF (8 mL), cooled to 000 and treated with NaH (199 mg, 60% in mineral oil). The mixture is stirred for 20 min and then treated dropwise with 2-(trimethylsilyl)ethoxymethylchloride (SEM-Cl, 742 µL). The mixture is stirred for 20 min at 0° C., for 20 min at room temperature and then partitioned between water and EtOAC. Aqueous 4 M HCl is added until a pH of 6 to 7 is reached. The phases are separated and the aqueous phase is extracted with EtOAC. The combined organic phases are dried (MgSO$_4$) and concentrated in vacuo. The residue is chromatographed on silica gel (petrole ether/EtOAC 100:0→90:10) to give the title compound.

LC (Method 1): $t_R$=1.23 min; Mass spectrum (ESI$^+$): m/z=404 [M+Na]$^+$.

Step 2: Methyl 4-[(6-{3-azabicyclo[3.1.0]hexan-3-yl}-2-methylpyridin-3-yl)(hydroxy)methyl]-1-{[2-(trimethylsilyl)ethoxy]methyl}-1H-pyrrole-2-carboxylate To a solution of methyl 4-iodo-1-{[2-(trimethylsilyl)ethoxy]methyl}-1H-pyrrole-2-carboxylate (1.18 g) in THF (15 mL) is added dropwise at −80° C. isopropylmagnesuim chloride-lithium chloride complex (iPrMgClxLiCl, 2.5 mL of a 1.3 M solution in THF). The mixture is stirred for 1 h and then treated dropwise with a solution of 6-{3-azabicy-clo-[3.1.0]hexan-3-yl}-2-methylpyridine-3-carbaldehyde (644 mg) in THF (6 mL). After stirring for 1.5 h, the reaction is quenched by addition of 10% aqueous NH₄Cl. The phases are separated and the aqueous phase is extracted with EtOAC. The combined organic phases are dried (MgSO₄) and concentrated in vacuo to give the title compound.

LC (Method 3): $t_R$=0.90 min; Mass spectrum (ESI⁺): m/z=548 [M+H]⁺.

Step 3: Methyl 4-[(6-{3-azabicyclo[3.1.0]hexan-3-yl}-2-methylpyridin-3-yl)methyl]-1-{[2-(trimethylsilyl)ethoxy]-methyl}-1H-pyrrole-2-carboxylate Methyl 4-[(6-{3-azabicyclo[3.1.0]hexan-3-yl}-2-methylpyridin-3-yl)(hydroxy)methyl]-1-{[2-(trimethylsilyl)ethoxy]-methyl}-1H-pyrrole-2-carboxylate (1.56 g) is dissolved in DCM (20 mL) and cooled to 0° C. Triethylsilane (3 mL) and BF₃xOEt₂ (1.17 mL) are added and the mixture is stirred for 40 min while warming room temperature. The mixture is carefully partitioned between saturated aqueous NaHCO₃ and DCM. The phases are separated and the aqueous phase is extracted with DCM. The combined organic phases are dried (MgSO₄) and concentrated in vacuo. The residue is chromatographed on silica gel (petrole ether/(EtOAC/MeOH 8:2) 100:0→80:20) to give the title compound.

LC (Method 1): $t_R$=0.94 min; Mass spectrum (ESI⁺): m/z=442 [M+H]⁺.

Step 4: 4-[(6-{3-Azabicyclo[3.1.0]hexan-3-yl}-2-methylpyridin-3-yl)methyl]-1-{[2-(trimethylsilyl)ethoxy]methyl}-1H-pyrrole-2-carboxylic acid A mixture of methyl 4-[(6-{3-azabicyclo[3.1.0]hexan-3-yl}-2-methylpyridin-3-yl)methyl]-1-{[2-(trimethylsilyl)-ethoxy]methyl}-1H-pyrrole-2-carboxylate (965 mg), 4 M aqueous NaOH (1.64 mL), THF (10 mL) and MeOH (10 mL) is stirred at 45° C. for 22 h. 4 M Aqueous NaOH (0.55 mL) is added and the mixture is stirred for 5 h at 60° C. After cooling to room temperature 4 M aqueous HCl (2.2 mL) is added and the mixture is partitioned EtOAC and brine. The phases are separated and the aqueous phase is twice extracted with EtOAC. The combined organic phases are dried (MgSO₄) and concentrated in vacuo to give the title compound.

LC (Method 1): $t_R$=0.88 min; Mass spectrum (ESI⁺): m/z=428 [M+H]⁺.

Intermediate 13

4-[(6-{3-Azabicyclo[3.1.0]hexan-3-yl}-2-methylpyridin-3-yl)methyl]-5-cyanothiophene-2-carboxylic acid

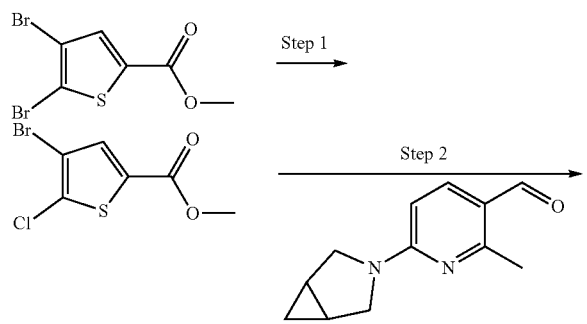

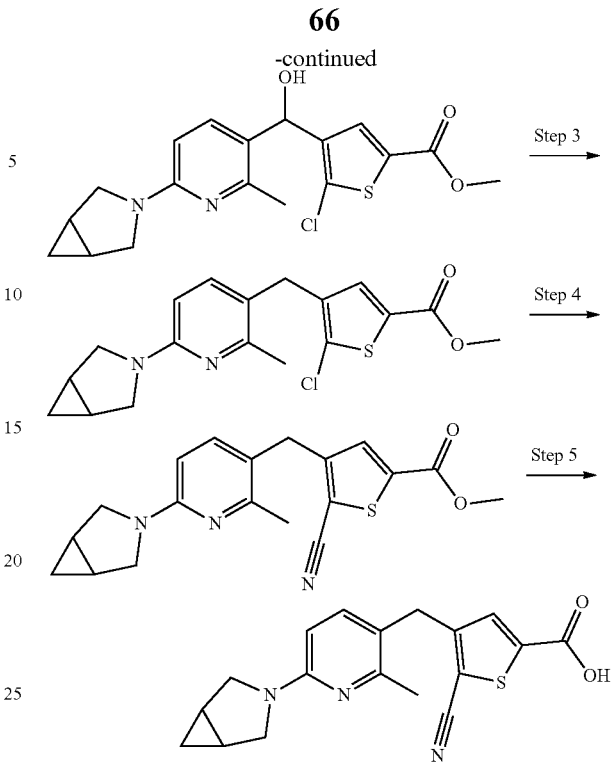

Step 1: Methyl 4-bromo-5-chlorothiophene-2-carboxylate

Methyl 4,4-dibromo-2-carboxylate (2 g) is dissolved in THF (25 mL) cooled to −25° C. and treated slowly with isopropylmagnesuim (iPrMgCl, 3.3 mL of a 2 M solution in THF). The mixture is stirred for 30 min, cooled to −60° C. and treated with N-chlorosuccinimide (0.89 g). Then the mixture is stirred for 30 min while warming to room temperature. The mixture is partitioned between 10% aqueous NH₄Cl and EtOAC. The phases are separated and the aqueous phase is extracted twice with EtOAC. The combined organic phases are dried (MgSO₄) and concentrated in vacuo. The residue is triturated with MeOH. The title compound is collected by filtration.

LC (Method 1): $t_R$=1.16 min.

Step 2: Methyl 4-[(6-{3-azabicyclo[3.1.0]hexan-3-yl}-2-methylpyridin-3-yl)(hydroxy)methyl]-5-chlorothiophene-2-carboxylate To a solution of methyl 4-bromo-5-chlorothiophene-2-carboxylate (900 mg) in THF (20 mL) is added dropwise at −20° C. isopropylmagnesuim chloride-lithium chloride complex (iPrMgClxLiCl, 2.7 mL of a 1.3 M solution in THF). The mixture is stirred for 30 min and is then treated dropwise with a solution of 6-{3-azabicyclo[3.1.0]hexan-3-yl}-2-methylpyridine-3-carbaldehyde (712 mg) in THF (20 mL). After stirring for 30 min at −20° C. and for 15 min at room temperature the reaction is quenched by addition of 1 M aqueous HCl. The aqueous phase is extracted with DCM. The organic phase is dried (MgSO₄) and concentrated in vacuo to give the title compound.

LC (Method 1): $t_R$=0.79 min; Mass spectrum (ESI⁺): m/z=379/381 (Cl) [M+H]⁺.

Step 3: Methyl 4-[(6-{3-azabicyclo[3.1.0]hexan-3-yl}-2-methylpyridin-3-yl)methyl]-5-chlorothiophene-2-carboxylate Methyl 4-[(6-{3-azabicyclo[3.1.0]hexan-3-yl}-2-methylpyridin-3-yl)(hydroxy)methyl]-5-chlorothiophene-2-carboxylate (1.17 g) is dissolved in DCM (20 mL) and cooled to 0° C. Triethylsilane (0.99 mL) and BF$_3$xOEt$_2$ (1.90 mL) are added and the mixture is stirred for 2 h at room temperature. Triethylsilane (1.98 mL) and BF$_3$xOEt$_2$ (3.80 mL) are added again and the mixture is stirred for 12 h at room temperature. The mixture is carefully partitioned between saturated aqueous NaHCO$_3$ and DCM. The phases are separated and the aqueous phase is extracted with DCM. The combined organic phases are dried (MgSO$_4$) and concentrated in vacuo. The residue is triturated with EtOAC and the title compound collected by filtration.

LC (Method 1): $t_R$=0.84 min; Mass spectrum (ESI$^+$): m/z=363/265 (Cl) [M+H]$^+$.

Step 4: Methyl 4-[(6-{3-azabicyclo[3.1.0]hexan-3-yl}-2-methylpyridin-3-yl)methyl]-5-cyanothiophene-2-carboxylate Under argon methyl 4-[(6-{3-azabicyclo[3.1.0]hexan-3-yl}-2-methylpyridin-3-yl)methyl]-5-chlorothiophene-2-carboxylate (150 mg), Zn(CN)$_2$ (27 mg), zinc (5.1 mg) and bis(tri-tert-butylphosphine)palladium(0) (11 mg) are dissolved dimethylacetamide (1 mL) and heated to 100° C. for 1 h. After cooling to room temperature the mixture is partitioned between water and EtOAC. The organic phase is dried (MgSO$_4$) and concentrated in vacuo. The residue is chromatographed on silica gel (petrole ether/EtOAC 80:20) to give the title compound.

LC (Method 1): $t_R$=0.80 min; Mass spectrum (ESI$^+$): m/z=354 [M+H]$^+$.

Step 5: 4-[(6-{3-Azabicyclo[3.1.0]hexan-3-yl}-2-methylpyridin-3-yl)methyl]-5-cyanothiophene-2-carboxylic acid A mixture of methyl 4-[(6-{3-azabicyclo[3.1.0]hexan-3-yl}-2-methylpyridin-3-yl)methyl]-5-cyanothiophene-2-carboxylate (58 mg), 4 M aqueous NaOH (100 µL), THF (1 mL) and MeOH (1 mL) is stirred for 30 min at room temperature. 4 M aqueous HCl (110 µL) is added, the mixture is stirred for 10 min and then evaporated in vacuo to give the crude product, which is directly used in the next step.

LC (Method 1): $t_R$=0.74 min; Mass spectrum (ESI$^+$): m/z=340 [M+H]$^+$.

Intermediate 14

2-[(6-{3-Azabicyclo[3.1.0]hexan-3-yl}-2-methylpyridin-3-yl)methyl]-2H-1,2,3,4-tetrazole-5-carboxylic acid

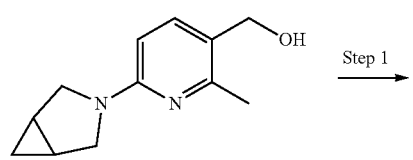

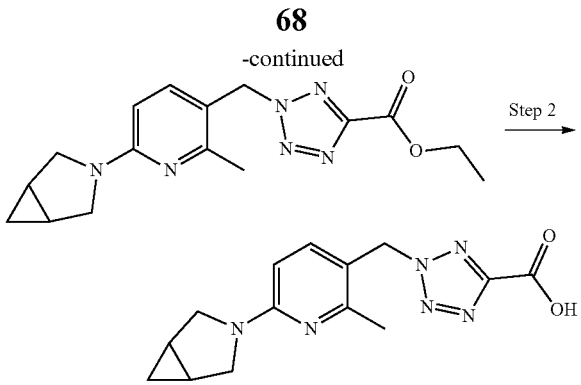

Step 1: Ethyl 2-[(6-{3-azabicyclo[3.1.0]hexan-3-yl}-2-methylpyridin-3-yl)methyl]-2H-1,2,3,4-tetrazole-5-carboxylate (6-{3-Azabicyclo[3.1.0]hexan-3-yl}-2-methylpyridin-3-yl)methanol (350 mg) is dissolved in THF (20 mL) and cooled to 0° C. Ethyl 1H-1,2,3,4-tetrazole-5-carboxylate (244 mg) and triphenyl phosphine (539 mg) are added. Di-isopropyl-azodicarboxylate (404 µL) is added dropwise and the mixture is stirred for 15 min and then warmed to room temperature. The mixture is partitioned between water and EtOAC. The organic phase is dried (MgSO$_4$) and concentrated in vacuo. The residue is chromatographed on silica gel (petrole ether/EtOAC 98:2→80:20) to give the title compound.

LC (Method 1): $t_R$=0.73 min; Mass spectrum (ESI$^+$): m/z=329 [M+H]$^+$.

Step 2: 2-[(6-{3-Azabicyclo[3.1.0]hexan-3-yl}-2-methylpyridin-3-yl)methyl]-2H-1,2,3,4-tetrazole-5-carboxylic acid A mixture of ethyl 2-[(6-{3-azabicyclo[3.1.0]hexan-3-yl}-2-methylpyridin-3-yl)methyl]-2H-1,2,3,4-tetrazole-5-carboxylate (60 mg), 4 M aqueous NaOH (200 µL) and THF (1 mL) and EtOH (1 mL) is stirred for 1 h at room temperature. 4 M aqueous HCl (210 µL) is added and the solvents are evaporated in vacuo. The residue is triturated with EtOH to give the title compound, which is directly used in the next step.

LC (Method 1): $t_R$=0.55 min; Mass spectrum (ESI$^+$): m/z=301 [M+H]$^+$.

Intermediate 15

2-[(6-{3-Azabicyclo[3.1.0]hexan-3-yl}-2-methylpyridin-3-yl)methyl]-2H-1,2,3-triazole-4-carboxylic acid

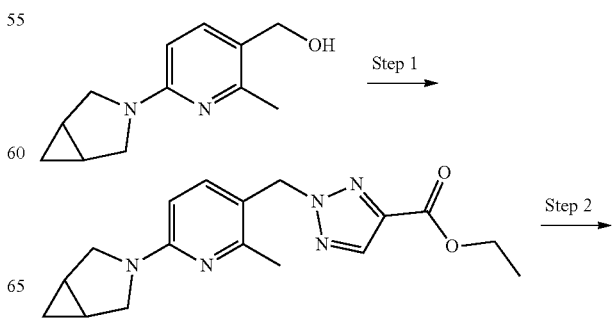

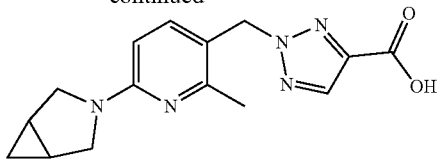

Step 1: Methyl 2-[(6-{3-azabicyclo[3.1.0]hexan-3-yl}-2-methylpyridin-3-yl)methyl]-2H-1,2,3-triazole-4-carboxylate (6-{3-Azabicyclo[3.1.0]hexan-3-yl}-2-methylpyridin-3-yl)methanol (250 mg) is dissolved in THF (20 mL) and cooled to 0° C. Methyl 1H-1,2,3-triazole-4-carboxylate (156 mg) and triphenyl phosphine (385 mg) are added. Di-isopropyl-azodicarboxylate (289 µL) is added dropwise and the mixture is stirred for 15 min and then warmed to room temperature. The mixture is partitioned between water and EtOAC. The organic phase is dried (MgSO$_4$) and concentrated in vacuo. The residue is chromatographed on silica gel (petrole ether/EtOAC 98:2→80:20) to give the title compound.

LC (Method 1): t$_R$=0.69 min; Mass spectrum (ESI$^+$): m/z=314 [M+H]$^+$.

Step 2: 2-[(6-{3-Azabicyclo[3.1.0]hexan-3-yl}-2-methylpyridin-3-yl)methyl]-2H-1,2,3-triazole-4-carboxylic acid A mixture of methyl 2-[(6-{3-azabicyclo[3.1.0]hexan-3-yl}-2-methylpyridin-3-yl)methyl]-2H-1,2,3-triazole-4-carboxylate (120 mg), 4 M aqueous NaOH (2 mL) and THF (3 mL) and MeOH (3 mL) is stirred for 1 h at room temperature. 4 M aqueous HCl (2.1 mL) is added and the solvents are evaporated in vacuo to give crude product, which is directly used in the next step.

LC (Method 1): t$_R$=0.63 min; Mass spectrum (ESI$^+$): m/z=300 [M+H]$^+$.

Intermediate 16

(6-{5-Azaspiro[2.3]hexan-5-yl}-2-methylpyridin-3-yl)methanol

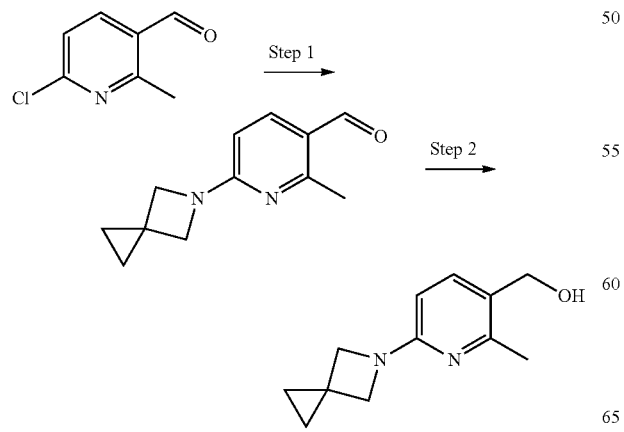

Step 1: 6-{5-Azaspiro[2.3]hexan-5-yl}-2-methylpyridine-3-carbaldehyde

6-Chloro-2-methylpyridine-3-carbaldehyde (0.5 g), 5-azaspiro[2.3]hexane trifluoroacetate (1.1 g) and KHCO$_3$ (1.6 g) are suspended in DMSO (70 mL) and heated to 80° C. for 16 h. The mixture is cooled, partitioned between water and EtOAC and the phases are separated. The organic phase is washed with brine. After drying (MgSO$_4$) the solvents are evaporated in vacuo. The residue is chromatographed on silica gel (petrole ether/EtOAC 99:1→50:50) to give the title compound.

LC (Method 1): t$_R$=0.59 min; Mass spectrum (ESI): m/z=203 [M+H]$^+$.

Step 2: (6-{5-Azaspiro[2.3]hexan-5-yl}-2-methylpyridin-3-yl)methanol

To a solution of 6-{5-azaspiro[2.3]hexan-5-yl}-2-methylpyridine-3-carbaldehyde (487 mg) in EtOH (6 mL) is added under ice-cooling NaBH$_4$ (110 mg). The mixture is stirred for 1 h at room temperature. The mixture is slowly treated with 2 M aqueous NaHCO$_3$ solution and extracted with EtOAC. The organic phase is washed with brine and dried (MgSO$_4$). The solvents are evaporated in vacuo to give the title compound.

LC (Method 1): t$_R$=0.62 min; Mass spectrum (ESI$^+$): m/z=205 [M+H]$^+$.

Intermediate 17

(2-{6,6-Difluoro-3-azabicyclo[3.1.0]hexan-3-yl}-4-methylpyrimidin-5-yl)methanol

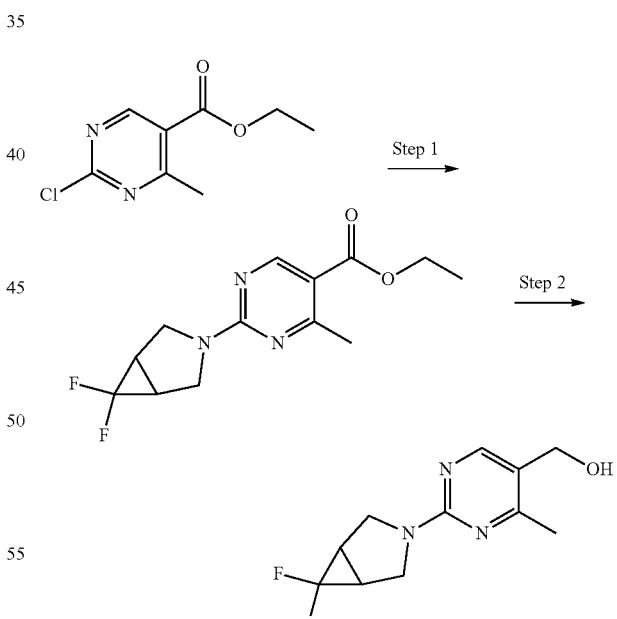

Step 1: Ethyl 2-{6,6-difluoro-3-azabicyclo[3.1.0]hexan-3-yl}-4-methylpyrimidine-5-carboxylate Ethyl-2-chloro-4-methylpyrimidine-5-carboxylate (5.0 g), 6,6-difluoro-3-azabicyclo[3.1.0]hexane hydrochloride (4.26 g) and K$_2$CO$_3$ (10.3 g) are suspended in DMF (50 mL) and heated to 90° C. for 1 h. The mixture is cooled, partitioned between water and EtOAC and the phases are separated. The organic phase is washed with brine. After drying (MgSO$_4$) the solvents are evaporated in vacuo to give the title compound.

LC (Method 1): t$_R$=1.065 min; Mass spectrum (ESI$^+$): m/z=284 [M+H]$^+$.

Step 2: (2-{6,6-Difluoro-3-azabicyclo[3.1.0]hexan-3-yl}-4-methylpyrimidin-5-yl)methanol To a solution ethyl 2-{6,6-difluoro-3-azabicyclo[3.1.0]hexan-3-yl}-4-methylpyrimidine-5-carboxylate (7.15 g) in THF (20 mL) is added LiBH$_4$ (16.62 mL; 2M solution in THF). The mixture is stirred for 20 min, MeOH (2.0 mL) is added and stirring continued for 16 h at room temperature. After cooling to 0° C. the mixture is slowly treated with water and stirred for 10 min. Then the mixture is extracted with EtOAC and the solvents are evaporated in vacuo to give the title compound.

LC (Method 1): t$_R$=0.64 min; Mass spectrum (ESI$^+$): m/z=242 [M+H]$^+$.

Intermediate 18

(2-{3-Azabicyclo[3.1.0]hexan-3-yl}-4-methylpyrimidin-5-yl)methanol

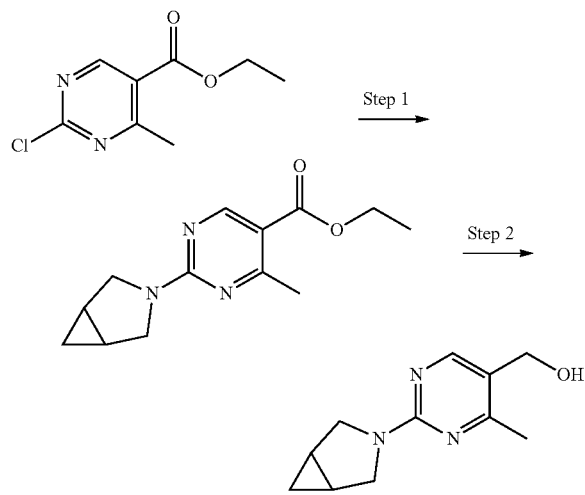

Step 1: Ethyl 2-{3-azabicyclo[3.1.0]hexan-3-yl}-4-methylpyrimidine-5-carboxylate Ethyl-2-chloro-4-methylpyrimidine-5-carboxylate (1.0 g), 3-azabicyclo[3.1.0]hexane hydrochloride (0.66 g) and K$_2$CO$_3$ (2.1 g) are suspended in DMF (15 mL) and heated to 100° C. for 1 h. The mixture is cooled, partitioned between water and EtOAC and the phases are separated. The organic phase is washed with brine. After drying (MgSO$_4$) the solvents are evaporated in vacuo to give the title compound.

LC (Method 1): t$_R$=1.04 min; Mass spectrum (ESI$^+$): m/z=248 [M+H]$^+$.

Step 2: (2-{3-Azabicyclo[3.1.0]hexan-3-yl}-4-methylpyrimidin-5-yl)methanol

A solution of ethyl 2-{3-azabicyclo[3.1.0]hexan-3-yl}-4-methylpyrimidine-5-carboxylate (1.2 g) in THF (10 mL) is cooled in an ice/acetone bath and diisobutylaluminiumhydride (10 mL; 1M solution in THF) is added. The mixture is stirred for 1 h under cooling. The mixture is slowly treated with water (0.75 mL) and 4 M aqueous NaOH (0.75 mL), stirred for 30 min and filtered through a pad of celite. After drying (MgSO$_4$) the mixture is concentrated in vacuo and the residue is chromatographed over silica gel (EtOAC/MeOH 100:0→50:50). The solvents are evaporated in vacuo to give the title compound.

LC (Method 1): t$_R$=0.58 min; Mass spectrum (ESI$^+$): m/z=206 [M+H]$^+$.

Intermediate 19

(2-{5-Azaspiro[2.3]hexan-5-yl}-4-methylpyrimidin-5-yl)methanol

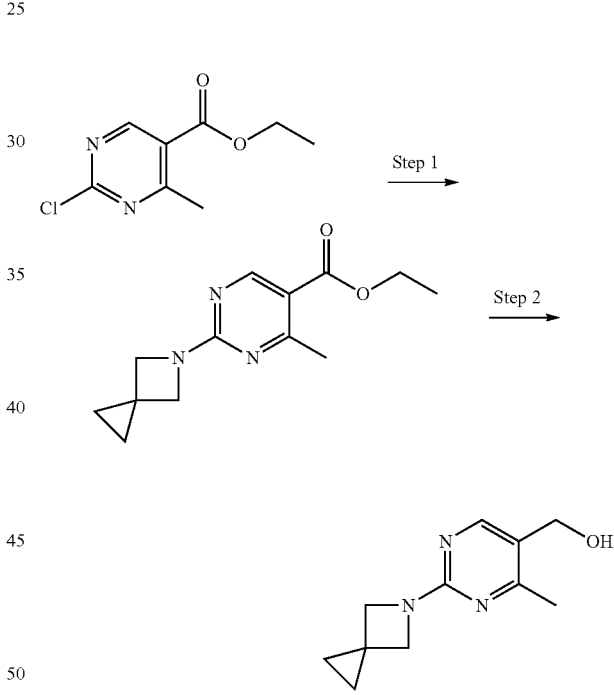

Intermediate 19 was prepared in analogy to Intermediate 18.

Starting materials Step 1: Ethyl-2-chloro-4-methyl pyrimidine-5-carboxylate (1 g), 5-azaspiro[2.3]hexane trifluoroacetate (1.1 g), K$_2$CO$_3$ (1.45 g) in DMF (10 mL).

LC (Method 1): tR=1.00 min; Mass spectrum (ESI+): m/z=248 [M+H]$^+$.

Starting materials Step 2: Ethyl 2-{5-azaspiro[2.3]hexan-5-yl}-4-methylpyrimidine-5-carboxylate (0.659 g), diisobutylaluminiumhydride (7 mL 1 M solution in THF) in 5 mL THF.

LC (Method 1): tR=0.60 min; Mass spectrum (ESI+): m/z=206 [M+H]$^+$.

Intermediate 20

Methyl 7-[(6-{6,6-difluoro-3-azabicyclo[3.1.0]hexan-3-yl}-2-methyl pyridin-3-yl)methyl]-7H-pyrrolo[2,3-d]pyrimidine-5-carboxylate

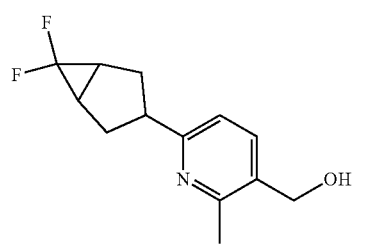

+

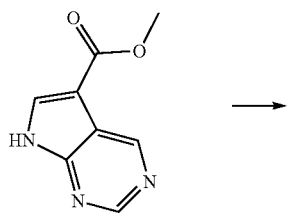

→

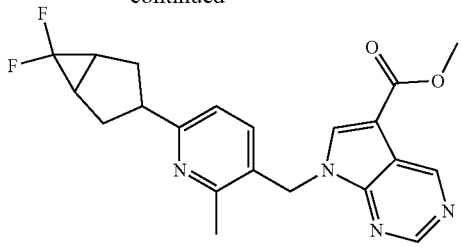

(6-{6,6-Difluoro-3-azabicyclo[3.1.0]hexan-3-yl}-2-methylpyridin-3-yl)methanol (150 mg) is dissolved in THF (8 mL) and cooled to −10° C. Methyl 7H-pyrrolo[2,3-d]pyrimidine-5-carboxylate (120 mg), tributyl phosphine (585 μL) are added. Di-tert.-butyl-azodicarboxylate (480 mg) is slowly added portionwise and the mixture is stirred at room temperature until completion of the reaction. Water is added and the mixture is extracted with EtOAC. The organic phase is washed with brine, dried (MgSO$_4$) and concentrated in vacuo. The residue is chromatographed on silica gel (petrole ether/EtOAC 80:20→0:100) to give the title compound.

LC (Method 1): $t_R$=0.67 min; Mass spectrum (ESI$^+$): m/z=400 [M+H]$^+$.

Intermediates 21-40 are prepared in analogy to Intermediate 20:

| Intermediate | Structure | $t_R$ | m/z [M+H]$^+$ | LC Method |
|---|---|---|---|---|
| 21 | 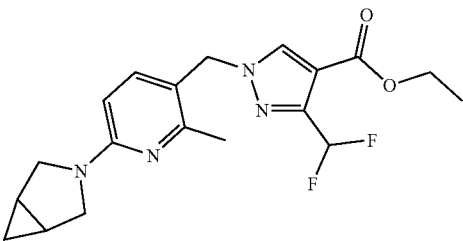 [SMILES: CCOC(=O)c1cn(Cc2ccc(N3CC4CC4C3)nc2C)nc1C(F)F] | 1.14 | 377 | Method 2 |
| 22 | 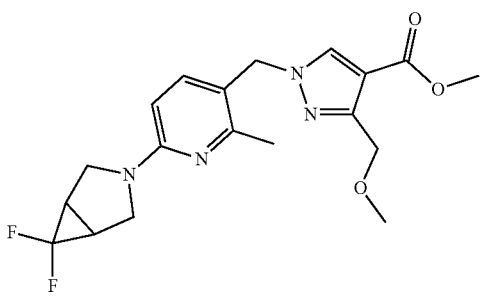 [SMILES: COCc1nn(Cc2ccc(N3CC4C(C3)C4(F)F)nc2C)cc1C(=O)OC] | 0.73 | 393 | Method 1 |
| 23 | 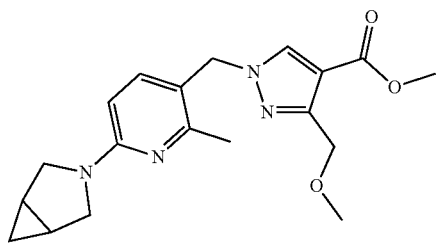 [SMILES: COCc1nn(Cc2ccc(N3CC4CC4C3)nc2C)cc1C(=O)OC] | 0.71 | 357 | Method 1 |

-continued

| Intermediate | Structure | $t_R$ | Mass spectrum (ESI+): m/z [M+H]$^+$ | LC Method |
|---|---|---|---|---|
| 24 | 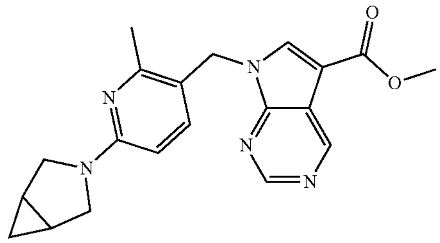 [SMILES: COC(=O)c1cn(Cc2ccc(N3CC4CC4C3)nc2C)c2ncncc12] | 0.65 | 364 | Method 1 |
| 25 | 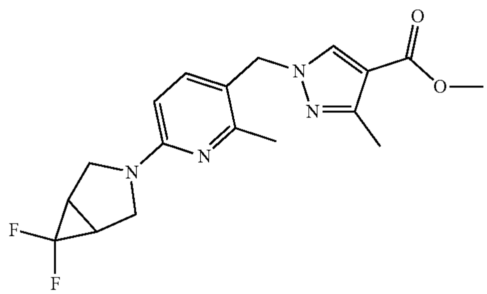 [SMILES: COC(=O)c1cn(Cc2ccc(N3CC4C(C3)C4(F)F)nc2C)nc1C] | 0.74 | 363 | Method 1 |
| 26 | 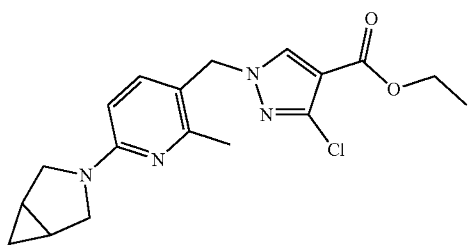 [SMILES: CCOC(=O)c1cn(Cc2ccc(N3CC4CC4C3)nc2C)nc1Cl] | 1.12 | 361 | Method 2 |
| 27 | 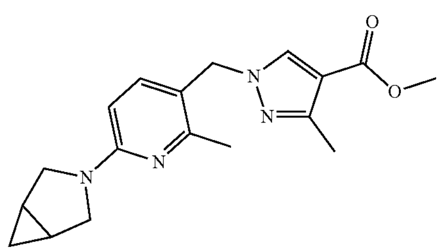 [SMILES: COC(=O)c1cn(Cc2ccc(N3CC4CC4C3)nc2C)nc1C] | 0.73 | 327 | Method 1 |
| 28 | 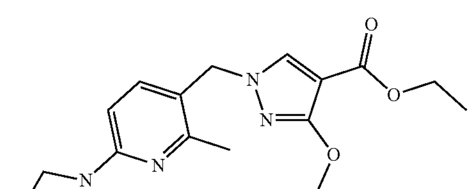 | 1.09 | 357 | Method 2 |
| 29 | 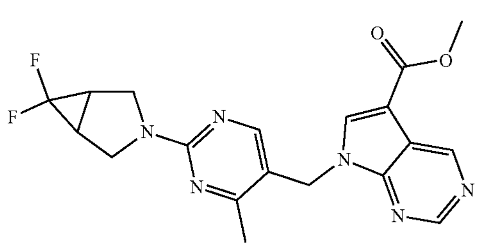 [SMILES: COC(=O)c1cn(Cc2cnc(N3CC4C(C3)C4(F)F)nc2C)c2ncncc12] | 0.84 | 401 | Method 1 |

-continued

| Intermediate | Structure | $t_R$ | Mass spectrum (ESI+): m/z [M+H]$^+$ | LC Method |
|---|---|---|---|---|
| 30 | 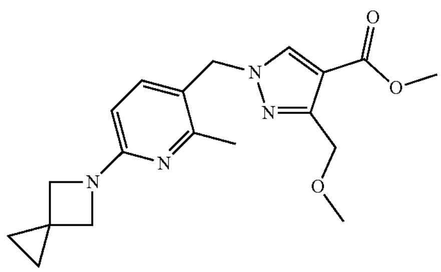 [SMILES: COCc1nn(Cc2ccc(N3CC4(CC4)C3)nc2C)cc1C(=O)OC] | 0.73 | 357 | Method 1 |
| 31 | 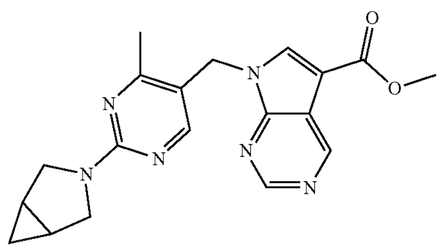 [SMILES: COC(=O)c1cn(Cc2cnc(N3CC4CC4C3)nc2C)c2ncncc12] | 0.77 | 365 | Method 1 |
| 32 | 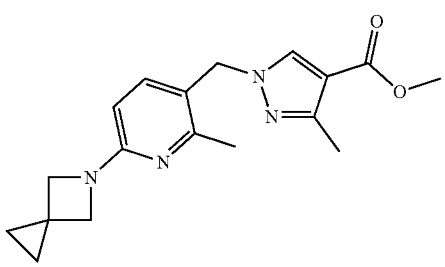 [SMILES: COC(=O)c1cn(Cc2ccc(N3CC4(CC4)C3)nc2C)nc1C] | 0.74 | 327 | Method 1 |
| 33 | 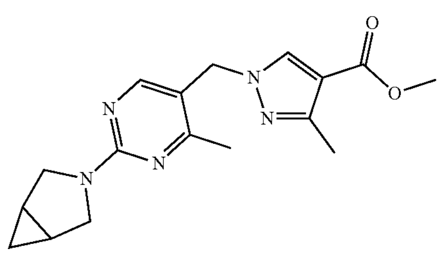 [SMILES: COC(=O)c1cn(Cc2cnc(N3CC4CC4C3)nc2C)nc1C] | 0.82 | 328 | Method 1 |
| 34 | 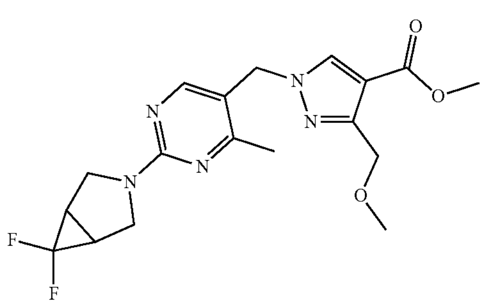 [SMILES: COCc1nn(Cc2cnc(N3CC4C(C3)C4(F)F)nc2C)cc1C(=O)OC] | 0.89 | 394 | Method 1 |

-continued

| Intermediate | Structure | $t_R$ | Mass spectrum (ESI+): m/z [M+H]+ | LC Method |
|---|---|---|---|---|
| 35 | 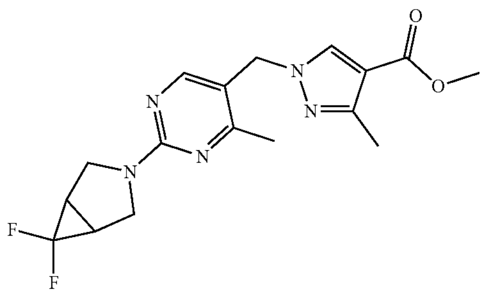 [SMILES: COC(=O)c1cn(Cc2cnc(N3CC4C(C3)C4(F)F)nc2C)nc1C] | 0.92 | 364 | Method 1 |
| 36 | 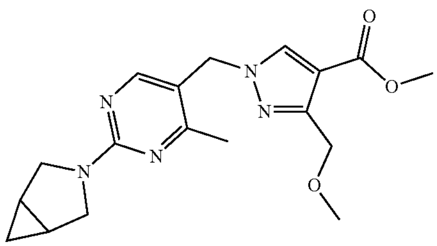 [SMILES: COCc1nn(Cc2cnc(N3CC4CC4C3)nc2C)cc1C(=O)OC] | 0.80 | 358 | Method 1 |
| 37 | 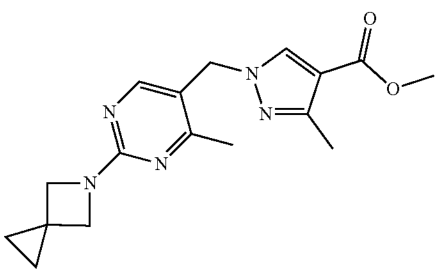 [SMILES: COC(=O)c1cn(Cc2cnc(N3CC4(CC4)C3)nc2C)nc1C] | 0.81 | 328 | Method 1 |
| 38 | 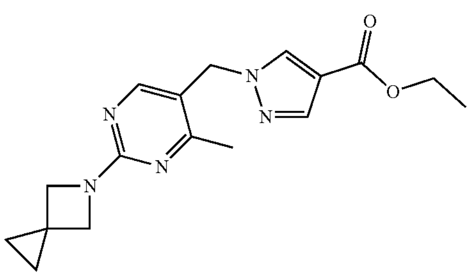 [SMILES: CCOC(=O)c1cnn(Cc2cnc(N3CC4(CC4)C3)nc2C)c1] | 0.95 | 328 | Method 2 |
| 39 | 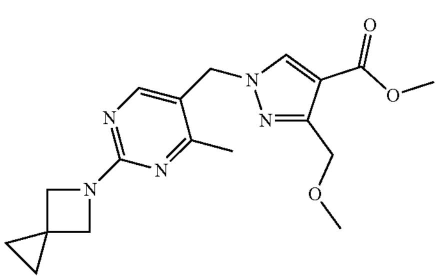 [SMILES: COCc1nn(Cc2cnc(N3CC4(CC4)C3)nc2C)cc1C(=O)OC] | 0.79 | 358 | Method 1 |

| Intermediate | Structure | $t_R$ | Mass spectrum (ESI+): m/z [M+H]$^+$ | LC Method |
| --- | --- | --- | --- | --- |
| 40 | 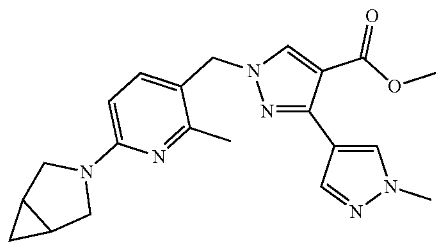 [SMILES: COC(=O)c1cn(Cc2ccc(N3CC4CC4C3)nc2C)nc1-c1cnn(C)c1] | 1.03 | 393 | Method 2 |

| Intermediate | Name | Name of Starting Material 1 | Name of Starting Material 2 |
| --- | --- | --- | --- |
| 21 | Ethyl 1-[(6-{3-azabicyclo[3.1.0]hexan-3-yl}-2-methylpyridin-3-yl)methyl]-3-(difluoromethyl)-1H-pyrazole-4-carboxylate | (6-{3-Azabicyclo[3.1.0]hexan-3-yl}-2-methylpyridin-3-yl)methanol | Ethyl 3-(difluoromethyl)-1H-pyrazole-4-carboxylate |
| 22 | Methyl 1-[(6-{6,6-difluoro-3-azabicyclo[3.1.0]hexan-3-yl}-2-methylpyridin-3-yl)methyl]-3-(methoxymethyl)-1H-pyrazole-4-carboxylate | (6-{6,6-Difluoro-3-azabicyclo[3.1.0]hexan-3-yl}-2-methylpyridin-3-yl)methanol | Methyl 3-(methoxymethyl)-1H-pyrazole-4-carboxylate |
| 23 | Methyl 1-[(6-{3-azabicyclo[3.1.0]hexan-3-yl}-2-methylpyridin-3-yl)methyl]-3-(methoxymethyl)-1H-pyrazole-4-carboxylate | (6-{3-Azabicyclo[3.1.0]hexan-3-yl}-2-methylpyridin-3-yl)methanol | Methyl 3-(methoxymethyl)-1H-pyrazole-4-carboxylate |
| 24 | Methyl 7-[(6-{3-azabicyclo[3.1.0]hexan-3-yl}-2-methylpyridin-3-yl)methyl]-7H-pyrrolo[2,3-d]pyrimidin-5-carboxylate | (6-{3-Azabicyclo[3.1.0]hexan-3-yl}-2-methylpyridin-3-yl)methanol | Methyl 7H-pyrrolo[2,3-d]pyrimidine-5-carboxylate |
| 25 | Methyl 1-[(6-{6,6-difluoro-3-azabicyclo[3.1.0]hexan-3-yl}-2-methylpyridin-3-yl)methyl]-3-methyl-1H-pyrazole-4-carboxylate | (6-{6,6-Difluoro-3-azabicyclo[3.1.0]hexan-3-yl}-2-methylpyridin-3-yl)methanol | Methyl 3-methyl-1H-pyrazole-4-carboxylate |
| 26 | Ethyl 1-[(6-{3-azabicyclo[3.1.0]hexan-3-yl}-2-methylpyridin-3-yl)methyl]-3-chloro-1H-pyrazole-4-carboxylate | (6-{3-Azabicyclo[3.1.0]hexan-3-yl}-2-methylpyridin-3-yl)methanol | Ethyl 3-chloro-1H-pyrazole-4-carboxylate |
| 27 | Methyl 1-[(6-{3-azabicyclo[3.1.0]hexan-3-yl}-2-methylpyridin-3-yl)methyl]-3-methyl-1H-pyrazole-4-carboxylate | (6-{3-Azabicyclo[3.1.0]hexan-3-yl}-2-methylpyridin-3-yl)methanol | Methyl 3-methyl-1H-pyrazole-4-carboxylate |
| 28 | Ethyl 1-[(6-{3-azabicyclo[3.1.0]hexan-3-yl}-2-methylpyridin-3-yl)methyl]-3-methoxy-1H-pyrazole-4-carboxylate | (6-{3-Azabicyclo[3.1.0]hexan-3-yl}-2-methylpyridin-3-yl)methanol | Ethyl 3-methoxy-1H-pyrazole-4-carboxylate |
| 29 | Methyl 7-[(2-{6,6-difluoro-3-azabicyclo[3.1.0]hexan-3-yl}-4-methylpyrimidin-5-yl)methyl]-7H-pyrrolo[2,3-d]pyrimidine-5-carboxylate | (2-{6,6-Difluoro-3-azabicyclo[3.1.0]hexan-3-yl}-4-methylpyrimidin-5-yl)methanol | Methyl 7H-pyrrolo[2,3-d]pyrimidine-5-carboxylate |
| 30 | Methyl 1-[(6-{5-azaspiro[2.3]hexan-5-yl}-2-methylpyridin-3-yl)methyl]-3-(methoxymethyl)-1H-pyrazole-4-carboxylate | (6-{5-Azaspiro[2.3]hexan-5-yl}-2-methylpyridin-3-yl)methanol | Methyl 3-(methoxymethyl)-1H-pyrazole-4-carboxylate |
| 31 | Methyl 7-[(2-{3-azabicyclo[3.1.0]hexan-3-yl}-4-methylpyrimidin-5-yl)methyl]-7H-pyrrolo[2,3-d]pyrimidine-5-carboxylate | (2-{3-Azabicyclo[3.1.0]hexan-3-yl}-4-methylpyrimidin-5-yl)methanol | Methyl 7H-pyrrolo[2,3-d]pyrimidine-5-carboxylate |
| 32 | Methyl 1-[(6-{5-azaspiro[2.3]hexan-5-yl}-2-methylpyridin-3-yl)methyl]-3-methyl-1H-pyrazole-4-carboxylate | (6-{5-Azaspiro[2.3]hexan-5-yl}-2-methylpyridin-3-yl)methanol | Methyl 3-methyl-1H-pyrazole-4-carboxylate |
| 33 | Methyl 1-[(2-{3-azabicyclo[3.1.0]hexan-3-yl}-4-methylpyrimidin-5-yl)methyl]-3-methyl-1H-pyrazole-4-carboxylate | (2-{3-Azabicyclo[3.1.0]hexan-3-yl}-4-methylpyrimidin-5-yl)methanol | Methyl 3-methyl-1H-pyrazole-4-carboxylate |
| 34 | Methyl 1-[(2-{6,6-difluoro-3-azabicyclo[3.1.0]hexan-3-yl}-4-methylpyrimidin-5-yl)methyl]-3-(methoxymethyl)-1H-pyrazole-4-carboxylate | (2-{6,6-Difluoro-3-azabicyclo[3.1.0]hexan-3-yl}-4-methylpyrimidin-5-yl)methanol | Methyl 3-(methoxymethyl)-1H-pyrazole-4-carboxylate |
| 35 | Methyl 1-[(2-{6,6-difluoro-3-azabicyclo[3.1.0]hexan-3-yl}-4-methylpyrimidin-5-yl)methyl]-3-methyl-1H-pyrazole-4-carboxylate | (2-{6,6-Difluoro-3-azabicyclo[3.1.0]hexan-3-yl}-4-methylpyrimidin-5-yl)methanol | Methyl 3-methyl-1H-pyrazole-4-carboxylate |

| Intermediate | Name | Name of Starting Material 1 | Name of Starting Material 2 |
|---|---|---|---|
| 36 | Methyl 1-[(2-{3-azabicyclo[3.1.0]-hexan-3-yl}-4-methylpyrimidin-5-yl)methyl]-3-methyl-1H-pyrazole-4-carboxylate | (2-{3-Azabicyclo[3.1.0]-hexan-3-yl}-4-methylpyrimidin-5-yl)methanol | Methyl 3-(methoxymethyl)-1H-pyrazole-4-carboxylate |
| 37 | Methyl 1-[(2-{5-azaspiro[2.3]hexan-5-yl}-4-methylpyrimidin-5-yl)methyl]-3-methyl-1H-pyrazole-4-carboxylate | (2-{5-Azaspiro[2.3]hexan-5-yl}-4-methylpyrimidin-5-yl)methanol | Methyl 3-methyl-1H-pyrazole-4-carboxylate |
| 38 | Ethyl 1-[(2-{5-azaspiro[2.3]hexan-5-yl}-4-methylpyrimidin-5-yl)methyl]-1H-pyrazole-4-carboxylate | (2-{5-Azaspiro[2.3]hexan-5-yl}-4-methylpyrimidin-5-yl)methanol | Ethyl 1H-pyrazole-4-carboxylate |
| 39 | Methyl 1-[(2-{5-azaspiro[2.3]hexan-5-yl}-4-methylpyrimidin-5-yl)methyl]-3-(methoxymethyl)-1H-pyrazole-4-carboxylate | (2-{5-Azaspiro[2.3]hexan-5-yl}-4-methylpyrimidin-5-yl)methanol | Methyl 3-(methoxymethyl)-1H-pyrazole-4-carboxylate |
| 40 | Methyl 1-[(6-{3-azabicyclo[3.1.0]-hexan-3-yl}-2-methylpyridin-3-yl)methyl]-3-(1-methyl-1H-pyrazol-4-yl)-1H-pyrazole-4-carboxylate | (6-{3-Azabicyclo[3.1.0]-hexan-3-yl}-2-methylpyridin-3-yl)methanol | Methyl 3-(1-methyl-1H-pyrazol-4-yl)-1H-pyrazole-4-carboxylate |

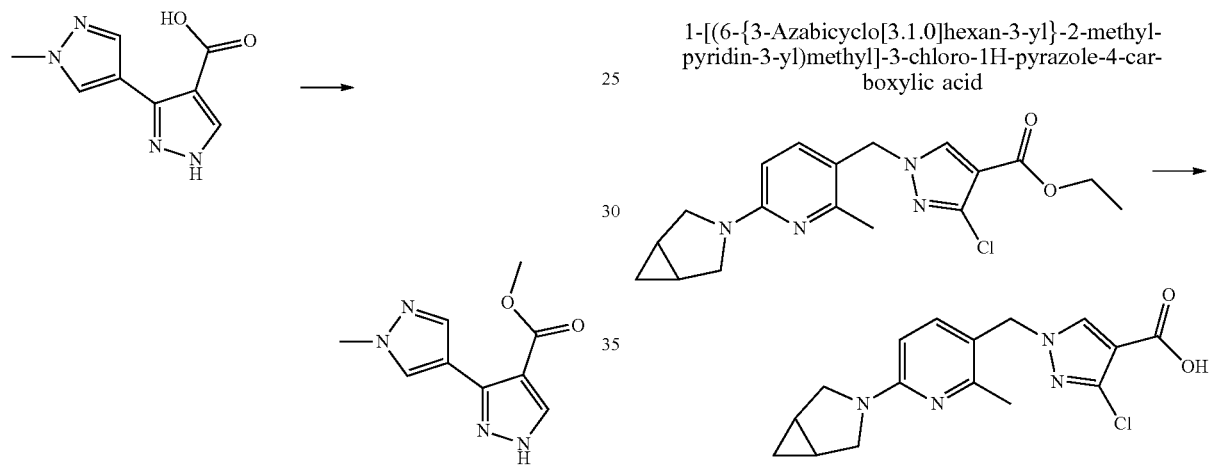

3-(1-Methyl-1H-pyrazol-4-yl)-1H-pyrazole-4-carboxylic acid (1 g) is dissolved in MeOH (50 mL). Thionylchloride (3 mL) is added, the mixture is stirred for 16 h at 50° C. and then concentrated in vacuo. The residue is dissolved in MeOH, filtered through a PL-HCO$_3$ MP SPE cartridge, washed with MeOH and concentrated in vacuo to give the title compound.

LC (Method 1): t$_R$=0.73 min; Mass spectrum (ESI$^+$): m/z=207 [M+H]$^+$.

Intermediate 41

1-[(6-{3-Azabicyclo[3.1.0]hexan-3-yl}-2-methyl-pyridin-3-yl)methyl]-3-chloro-1H-pyrazole-4-carboxylic acid A mixture ethyl 1-[(6-{3-azabicyclo[3.1.0]hexan-3-yl}-2-methylpyridin-3-yl)methyl]-3-chloro-1H-pyrazole-4-carboxylate (124 mg), 1 M NaOH in water (2 mL), EtOH (2 mL) and 1,4-dioxane (5 mL) is stirred at 50° C. for ~2 h. After cooling to room temperature 4 M aqueous HCl (0.5 mL) is added and the solvents are evaporated in vacuo to give the title compound (containing NaCl).

LC (Method 1): t$_R$=0.71 min; Mass spectrum (ESI$^+$): m/z=333/335 (Cl) [M+H]$^+$.

Intermediates 42-61 are prepared in analogy to Intermediate 41:

| Intermediate | Structure | t$_R$ | Mass spectrum (ESI+): m/z [M+H]$^+$ | LC Method |
|---|---|---|---|---|
| 42 | 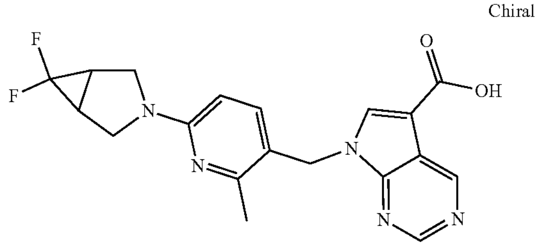 [SMILES: Cc1nc(N2CC3C(C2)C3(F)F)ccc1Cn1cc(C(=O)O)c2cncnc21] | Chiral 0.28 | 386 | Method 4 |

-continued

| Intermediate | Structure | $t_R$ | Mass spectrum (ESI+): m/z [M+H]+ | LC Method |
|---|---|---|---|---|
| 43 | 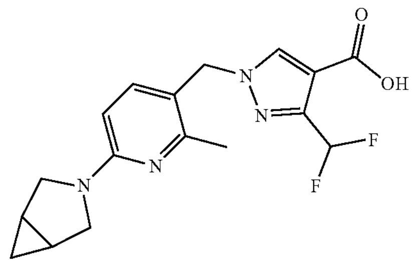 [SMILES: Cc1nc(N2CC3CC3C2)ccc1Cn1cc(C(=O)O)c(C(F)F)n1] | 0.72 | 349 | Method 1 |
| 44 | 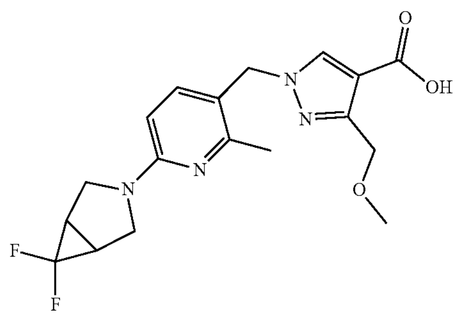 [SMILES: COCc1nn(Cc2ccc(N3CC4C(C3)C4(F)F)nc2C)cc1C(=O)O] | 0.31 | 379 | Method 4 |
| 45 | 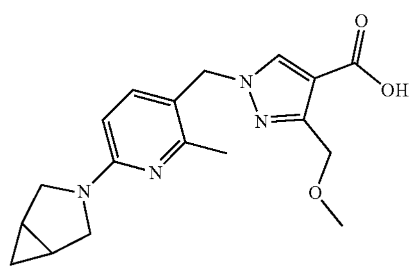 [SMILES: COCc1nn(Cc2ccc(N3CC4CC4C3)nc2C)cc1C(=O)O] | 0.67 | 343 | Method 1 |
| 46 | 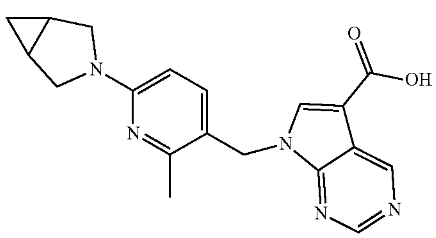 [SMILES: Cc1nc(N2CC3CC3C2)ccc1Cn1cc(C(=O)O)c2cncnc21] | 0.63 | 350 | Method 1 |
| 47 | 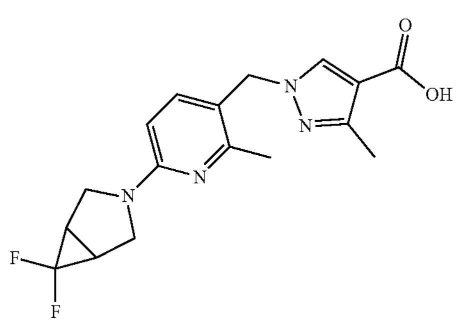 [SMILES: Cc1nc(N2CC3C(C2)C3(F)F)ccc1Cn1cc(C(=O)O)c(C)n1] | 0.32 | 349 | Method 4 |

-continued

| Intermediate | Structure | $t_R$ | Mass spectrum (ESI+): m/z [M+H]+ | LC Method |
|---|---|---|---|---|
| 48 | 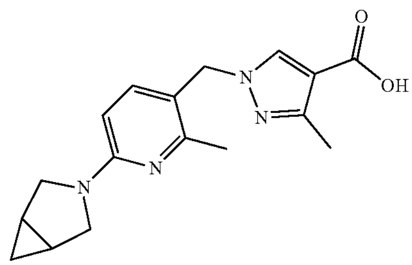 | 0.68 | 313 | Method 1 |
| 49 | 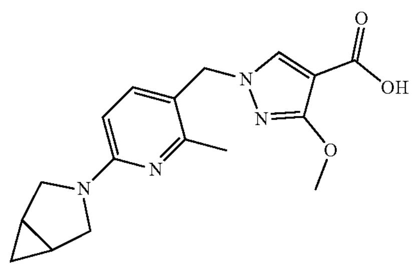 [SMILES: COc1nn(Cc2ccc(N3CC4CC4C3)nc2C)cc1C(=O)O] | 0.67 | 329 | Method 1 |
| 50 | 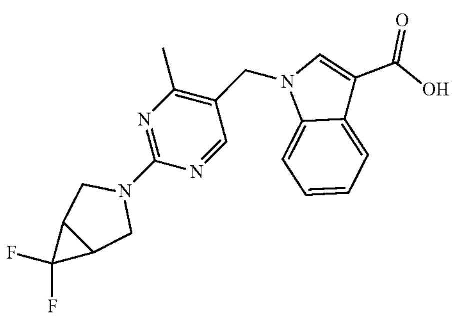 [SMILES: Cc1nc(N2CC3C(C2)C3(F)F)ncc1Cn1cc(C(=O)O)c2ccccc21] | 0.77 | 387 | Method 1 |
| 51 | 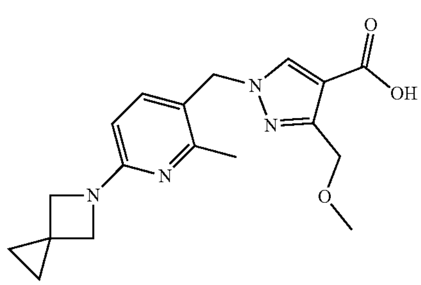 | 0.32 | 343 | Method 4 |
| 52 | 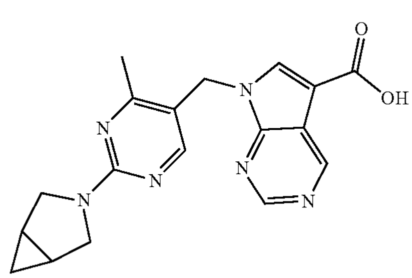 [SMILES: Cc1nc(N2CC3CC3C2)ncc1Cn1cc(C(=O)O)c2cncnc21] | 0.35 | 351 | Method 4 |

-continued

| Intermediate | Structure | $t_R$ | Mass spectrum (ESI+): m/z [M+H]+ | LC Method |
|---|---|---|---|---|
| 53 | 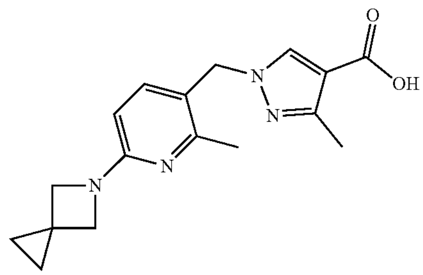 [SMILES: Cc1nc(N2CC3(CC3)C2)ccc1Cn1cc(C(=O)O)c(C)n1] | 0.33 | 313 | Method 4 |
| 54 | 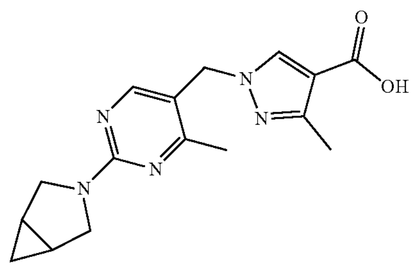 [SMILES: Cc1nc(N2CC3CC3C2)ncc1Cn1cc(C(=O)O)c(C)n1] | 0.39 | 314 | Method 4 |
| 55 | 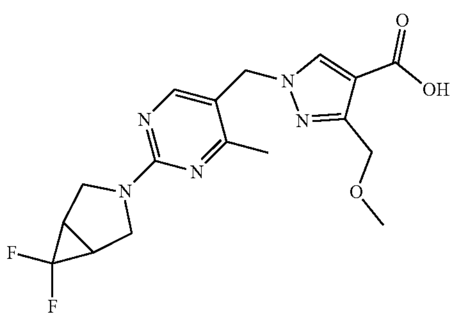 [SMILES: COCc1nn(Cc2cnc(N3CC4C(C3)C4(F)F)nc2C)cc1C(=O)O] | 0.47 | 380 | Method 4 |
| 56 | 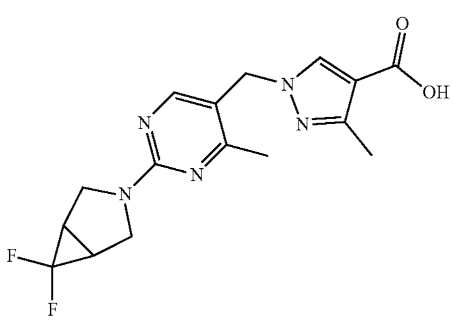 [SMILES: Cc1nc(N2CC3C(C2)C3(F)F)ncc1Cn1cc(C(=O)O)c(C)n1] | 0.48 | 350 | Method 4 |
| 57 | 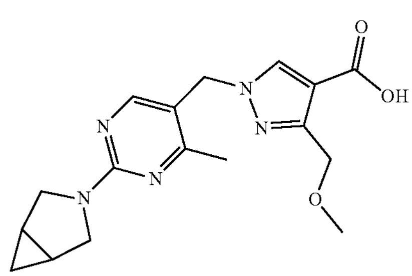 [SMILES: COCc1nn(Cc2cnc(N3CC4CC4C3)nc2C)cc1C(=O)O] | 0.74 | 344 | Method 1 |

-continued

| Intermediate | Structure | $t_R$ | Mass spectrum (ESI+): m/z [M+H]+ | LC Method |
|---|---|---|---|---|
| 58 | 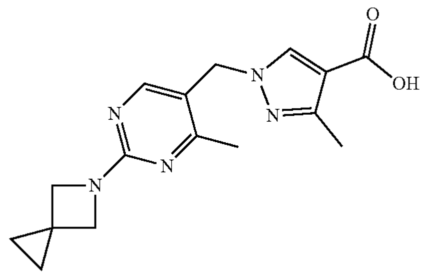 [SMILES: Cc1nc(N2CC3(CC3)C2)ncc1Cn1cc(C(=O)O)c(C)n1] | 0.39 | 314 | Method 4 |
| 59 | 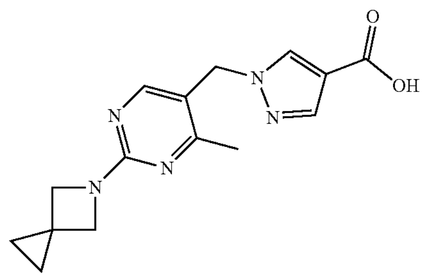 [SMILES: Cc1nc(N2CC3(CC3)C2)ncc1Cn1cc(C(=O)O)cn1] | 0.56 | 328 | Method 2 |
| 60 | 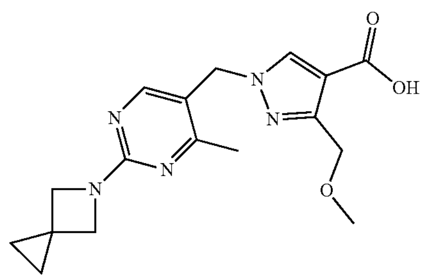 [SMILES: COCc1nn(Cc2cnc(N3CC4(CC4)C3)nc2C)cc1C(=O)O] | 0.38 | 344 | Method 4 |
| 61 | 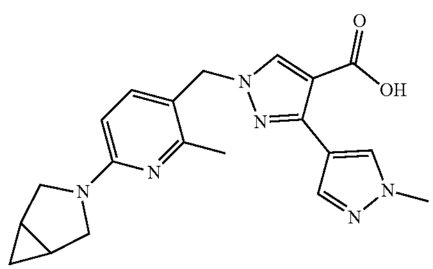 [SMILES: Cc1nc(N2CC3CC3C2)ccc1Cn1cc(C(=O)O)c(-c2cnn(C)c2)n1] | 0.70 | 379 | Method 1 |

| Intermediate | Name | Name of Starting Material |
|---|---|---|
| 42 | 7-[(6-{6,6-Difluoro-3-azabicyclo[3.1.0]hexan-3-yl}-2-methylpyridin-3-yl)methyl]-7H-pyrrolo[2,3-d]pyrimidine-5-carboxylic acid | Methyl 7-[(6-{6,6-difluoro-3-azabicyclo[3.1.0]hexan-3-yl}-2-methylpyridin-3-yl)methyl]-7H-pyrrolo[2,3-d]pyrimidine-5-carboxylate |
| 43 | 1-[(6-{3-Azabicyclo[3.1.0]hexan-3-yl}-2-methylpyridin-3-yl)methyl]-3-(difluoromethyl)-1H-pyrazole-4-carboxylic acid | Ethyl 1-[(6-{3-azabicyclo[3.1.0]hexan-3-yl}-2-methylpyridin-3-yl)methyl]-3-(difluoromethyl)-1H-pyrazole-4-carboxylate |
| 44 | 1-[(6-{6,6-Difluoro-3-azabicyclo[3.1.0]hexan-3-yl}-2-methylpyridin-3-yl)methyl]-3-(methoxymethyl)-1H-pyrazole-4-carboxylic acid | Methyl 1-[(6-{6,6-difluoro-3-azabicyclo[3.1.0]hexan-3-yl}-2-methylpyridin-3-yl)methyl]-3-(methoxymethyl)-1H-pyrazole-4-carboxylate |
| 45 | 1-[(6-{3-Azabicyclo[3.1.0]hexan-3-yl}-2-methylpyridin-3-yl)methyl]-3-(methoxymethyl)-1H-pyrazole-4-carboxylic acid | Methyl 1-[(6-{3-azabicyclo[3.1.0]hexan-3-yl}-2-methylpyridin-3-yl)methyl]-3-(methoxymethyl)-1H-pyrazole-4-carboxylate |

-continued

| Intermediate | Name | Name of Starting Material |
|---|---|---|
| 46 | 7-[(6-{3-Azabicyclo[3.1.0]hexan-3-yl}-2-methylpyridin-3-yl)methyl]-7H-pyrrolo[2,3-d]pyrimidine-5-carboxylic acid | Methyl 7-[(6-{3-azabicyclo[3.1.0]hexan-3-yl}-2-methylpyridin-3-yl)methyl]-7H-pyrrolo[2,3-d]pyrimidine-5-carboxylate |
| 47 | 1-[(6-{6,6-Difluoro-3-azabicyclo[3.1.0]hexan-3-yl}-2-methylpyridin-3-yl)methyl]-3-methyl-1H-pyrazole-4-carboxylic acid | Methyl 1-[(6-{6,6-difluoro-3-azabicyclo[3.1.0]hexan-3-yl}-2-methylpyridin-3-yl)methyl]-3-methyl-1H-pyrazole-4-carboxylate |
| 48 | 1-[(6-{3-Azabicyclo[3.1.0]hexan-3-yl}-2-methylpyridin-3-yl)methyl]-3-methyl-1H-pyrazole-4-carboxylic acid | Methyl 1-[(6-{3-azabicyclo[3.1.0]hexan-3-yl}-2-methylpyridin-3-yl)methyl]-3-methyl-1H-pyrazole-4-carboxylate |
| 49 | 1-[(6-{3-Azabicyclo[3.1.0]hexan-3-yl}-2-methylpyridin-3-yl)methyl]-3-methoxy-1H-pyrazole-4-carboxylic acid | Ethyl 1-[(6-{3-azabicyclo[3.1.0]hexan-3-yl}-2-methylpyridin-3-yl)methyl]-3-methoxy-1H-pyrazole-4-carboxylate |
| 50 | 7-[(2-{6,6-Difluoro-3-azabicyclo[3.1.0]hexan-3-yl}-4-methylpyrimidin-5-yl)methyl]-7H-pyrrolo[2,3-d]pyrimidine-5-carboxylic acid | Methyl 7-[(2-{6,6-difluoro-3-azabicyclo[3.1.0]hexan-3-yl}-4-methylpyrimidin-5-yl)methyl]-7H-pyrrolo[2,3-d]pyrimidine-5-carboxylate |
| 51 | 1-[(6-{5-Azaspiro[2.3]hexan-5-yl}-2-methylpyridin-3-yl)methyl]-3-(methoxymethyl)-1H-pyrazole-4-carboxylic acid | Methyl 1-[(6-{5-azaspiro[2.3]hexan-5-yl}-2-methylpyridin-3-yl)methyl]-3-(methoxymethyl)-1H-pyrazole-4-carboxylate |
| 52 | 7-[(2-{3-Azabicyclo[3.1.0]hexan-3-yl}-4-methylpyrimidin-5-yl)methyl]-7H-pyrrolo[2,3-d]pyrimidine-5-carboxylic acid | Methyl 7-[(2-{3-azabicyclo[3.1.0]hexan-3-yl}-4-methylpyrimidin-5-yl)methyl]-7H-pyrrolo[2,3-d]pyrimidine-5-carboxylate |
| 53 | 1-[(6-{5-Azaspiro[2.3]hexan-5-yl}-2-methylpyridin-3-yl)methyl]-3-methyl-1H-pyrazole-4-carboxylic acid | Methyl 1-[(6-{5-azaspiro[2.3]hexan-5-yl}-2-methylpyridin-3-yl)methyl]-3-methyl-1H-pyrazole-4-carboxylate |
| 54 | 1-[(2-{3-Azabicyclo[3.1.0]hexan-3-yl}-4-methylpyrimidin-5-yl)methyl]-3-methyl-1H-pyrazole-4-carboxylic acid | Methyl 1-[(2-{3-azabicyclo[3.1.0]hexan-3-yl}-4-methylpyrimidin-5-yl)methyl]-3-methyl-1H-pyrazole-4-carboxylate |
| 55 | 1-[(2-{6,6-Difluoro-3-azabicyclo[3.1.0]hexan-3-yl}-4-methylpyrimidin-5-yl)methyl]methyl]-3-(methoxymethyl)-1H-pyrazole-4-carboxylic acid | Methyl 1-[(2-{6,6-difluoro-3-azabicyclo[3.1.0]hexan-3-yl}-4-methylpyrimidin-5-yl)methyl]-3-(methoxymethyl)-1H-pyrazole-4-carboxylate |
| 56 | 1-[(2-{6,6-Difluoro-3-azabicyclo[3.1.0]hexan-3-yl}-4-methylpyrimidin-5-yl)methyl]-3-methyl-1H-pyrazole-4-carboxylic acid | Methyl 1-[(2-{6,6-difluoro-3-azabicyclo[3.1.0]hexan-3-yl}-4-methylpyrimidin-5-yl)methyl]-3-methyl-1H-pyrazole-4-carboxylate |
| 57 | 1-[(2-{3-Azabicyclo[3.1.0]hexan-3-yl}-4-methylpyrimidin-5-yl)methyl]-3-(methoxymethyl)-1H-pyrazole-4-carboxylic acid | Methyl 1-[(2-{3-azabicyclo[3.1.0]hexan-3-yl}-4-methylpyrimidin-5-yl)methyl]-3-(methoxymethyl)-1H-pyrazole-4-carboxylate |
| 58 | 1-[(2-{5-Azaspiro[2.3]hexan-5-yl}-4-methylpyrimidin-5-yl)methyl]-3-methyl-1H-pyrazole-4-carboxylic acid | Methyl 1-[(2-{5-azaspiro[2.3]hexan-5-yl}-4-methylpyrimidin-5-yl)methyl]-3-methyl-1H-pyrazole-4-carboxylate |
| 59 | 1-[(2-{5-Azaspiro[2.3]hexan-5-yl}-4-methylpyrimidin-5-yl)methyl]-1H-pyrazole-4-carboxylic acid | Ethyl 1-[(2-{5-azaspiro[2.3]hexan-5-yl}-4-methylpyrimidin-5-yl)methyl]-1H-pyrazole-4-carboxylate |
| 60 | 1-[(2-{5-Azaspiro[2.3]hexan-5-yl}-4-methylpyrimidin-5-yl)methyl]-3-(methoxymethyl)-1H-pyrazole-4-carboxylic acid | Methyl 1-[(2-{5-azaspiro[2.3]hexan-5-yl}-4-methylpyrimidin-5-yl)methyl]-3-(methoxymethyl)-1H-pyrazole-4-carboxylate |
| 61 | 1-[(6-{3-Azabicyclo[3.1.0]hexan-3-yl}-2-methylpyridin-3-yl)methyl]-3-(1-methyl-1H-pyrazol-4-yl)-1H-pyrazole-4-carboxylic acid | Methyl 1-[(6-{3-azabicyclo[3.1.0]hexan-3-yl}-2-methylpyridin-3-yl)methyl]-3-(1-methyl-1H-pyrazol-4-yl)-1H-pyrazole-4-carboxylate |

1-[(6-{5-Azaspiro[2.3]hexan-5-yl}-2-methylpyridin-3-yl)methyl]-1H-pyrazole-4-carboxylic acid

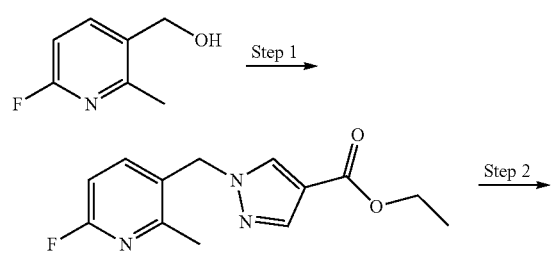

-continued

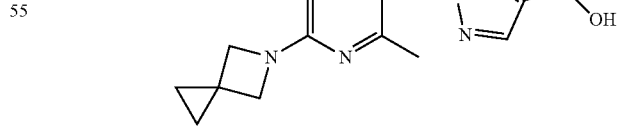

Step 1: Ethyl 1-[(6-fluoro-2-methylpyridin-3-yl)methyl]-1H-pyrazole-4-carboxylate (6-Fluoro-2-methylpyridin-3-yl)methanol (4.12 g) is dissolved in THF (50 mL) and cooled to −10° C. Ethyl 1H-pyrazole-4-carboxylate (4.43 g) and tributyl phosphine (9 mL) are added. Di-tert.-butyl-azodicarboxylate (7.4 g) is slowly added portionwise, the mixture is stirred at room temperature for 45 min and concentrated in vacuo. The residue is chromatographed on silica gel (cyclohexane/ EtOAC) to give the title compound.

LC (Method 2): $t_R$=0.88 min; Mass spectrum (ESI$^+$): m/z=264 [M+H]$^+$.

Step 2: 1-[(6-{5-Azaspiro[2.3]hexan-5-yl}-2-methylpyridin-3-yl)methyl]-1H-pyrazole-4-carboxylic acid Ethyl 1-[(6-fluoro-2-methylpyridin-3-yl)methyl]-1H-pyrazole-4-carboxylate (0.5 g) is dissolved in DMSO (2 mL). 5-Azaspiro[2.3]hexane trifluoroacetate (1.2 g) and DIPEA (2 mL) are added and the mixture is stirred for 16 h at 100° C. and additional 5 h at 120° C. After cooling to room temperature, the N,N-diisopropyl-ethylamine phase is removed, 4 M NaOH (4 mL) is added and stirred at 60° C. for 2 h. 4 M aqueous HCl (4 mL) is added and the mixture is purified by HPLC on reversed phase (ACN, water) to give the title compound.

LC (Method 1): $t_R$=0.68 min; Mass spectrum (ESI$^+$): m/z=299 [M+H]$^+$.

Intermediate 63

7-[(2-{5-Azaspiro[2.3]hexan-5-yl}-4-methylpyrimidin-5-yl)methyl]-7H-pyrrolo[2,3-d]pyrimidine-5-carboxylic acid

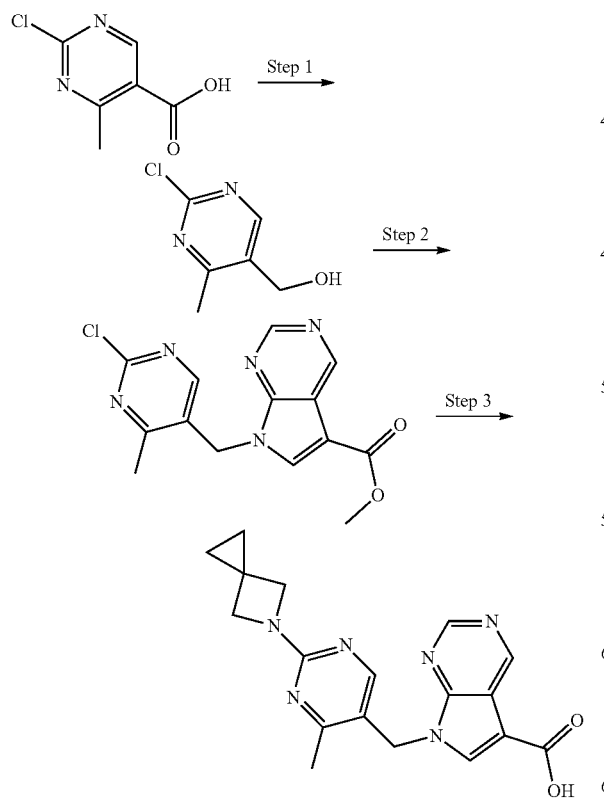

Step 1: (2-Chloro-4-methylpyrimidin-5-yl)methanol

2-Chloro-4-methylpyrimidine-5-carboxylic acid (7 g) is dissolved in dimethoxyethane (200 mL) and N-methylmorpholine (4.2 mL) is added. The mixture is cooled to 0° C., isobutylchloroformate (5.1 mL) is added and the mixture is stirred for 30 min at 0° C. Then the mixture is filtered through celite, cooled to 0° C., a solution of NaBH$_4$ (1.6 g) in water (20 mL) is added and the mixture is stirred for 15 min. Water is added and the mixture is extracted with EtOAC. The organic phase is washed with brine, dried (MgSO$_4$) and concentrated in vacuo. The residue is chromatographed on silica gel (DCM/MeOH 97:3-50:50) to give the title compound.

LC (Method 1): $t_R$=0.50 min; Mass spectrum (ESI$^+$): m/z=159/161 (Cl) [M+H]$^+$.

Step 2: Methyl 7-[(2-chloro-4-methyl pyrimidin-5-yl)methyl]-7H-pyrrolo[2,3-d]pyrimidine-5-carboxylate (2-Chloro-4-methylpyrimidin-5-yl)methanol (475 mg) is dissolved in THF (10 mL) and DMSO (2 mL) and cooled to –10° C. Methyl 7H-pyrrolo[2,3-d]pyrimidine-5-carboxylate (530 mg), tributyl phosphine (890 µL) are added. Di-tert.-butyl-azodicarblylate (750 mg) is slowly added portionwise and the mixture is stirred at room temperature for about 30 min. The mixture is purified by HPLC on reversed phase (ACN, water) to give the title compound.

LC (Method 1): $t_R$=0.80 min; Mass spectrum (ESI$^+$): m/z=318/320 (Cl) [M+H]$^+$.

Step 3: 7-[(2-{5-Azaspiro[2.3]hexan-5-yl}-4-methylpyrimidin-5-yl)methyl]-7H-pyrrolo[2,3-d]pyrimidine-5-carboxylic acid Methyl 7-[(2-chloro-4-methylpyrimidin-5-yl)methyl]-7H-pyrrolo[2,3-d]pyrimidine-5-carboxylate (200 mg) is dissolved in DMSO (2 mL). 5-Azaspiro[2.3]hexane trifluoroacetate (250 mg) and DIPEA (0.35 mL) are added and the mixture is stirred for 6 h at 80° C. After cooling to room temperature, 4 M NaOH (1 mL) is added and stirred at 60° C. for 2 h. 4 M aqueous HCl (1 mL) is added and the mixture is purified by HPLC on reversed phase (ACN, water) to give the title compound.

LC (Method 1): $t_R$=0.72 min; Mass spectrum (ESI$^+$): m/z=351 [M+H]$^+$.

Intermediate 64

1-[(6-Fluoro-2-methylpyridin-3-yl)methyl]-N-[(6R)-3-methyl-2-{[2-(trimethylsilyl)ethoxy]methyl}-2H,4H,5H,6H-cyclopenta[c]pyrazol-6-yl]-1H-pyrazole-4-carboxamide

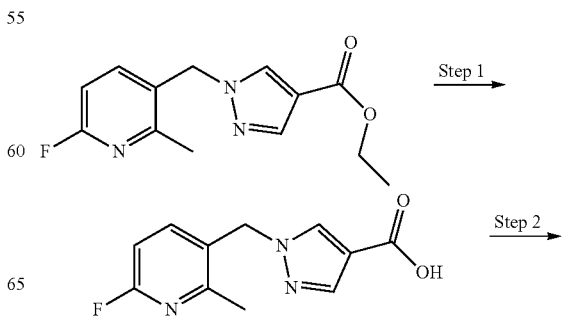

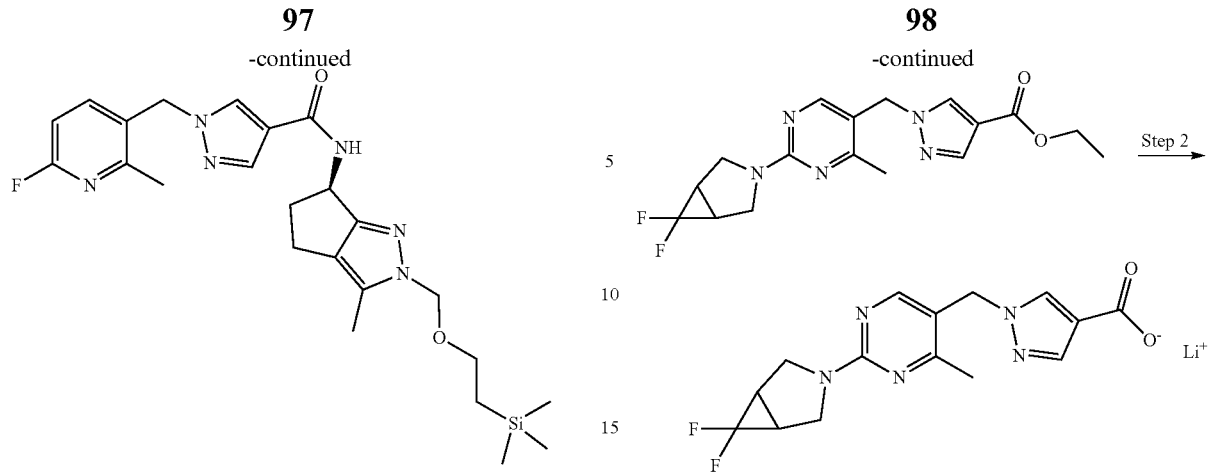

Step 1: 1-[(6-Fluoro-2-methylpyridin-3-yl)methyl]-
1H-pyrazole-4-carboxylic acid Ethyl 1-[(6-fluoro-2-methylpyridin-3-yl)methyl]-1H-pyrazole-4-carboxylate (9.1 g) is dissolved in THF (150 mL), a solution of LiOH (1.7 g) in water (15 mL) is added and the mixture is stirred for 3 d at 60° C. Acetic acid (3.8 mL) is added and the mixture is concentrated in vacuo. Water is added and the mixture is extracted with DCM/isopropanol 9:1. The organic phase is washed with brine, dried (MgSO₄) and concentrated in vacuo to give the title compound.

LC (Method 1): $t_R$=0.72 min; Mass spectrum (ESI⁺): m/z=236 [M+H]⁺.

Step 2: 1-[(6-Fluoro-2-methylpyridin-3-yl)methyl]-
N-[(6R)-3-methyl-2-{[2-(trimethylsilyl)ethoxy]
methyl}-2H,4H,5H,6H-cyclopenta[c]pyrazol-6-yl]-
1H-pyrazole-4-carboxamide To a solution of 1-[(6-fluoro-2-methylpyridin-3-yl)methyl]-1H-pyrazole-4-carboxylic acid (1 g) in DMF (10 mL) is added DIPEA (900 µL) and O-(7-azabenzotriazol-1-yl)-N,N,N',N'-tetramethyluronium-hexafluorophosphat (HATU, 1.8 g) and the mixture is stirred for 5 min. (6R)-3-Methyl-2-{[2-(trimethylsilyl)ethoxy]-methyl}-2H,4H,5H,6H-cyclopenta[c]pyrazol-6-amine (1.15 g) is added and the mixture is stirred for 1 h. The mixture is partitioned between water and EtOAC. The organic phase is washed with brine, dried (MgSO₄) and the solvents are evaporated in vacuo. The residue is chromatographed on silica gel (DCM/MeOH 98:2) to give the title compound.

LC (Method 1): $t_R$=1.08 min; Mass spectrum (ESI⁺): m/z=485 [M+H]⁺.

Intermediate 65

1-[(2-{6,6-Difluoro-3-azabicyclo[3.1.0]hexan-3-yl}-
4-methylpyrimidin-5-yl)methyl]-1H-pyrazole-4-
carboxylic acid, lithium salt

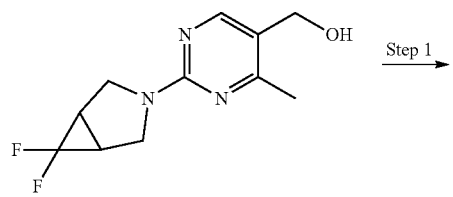

Step 1: Ethyl 1-[(2-{6,6-difluoro-3-azabicyclo
[3.1.0]hexan-3-yl}-4-methylpyrimidin-5-yl)methyl]-
1H-pyrazole-4-carboxylate 2-{6,6-Difluoro-3-azabicyclo[3.1.0]hexan-3-yl}-4-methylpyrimidin-5-yl)methanol (100 mg) is dissolved in THF (2 mL) and cooled to 0° C. Ethyl 1H-pyrazole-4-carboxylate (58 mg) and triphenyl phosphine (120 mg) are added. Di-tert.-butyl-azodicarboxylate (105 mg) is added and the mixture is stirred for 3 h while warming to room temperature. Saturated aqueous NaHCO₃ is added, the mixture is vigorously stirred for 10 min and then extracted with EtOAC. The organic phase is washed with brine, dried (MgSO₄) and concentrated in vacuo. The residue is chromatographed on silica gel (cyclohexane/EtOAC 50:50→0:100) to give the title compound.

LC (Method 1): $t_R$=0.94 min; Mass spectrum (ESI⁺): m/z=364 [M+H]⁺.

Step 2: 1-[(2-{6,6-Difluoro-3-azabicyclo[3.1.0]
hexan-3-yl}-4-methylpyrimidin-5-yl)methyl]-1H-
pyrazole-4-carboxylic acid, lithium salt A mixture of ethyl 1-[(2-{6,6-difluoro-3-azabicyclo[3.1.0]hexan-3-yl}-4-methylpyrimidin-5-yl)methyl]-1H-pyrazole-4-carboxylate (74 mg), THF (2 mL), water (0.5 mL), MeOH (1 mL) and LiOH (7.3 mg) is stirred at 50° C. for 12 h. The solvents are evaporated in vacuo to give the title compound.

LC (Method 1): $t_R$=0.77 min; Mass spectrum (ESI⁺): m/z=336 [M-Li+2H]⁺.

Intermediate 66

1-[(2-{6,6-Difluoro-3-azabicyclo[3.1.0]hexan-3-yl}-
4-methylpyrimidin-5-yl)methyl]-1H-1,2,3-triazole-4-
carboxylic acid

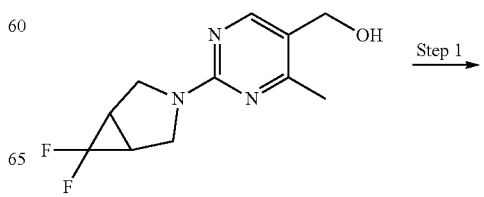

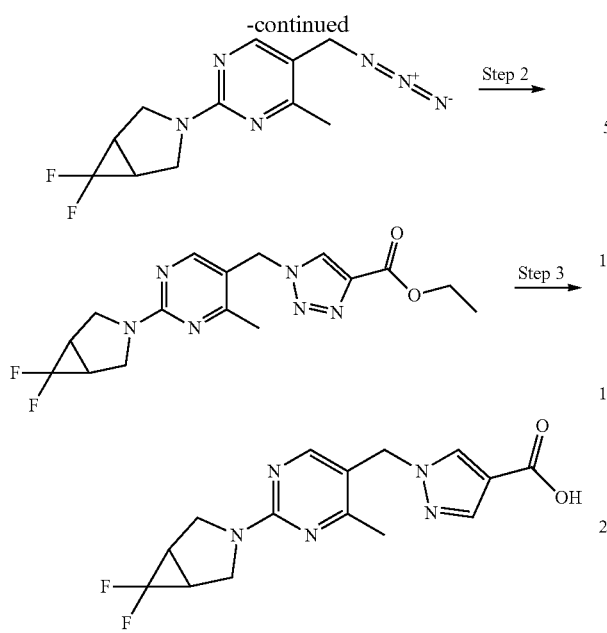

Step 1: 3-[5-(Azidomethyl)-4-methylpyrimidin-2-yl]-6,6-difluoro-3-azabicyclo[3.1.0]hexane Under argon DBU (1.5 mL) is added to a solution of (2-{6,6-difluoro-3-azabicyclo[3.1.0]hexan-3-yl}-4-methylpyrimidin-5-yl)methanol (2 g) in toluene (15 mL) and ACN (15 mL). The mixture is cooled to 0° C. and diphenylphosphorylazide (1.9 mL) is added dropwise over 1 h. The mixture is stirred for 12 h while warming to room temperature. Then the mixture is partitioned between EtOAC and 5% aqueous NaHCO$_3$. The organic phase is washed with brine, dried (MgSO$_4$) and concentrated in vacuo. The residue is chromatographed on silica gel (cyclohexane/EtOAC 70:30→50:50) to give the title compound.

LC (Method 1): $t_R$=0.90 min; Mass spectrum (ESI$^+$): m/z=267 [M+H]$^+$.

Step 2: Ethyl 1-[(2-{6,6-difluoro-3-azabicyclo[3.1.0]hexan-3-yl}-4-methylpyrimidin-5-yl)methyl]-1H-1,2,3- triazole-4-carboxylate 3-[5-(Azidomethyl)-4-methylpyrimidin-2-yl]-6,6-difluoro-3-azabicyclo[3.1.0]hexane (1.45 g), ethyl propiolate (0.42 mL), CuSO$_4$ (88 mg) and L-ascorbic acid sodium salt (656 mg) are dissolved in tert.-butanol (20 mL) and water (20 mL) and stirred for 12 h at room temperature. Ethyl propiolate (0.42 mL), CuSO$_4$ (88 mg) and L-ascorbic acid sodium salt (656 mg) are added and the mixture is again stirred for 12 h. Then the mixture is partitioned between DCM and half-saturated aqueous NaHCO$_3$. The organic phase is washed with brine, dried (MgSO$_4$) and concentrated in vacuo to give the title compound.

LC (Method 2): $t_R$=0.92 min; Mass spectrum (ESI$^+$): m/z=365 [M+H]$^+$.

Step 3: 1-[(2-{6,6-Difluoro-3-azabicyclo[3.1.1]hexan-3-yl}-4-methylpyrimidin-5-yl)methyl]-1H-1,2,3-triazole-4-carboxylic acid A mixture of ethyl 1-[(2-{6,6-difluoro-3-azabicyclo[3.1.0]hexan-3-yl}-4-methylpyrimidin-5-yl)methyl]-1H-1,2,3-triazole-4-carboxylate (1.45 g), THF (10 mL), water (10 mL), MeOH (5 mL) and LiOH (251 mg) is stirred at room temperature for 48 h. The mixture is cooled to 0° C. and treated with 1 M aqueous HCl (6 mL). The precipitated product is collected by filtration and dried in vacuo.

LC (Method 1): $t_R$=0.76 min; Mass spectrum (ESI$^+$): m/z=337 [M+H]$^+$.

Intermediate 67

1-[(6-{3-Azabicyclo[3.1.0]hexan-3-yl}-2-methylpyridin-3-yl)methyl]-1H-1,2,3-triazole-4-carboxylic acid

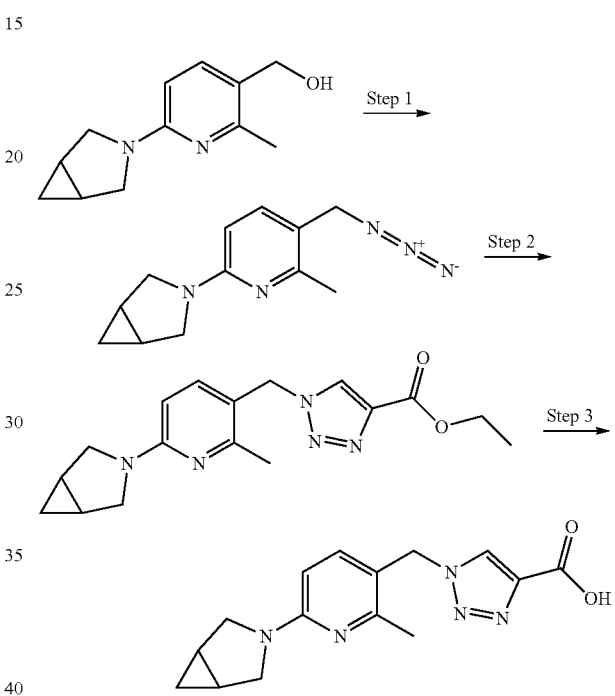

Step 1: 3-[5-(Azidomethyl)-6-methylpyridin-2-yl]-3-azabicyclo[3.1.0]hexane

Under argon DBU (0.5 mL) is added to a solution of (6-{3-azabicyclo[3.1.0]hexan-3-yl}-2-methylpyridin-3-yl)methanol (500 mg) in toluene (5 mL) and ACN (5 mL). The mixture is cooled to 0° C. and diphenylphosphorylazide (0.5 mL) is added dropwise over 1 h. The mixture is stirred for 2 h while warming to room temperature. Then the mixture is partitioned between EtOAC and saturated aqueous Na$_2$CO$_3$. The organic phase is washed with brine, dried (MgSO$_4$) and concentrated in vacuo. The residue is chromatographed on silica gel (cyclohexane/EtOAC 90:10→40:60) to give the title compound.

LC (Method 1): $t_R$=0.70 min; Mass spectrum (ESI$^+$): m/z=230 [M+H]$^+$.

Step 2: Ethyl 1-[(6-{3-azabicyclo[3.1.10]hexan-3-yl}-2-methylpyridin-3-yl)methyl]-1H-1,2,3-triazole-4- carboxylate 3-[5-(Azidomethyl)-6-methylpyridin-2-yl]-3-azabicyclo[3.1.0]hexane (350 mg), ethyl propiolate (0.18 mL), CuSO$_4$ (80 mg) and L-ascorbic acid sodium salt (306 mg) are dissolved in tert.-butanol (6 mL) and water (6 mL) and stirred for 6 h at room temperature. Ethyl propiolate (0.1 mL), CuSO₄ (40 mg) and L-ascorbic acid sodium salt (200 mg) are added and the mixture is again stirred for 12 h. Then the mixture is partitioned between DCM and water. The organic phase is washed with brine, dried (MgSO₄) and concentrated. The residue is chromatographed on silica gel (cyclohexane/EtOAC 90:10→0:100) to give the title compound.

LC (Method 1): $t_R$=0.69 min; Mass spectrum (ESI⁺): m/z=328 [M+H]⁺.

Step 3: 1-[(6-{3-Azabicyclo[3.1.0]hexan-3-yl}-2-methylpyridin-3-yl)methyl]-1H-1,2,3-triazole-4-carboxylic acid A mixture of ethyl 1-[(6-{3-azabicyclo[3.1.0]hexan-3-yl}-2-methylpyridin-3-yl)methyl]-1H-1,2,3-triazole-4-carboxylate (40 mg), EtOH (2 mL) and 1 M aqueous NaOH (400 µL) is stirred at room temperature for 16 h. After addition of 1 M aqueous HCl (400 µL) the solvents are evaporated in vacuo to give the crude product which is directly used in the next step.

LC (Method 1): $t_R$=0.57 min; Mass spectrum (ESI⁺): m/z=300 [M+H]⁺.

Intermediate 68

1-[(6-{3-Azabicyclo[3.1.0]hexan-3-yl}-2-methylpyridin-3-yl)methyl]-N-[(6R)-3-methyl-2-{[2-(trimethylsilyl)ethoxy]methyl}-2H,4H,5H,6H-cyclopenta[c]pyrazol-6-yl]-1H-1,2,3-triazole-4-carboxamide

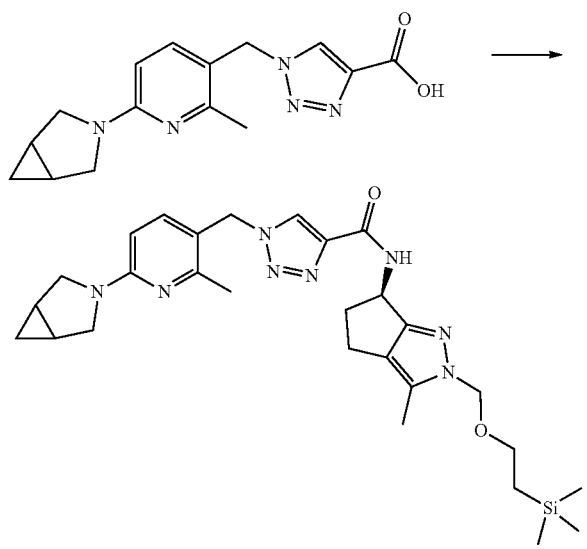

To a solution of 1-[(6-{3-azabicyclo[3.1.0]hexan-3-yl}-2-methylpyridin-3-yl)methyl]-1H-1,2,3-triazole-4-carboxylic acid (32 mg) in DMF (1 mL) is added DIPEA (28 µL) and O-(7-azabenzotriazol-1-yl)-N,N,N',N'-tetramethyluronium-hexafluorophosphat (HATU, 20 mg) and the mixture is stirred for 10 min. (6R)-3-Methyl-2-{[2-(trimethylsilyl)ethoxy]methyl}-2H,4H,5H,6H-cyclopenta[c]pyrazol-6-amine (14.3 mg) is added and the mixture is stirred for 12 h. The mixture is partitioned between water and EtOAC. The organic phase is washed with brine and dried (MgSO₄). The solvents are evaporated in vacuo to give the title compound.

LC (Method 1): $t_R$=0.95 min; Mass spectrum (ESI⁺): m/z=549 [M+H]⁺.

Intermediate 69

1-[(2-{3-Azabicyclo[3.1.0]hexan-3-yl}-4-methylpyrimidin-5-yl)methyl]-1H-1,2,3-triazole-4-carboxylic acid

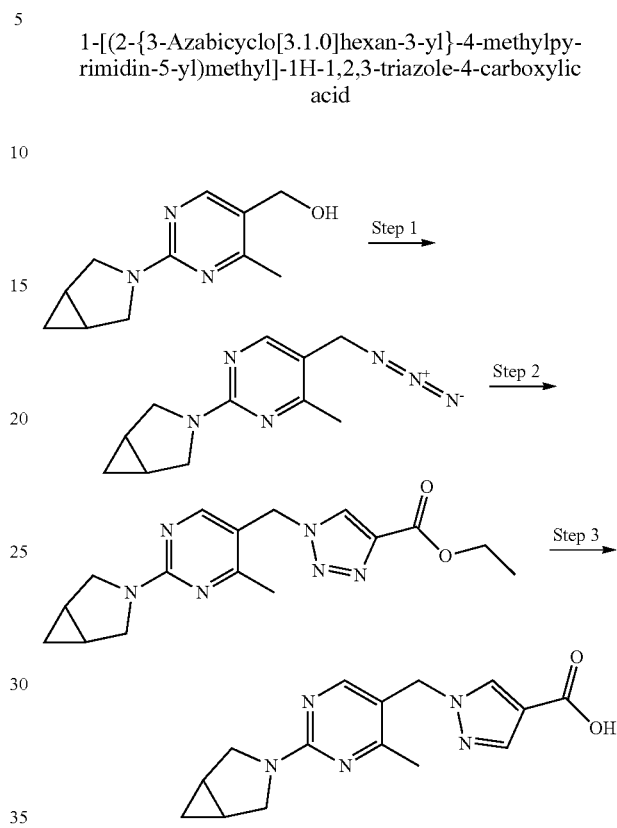

Step 1: 3-[5-(Azidomethyl)-4-methylpyrimidin-2-yl]-3-azabicyclo[3.1.0]hexane

Under argon DBU (11.2 mL) is added to a solution of (2-{3-azabicyclo[3.1.0]hexan-3-yl}-4-methylpyrimidin-5-yl)methanol (3.88 g) in toluene (80 mL) and ACN (80 mL). The mixture is cooled to 0° C. and diphenylphosphorylazide (14.7 mL) is added dropwise over 1 h. The mixture is stirred for 12 h while warming to room temperature. Then the mixture is partitioned between EtOAC and half-saturated aqueous NaHCO₃. The aqueous phase is extracted for three times with EtOAC. The combined organic phases are washed with brine. MgSO₄ and silica gel are added and the mixture is stirred for 30 min. The solids are filtered off and the solvents are evaporated in vacuo to give the title compound.

LC (Method 1): $t_R$=0.75 min; Mass spectrum (ESI⁺): m/z=231 [M+H]⁺.

Step 2: Ethyl 1-[(2-{3-azabicyclo[3.1.0]hexan-3-yl}-4-methylpyrimidin-5-yl)methyl]-1H-1,2,3-triazole-4-carboxylate 3-[5-(Azidomethyl)-4-methylpyrimidin-2-yl]-3-azabicyclo[3.1.0]hexane (15.8 g), ethyl propiolate (6.2 mL), CuSO₄ (1.8 g) and L-ascorbic acid sodium salt (11.1 g) are dissolved in tert.-butanol (200 mL) and water (200 mL) and stirred for 5 d at room temperature. Then the mixture is partitioned between DCM and saturated aqueous NaHCO₃. The aqueous phase is twice extracted with DCM and the combined organic phases are washed with brine, dried (MgSO₄) and concentrated. The residue is chromatographed on silica gel (cyclohexane/EtOAC/MeOH 30:70:0→0:90:10) to give the title compound.

LC (Method 1): t$_R$=0.79 min; Mass spectrum (ESI⁺): m/z=329 [M+H]⁺.

Step 3: 1-[(2-{3-Azabicyclo[3.1.1]hexan-3-yl}-4-methylpyrimidin-5-yl)methyl]-1H-1,2,3-triazole-4-carboxylic acid A mixture of ethyl 1-[(2-{3-azabicyclo[3.1.0]hexan-3-yl}-4-methylpyrimidin-5-yl)methyl]-1H-1,2,3-triazole-4-carboxylate (16.1 g), EtOH (150 mL) and 4 M aqueous NaOH (15 mL) is stirred at 50° C. for 12 h. The mixture is concentrated in vacuo. After addition of 4 M aqueous HCl (15 mL) the mixture is stirred for 1 h. The precipitate is collected by filtration, washed with water and dried in vacuo to give the title compound.

LC (Method 1): t$_R$=0.65 min; Mass spectrum (ESI⁺): m/z=301 [M+H]⁺.

Intermediate 70

1-[(2-{3-Azabicyclo[3.1.0]hexan-3-yl}-4-methylpyrimidin-5-yl)methyl]-N-[(6R)-3-methyl-2-{[2-(trimethylsilyl)ethoxy]methyl}-2H,4H,5H,6H-cyclopenta[c]pyrazol-6-yl]-1H-1,2,3-triazole-4-carboxamide

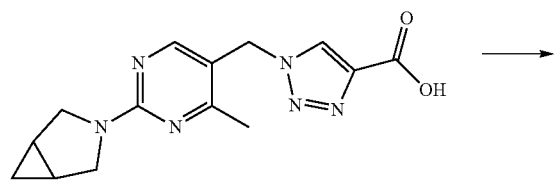

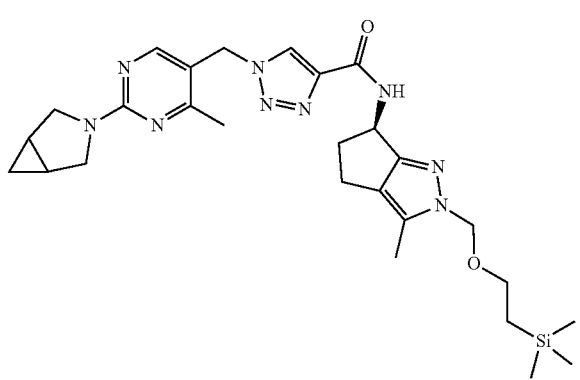

To a solution of 1-[(2-{3-azabicyclo[3.1.0]hexan-3-yl}-4-methylpyrimidin-5-yl)methyl]-1H-1,2,3-triazole-4-carboxylic acid (50 mg) in DMF (0.5 mL) is added DIPEA (60 µL) and O-(7-azabenzotriazol-1-yl)-N,N,N',N'-tetramethyl-uronium-hexafluorophosphat (HATU, 66 mg) and the mixture is stirred for 5 min. (6R)-3-Methyl-2-{[2-(trimethylsilyl)ethoxy]methyl}-2H,4H,5H,6H-cyclopenta[c]pyrazol-6-amine (47 mg) is added and the mixture is stirred for 6 h. The mixture is purified by HPLC on reversed phase (ACN, water) to give the title compound.

LC (Method 2): t$_R$=1.16 min; Mass spectrum (ESI⁺): m/z=550 [M+H]⁺.

Intermediate 71

Ethyl 1-[(6-{5-azaspiro[2.3]hexan-5-yl}-2-methyl-pyrimidin-3-yl)methyl]-1H-imidazole-4-carboxylate

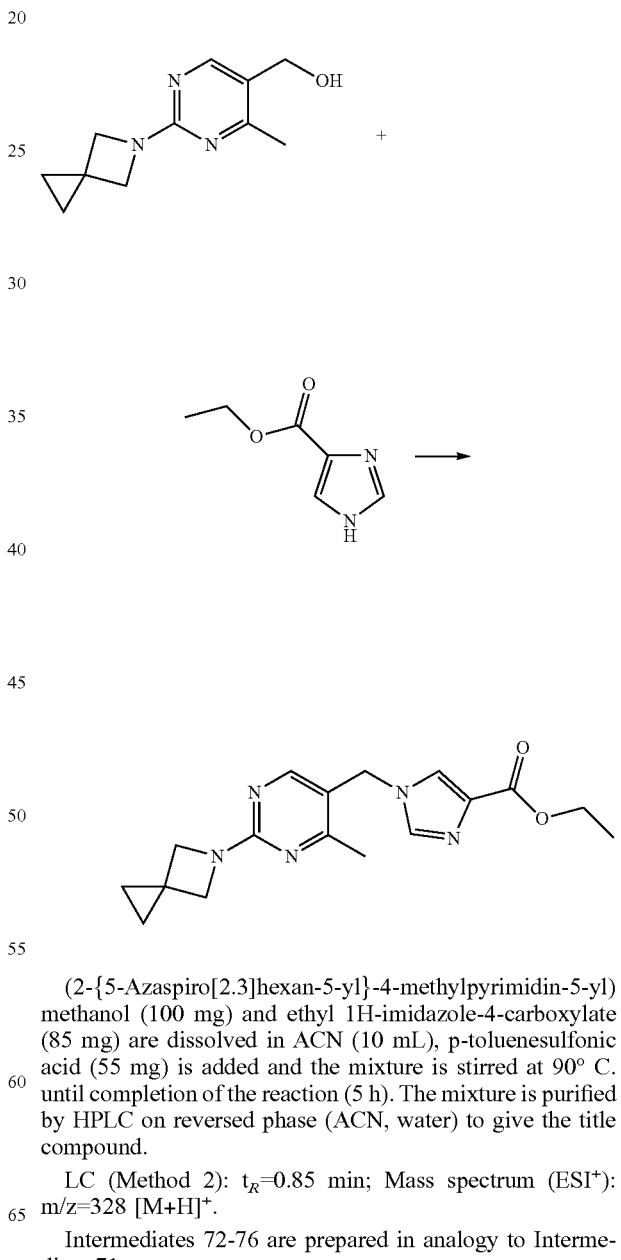

(2-{5-Azaspiro[2.3]hexan-5-yl}-4-methylpyrimidin-5-yl)methanol (100 mg) and ethyl 1H-imidazole-4-carboxylate (85 mg) are dissolved in ACN (10 mL), p-toluenesulfonic acid (55 mg) is added and the mixture is stirred at 90° C. until completion of the reaction (5 h). The mixture is purified by HPLC on reversed phase (ACN, water) to give the title compound.

LC (Method 2): t$_R$=0.85 min; Mass spectrum (ESI⁺): m/z=328 [M+H]⁺.

Intermediates 72-76 are prepared in analogy to Intermediate 71:

| Intermediate | Structure | $t_R$ | Mass spectrum (ESI+): m/z [M+H]+ | LC Method |
|---|---|---|---|---|
| 72 | 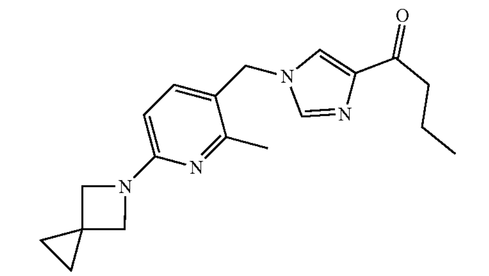 [SMILES: CCCC(=O)c1cn(Cc2ccc(N3CC4(CC4)C3)nc2C)cn1] | 0.93 | 327 | Method 2 |
| 73 | 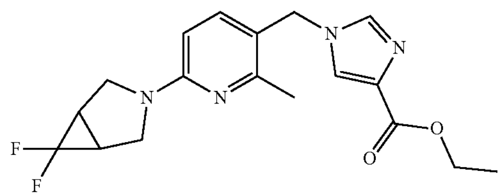 [SMILES: CCOC(=O)c1cn(Cc2ccc(N3CC4C(C3)C4(F)F)nc2C)cn1] | 0.94 | 223 (fragment) | Method 2 |
| 74 | 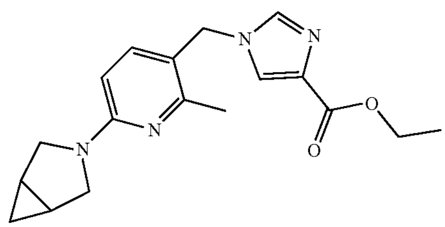 [SMILES: CCOC(=O)c1cn(Cc2ccc(N3CC4CC4C3)nc2C)cn1] | 0.98 | 327 | Method 2 |
| 75 | 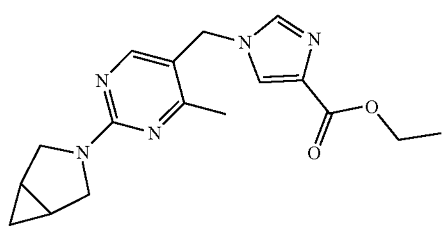 [SMILES: CCOC(=O)c1cn(Cc2cnc(N3CC4CC4C3)nc2C)cn1] | 0.89 | 328 | Method 2 |
| 76 | 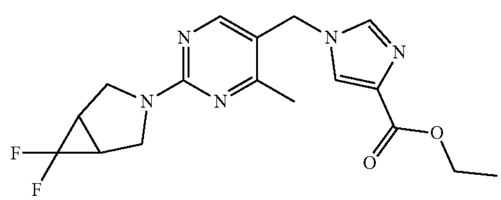 [SMILES: CCOC(=O)c1cn(Cc2cnc(N3CC4C(C3)C4(F)F)nc2C)cn1] | 0.88 | 364 | Method 2 |

| Intermediate | Name | Name of StartingMaterial 1 | Name of Starting Material 2 |
|---|---|---|---|
| 72 | Ethyl 1-[(6-{5-azaspiro[2.3]hexan-5-yl}-2-methylpyridin-3-yl)methyl]-1H-imidazole-4-carboxylate | (2-{5-Azaspiro[2.3]hexan-5-yl}-4-methylpyridin-5-yl)methanol | Ethyl 1H-imidazole-4-carboxylate |
| 73 | Ethyl 1-[(6-{6,6-difluoro-3-azabicyclo[3.1.0]hexan-3-yl}-2-methylpyridin-3-yl)methyl]-1H-imidazole-4-carboxylate | (6-{6,6-Difluoro-3-azabicyclo[3.1.0]hexan-3-yl}-2-methylpyridin-3-yl)methanol | Ethyl 1H-imidazole-4-carboxylate |
| 74 | Ethyl 1-[(6-{3-azabicyclo[3.1.0]hexan-3-yl}-2-methylpyridin-3-yl)methyl]-1H-imidazole-4-carboxylate | (6-{3-Azabicyclo[3.1.0]hexan-3-yl}-2-methyl-pyridin-3-yl)methanol | Ethyl 1H-imidazole-4-carboxylate |
| 75 | Ethyl 1-[(6-{3-azabicyclo[3.1.0]hexan-3-yl}-2-methylpyrimidin-3-yl)methyl]-1H-imidazole-4-carboxylate | (6-{3-Azabicyclo[3.1.0]-hexan-3-yl}-2-methyl-pyrimidin-3-yl)methanol | Ethyl 1H-imidazole-4-carboxylate |

-continued

| Intermediate | Name | Name of StartingMaterial 1 | Name of Starting Material 2 |
|---|---|---|---|
| 76 | Ethyl 1-[(6-{6,6-difluoro-3-azabicyclo[3.1.0]hexan-3-yl}-2-methylpyrimidin-3-yl)methyl]-1H-imidazole-4-carboxylate | (6-{6,6-Difluoro-3-azabicyclo[3.1.0]hexan-3-yl}-2-methylpyrimidin-3-yl)methanol | Ethyl 1H-imidazole-4-carboxylate |

Intermediates 77-82 are pr prepared in analogy to Intermediate 41:

| Intermediate | Structure | $t_R$ | Mass spectrum (ESI+): m/z [M+H]$^+$ | LC Method |
|---|---|---|---|---|
| 77 | 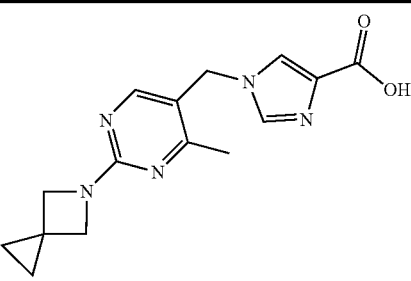 | 0.58 | 300 | Method 2 |
| 78 | 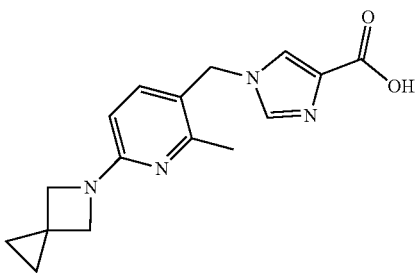 [SMILES: Cc1nc(N2CC3(CC3)C2)ncc1Cn1cnc(C(=O)O)c1] | 0.63 | 299 | Method 2 |
| 79 | 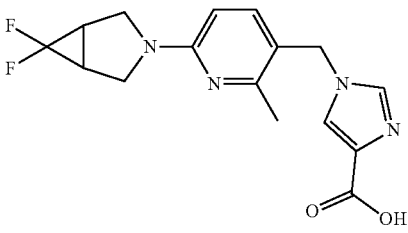 [SMILES: Cc1nc(N2CC3C(C2)C3(F)F)ccc1Cn1cnc(C(=O)O)c1] | 0.64 | 335 | Method 2 |
| 80 | 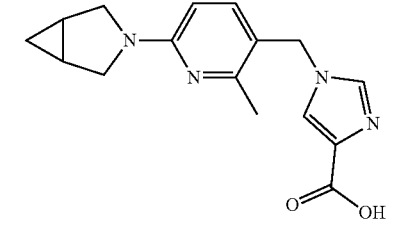 [SMILES: Cc1nc(N2CC3CC3C2)ccc1Cn1cnc(C(=O)O)c1] | 0.63 | 299 | Method 2 |
| 81 | 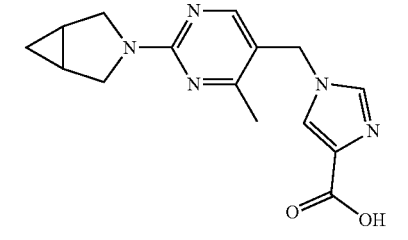 [SMILES: Cc1nc(N2CC3CC3C2)ncc1Cn1cnc(C(=O)O)c1] | 0.60 | 300 | Method 2 |

| Intermediate | Structure | $t_R$ | Mass spectrum (ESI+): m/z [M+H]+ | LC Method |
|---|---|---|---|---|
| 82 | 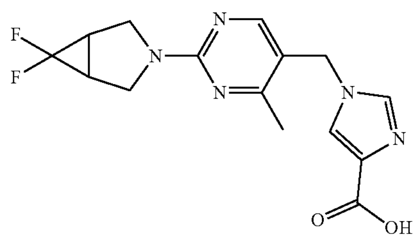 [SMILES: Cc1nc(N2CC3C(C2)C3(F)F)ncc1Cn1cnc(C(=O)O)c1] | 0.60 | 336 | Method 2 |

| Intermediate | Name | Name of Starting Material |
|---|---|---|
| 77 | 1-[(6-{5-Azaspiro[2.3]hexan-5-yl}-2-methylpyrimidin-3-yl)methyl]-1H-imidazole-4-carboxylic acid | Ethyl 1-[(6-{5-azaspiro[2.3]hexan-5-yl}-2-methylpyrimidin-3-yl)methyl]-1H-imidazole-4-carboxylate |
| 78 | 1-[(6-{5-Azaspiro[2.3]hexan-5-yl}-2-methylpyridin-3-yl)methyl]-1H-imidazole-4-carboxylic acid | Ethyl 1-[(6-{5-azaspiro[2.3]hexan-5-yl}-2-methylpyridin-3-yl)methyl]-1H-imidazole-4-carboxylate |
| 79 | 1-[(6-{6,6-Difluoro-3-azabicyclo[3.1.0]hexan-3-yl}-2-methylpyridin-3-yl)methyl]-1H-imidazole-4-carboxylic acid | Ethyl 1-[(6-{6,6-difluoro-3-azabicyclo[3.1.0]hexan-3-yl}-2-methylpyridin-3-yl)methyl]-1H-imidazole-4-carboxylic |
| 80 | 1-[(6-{3-Azabicyclo[3.1.0]hexan-3-yl}-2-methylpyridin-3-yl)methyl]-1H-imidazole-4-carboxylic acid | Ethyl 1-[(6-{3-azabicyclo[3.1.0]hexan-3-yl}-2-methylpyridin-3-yl)methyl]-1H-imidazole-4-carboxylate |
| 81 | 1-[(6-{3-Azabicyclo[3.1.0]hexan-3-yl}-2-methylpyrimidin-3-yl)methyl]-1H-imidazole-4-carboxylic acid | Ethyl 1-[(6-{3-azabicyclo[3.1.0]hexan-3-yl}-2-methylpyrimidin-3-yl)methyl]-1H-imidazole-4-carboxylate |
| 82 | 1-[(6-{6,6-Difluoro-3-azabicyclo[3.1.0]hexan-3-yl}-2-methylpyrimidin-3-yl)methyl]-1H-imidazole-4-carboxylic acid | Ethyl 1-[(6-{6,6-difluoro-3-azabicyclo[3.1.0]hexan-3-yl}-2-methylpyrimidin-3-yl)methyl]-1H-imidazole-4-carboxylate |

Intermediate 83

1-({6-[(1R,5S,6R)-6-(Hydroxymethyl)-3-azabicyclo[3.1.0]hexan-3-yl]-2-methylpyridin-3-yl}methyl)-N-[(6R)- 3-methyl-2-{[2-(trimethylsilyl)ethoxy]methyl}-2H,4H,5H,6H-cyclopenta[c]pyrazol-6-yl]-1H-pyrazole-4-carboxamide

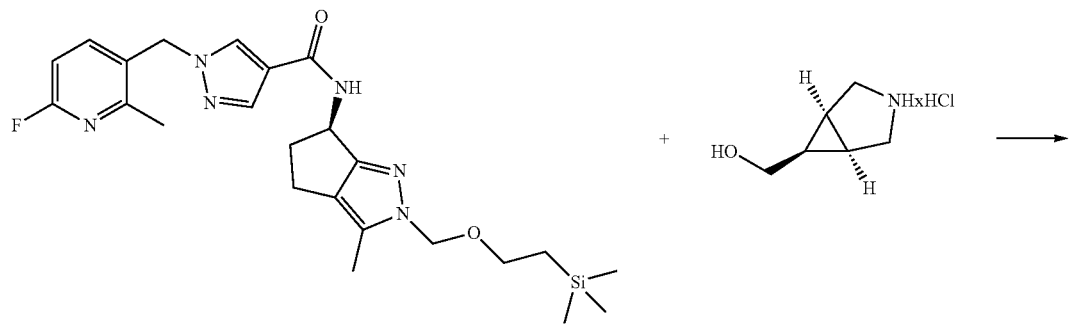

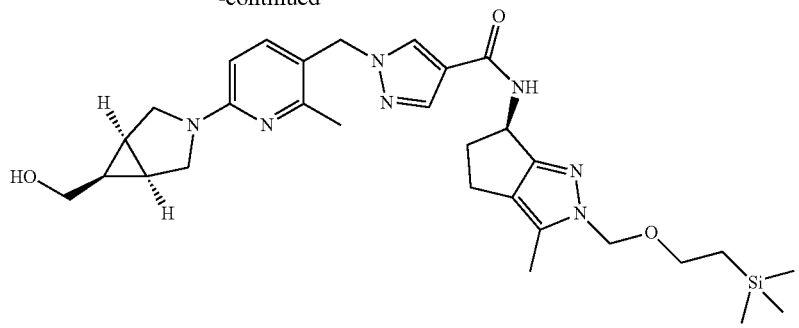

A mixture of 1-[(6-fluoro-2-methylpyridin-3-yl)methyl]-N-[(6R)-3-methyl-2-{[2-(trimethylsilyl)ethoxy]methyl}-2H,4H,5H,6H-cyclopenta[c]pyrazol-6-yl]-1H-pyrazole-4-carboxamide (60 mg), [(1R,5S,6R)-3-azabicyclo[3.1.0]-hexan-6-yl]methanol hydrochloride (see: *Bioorg. Med. Chem. Lett.* 2010, 4741-4744; 80 mg) and DIPEA (100 μL) in DMSO (1 mL) is heated for 4 h to 60° C. [(1R,5S,6R)-3-Azabicyclo[3.1.0]hexan-6-yl]methanol hydrochloride (60 mg) and DIPEA (75 μL) are added and the mixture is stirred for 24 h to 11000. The mixture is diluted with EtOAC and washed successively with water and brine. The organic phase is dried (MgSO$_4$) and concentrated in vacuo. The residue is chromatographed on Al$_2$O$_3$(DCM/MeOH 95:5→85:15) to give the title compound.

LC (Method 1): $t_R$=0.98 min; Mass spectrum (ESI$^+$): m/z=578 [M+H]$^+$.

Intermediate 84

[(1R,5S,6S)-3-[5-(Hydroxymethyl)-6-methylpyridin-2-yl]-3-azabicyclo[3.1.0]hexan-6-yl]methanol

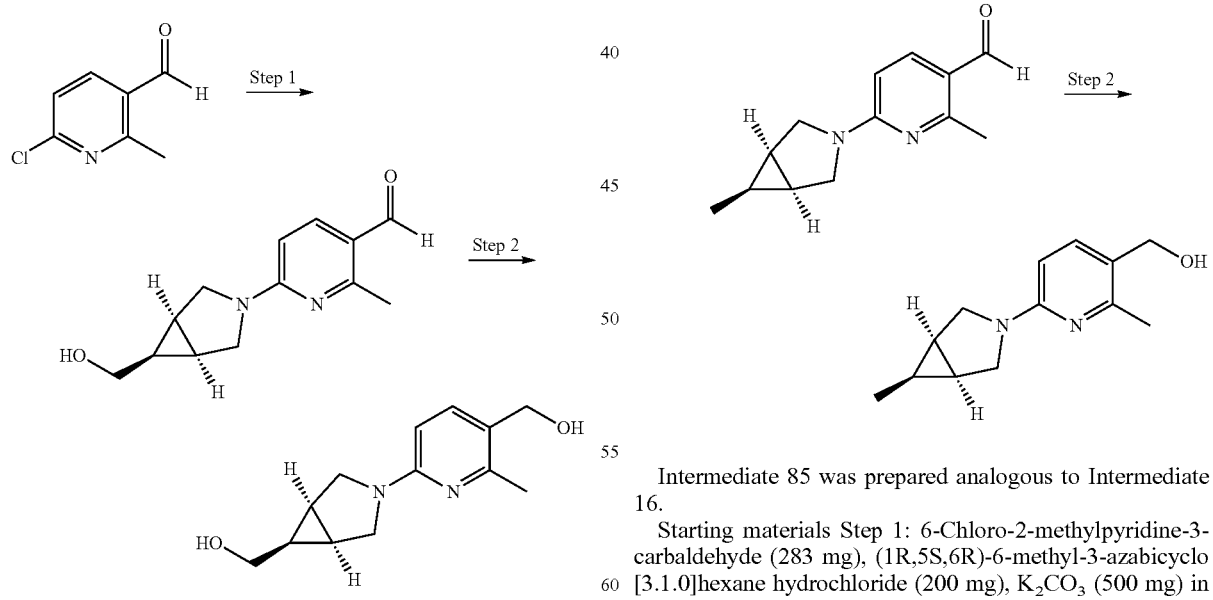

Intermediate 84 was prepared analogous to Intermediate 16.

Starting materials Step 1: 6-Chloro-2-methylpyridine-3-carbaldehyde (280 mg), [(1R,5S,6S)-3-azabicyclo[3.1.0]-hexan-6-yl]methanol hydrochloride (444 mg), K$_2$CO$_3$ (400 mg) in DMSO (5 mL).

LC (Method 2): $t_R$=0.76 min; Mass spectrum (ESI$^+$): m/z=233 [M+H]$^+$.

Starting materials Step 2: 6-[(1R,5S,6S)-6-(Hydroxymethyl)-3-azabicyclo[3.1.0]hexan-3-yl]-2-methylpyridine-3-carbaldehyde (74 mg), sodiumborohydride (18 mg) in EtOH (4 mL) and THF (1.5 mL).

LC (Method 2): $t_R$=0.71 min; Mass spectrum (ESI$^+$): m/z=235 [M+H]$^+$.

Intermediate 85

{2-Methyl-6-[(1R,5S,6S)-6-methyl-3-azabicyclo[3.1.0]hexan-3-yl]pyridin-3-yl}methanol Intermediate 85 was prepared analogous to Intermediate 16.

Starting materials Step 1: 6-Chloro-2-methylpyridine-3-carbaldehyde (283 mg), (1R,5S,6R)-6-methyl-3-azabicyclo[3.1.0]hexane hydrochloride (200 mg), K$_2$CO$_3$ (500 mg) in DMF (5 mL).

LC (Method 2): $t_R$=1.01 min; Mass spectrum (ESI$^+$): m/z=217 [M+H]$^+$.

Starting materials Step 2: 2-Methyl-6-[(1R,5S,6S)-6-methyl-3-azabicyclo[3.1.0]hexan-3-yl]pyridine-3-carbaldehyde (217 mg), sodiumborohydride (93 mg) in EtOH (4 mL) and THF (1 mL).

LC (Method 2): $t_R$=0.91 min; Mass spectrum (ESI⁺): m/z=219 [M+H]⁺.

Intermediate 86

(2-{5-Azaspiro[2.3]hexan-5-yl}-4-methylpyrimidin-5-yl)methanol

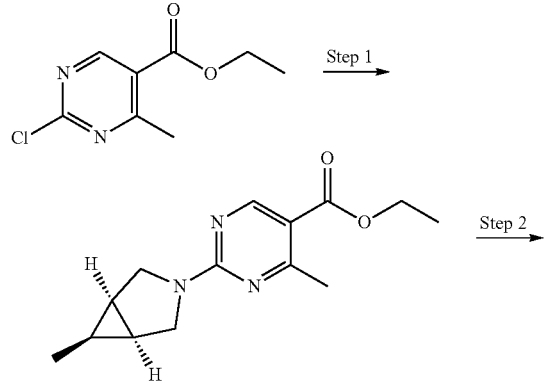

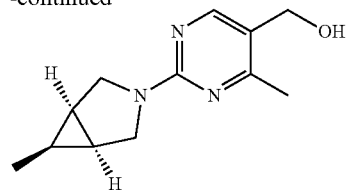

Intermediate 86 was prepared analogous to Intermediate 17.

Starting materials Step 1: Ethyl-2-chloro-4-methylpyrimidine-5-carboxylate (350 mg), (1R,5S,6R)-6-methyl-3-azabicyclo[3.1.0]hexane hydrochloride (200 mg), K₂CO₃ (500 mg) in DMF (5 mL).

LC (Method 2): $t_R$=1.12 min; Mass spectrum (ESI⁺): m/z=262 [M+H]⁺.

Starting materials Step 2: Ethyl 2-{5-azaspiro[2.3]hexan-5-yl}-4-methylpyrimidine-5-carboxylate (0.659 g), LiBH₄ (49 mg) and MeOH (0.2 mL) in THF (5 mL).

LC (Method 2): $t_R$=0.83 min; Mass spectrum (ESI⁺): m/z=220 [M+H]⁺.

Intermediates 87-93 are prepared in analogy to Intermediate 71:

| Intermediate | Structure | $t_R$ | Mass spectrum (ESI+): m/z [M + H]⁺ | LC Method |
|---|---|---|---|---|
| 87 | 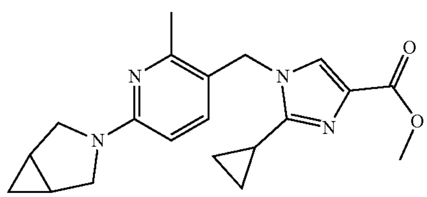 [SMILES: COC(=O)c1cn(Cc2ccc(N3CC4CC4C3)nc2C)c(C2CC2)n1] | 1.01 | 353 | Method 2 |
| 88 | 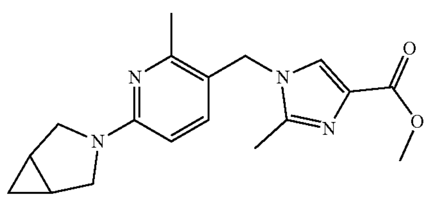 [SMILES: COC(=O)c1cn(Cc2ccc(N3CC4CC4C3)nc2C)c(C)n1] | 0.95 | 327 | Method 2 |
| 89 | 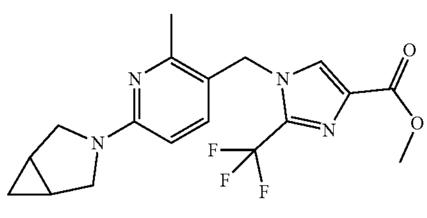 [SMILES: COC(=O)c1cn(Cc2ccc(N3CC4CC4C3)nc2C)c(C(F)(F)F)n1] | 1.09 | 381 | Method 2 |
| 90 | 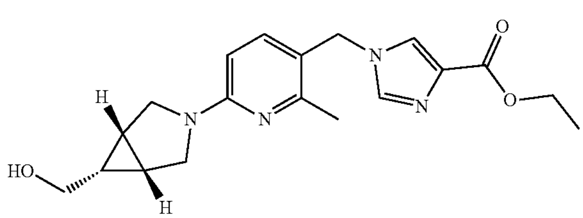 [SMILES: CCOC(=O)c1cn(Cc2ccc(N3C[C@@H]4[C@H](CO)[C@@H]4C3)nc2C)cn1] | 0.81 | 217 (fragment) | Method 2 |

-continued

| Intermediate | Structure | $t_R$ | Mass spectrum (ESI+): m/z [M + H]+ | LC Method |
|---|---|---|---|---|
| 91 | 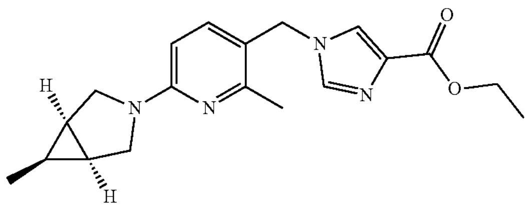 | 1.02 | 341 | Method 2 |
| 92 | 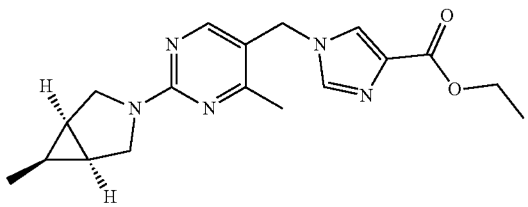 [SMILES: CCOC(=O)c1cn(Cc2cnc(N3C[C@@H]4[C@H](C)[C@@H]4C3)nc2C)cn1] | 0.94 | 342 | Method 2 |
| 93 | 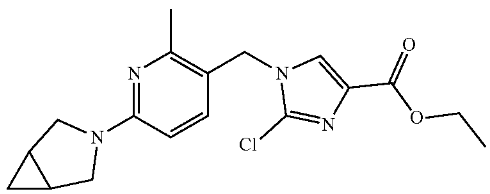 [SMILES: CCOC(=O)c1cn(Cc2ccc(N3CC4CC4C3)nc2C)c(Cl)n1] | 1.06 | 361/363 (Cl) | Method 2 |

| Intermediate | Name | Name of Starting Material 1 | Name of Starting Material 2 |
|---|---|---|---|
| 87 | Methyl 1-[(6-{3-azabicyclo[3.1.0]hexan-3-yl}-2-methylpyridin-3-yl)methyl]-2-cyclopropyl-1H-imidazole-4-carboxylate | [6-(3-Aza-bicyclo[3.1.0]-hex-3-yl)-2-methyl-pyridin-3-yl]-methanol | Methyl 2-cyclopropyl-1H-imidazole-4-carboxylate |
| 88 | Methyl 1-[(6-{3-azabicyclo[3.1.0]hexan-3-yl}-2-methylpyridin-3-yl)methyl]-2-methyl-1H-imidazole-4-carboxylate | [6-(3-Aza-bicyclo[3.1.0]-hex-3-yl)-2-methyl-pyridin-3-yl]-methanol | Methyl 2-methyl-1H-imidazole-4-carboxylate |
| 89 | Methyl 1-[(6-{3-azabicyclo[3.1.0]hexan-3-yl}-2-methylpyridin-3-yl)methyl]-2-(trifluoromethyl)-1H-imidazole-4-carboxylate | [6-(3-Aza-bicyclo[3.1.0]-hex-3-yl)-2-methyl-pyridin-3-yl]-methanol | Methyl 2-(trifluoromethyl)-1H-imidazole-4-carboxylate hydrochloride |
| 90 | Ethyl 1-({6-[(1R,5S,6S)-6-(hydroxymethyl)-3-azabicyclo[3.1.0]hexan-3-yl]-2-methylpyridin-3-yl}methyl)-1H-imidazole-4-carboxylate | [(1R,5S,6S)-3-[5-(Hydroxymethyl)-6-methylpyri-din-2-yl]-3-azabicyclo-[3.1.0]hexan-6-yl]-methanol | Ethyl 1H-imidazole-4-carboxylate |
| 91 | Ethyl 1-({2-methyl-6-[(1R,5S,6S)-6-methyl-3-azabicyclo[3.1.0]hexan-3-yl]pyridin-3-yl}methyl)-1H-imidazole-4-carboxylate | {2-Methyl-6-[(1R,5S,6S)-6-methyl-3-azabicyclo[3.1.0]hexan-3-yl]pyridin-3-yl}methanol | Ethyl 1H-imidazole-4-carboxylate |
| 92 | Ethyl 1-({2-methyl-6-[(1R,5S,6S)-6-methyl-3-azabicyclo[3.1.0]hexan-3-yl]pyrimidin-3-yl}methyl)-1H-imidazole-4-carboxylate | {2-Methyl-6-[(1R,5S,6S)-6-methyl-3-azabicyclo[3.1.0]hexan-3-yl]pyridin-3-yl}methanol | Ethyl 1H-imidazole-4-carboxylate |
| 93 | Ethyl 1-[(6-{3-azabicyclo[3.1.0]hexan-3-yl}-2-methylpyridin-3-yl)methyl]-2-chloro-1H-imidazole-4-carboxylate | [6-(3-Aza-bicyclo[3.1.0]-hex-3-yl)-2-methyl-pyridin-3-yl]-methanol | Methyl 2-chloro-1H-imidazole-4-carboxylate |

Intermediates 94-100 are prepared in analogy to Intermediate 41:

| Intermediate | Structure | $t_R$ | Mass spectrum (ESI+): m/z [M + H]+ | LC Method |
|---|---|---|---|---|
| 94 | 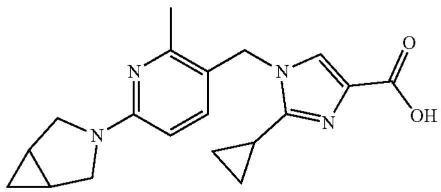 [SMILES: Cc1nc(N2CC3CC3C2)ccc1Cn1cc(C(=O)O)nc1C1CC1] | 0.67 | 339 | Method 2 |
| 95 | 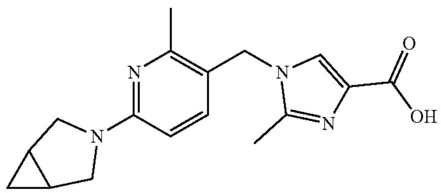 | 0.64 | 313 | Method 2 |
| 96 | 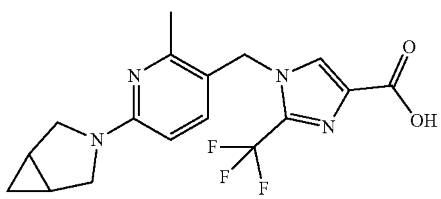 [SMILES: Cc1nc(N2CC3CC3C2)ccc1Cn1cc(C(=O)O)nc1C(F)(F)F] | 0.72 | 367 | Method 2 |
| 97 | 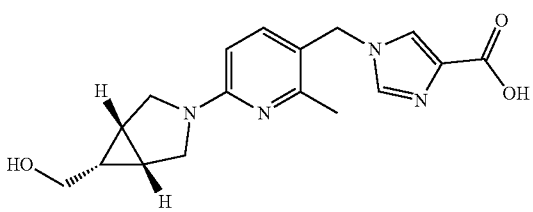 [SMILES: Cc1nc(N2C[C@@H]3[C@H](CO)[C@@H]3C2)ccc1Cn1cnc(C(=O)O)c1] | 0.55 | 329 | Method 2 |
| 98 | 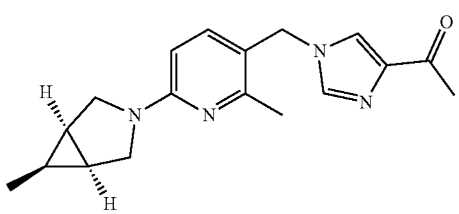 [SMILES: CC(=O)c1cn(Cc2ccc(N3C[C@@H]4[C@H](C)[C@@H]4C3)nc2C)cn1] | 0.56 | 313 | Method 2 |
| 99 | 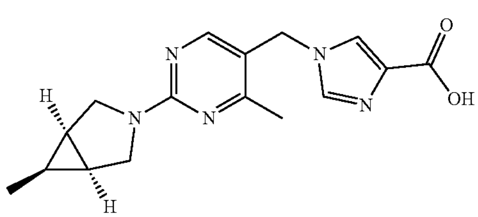 [SMILES: Cc1nc(N2C[C@@H]3[C@H](C)[C@@H]3C2)ncc1Cn1cnc(C(=O)O)c1] | 0.69 | 314 | Method 2 |
| 100 | 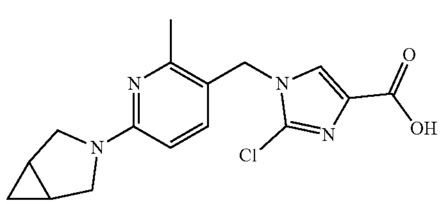 [SMILES: Cc1nc(N2CC3CC3C2)ccc1Cn1cc(C(=O)O)nc1Cl] | 0.65 | 333/335 (Cl) | Method 1 |

| Intermediate | Name | Name of Starting Material |
|---|---|---|
| 94 | 1-[(6-{3-Azabicyclo[3.1.0]hexan-3-yl}-2-methylpyridin-3-yl)methyl]-2-cyclopropyl-1H-imidazole-4-carboxylic acid | Methyl 1-[(6-{3-azabicyclo[3.1.0]hexan-3-yl}-2-methylpyridin-3-yl)methyl]-2-cyclopropyl-1H-imidazole-4-carboxylate |
| 95 | 1-[(6-{3-Azabicyclo[3.1.0]hexan-3-yl}-2-methylpyridin-3-yl)methyl]-2-methyl-1H-imidazole-4-carboxylic acid | Methyl 1-[(6-{3-azabicyclo[3.1.0]hexan-3-yl}-2-methylpyridin-3-yl)methyl]-2-methyl-1H-imidazole-4-carboxylate |
| 96 | 1-[(6-{3-Azabicyclo[3.1.0]hexan-3-yl}-2-methylpyridin-3-yl)methyl]-2-(trifluoromethyl)-1H-imidazole-4-carboxylic acid | Methyl 1-[(6-{3-azabicyclo[3.1.0]hexan-3-yl}-2-methylpyridin-3-yl)methyl]-2-(trifluoromethyl)-1H-imidazole-4-carboxylate |
| 97 | 1-({6-[(1R,5S,6S)-6-(Hydroxymethyl)-3-azabicyclo[3.1.0]hexan-3-yl]-2-methylpyridin-3-yl}methyl)-1H-imidazole-4-carboxylic acid | Ethyl 1-({6-[(1R,5S,6S)-6-(hydroxymethyl)-3-azabicyclo[3.1.0]hexan-3-yl]-2-methylpyridin-3-yl}methyl)-1H-imidazole-4-carboxylate |
| 98 | 1-({4-Methyl-2-[(1R,5S,6R)-6-methyl-3-azabicyclo[3.1.0]hexan-3-yl]pyridin-5-yl}methyl)-1H-imidazole-4-carboxylic acid | Ethyl 1-({2-methyl-6-[(1R,5S,6S)-6-methyl-3-azabicyclo[3.1.0]hexan-3-yl]pyridin-3-yl}methyl)-1H-imidazole-4-carboxylate |
| 99 | 1-({4-Methyl-2-[(1R,5S,6R)-6-methyl-3-azabicyclo[3.1.0]hexan-3-yl]pyrimidin-5-yl}methyl)-1H-imidazole-4-carboxylic acid | Ethyl 1-({2-methyl-6-[(1R,5S,6S)-6-methyl-3-azabicyclo[3.1.0]hexan-3-yl]pyrimidin-3-yl}methyl)-1H-imidazole-4-carboxylate |
| 100 | 1-[(6-{3-Azabicyclo[3.1.0]hexan-3-yl}-2-methylpyridin-3-yl)methyl]-2-chloro-1H-imidazole-4-carboxylic acid | Ethyl 1-[(6-{3-azabicyclo[3.1.0]hexan-3-yl}-2-methylpyridin-3-yl)methyl]-2-chloro-1H-imidazole-4-carboxylate |

Intermediate 101

1-[(6-{3-Azabicyclo[3.1.0]hexan-3-yl}-2-methylpyridin-3-yl)methyl]-3-(2-hydroxypropan-2-yl)-1H-pyrazole-4- carboxylic acid

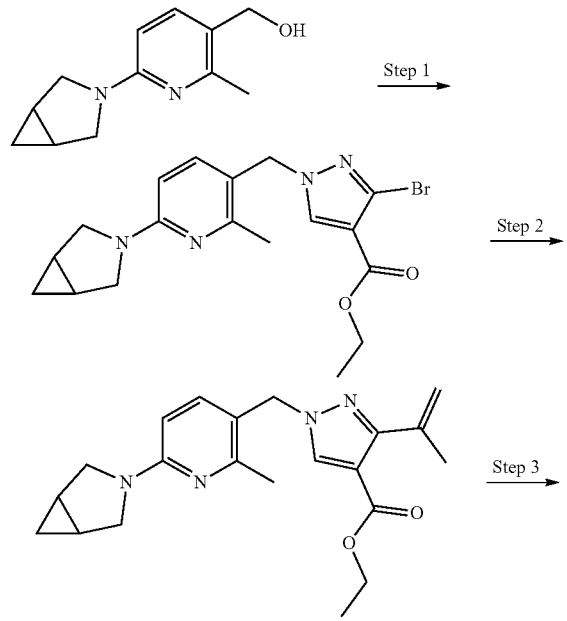

Step 1: Ethyl 1-[(6-{3-azabicyclo[3.1.0]hexan-3-yl}-2-methylpyridin-3-yl)methyl]-3-bromo-1H-pyrazole-4- carboxylate

[6-(3-Aza-bicyclo[3.1.0]hex-3-yl)-2-methyl-pyridin-3-yl]-methanol (612 mg) is dissolved in THF (20 mL) and cooled to −10° C. Ethyl 5-bromo-1H-pyrazole-4-carboxylate (690 mg) and tributyl phosphine (667 µL) are added. Di-tert.-butyl-azodicarboxylate (759 mg) is slowly added portionwise and the mixture is stirred at room temperature until completion of the reaction. The mixture is purified by HPLC on reversed phase (ACN, water) to give the title compound.

LC (Method 2): $t_R$=1.14 min; Mass spectrum (ESI$^+$): m/z=405/407 (Br) [M+H]$^+$.

Step 2: Ethyl 1-[(6-{3-azabicyclo[3.1.0]hexan-3-yl}-2-methylpyridin-3-yl)methyl]-3-(prop-1-en-2-yl)-1H- pyrazole-4-carboxylate; trifluoroacetic acid Ethyl 1-[(6-{3-azabicyclo[3.1.0]hexan-3-yl}-2-methylpyridin-3-yl)methyl]-3-bromo-1H-pyrazole-4-carboxylate (122 mg), 4,4,5,5-tetramethyl-2-(prop-1-en-2-yl)-1,3,2-dioxaborolane (100 mg) and Cs$_2$CO$_3$ (195 mg) are dissolved in 1,4-dioxane (5 mL) and water (1 mL) under inert atmosphere.

1,1'-Bis(diphenylphosphino)ferrocenepalladium(II) dichloride DCM (7.4 mg) is added an the mixture stirred for 2 h at 100° C. The mixture is purified by HPLC on reversed phase (TFA, ACN, water) to give the title compound.

LC (Method 1): $t_R$=0.85 min; Mass spectrum (ESI$^+$): m/z=367 [M+H]$^+$.

Step 3: 1-[(6-{3-Azabicyclo[3.1.0]hexan-3-yl}-2-methyl pyridin-3-yl)methyl]-3-(2-hydroxypropan-2-yl)-1H- pyrazole-4-carboxylic acid; trifluoroacetic acid Ethyl 1-[(6-{3-azabicyclo[3.1.0]hexan-3-yl}-2-methylpyridin-3-yl)methyl]-3-(prop-1-en-2-yl)-1H-pyrazole-4-carboxylate; trifluoroacetic acid (135 mg) is dissolved in aqueous HCl (20 mL; 4 M), stirred at 50° C. for 16 h and concentrated in vacuo. The residue is dissolved in MeOH (5 mL) and aqueous NaOH (3 mL; 1 M) and stirred at room temperature for 1 h. The mixture is neutralized with aqueous HCl and purified by HPLC on reversed phase (TFA, ACN, water) to give the title compound.

LC (Method 1): $t_R$=0.72 min; Mass spectrum (ESI$^+$): m/z=357 [M+H]$^+$.

Intermediate 102

1-[(6-{3-Azabicyclo[3.1.0]hexan-3-yl}-2-methyl-pyridin-3-yl)methyl]-N-[(6R)-3-methyl-2-{[2-(trim-ethylsilyl)ethoxy]methyl}-2H,4H,5H,6H-cyclopenta[c]pyrazol-6-yl]-1H-1,2,4-triazole-3-carboxamide

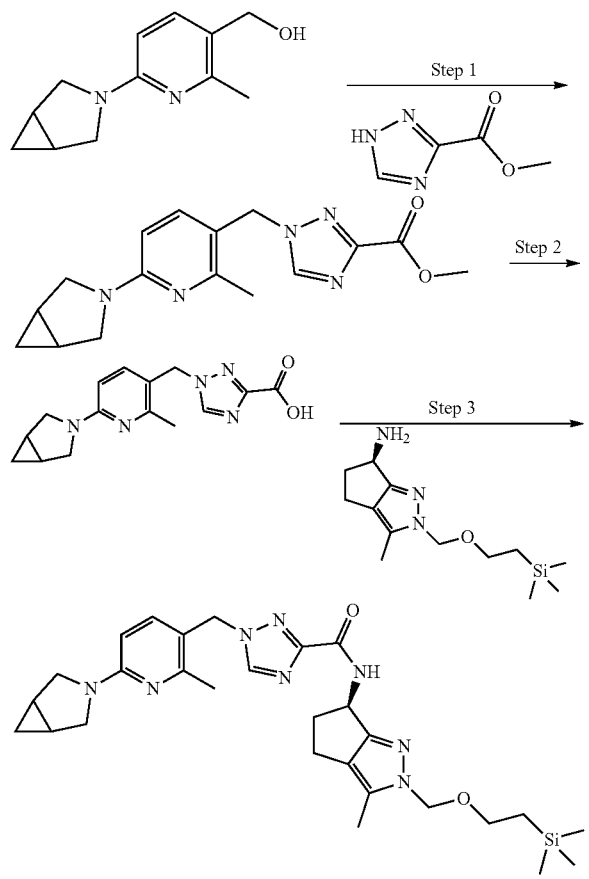

Step 1: Methyl 1-[(6-{3-azabicyclo[3.1.0]hexan-3-yl}-2-methylpyridin-3-yl)methyl]-1H-1,2,4-triazole-3-carboxylate (6-{3-Azabicyclo[3.1.0]hexan-3-yl}-2-methylpyridin-3-yl)methanol (100 mg) and methyl 1H-1,2,4-triazole-3-carboxylate (85 mg) are dissolved in ACN (10 mL), p-toluene-sulfonic acid (55 mg) is added and the mixture is stirred at 85° C. for 12 h. The mixture is purified by HPLC on reversed phase (ACN, water) to give the title compound.

LC (Method 1): $t_R$=0.63 min; Mass spectrum (ESI$^+$): m/z=314 [M+H]$^+$.

Step 2: 1-[(6-{3-Azabicyclo[3.1.0]hexan-3-yl}-2-methylpyridin-3-yl)methyl]-1H-1,2,4-triazole-3-carboxylic acid Methyl 1-[(6-{3-azabicyclo[3.1.0]hexan-3-yl}-2-methyl-pyridin-3-yl)methyl]-1H-1,2,4-triazole-3-carboxylate (53 mg) is dissolved in THF (1 mL) and EtOH (1 mL). A 4 M aqueous solution of KOH (106 μL) is added and the mixture is stirred for 2 h at 50° C. Then 4 M aqueous HCl (106 μL) is added and the solvents are evaporated in vacuo to give the title compound which is used directly in the next step.

LC (Method 1): $t_R$=0.55 min; Mass spectrum (ESI$^+$): m/z=300 [M+H]$^+$.

Step 3: 1-[(6-{3-Azabicyclo[3.1.0]hexan-3-yl}-2-methylpyridin-3-yl)methyl]-N-[(6R)-3-methyl-2-{[2-(trimethylsilyl)ethoxy]methyl}-2H,4H,5H,6H-cyclopenta[c]pyrazol-6-yl]-1H-1,2,4-triazole-3-carboxamide To a solution of 1-[(6-{3-azabicyclo[3.1.0]hexan-3-yl}-2-methylpyridin-3-yl)methyl]-1H-1,2,4-triazole-3-carboxylic acid (67 mg) in DMF (0.5 mL) are added DIPEA (86 μL) and O-(7-azabenzotriazol-1-yl)-N,N,N',N'-tetramethyl-uronium-hexafluorophosphat (HATU, 32 mg) and the mixture is stirred for 10 min. (6R)-3-Methyl-2-{[2-(trimethyl-silyl)ethoxy]methyl}-2H,4H,5H,6H-cyclopenta[c]pyrazol-6-amine (23 mg) is added and the mixture is stirred for 2 h. The mixture is partitioned between water and EtOAC. The aqueous phase is extracted with EtOAC. The combined organic phases are dried (MgSO$_4$) and the solvents are evaporated in vacuo to give the title compound which is directly used in the next step.

LC (Method 1): $t_R$=0.91 min; Mass spectrum (ESI$^+$): m/z=549 [M+H]$^+$.

Intermediate 103

Methyl 1-[(6-{3-azabicyclo[3.1.0]hexan-3-yl}-2-methylpyridin-3-yl)methyl]-3-{[(6R)-3-methyl-2-{[2-(trimethylsilyl)ethoxy]methyl}-2H,4H,5H,6H-cyclopenta[c]pyrazol-6-yl]carbamoyl}-1H-indole-5-carboxylate

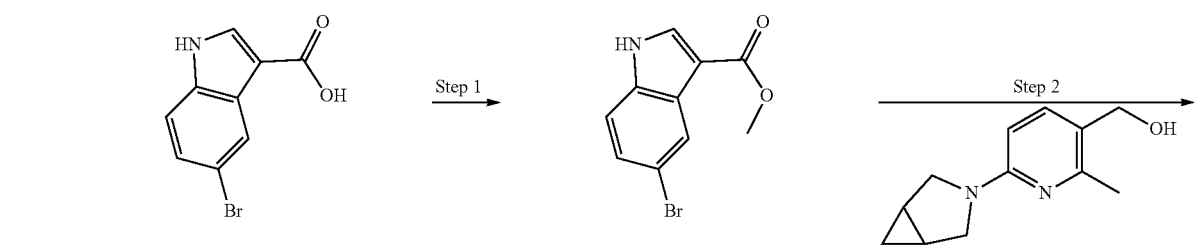

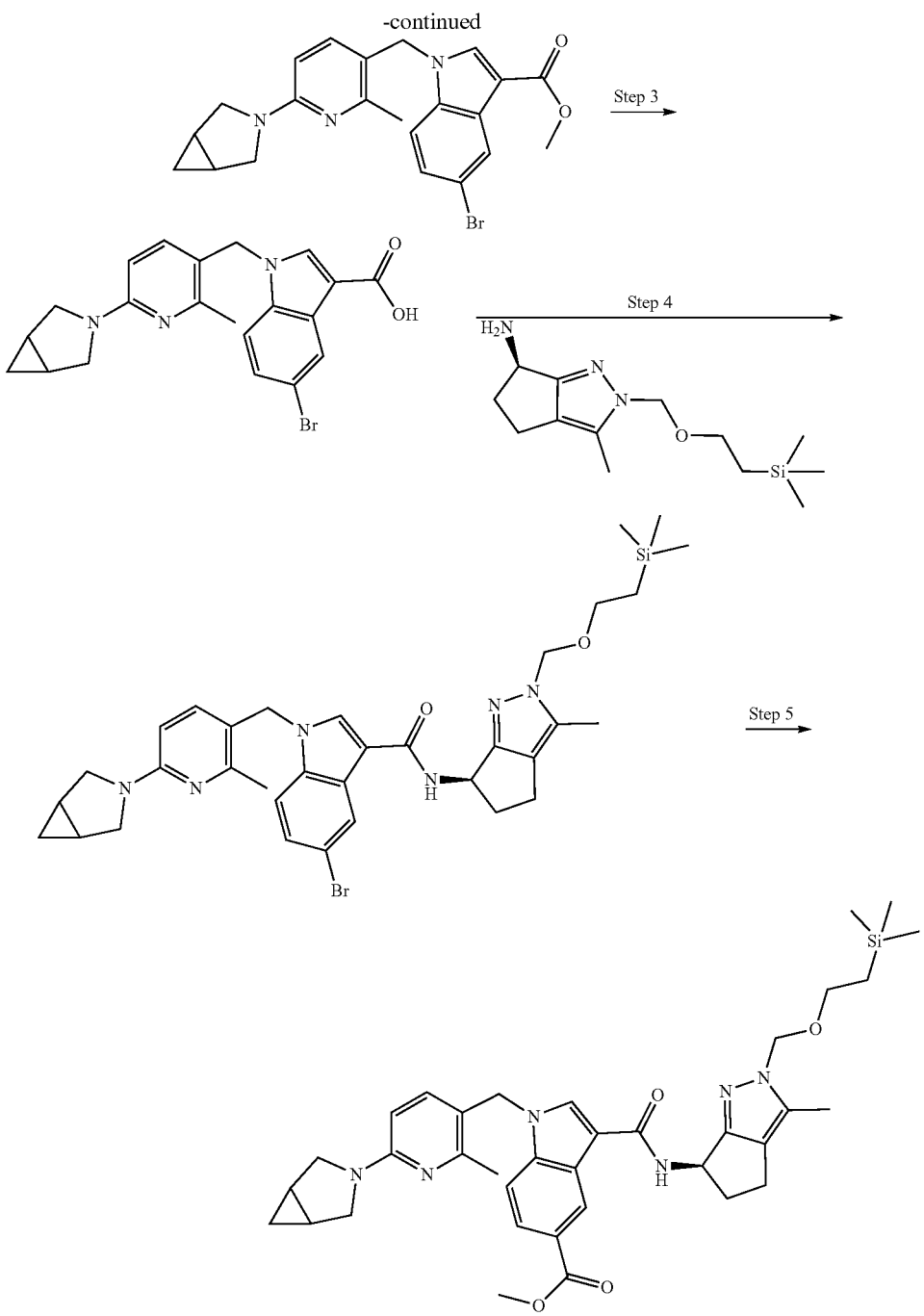

Step 1: Methyl 5-bromo-1H-indole-3-carboxylate

To a solution of 5-bromo-1H-indole-3-carboxylic acid (5.2 g) in MeOH (50 mL) is added dropwise thionylchloride (3.15 mL). The mixture is stirred for 12 h at room temperature. The solvent is evaporated in vacuo and the residue triturated with diethylether. The precipitate is collected by filtration to give the title compound.

LC (Method 1): $t_R$=0.94 min; Mass spectrum (ESI$^+$): m/z=254/256 (Br) [M+H]$^+$.

Step 2: Methyl 1-[(6-{3-azabicyclo[3.1.0]hexan-3-yl}-2-methylpyridin-3-yl)methyl]-5-bromo-1H-indole-3- carboxylate (6-{3-Azabicyclo[3.1.0]hexan-3-yl}-2-methylpyridin-3-yl)methanol (50 mg) is dissolved in THF (2 mL) and cooled to 0° C. Methyl 5-bromo-1H-indole-3-carboxylate (65 mg) and tributyl phosphine (85 μL) are added. Di-tert.-butyl-azodicarboxylate (70 mg) is slowly added portionwise and the mixture is stirred for 12 h. Saturated aqueous NaHCO$_3$ is added, the mixture is vigorously stirred for 10 min and then extracted with EtOAC. The organic phase is washed with brine, dried (MgSO$_4$) and concentrated in vacuo. The residue is chromatographed on silica gel (DCM/MeOH 95:5→80:20) to give the title compound.

LC (Method 1): $t_R$=0.95 min; Mass spectrum (ESI+): m/z=440/442 (Br) [M+H]+.

Step 3: 1-[(6-{3-Azabicyclo[3.1.0]hexan-3-yl}-2-methylpyridin-3-yl)methyl]-5-bromo-1H-indole-3-carboxylic acid A mixture of methyl 1-[(6-{3-azabicyclo[3.1.0]hexan-3-yl}-2-methylpyridin-3-yl)methyl]-5-bromo-1H-indole-3-carboxylate (33 mg), 1 M solution of KOH in EtOH (150 µL) and THF (2 mL) is stirred for 12 h at 90° C. Then 1 M aqueous NaOH (150 µL) is added and the mixture is stirred for 12 h at 90° C. The mixture is diluted with water, neutralized by addition of acetic acid and extracted three times with DCM/isopropanol 9:1. The combined organic phases are washed with brine, dried (MgSO4) and evaporated in vacuo to give the title compound which is directly used in the next step.

LC (Method 1): $t_R$=0.86 min; Mass spectrum (ESI): m/z=426/428 (Br) [M+H]+.

Step 4: 1-[(6-{3-Azabicyclo[3.1.0]hexan-3-yl}-2-methylpyridin-3-yl)methyl]-5-bromo-N-[(6R)-3-methyl-2-{[2-(trimethylsilyl)ethoxy]methyl}-2H,4H,5H,6H-cyclopenta[c]pyrazol-6-yl]-1H-indole-3-carboxamide To a solution of 1-[(6-{3-azabicyclo[3.1.0]hexan-3-yl}-2-methylpyridin-3-yl)methyl]-5-bromo-1H-indole-3-carboxylic acid (30 mg) in DMF (3 mL) are added DIPEA (35 µL) and O-(7-azabenzotriazol-1-yl)-N,N,N',N'-tetramethyluronium-hexafluorophosphat (HATU, 40 mg) and the mixture is stirred for 5 min. (6R)-3-Methyl-2-{[2-(trimethylsilyl)ethoxy]methyl}-2H,4H,5H,6H-cyclopenta[c]pyrazol-6-amine (22 mg) is added and the mixture is stirred for 1 h. The mixture is partitioned between water and EtOAC. The aqueous phase is extracted with ethylacetate. The combined organic phases are dried (MgSO4) and the solvents are evaporated in vacuo. The residue is chromatographed on silica gel (DCM/MeOH 98:2-90:10) to give the title compound.

LC (Method 1): $t_R$=1.02 min; Mass spectrum (ESI): m/z=675/677 (Br) [M+H]+.

Step 5: Methyl 1-[(6-{3-azabicyclo[3.1.0]hexan-3-yl}-2-methylpyridin-3-yl)methyl]-3-{[(6R)-3-methyl-2-{[2-(trimethylsilyl)ethoxy]methyl}-2H,4H,5H,6H-cyclopenta[c]pyrazol-6-yl]carbamoyl}-1H-indole-5-carboxylate A solution of 1-[(6-{3-azabicyclo[3.1.0]hexan-3-yl}-2-methylpyridin-3-yl)methyl]-5-bromo-N-[(6R)-3-methyl-2-{[2-(trimethylsilyl)ethoxy]methyl}-2H,4H,5H,6H-cyclopenta[c]pyrazol-6-yl]-1H-indole-3-carboxamide (25 mg) and triethylamine (50 µL) in MeOH (10 mL) is purged for 10 min with argon. 1,1'-Bis(diphenylphosphino)ferrocene-palladium(II) dichloride (10 mg) is added and the mixture is stirred for 20 h at 100° C. under an carbon monoxide atmosphere (8 bar). Then the solvents are evaporated in vacuo and the residue is chromatographed on silica gel (petrole ether/EtOAC 90:10→0:100) to give the title compound.

LC (Method 1): $t_R$=0.97 min; Mass spectrum (ESI+): m/z=655 [M+H]+.

Intermediate 104

(6R)-3-Methyl-1H,4H,5H,6H-cyclopenta[c]pyrazol-6-amine dihydrochloride

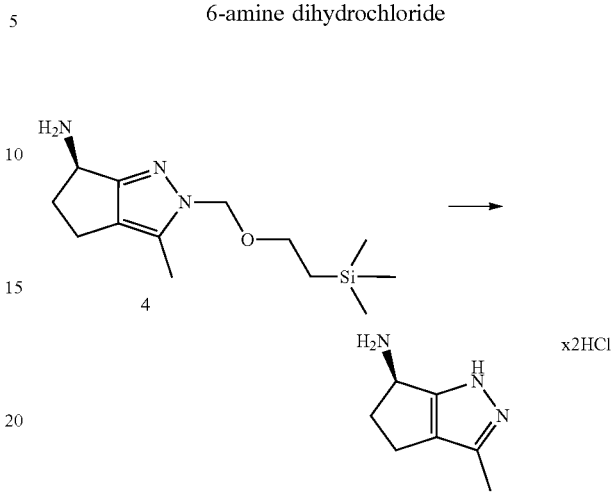

A solution of (6R)-3-methyl-2-{[2-(trimethylsilyl)ethoxy]methyl}-2H,4H,5H,6H-cyclopenta[c]pyrazol-6-amine (1.58 g) in MeOH (20 mL) is treated with 4 N HCl in 1,4-dioxane (6 mL) and stirred for 12 h. The reaction mixture is concentrated under vacuum and the residue is dissolved in concentrated hydrochloric acid (10 mL). The mixture is sonicated for 10 min and concentrated under vacuum. The residue is dissolved in water and ACN and the solvents are removed by lyophilization to give the title compound, which is directly used in the next step.

Mass spectrum (ESI+): m/z=138 [M+H]+.

Intermediate 105

5-[(6-{3-Azabicyclo[3.1.0]hexan-3-yl}-2-methylpyridin-3-yl)methyl]-1H-pyrrole-2-carboxylic acid

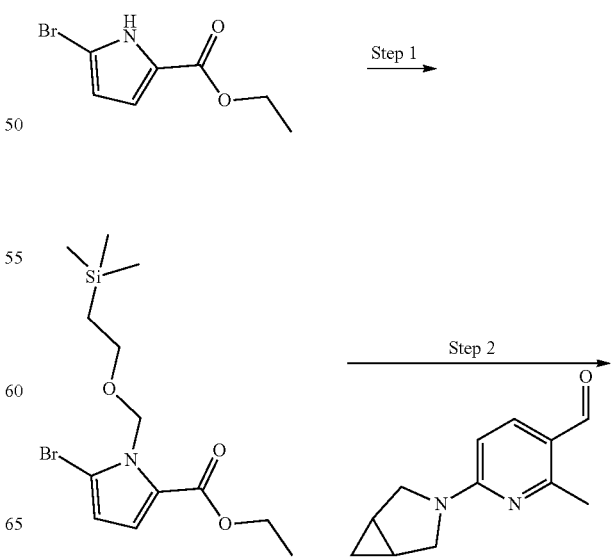

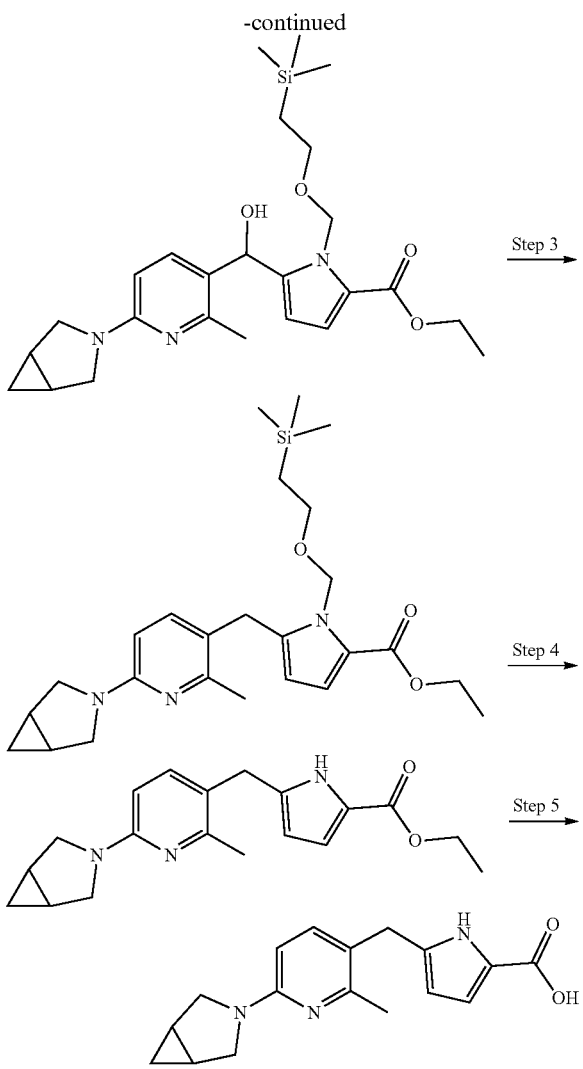

Step 1: Ethyl 5-bromo-1-{[2-(trimethylsilyl)ethoxy]methyl}-1H-pyrrole-2-carboxylate Ethyl 5-bromo-1H-pyrrole-2-carboxylate (1 g) is dissolved in THF (15 mL), treated with triethylamine (767 μL) and stirred for 10 min. 2-(Trimethylsilyl)ethoxymethylchloride (SEM-Cl, 846 μL) is added and the mixture is stirred for 1 h. Triethylamine (140 μL) and 2-(trimethylsilyl)ethoxymethylchloride (SEM-Cl, 160 μL) are added and stirring is continued for 45 min. The mixture is partitioned between water and EtOAC. The aqueous phase is extracted with EtOAC and the combined organic phases are dried (MgSO$_4$). The solvents are evaporated in vacuo and the residue is chromatographed on silica gel (petrole ether/EtOAC 100:0→95:5) to give the title compound.

LC (Method 1): $t_R$=1.30 min; Mass spectrum (ESI): m/z=370 [M+Na]$^+$.

Step 2: Ethyl 5-[(6-{3-azabicyclo[3.1.0]hexan-3-yl}-2-methylpyridin-3-yl)(hydroxy)methyl]-1-{[2-(trimethylsilyl)ethoxy]methyl}-1H-pyrrole-2-carboxylate To a solution of ethyl 5-bromo-1-{[2-(trimethylsilyl)ethoxy]methyl}-1H-pyrrole-2-carboxylate (750 mg) in THF (9 mL) is added dropwise at 0° C. isopropylmagnesuim chloride-lithium chloride complex (iPrMgClxLiCl, 1.71 mL of a 1.3 M solution in THF). The mixture is stirred for 30 min at 0° C. and then allowed to warm to room temperature. Isopropylmagnesuim chloride-lithium chloride complex (iPrMgClxLiCl, 170 μL of a 1.3 M solution in THF) is added the mixture is stirred for 10 min and then treated with a solution of 6-{3-azabicyclo[3.1.0]hexan-3-yl}-2-methylpyridine-3-carbaldehyde (450 mg) in THF (4.5 mL). The mixture is stirred for 12 h and then partitioned between saturated aqueous NH$_4$Cl and EtOAC. The aqueous is extracted with EtOAC and the combined organic phases are dried (MgSO$_4$). The solvents are evaporated in vacuo and the residue is purified by HPLC on reversed phase (ACN, water) to give the title compound.

LC (Method 1): $t_R$=0.98 min; Mass spectrum (ESI$^+$): m/z=472 [M+H]$^+$.

Step 3: Ethyl 5-[(6-{3-azabicyclo[3.1.1]hexan-3-yl}-2-methylpyridin-3-yl)methyl]-1-{[2-(trimethylsilyl)ethoxy]methyl}-1H-pyrrole-2-carboxylate Ethyl 5-[(6-{3-azabicyclo[3.1.0]hexan-3-yl}-2-methylpyridin-3-yl)(hydroxy)methyl]-1-{[2-(trimethylsilyl)ethoxy]-methyl}-1H-pyrrole-2-carboxylate (520 mg) is dissolved in 1,2-dichloroethane (8 mL) and cooled to 0° C. Triethylsilane (711 μL) and TFA (300 μL) are added and the mixture is stirred for 2 h while warming room temperature. Triethylsilane (360 μL) and TFA (150 μL) are added and the mixture is stirred for additional 2 h. The mixture is carefully partitioned between saturated aqueous NaHCO$_3$ and DCM. The phases are separated and the aqueous phase is extracted with DCM. The combined organic phases are dried (MgSO$_4$) and concentrated in vacuo to give the title compound.

LC (Method 1): $t_R$=1.04 min; Mass spectrum (ESI$^+$): m/z=456 [M+H]$^+$.

Step 4: Ethyl 5-[(6-{3-azabicyclo[3.1.0]hexan-3-yl}-2-methylpyridin-3-yl)methyl]-1H-pyrrole-2-carboxylate A mixture of ethyl 5-[(6-{3-azabicyclo[3.1.0]hexan-3-yl}-2-methylpyridin-3-yl)methyl]-1-{[2-(trimethylsilyl)ethoxy]-methyl}-1H-pyrrole-2-carboxylate (520 mg), DCM (6 mL) and TFA (3 mL) is stirred for 3.5 h at room temperature. The solvents are evaporated in vacuo, the residue is dissolved in 7 M NH$_3$ in MeOH and the mixture is stirred for 18 h at room temperature. The solvents are evaporated in vacuo and the residue is purified by HPLC on reversed phase (ACN, water) to give the title compound.

LC (Method 1): $t_R$=0.81 min; Mass spectrum (ESI$^+$): m/z=326 [M+H]$^+$.

Step 5: 5-[(6-{3-Azabicyclo[3.1.0]hexan-3-yl}-2-methylpyridin-3-yl)methyl]-1H-pyrrole-2-carboxylic acid A mixture of ethyl 5-[(6-{3-azabicyclo[3.1.0]hexan-3-yl}-2-methylpyridin-3-yl)methyl]-1H-pyrrole-2-carboxylate (150 mg), 4 M aqueous NaOH (500 μL), THF (2 mL) and MeOH (2 mL) is stirred at 85° C. for 12 h. After cooling to room temperature 4 M aqueous HCl (500 μL) is added and the mixture is partitioned EtOAC and brine. The phases are separated and the aqueous phase is extracted three times with EtOAC. The combined organic phases are dried (MgSO$_4$) and concentrated in vacuo to give the title compound.

LC (Method 1): t$_R$=0.70 min; Mass spectrum (ESI$^+$): m/z=298 [M+H]$^+$.

Intermediates 108-109 are prepared in analogy to Intermediate 71:

| Intermediate | Structure | t$_R$ | Mass spectrum (ESI+): m/z [M + H]$^+$ | LC Method |
|---|---|---|---|---|
| 108 | 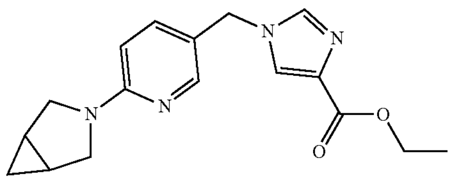 [SMILES: CCOC(=O)c1cn(Cc2ccc(N3CC4CC4C3)nc2)cn1] | 0.89 | 313 | Method 2 |
| 109 | 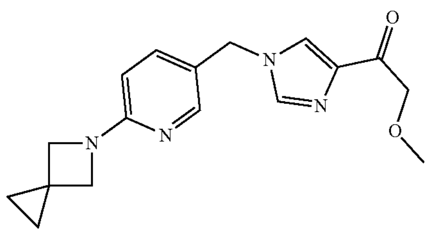 [SMILES: COCC(=O)c1cn(Cc2ccc(N3CC4(CC4)C3)nc2)cn1] | 0.88 | 313 | Method 2 |

| Intermediate | Name | Name of Starting Material 1 | Name of Starting Material 2 |
|---|---|---|---|
| 108 | Ethyl 1-[(6-{3-azabicyclo [3.1.0]-hexan-3-yl}pyridin-3-yl)methyl]-1H-imidazole-4-carboxylate | (6-{3-Azabicyclo [3.1.0]-hexan-3-yl} pyridin-3-yl) methanol | Ethyl 1H-imidazole-4-carboxylate |
| 109 | Ethyl 1-[(6-{5-azaspiro [2.3] hexan-5-yl}pyridin-3-yl) methyl]-1H-imidazole-4-carboxylate | (6-{5-Azaspiro[2.3] hexan-5-yl}pyridin-3-yl)methanol | Ethyl 1H-imidazole-4-carboxylate |

Intermediates 110-111 are prepared in analogy to Intermediate 41:

| Intermediate | Structure | t$_R$ | Mass spectrum (ESI+): m/z [M + H]$^+$ | LC Method |
|---|---|---|---|---|
| 110 | 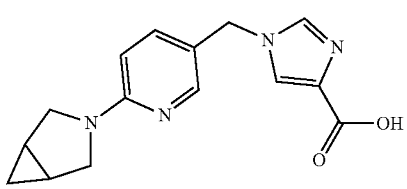 [SMILES: O=C(O)c1cn(Cc2ccc(N3CC4CC4C3)nc2)cn1] | 0.89 | 313 | Method 2 |
| 111 | 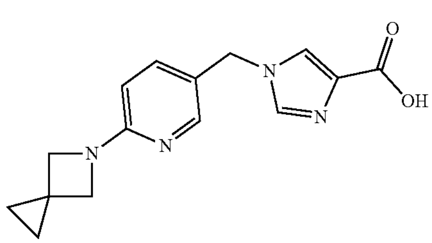 [SMILES: O=C(O)c1cn(Cc2ccc(N3CC4(CC4)C3)nc2)cn1] | 0.88 | 313 | Method 2 |

| Intermediate | Structure | $t_R$ | Mass spectrum (ESI+): m/z [M + H]⁺ | LC Method |
|---|---|---|---|---|
| 112 | 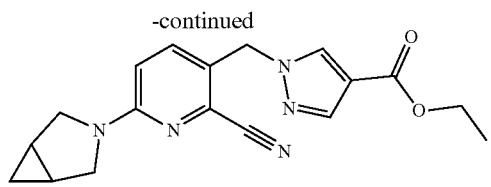 | 0.66 | 310 | Method 2 |

| Intermediate | Name | Name of Starting Material |
|---|---|---|
| 110 | 1-[(6-{3-Azabicyclo[3.1.0]hexan-3-yl}pyridin-3-yl)methyl]-1H-imidazole-4-carboxylic acid | Ethy 1-[(6-{3-azabicyclo [3.1.0]hexan-3-yl}-pyridin-3-yl)methyl]-1H-imidazole-4-carboxylate |
| 111 | 1-[(6-{5-Azaspiro[2.3]hexan-5-yl}pyridin-3-yl)methyl]-1H-imidazole-4-carboxylic acid | Ethyl 1-[(6-{5-azaspiro[2.3] hexan-5-yl}-pyridin-3-yl)methyl]-1H-imidazole-4-carboxylate |
| 112 | 1-[(6-{3-Azabicyclo[3.1.0]hexan-3-yl}-2-cyanopyridin-3-yl)methyl]-1H-pyrazole-4-carboxylic acid | Ethyl 1-[(6-{3-azabicyclo[3.1.0]hexan-3-yl}-2-cyanopyridin-3-yl)methyl]-1H-pyrazole-4-carboxylate |

Intermediate 113

Ethyl 1-[(6-{3-azabicyclo[3.1.0]hexan-3-yl}-2-cyanopyridin-3-yl)methyl]-1H-pyrazole-4-carboxylate

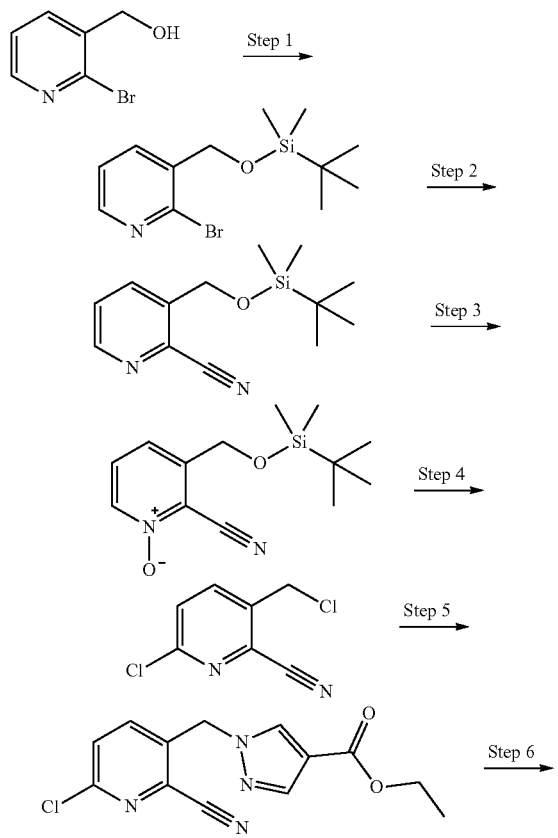

Step 1: 2-Bromo-3-{[(tert-butyldimethylsilyl)oxy]methyl}pyridine

To a mixture of (2-bromopyridin-3-yl)methanol (25.0 g) and imidazole (18.1 g) in DMF (300 mL) is added tert-butyl-dimethyl-silylchloride (23.9 g) at 20° C. under nitrogen, and then the mixture is stirred at 20° C. for 1 h. The mixture is diluted with water (500 mL) and extracted with EtOAC. The combined organic layers are washed with brine, dried (NaSO₄), filtered and concentrated under reduced pressure. The residue is purified by chromatography on silica gel (petroleum ether/EtOAC 50:1→10:1) to give the title compound.

TLC: $R_f$=0.8 (silica; petroleum ether/EtOAC 2:1).

Step 2: 3-{[(Tert-butyldimethylsilyl)oxy]methyl}pyridine-2-carbonitrile

A mixture of 2-bromo-3-{[(tert-butyldimethylsilyl)oxy]methyl}pyridine (8.0 g) and Zn(CN)₂ (6.2 g) in DMF (100 mL) is purged with nitrogen for 5 min. Pd(PPh₃)₄(1.5 g) is added in portions at 20° C. under nitrogen, and then the mixture is heated to 120° C. and stirred for 4 h. The mixture is filtered and the filtrate is concentrated under reduced pressure. The residue is purified by chromatography on silica gel (petroleum ether/EtOAC 100:1→10:1) to give the title compound.

TLC: $R_f$=0.4 (silica; petroleum ether/EtOAC 5:1).

Step 3: 3-{[(Tert-butyldimethylsilyl)oxy]methyl}-2-cyanopyridin-1-ium-1-olate To a mixture of 3-{[(tert-butyldimethylsilyl)oxy]methyl}pyridine-2-carbonitrile (4.5 g) in CHCl$_3$ (50 mL) is added 3-chloroperbenzoic acid (4.67 g) in portions at 20° C. under nitrogen. The mixture is heated to 70° C. and stirred for 16 h. Saturated aqueous NaHCO$_3$ (10 mL) is added to the reaction mixture. The mixture is diluted with water (100 mL) and extracted three times with DCM. The combined organic layers are washed with brine, dried (Na$_2$SO$_4$), filtered and concentrated under reduced pressure. The residue is purified by chromatography on silica gel (petroleum ether/EtOAC 50:1→5:1) to give the title compound.

TLC: R$_f$=0.1 (silica; petroleum ether/EtOAC 5:1).

Step 4: 6-Chloro-3-(chloromethyl)pyridine-2-carbonitrile

A mixture of 3-{[(tert-butyldimethylsilyl)oxy]methyl}-2-cyanopyridin-1-ium-1-olate (3.5 g) in POCl$_3$ (30 mL) is stirred at 80° C. for 1 hour and concentrated under reduced pressure. The mixture is added to saturated aqueous NaHCO$_3$ (10 mL) and then diluted with water (100 mL) and extracted three times with DCM. The combined organic layers are washed with brine, dried (Na$_2$SO$_4$), filtered and concentrated under reduced pressure. The residue is purified by chromatography on silica gel (petroleum ether/EtOAC 50:1→2:1) to give the title compound.

Mass spectrum (ESI$^+$): m/z=187/189 (Cl) [M+H]$^+$.

Step 5: Ethyl 1-[(6-chloro-2-cyanopyridin-3-yl)methyl]-1H-pyrazole-4-carboxylate 6-Chloro-3-(chloromethyl)pyridine-2-carbonitrile (37 mg) and ethyl 1H-pyrazole-4-carboxylate (30 mg) are dissolved in THF (2 mL), Cs$_2$CO$_3$ (100 mg) is added and the mixture stirred for 8 h at room temperature. The mixture is purified by HPLC on reversed phase (ACN, water) to give the title compound.

LC (Method 2): t$_R$=0.94 min; Mass spectrum (ESI): m/z=291/293 (Cl) [M+H]$^+$.

Step 6: Ethyl 1-[(6-{3-azabicyclo[3.1.0]hexan-3-yl}-2-cyanopyridin-3-yl)methyl]-1H-pyrazole-4-carboxylate Ethyl 1-[(6-chloro-2-cyanopyridin-3-yl)methyl]-1H-pyrazole-4-carboxylate (30 mg), 3-azabicyclo[3.1.0]hexane hydrochloride (25 mg) and KHCO$_3$ (60 mg) are suspended in DMSO (1 mL) and stirred at 50° C. for 16 h and additional 8 h at 70° C. The mixture is purified by HPLC on reversed phase (ACN, water) to give the title compound.

LC (Method 2): t$_R$=1.05 min; Mass spectrum (ESI): m/z=338 (Cl) [M+H]$^+$.

Intermediate 114

(6-{5-Azaspiro[2.3]hexan-5-yl}pyridin-3-yl)methanol

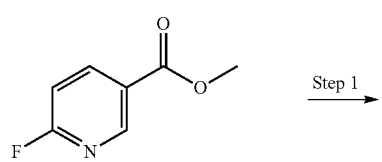

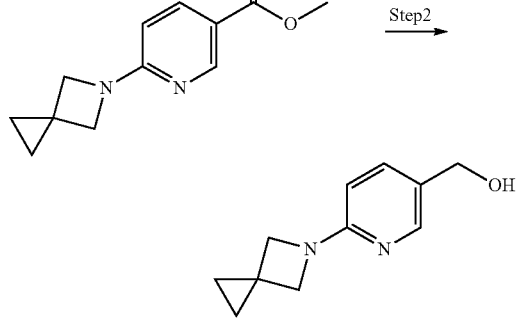

Step 1: Methyl 6-{5-azaspiro[2.3]hexan-5-yl}pyridine-3-carboxylate

A mixture of methyl 6-fluoropyridine-3-carboxylate (155 mg), 5-azaspiro[2.3]hexane trifluoroacetate (300 mg) and K$_2$CO$_3$ (500 mg) in DMF (5 mL) is stirred for 12 h at room temperature. The mixture is filtered, concentrated in vacuo and purified by HPLC on reversed phase (ACN, water) to give the title compound.

LC (Method 1): t$_R$=0.69 min; Mass spectrum (ESI): m/z=219 [M+H]$^+$.

Step 2: (6-{5-Azaspiro[2.3]hexan-5-yl}pyridin-3-yl)methanol

To a solution methyl 6-{5-azaspiro[2.3]hexan-5-yl}pyridine-3-carboxylate (172 mg) in THF (3 mL) are added LiBH$_4$ (27 mg) and MeOH (100 μL). The mixture is stirred for 12 h at 60° C. LiBH$_4$ (5 mg) is added and the mixture is stirred for 2 h at 60° C. LiBH$_4$ (5 mg) is added and the mixture is stirred for 1 h at 6000. The mixture is cooled to room temperature, treated with 1 M aqueous HCl (1.5 mL), concentrated in vacuo and purified by HPLC on reversed phase (ACN, water) to give the title compound.

LC (Method 2): t$_R$=0.76 min; Mass spectrum (ESI$^+$): m/z=191 [M+H]$^+$.

Intermediate 115

6-{3-Azabicyclo[3.1.0]hexan-3-yl}pyridin-3-yl)methanol

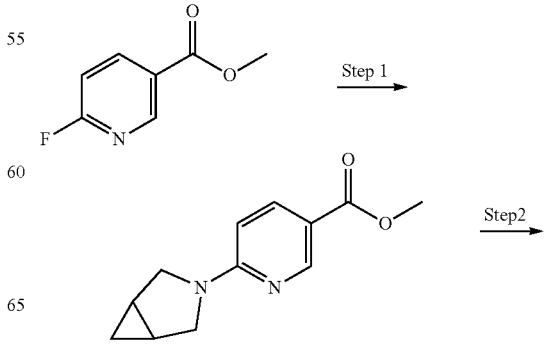

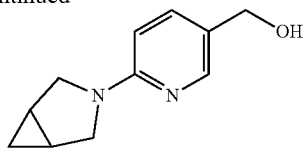

Step 1: Methyl 6-{3-azabicyclo[3.1.0]hexan-3-yl}pyridine-3-carboxylate

A mixture of methyl 6-fluoropyridine-3-carboxylate (6 g), 3-azabicyclo[3.1.0]hexane hydrochloride (4.7 g) and K₂CO₃ (14 g) in DMF (60 mL) is stirred for 12 h at room temperature. The mixture is diluted with water. The precipitate is collected by filtration, washed with water and dried in vacuo to give the title compound.

LC (Method 1): $t_R$=0.66 min; Mass spectrum (ESI⁺): m/z=219 [M+H]⁺.

Step 2: 6-{3-Azabicyclo[3.1.0]hexan-3-yl}pyridin-3-yl)methanol

To a solution methyl 6-{3-azabicyclo[3.1.0]hexan-3-yl}pyridine-3-carboxylate (8 g) in THF (60 mL) are added LiBH₄ (20 mL of a 2 M solution in THF) and MeOH (3 mL). The mixture is stirred for 12 h at 60° C. LiBH₄ (5 mL of a 2 M solution in THF) is added and the mixture is stirred for 2 h at 60° C. The mixture is cooled to room temperature, treated with water (5 mL), concentrated in vacuo and partitioned between water and EtOAC. The aqueous phase is extracted with EtOAC and the combined organic phases are dried (MgSO₄). The residue is dissolved in DCM and filtered over silica gel, which is further rinsed with DCM. The combined organic phases are concentrated in vacuo to give the title compound.

LC (Method 2): $t_R$=0.79 min; Mass spectrum (ESI⁺): m/z=191 [M+H]⁺.

Synthesis of Examples

Example 1

1-[(6-{3-Azabicyclo[3.1.0]hexan-3-yl}-2-methyl-pyridin-3-yl)methyl]-N-{3-methyl-1H,4H,5H,6H-cyclopenta[c]pyrazol-6-yl}-1H-pyrazole-4-carboxamide

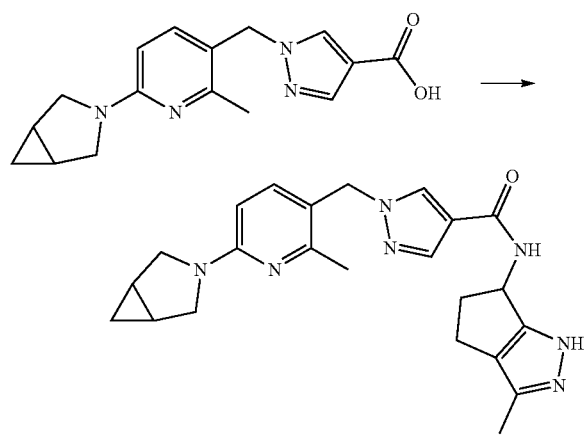

A solution of 1-[(6-{3-azabicyclo[3.1.0]hexan-3-yl}-2-methylpyridin-3-yl)methyl]-1H-pyrazole-4-carboxylic acid (17 mg), DIPEA (40 µL) and O-(7-azabenzotriazol-1-yl)-N,N,N',N'-tetramethyluronium-hexafluorophosphat (HATU, 22 mg) in DMF (2 mL) is stirred for 5 min. 3-Methyl-1H,4H,5H,6H-cyclopenta[c]pyrazol-6-amine dihydrochloride (10 mg) is added and the mixture is stirred for 1 h. The mixture is purified by HPLC on reversed phase (ACN, water) to give the title compound.

LC (Method 2): $t_R$=0.94 min; Mass spectrum (ESI⁺): m/z=418 [M+H]⁺.

Example 2

1-[(6-{3-Azabicyclo[3.1.0]hexan-3-yl}-2-methyl-pyridin-3-yl)methyl]-N-[(6S)-3-methyl-1H,4H,5H,6H-cyclopenta[c]pyrazol-6-yl]-1H-pyrazole-4-carboxamide

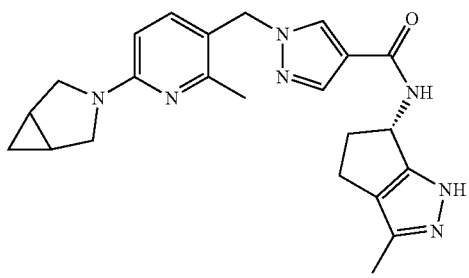 [SMILES: Cc1nc(N2CC3CC3C2)ccc1Cn1cc(C(=O)N[C@H]2CCc3c(C)n[nH]c32)cn1]

The title compound is obtained from the racemic mixture upon SFC separation on chiral phase (column: CHIRAL ART® Amylose SA, 5 µm, 250 mm×20 mm; eluent: scCO₂/(20 mM NH₃ in MeOH) 70:30, 40° C., 120 bar, 10 mL/min); $t_R$=4.1 min.

LC (Method 1): $t_R$=0.66 min; Mass spectrum (ESI⁺): m/z=418 [M+H]⁺.

Example 3

1-[(6-{3-Azabicyclo[3.1.0]hexan-3-yl}-2-methyl-pyridin-3-yl)methyl]-N-[(6R)-3-methyl-1H,4H,5H,6H-cyclopenta[c]pyrazol-6-yl]-1H-pyrazole-4-carboxamide

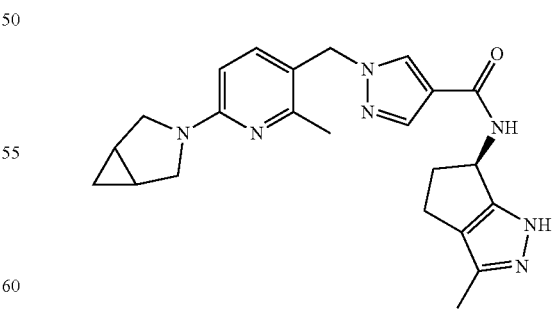

The title compound is obtained from the racemic mixture upon SFC separation on chiral phase (column: CHIRAL ART® Amylose SA, 5 µm, 250 mm×20 mm; eluent: scCO₂/(20 mM NH₃ in MeOH) 70:30, 40° C., 120 bar, 10 mL/min); $t_R$=3.5 min.

LC (Method 1): $t_R$=0.66 min; Mass spectrum (ESI⁺): m/z=418 [M+H]⁺.

Example 4

1-[(6-{6,6-Difluoro-3-azabicyclo[3.1.0]hexan-3-yl}-2-methylpyridin-3-yl)methyl]-N-[(6S)-3-methyl-1H,4H,5H,6H-cyclopenta[c]pyrazol-6-yl]-1H-pyrazole-4-carboxamide

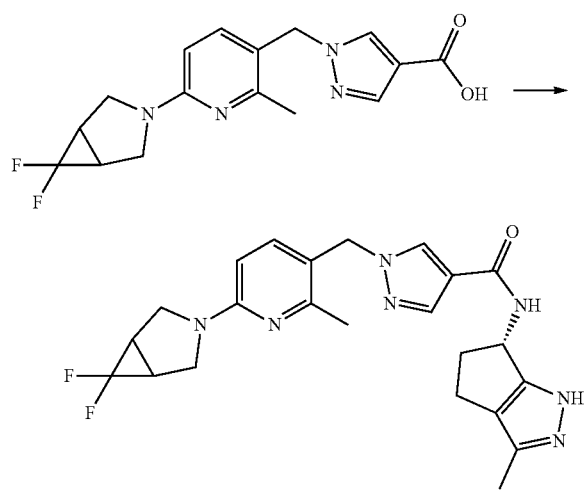

A solution of 1-[(6-{6,6-difluoro-3-azabicyclo[3.1.0]hexan-3-yl}-2-methylpyridin-3-yl)methyl]-1H-pyrazole-4-carboxylic acid (24 mg), DIPEA (40 μL) and O-(7-azabenzotriazol-1-yl)-N,N,N',N'-tetramethyluronium-hexafluorophosphat (HATU, 30 mg) in DMF (2 mL) is stirred for 5 min. (6S)-3-Methyl-1H,4H,5H,6H-cyclopenta[c]pyrazol-6-amine (10 mg) is added and the mixture is stirred for 3 h. The mixture is purified by HPLC on reversed phase (ACN, water) to give the title compound.

LC (Method 2): $t_R$=0.92 min; Mass spectrum (ESI⁺): m/z=454 [M+H]⁺.

Example 5

1-[(6-{6,6-Difluoro-3-azabicyclo[3.1.0]hexan-3-yl}-2-methylpyridin-3-yl)methyl]-N-[(6R)-3-methyl-1H,4H,5H,6H-cyclopenta[c]pyrazol-6-yl]-1H-pyrazole-4-carboxamide

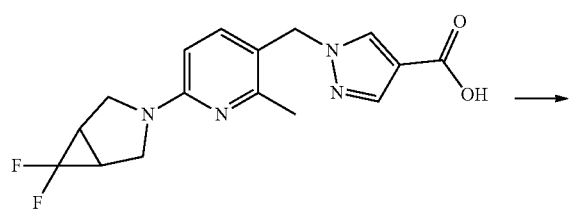

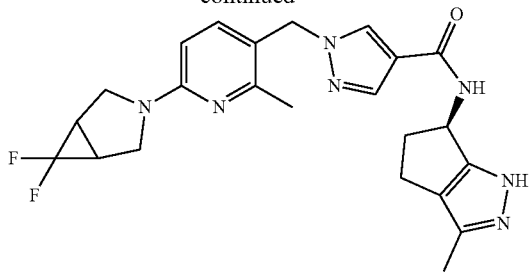

A solution of 1-[(6-{6,6-difluoro-3-azabicyclo[3.1.0]hexan-3-yl}-2-methylpyridin-3-yl)methyl]-1H-pyrazole-4-carboxylic acid (24 mg), DIPEA (40 μL) and O-(7-azabenzotriazol-1-yl)-N,N,N',N'-tetramethyluronium-hexafluorophosphat (HATU, 30 mg) in DMF (2 mL) is stirred for 5 min. (6R)-3-Methyl-1H,4H,5H,6H-cyclopenta[c]pyrazol-6-amine (10 mg) is added and the mixture is stirred for 3 h. The mixture is purified by HPLC on reversed phase (ACN, water) to give the title compound.

LC (Method 2): $t_R$=0.92 min; Mass spectrum (ESI⁺): m/z=454 [M+H]⁺.

Alternatively, the compound is obtained from 1-[(6-{6,6-difluoro-3-azabicyclo[3.1.0]hexan-3-yl}-2-methylpyridin-3-yl)methyl]-N-[(6R)-3-methyl-2-{[2-(trimethylsilyl)ethoxy]methyl}-2H,4H,5H,6H-cyclopenta[c]pyrazol-6-yl]-1H-pyrazole-4-carboxamide upon cleaving off the protective group, 2-(trimethylsilyl)ethyloxymethyl, using TFA in DCM at ambient temperature.

Example 6

4-[(6-{3-Azabicyclo[3.1.0]hexan-3-yl}-2-methylpyridin-3-yl)methyl]-N-[(6R)-3-methyl-1H,4H,5H,6H-cyclopenta[c]pyrazol-6-yl]thiophene-2-carboxamide

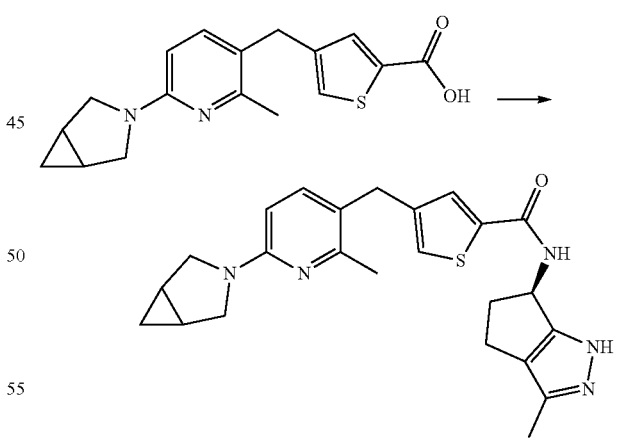

A solution of 4-[(6-{3-Azabicyclo[3.1.0]hexan-3-yl}-2-methylpyridin-3-yl)methyl]thiophene-2-carboxylic acid (50 mg), DIPEA (82 μL) and O-(7-azabenzotriazol-1-yl)-N,N,N',N'-tetramethyluronium-hexafluorophosphat (HATU, 67 mg) in DMF (1.5 mL) is stirred for 15 min. Thereto a solution of (6R)-3-methyl-1H,4H,5H,6H-cyclopenta[c]pyrazol-6-amine (23 mg) in DMF (1 mL) is added and the mixture is stirred for 1.5 h. The mixture is purified by HPLC on reversed phase (ACN, water) to give the title compound.

LC (Method 2): $t_R$=1.06 min; Mass spectrum (ESI⁺): m/z=434 [M+H]⁺.

Example 7

4-[(6-{3-Azabicyclo[3.1.0]hexan-3-yl}-2-methyl-pyridin-3-yl)methyl]-N-[(6R)-3-methyl-1H,4H,5H,6H-cyclopenta[c]pyrazol-6-yl]-1H-pyrrole-2-carboxamide

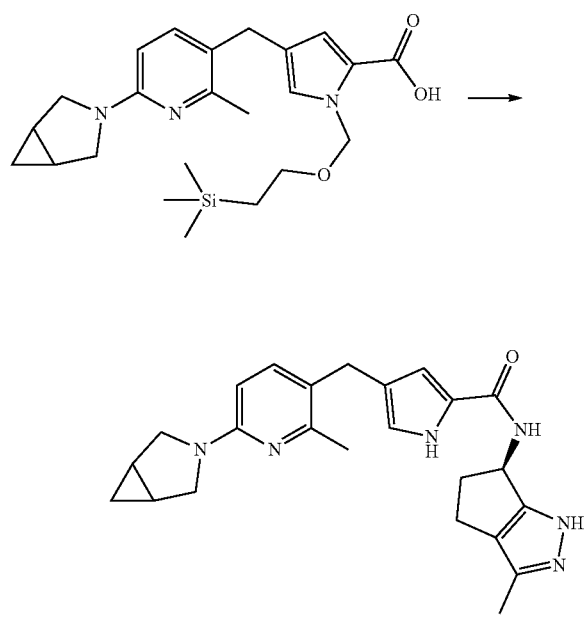

A solution of 4-[(6-{3-azabicyclo[3.1.0]hexan-3-yl}-2-methylpyridin-3-yl)methyl]-1-{[2-(trimethylsilyl)ethoxy]methyl}-1H-pyrrole-2-carboxylic acid (50 mg), DIPEA (60 µL) and O-(7-azabenzotriazol-1-yl)-N,N,N',N'-tetramethyl-uronium-hexafluorophosphat (HATU, 49 mg) in DMF (1.5 mL) is stirred for 15 min. Thereto a solution of (6R)-3-methyl-1H,4H,5H,6H-cyclopenta[c]pyrazol-6-amine (16 mg) in DMF (1 mL) is added and the mixture is stirred for 1.5 h. The mixture is partitioned between water and diethylether. The phases are separated and the aqueous phase is extracted with diethylether. The combined organic phases are dried (MgSO₄) and concentrated in vacuo. The residue is dissolved in DCM (3 mL) and TFA (1.5 mL). After stirring for 1.5 h the solvents are evaporated in vacuo and the residue is dissolved in MeOH (2 mL), 4 M aqueous NaOH (0.3 mL) and THF (2 mL). The mixture is stirred for 30 min and then purified by HPLC on reversed phase (ACN, water) to give the title compound.

LC (Method 1): $t_R$=1.01 min; Mass spectrum (ESI⁺): m/z=417 [M+H]⁺.

Alternatively, the compound is directly obtained from 4-[(6-{3-azabicyclo[3.1.0]hexan-3-yl}-2-methylpyridin-3-yl)methyl]-1H-pyrrole-2-carboxylic acid and (6R)-3-methyl-1H,4H,5H,6H-cyclopenta[c]pyrazol-6-amine following the coupling procedure described above.

Example 8

4-[(6-{3-Azabicyclo[3.1.0]hexan-3-yl}-2-methyl-pyridin-3-yl)methyl]-5-cyano-N-[(6R)-3-methyl-1H,4H,5H,6H-cyclopenta[c]pyrazol-6-yl]thiophene-2-carboxamide

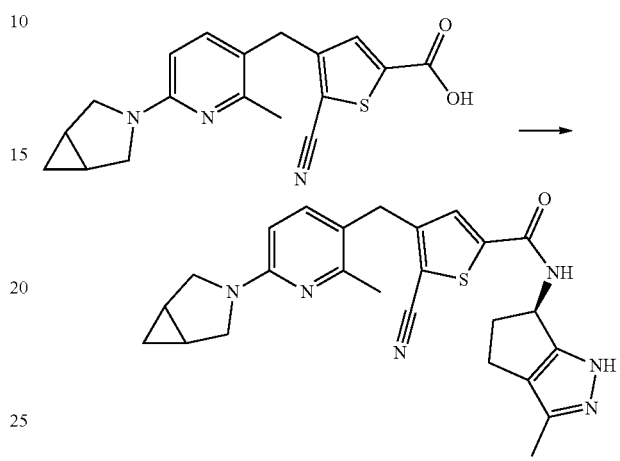

A solution of 4-[(6-{3-azabicyclo[3.1.0]hexan-3-yl}-2-methylpyridin-3-yl)methyl]-5-cyanothiophene-2-carboxylic acid (45 mg), DIPEA (91 µL) and O-(7-azabenzotriazol-1-yl)-N,N,N',N'-tetramethyluronium-hexafluorophosphat (HATU, 42 mg) in DMF (2 mL) is stirred for 15 min. (6R)-3-Methyl-1H,4H,5H,6H-cyclopenta[c]pyrazol-6-amine (15 mg) is added and the mixture is stirred for 30 min. The mixture is diluted with MeOH and purified by HPLC on reversed phase (ACN, water) to give the title compound.

LC (Method 1): $t_R$=0.75 min; Mass spectrum (ESI⁺): m/z=459 [M+H]⁺.

Example 9

2-[(6-{3-Azabicyclo[3.1.0]hexan-3-yl}-2-methyl-pyridin-3-yl)methyl]-N-[(6R)-3-methyl-1H,4H,5H,6H-cyclopenta[c]pyrazol-6-yl]-2H-1,2,3,4-tetrazole-5-carboxamide

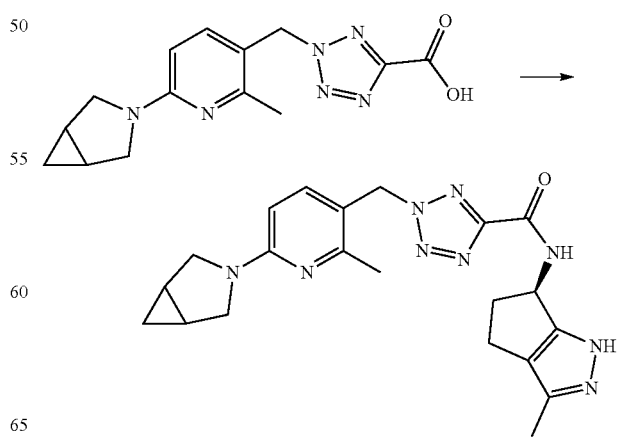

A solution of 2-[(6-{3-azabicyclo[3.1.0]hexan-3-yl}-2-methylpyridin-3-yl)methyl]-2H-1,2,3,4-tetrazole-5-carboxylic acid (40 mg), DIPEA (114 µL) and O-(7-azabenzotriazol-1-yl)-N,N,N',N'-tetramethyluronium-hexafluorophosphat (HATU, 53 mg) in DMF (2 mL) is stirred for 15 min. (6R)-3-Methyl-1H,4H,5H,6H-cyclopenta[c]pyrazol-6-amine (18 mg) is added and the mixture is stirred for 30 min. The mixture is partitioned between water and EtOAC. The aqueous phase is extracted three times with EtOAC. The combined organic phases are dried (Na$_2$SO$_4$) and concentrated. The residue is purified by HPLC on reversed phase (ACN, water) to give the title compound.

LC (Method 1): t$_R$=0.67 min; Mass spectrum (ESI$^+$): m/z=420 [M+H]$^+$.

Example 10

2-[(6-{3-Azabicyclo[3.1.0]hexan-3-yl}-2-methyl-pyridin-3-yl)methyl]-N-[(6R)-3-methyl-1H,4H,5H, 6H- cyclopenta[c]pyrazol-6-yl]-2H-1,2,3-triazole-4-carboxamide

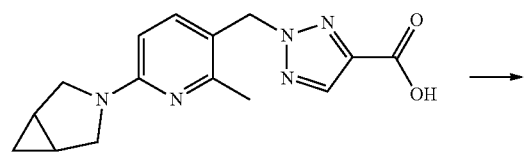

A solution of 2-[(6-{3-azabicyclo[3.1.0]hexan-3-yl}-2-methylpyridin-3-yl)methyl]-2H-1,2,3-triazole-4-carboxylic acid (45 mg), DIPEA (128 µL) and O-(7-azabenzotriazol-1-yl)-N,N,N',N'-tetramethyluronium-hexafluorophosphat (HATU, 60 mg) in DMF (2 mL) is stirred for 15 min. (6R)-3-Methyl-1H,4H,5H,6H-cyclopenta[c]pyrazol-6-amine (21 mg) is added and the mixture is stirred for 30 min. The mixture is partitioned between water and EtOAC. The aqueous phase is extracted three times with EtOAC. The combined organic phases are dried (Na$_2$SO$_4$) and concentrated. The residue is purified by HPLC on reversed phase (ACN, water) to give the title compound.

LC (Method 1): t$_R$=0.68 min; Mass spectrum (ESI$^+$): m/z=419 [M+H]$^+$.

Example 11

1-[(6-{5-azaspiro[2.3]hexan-5-yl}-2-methylpyridin-3-ylmethyl]-N-[(6R)-3-methyl-1H,4H,5H,6H-cyclopenta[c]pyrazol-6-yl]-1H-pyrazole-4-carboxamide

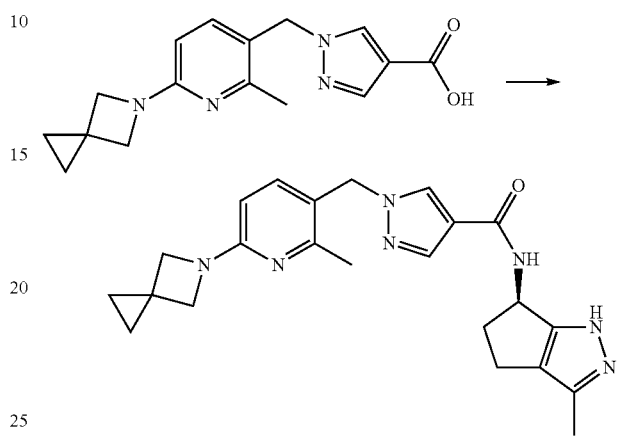

To a solution of 1-[(6-{5-azaspiro[2.3]hexan-5-yl})-2-methylpyridin-3-yl)methyl]-1H-pyrazole-4-carboxylic acid (41 mg) and (6R)-3-methyl-1H,4H,5H,6H-cyclopenta[c]pyrazol-6-amine (40 mg) in DMF (2 mL) are added DIPEA (50 µL) and O-(7-azabenzotriazol-1-yl)-N,N,N',N'-tetramethyluronium-hexafluorophosphat (HATU, 40 mg) and the mixture is stirred for 1 h. The mixture is purified by HPLC on reversed phase (ACN, water) to give the title compound.

LC (Method 2): t$_R$=0.91 min; Mass spectrum (ESI$^+$): m/z=418 [M+H]$^+$.

Example 12

1-[(6-{3-Azabicyclo[3.1.0]hexan-3-yl}-2-methyl-pyridin-3-yl)methyl]-3-chloro-N-[(6R)-3-methyl-1H, 4H,5H,6H-cyclopenta[c]pyrazol-6-yl]-1H-pyrazole-4-carboxamide

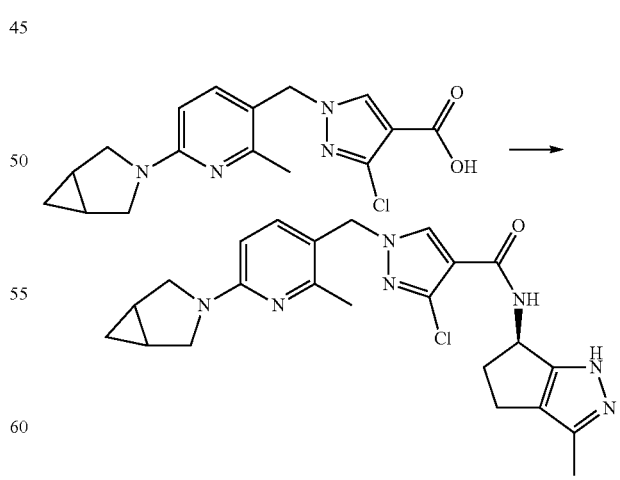

To a solution of 1-[(6-{3-azabicyclo[3.1.0]hexan-3-yl}-2-methylpyridin-3-yl)methyl]-3-chloro-1H-pyrazole-4-carboxylic acid (20 mg) and (6R)-3-methyl-2-{[2-(trimethylsilyl)ethoxy]methyl}-2H,4H,5H,6H-cyclopenta[c]pyrazol-6- amine (16 mg) in DMF (2 mL) are added DIPEA (40 μL) and O-(7-azabenzotriazol-1-yl)-N,N,N',N'-tetramethyluronium-hexafluorophosphat (HATU, 22.8 mg). The mixture is stirred for 2 h and the solvents are evaporated in vacuo. The residue is treated with TFA (1 mL) and stirred for 16 h. The mixture is purified by HPLC on reversed phase (ACN, water) to give the title compound.

LC (Method 6): $t_R$=0.82 min; Mass spectrum (ESI$^+$): m/z=452/454 (Cl) [M+H]$^+$.

Examples 13-33 are prepared analogous to example 12:

| Intermediate | Structure | $t_R$ | Mass spectrum (ESI+): m/z [M + H]$^+$ | LC Method |
|---|---|---|---|---|
| 13 | 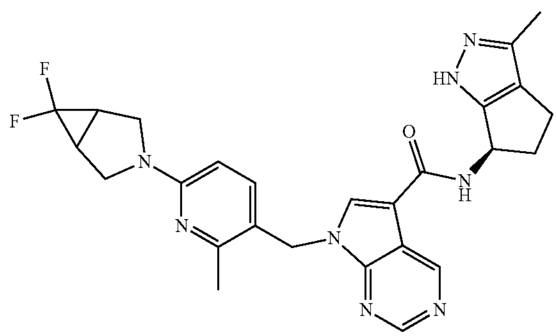 [SMILES: Cc1nc(N2CC3C(C2)C3(F)F)ccc1Cn1cc(C(=O)N[C@@H]2CCc3c(C)n[nH]c32)c2cncnc21] | 0.37 | 505.5 | Method 5 |
| 14 | 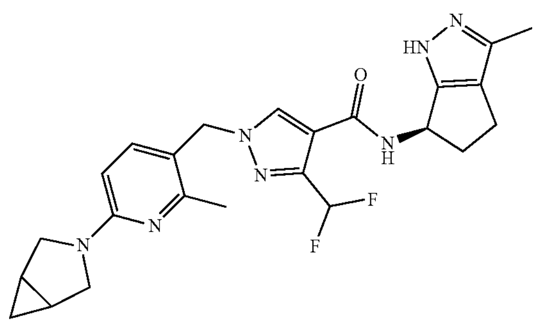 [SMILES: Cc1nc(N2CC3CC3C2)ccc1Cn1cc(C(=O)N[C@@H]2CCc3c(C)n[nH]c32)c(C(F)F)n1] | 0.44 | 468.5 | Method 5 |
| 15 | 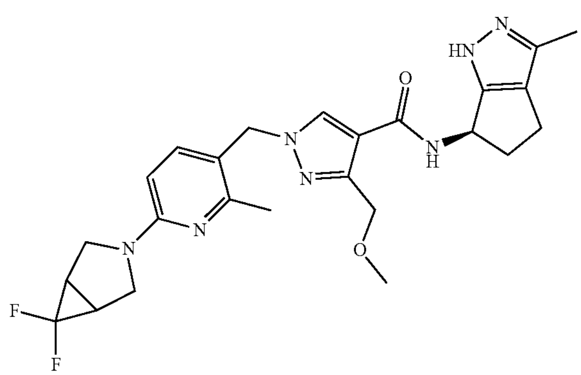 [SMILES: COCc1nn(Cc2ccc(N3CC4C(C3)C4(F)F)nc2C)cc1C(=O)N[C@@H]1CCc2c(C)n[nH]c21] | 0.44 | 498.5 | Method 5 |
| 16 | 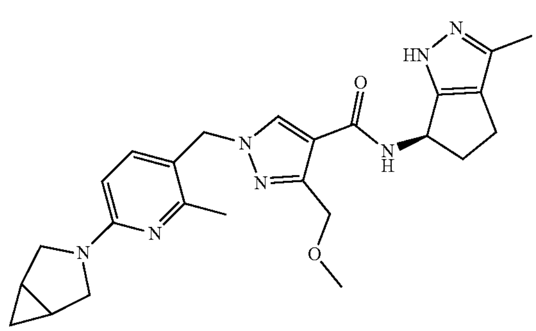 [SMILES: COCc1nn(Cc2ccc(N3CC4CC4C3)nc2C)cc1C(=O)N[C@@H]1CCc2c(C)n[nH]c21] | 0.43 | 462.5 | Method 5 |

-continued

| Intermediate | Structure | $t_R$ | Mass spectrum (ESI+): m/z [M + H]⁺ | LC Method |
|---|---|---|---|---|
| 17 | 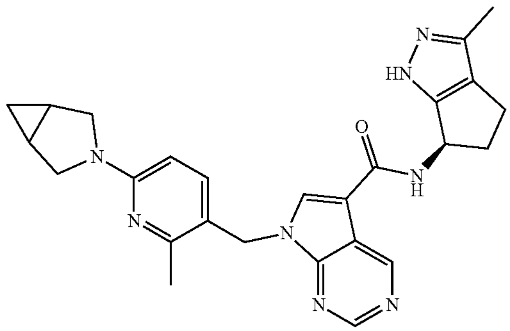 [SMILES: Cc1nc(N2CC3CC3C2)ccc1Cn1cc(C(=O)N[C@@H]2CCc3c(C)n[nH]c32)c2cncnc21] | 0.36 | 469.5 | Method 5 |
| 18 | 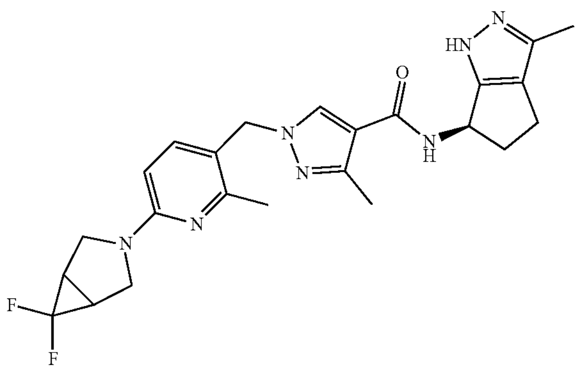 [SMILES: Cc1nc(N2CC3C(C2)C3(F)F)ccc1Cn1cc(C(=O)N[C@@H]2CCc3c(C)n[nH]c32)c(C)n1] | 0.41 | 468.5 | Method 5 |
| 19 | 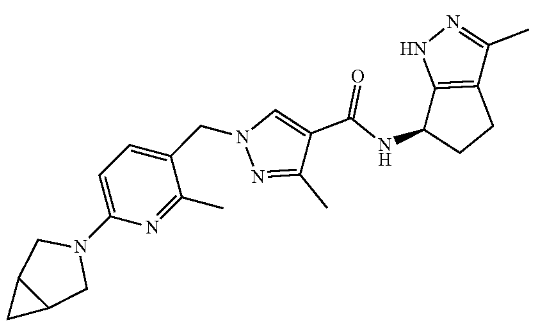 [SMILES: Cc1nc(N2CC3CC3C2)ccc1Cn1cc(C(=O)N[C@@H]2CCc3c(C)n[nH]c32)c(C)n1] | 0.39 | 432.5 | Method 5 |
| 20 | 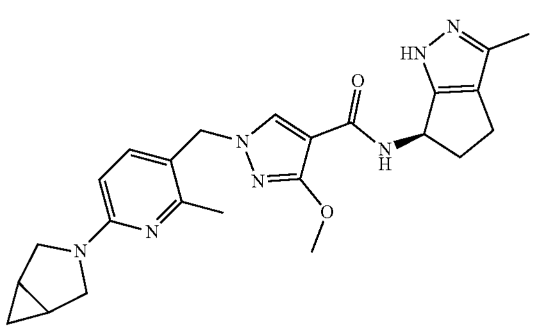 [SMILES: COc1nn(Cc2ccc(N3CC4CC4C3)nc2C)cc1C(=O)N[C@@H]1CCc2c(C)n[nH]c21] | 0.44 | 448.5 | Method 5 |

-continued

| Intermediate | Structure | $t_R$ | Mass spectrum (ESI+): m/z [M + H]+ | LC Method |
|---|---|---|---|---|
| 21 | 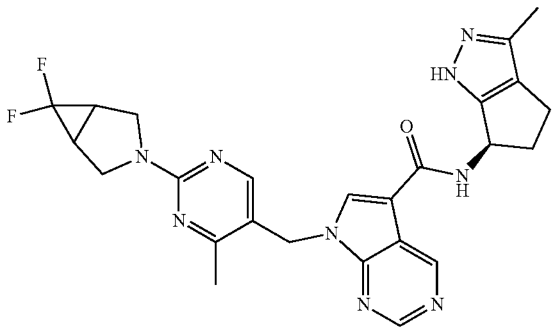 [SMILES: Cc1nc(N2CC3C(C2)C3(F)F)ncc1Cn1cc(C(=O)N[C@@H]2CCc3c(C)n[nH]c32)c2cncnc21] | 0.49 | 506.5 | Method 5 |
| 22 | 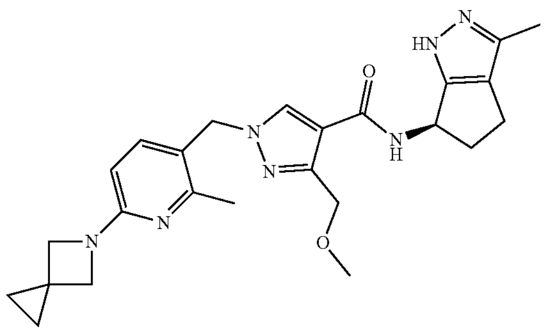 [SMILES: COCc1nn(Cc2ccc(N3CC4(CC4)C3)nc2C)cc1C(=O)N[C@@H]1CCc2c(C)n[nH]c21] | 0.44 | 462.5 | Method 5 |
| 23 | 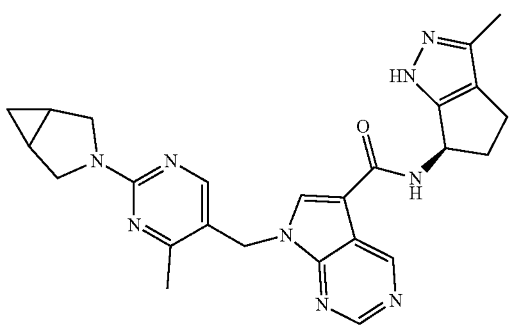 [SMILES: Cc1nc(N2CC3CC3C2)ncc1Cn1cc(C(=O)N[C@@H]2CCc3c(C)n[nH]c32)c2cncnc21] | 0.44 | 470.5 | Method 5 |
| 24 | 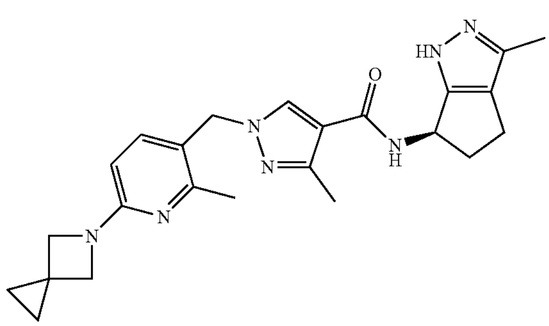 [SMILES: Cc1nc(N2CC3(CC3)C2)ccc1Cn1cc(C(=O)N[C@@H]2CCc3c(C)n[nH]c32)c(C)n1] | 0.41 | 432.5 | Method 5 |

| Intermediate | Structure | $t_R$ | Mass spectrum (ESI+): m/z [M + H]+ | LC Method |
|---|---|---|---|---|
| 25 | 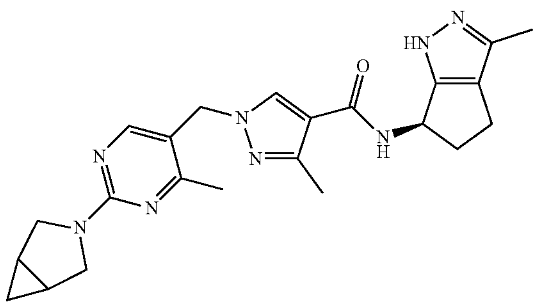 [SMILES: Cc1nc(N2CC3CC3C2)ncc1Cn1cc(C(=O)N[C@@H]2CCc3c(C)n[nH]c32)c(C)n1] | 0.45 | 433.5 | Method 5 |
| 26 | 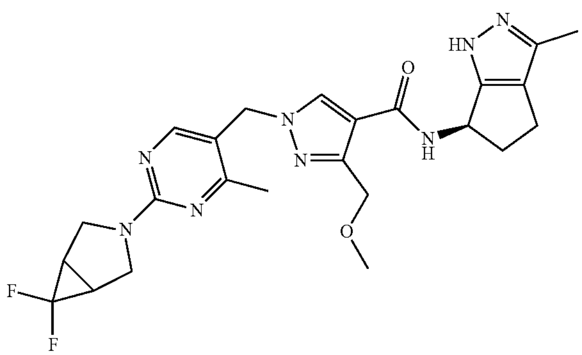 [SMILES: COCc1nn(Cc2cnc(N3CC4C(C3)C4(F)F)nc2C)cc1C(=O)N[C@@H]1CCc2c(C)n[nH]c21] | 0.58 | 499.5 | Method 5 |
| 27 | 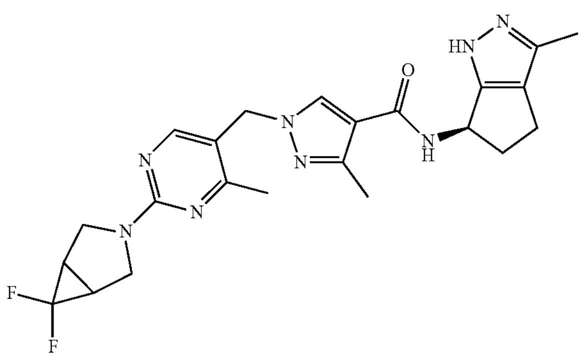 [SMILES: Cc1nc(N2CC3C(C2)C3(F)F)ncc1Cn1cc(C(=O)N[C@@H]2CCc3c(C)n[nH]c32)c(C)n1] | 0.53 | 469.5 | Method 5 |
| 28 | 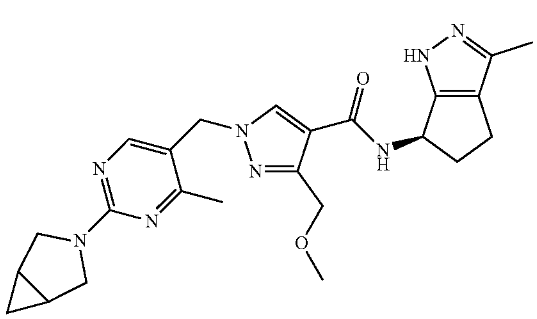 [SMILES: COCc1nn(Cc2cnc(N3CC4CC4C3)nc2C)cc1C(=O)N[C@@H]1CCc2c(C)n[nH]c21] | 0.49 | 463.5 | Method 5 |

-continued

| Intermediate | Structure | $t_R$ | Mass spectrum (ESI+): m/z [M + H]+ | LC Method |
|---|---|---|---|---|
| 29 | 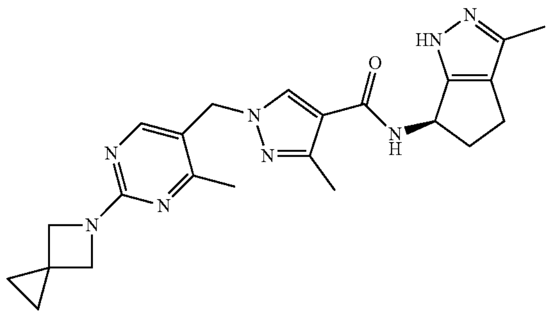 [SMILES: Cc1nc(N2CC3(CC3)C2)ncc1Cn1cc(C(=O)N[C@@H]2CCc3c(C)n[nH]c32)c(C)n1] | 0.45 | 433.5 | Method 5 |
| 30 | 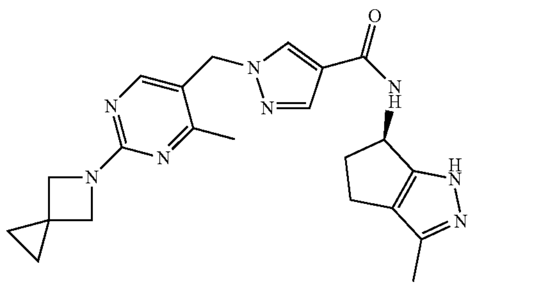 [SMILES: Cc1nc(N2CC3(CC3)C2)ncc1Cn1cc(C(=O)N[C@@H]2CCc3c(C)n[nH]c32)cn1] | 0.43 | 419.5 | Method 5 |
| 31 | 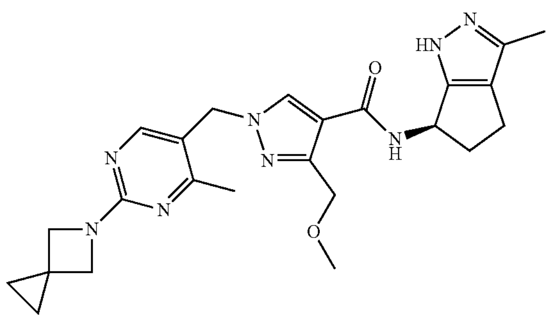 [SMILES: COCc1nn(Cc2cnc(N3CC4(CC4)C3)nc2C)cc1C(=O)N[C@@H]1CCc2c(C)n[nH]c21] | 0.49 | 463.5 | Method 5 |
| 32 | 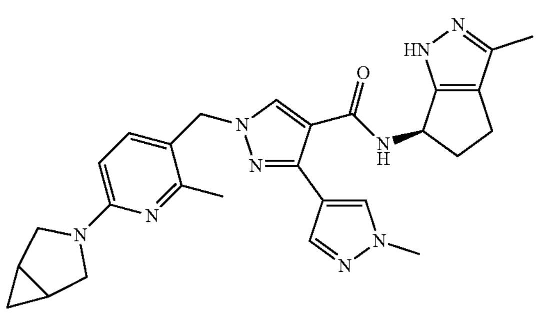 [SMILES: Cc1nc(N2CC3CC3C2)ccc1Cn1cc(C(=O)N[C@@H]2CCc3c(C)n[nH]c32)c(-c2cnn(C)c2)n1] | 0.40 | 498.5 | Method 5 |
| 33 | 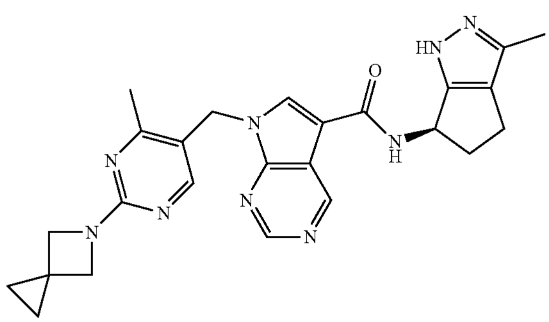 [SMILES: Cc1nc(N2CC3(CC3)C2)ncc1Cn1cc(C(=O)N[C@@H]2CCc3c(C)n[nH]c32)c2cncnc21] | 0.43 | 470.5 | Method 5 |

| Example | Name | Starting Material |
|---|---|---|
| 13 | 7-[(6-{6,6-Difluoro-3-azabicyclo[3.1.0]hexan-3-yl}-2-methylpyridin-3-yl)methyl]-N-[(6R)-3-methyl-1H,4H,5H,6H-cyclopenta[c]pyrazol-6-yl]-7H-pyrrolo[2,3-d]pyrimidine-5-carboxamide | 7-[(6-{6,6-Difluoro-3-azabicyclo[3.1.0]-hexan-3-yl}-2-methylpyridin-3-yl)methyl]-7H-pyrrolo[2,3-d]pyrimidine-5-carboxylic acid |
| 14 | 1-[(6-{3-Azabicyclo[3.1.0]hexan-3-yl}-2-methyl-pyridin-3-y)methyl]-3-(difluoromethyl)-N-[(6R)-3-methyl-1H,4H,5H,6H-cyclopenta[c]pyrazol-6-yl]-1H-pyrazole-4-carboxamide | 1-[(6-{3-Azabicyclo[3.1.0]hexan-3-yl}-2-methylpyridin-3-yl)methyl]-3-(difluoro-methyl)-1H-pyrazole-4-carboxylic acid |
| 15 | 1-[(6-{6,6-Difluoro-3-azabicyclo[3.1.0]hexan-3-yl}-2-methylpyridin-3-yl)methyl]-3-(methoxymethyl)-N-[(6R)-3-methyl-1H,4H,5H,6H-cyclopenta[c]-pyrazol-6-yl]-1H-pyrazole-4-carboxamide | 1-[(6-{6,6-Difluoro-3-azabicyclo[3.1.0]-hexan-3-yl}-2-methylpyridin-3-yl)methyl]-3-(methoxymethyl)-1H-pyrazole-4-carboxylic acid |
| 16 | 1-[(6-{3-Azabicyclo[3.1.0]hexan-3-yl}-2-methyl-pyridin-3-yl)methyl]-3-(methoxymethyl)-N-[(6R)-3-methyl-1H,4H,5H,6H-cyclopenta[c]pyrazol-6-yl]-1H-pyrazole-4-carboxamide | 1-[(6-{3-Azabicyclo[3.1.0]hexan-3-yl}-2-methylpyridin-3-yl)methyl]-3-(methoxy-methyl)-1H-pyrazole-4-carboxylic acid |
| 17 | 7-[(6-{3-Azabicyclo[3.1.0]hexan-3-yl}-2-methyl-pyridin-3-yl)methyl]-N-[(6R)-3-methyl-1H,4H,5H,6H-cylcopenta[c]pyrazol-6-yl]-7H-pyrrolo[2,3-d]pyrimidine-5-carboxamide | 7-[(6-{3-Azabicyclo[3.1.0]hexan-3-yl}-2-methylpyridin-3-yl)methyl]-7H-pyrrolo[2,3-d]pyrimidine-5-carboxylic acid |
| 18 | 1-[(6-{6,6-Difluoro-3-azabicyclo[3.1.0]hexan-3-yl}-2-methylpyridin-3-yl)methyl]-3-methyl-3-methyl-N-[(6R)-3-methyl-1H,4H,5H,6H-cyclopenta[c]pyrazol-6-yl]-1H-pyrazole-4-carboxamide | 1-[(6-{6,6-Difluoro-3-azabicyclo[3.1.0]-hexan-3-yl}-2-methylpyridin-3-yl)methyl]-3-methyl-1H-pyrazole-4-carboxylic acid |
| 19 | 1-[(6-{3-Azabicyclo[3.1.0]hexan-3-yl}-2-methyl-pyridin-3-yl)methyl]-3-methyl-N-[(6R)-3-methyl-1H,4H,5H,6H-cyclopenta[c]pyrazol-6-yl]-1H-pyrazole-4-carboxamide | 1-[(6-{3-Azabicyclo[3.1.0]hexan-3-yl}-2-methylpyridin-3-yl)methyl]-3-methyl-1H-pyrazole-4-carboxylic acid |
| 20 | 1-[(6-{3-Azabicyclo[3.1.0]hexan-3-yl}-2-methyl-pyridin-3-yl)methyl]-3-methoxy-N-[(6R)-3-methyl-1H,4H,5H,6H-cyclopenta[c]pyrazol-6-yl]-1H-pyrazole-4-carboxamide | 1-[(6-{3-Azabicyclo[3.1.0]hexan-3-yl}-2-methylpyridin-3-yl)methyl]-3-methoxy-1H-pyrazole-4-carboxylic acid |
| 21 | 7-[(2-{6,6-Difluoro-3-azabicyclo[3.1.0]hexan-3-yl}-4-methylpyrimidin-5-yl)methyl]-N-[(6R)-3-methyl-1H,4H,5H,6H-cyclopenta[c]pyrazol-6-yl]-7H-pyrrolo[2,3-d]pyrimidine-5-carboxamide | 7-[(2-{6,6-Difluoro-3-azabicyclo[3.1.0]-hexan-3-yl}-4-methylpyrimidin-5-yl)methyl]-7H-pyrrolo[2,3-d]pyrimidine-5-carboxylic acid |
| 22 | 1-[(6-{5-Azaspiro[2.3]hexan-5-yl}-2-methylpyridin-3-yl)methyl]-3-(methoxymethyl)-N-[(6R)-3-methyl-1H,4H,5H,6H-cyclopenta[c]pyrazol-6-yl]-1H-pyrazole-4-carboxamide | 1-[(6-{5-Azaspiro[2.3]hexan-5-yl}-2-methylpyridin-3-yl)methyl]-3-(methoxy-methyl)-1H-pyrazole-4-carboxylic acid |
| 23 | 7-[(2-{3-Azabicyclo[3.1.0]hexan-3-yl}-4-methyl-pyrimidin-5-yl)methyl]-N-[(6R)-3-methyl-1H,4H,5H,6H-cyclopenta[c]pyrazol-6-yl]-7H-pyrrolo[2,3-d]pyrimidine-5-carboxamide | 7-[(2-{3-Azabicyclo[3.1.0]hexan-3-yl}-4-methylpyrimidin-5-yl)methyl]-7H-pyrrolo-[2,3-d]pyrimidine-5-carboxylic acid |
| 24 | 1-[(6-{5-Azaspiro[2.3]hexan-5-yl}-2-methylpyridin-3-yl)methyl]-3-methyl-N-[(6R)-3-methyl 1H,4H,5H,6H-cyclopenta[c]pyrazol-6-yl]-1H-pyrazole-4-carboxamide | 1-[(6-{5-Azaspiro[2.3]hexan-5-yl}-2-methyl-pyridin-3-yl)methyl]-3-methyl-1H-pyrazole-4-carboxylic acid |
| 25 | 1-[(2-{3-Azabicyclo[3.1.0]hexan-3-yl}-4-methyl-pyrimidin-5-yl)methyl]-3-methyl-N-[(6R)-3-methyl-1H,4H,5H,6H-cyclopenta[c]pyrazol-6-yl]-1H-pyrazole-4-carboxamide | 1-[(2-{3-Azabicyclo[3.1.0]hexan-3-yl}-4-methylpyrimidin-5-yl)methyl]-3-methyl-1H-pyrazole-4-carboxylic acid |
| 26 | 1-[(2-{6,6-Difluoro-3-azabicyclo[3.1.0]hexan-3-yl}-4-methylpyrimidin-5-yl)methyl]-3-(methoxy-methyl)-N-[(6R)-3-methyl-1H,4H,5H,6H-cyclo-penta[c]pyrazol-6-yl]-1H-pyrazole-4-carboxamide | 1-[(2-{6,6-Difluoro-3-azabicyclo[3.1.0]-hexan-3-yl}-4-methylpyrimidin-5-yl)methyl]-3-(methoxymethyl)-1H-pyrazole-4-carboxylic acid |
| 27 | 1-[(2-{6,6-Difluoro-3-azabicyclo[3.1.0]hexan-3-yl}-4-methylpyrimidin-5-yl)methyl]-3-methyl-N-[(6R)-3-methyl-1H,4H,5H,6H-cyclopenta[c]pyrazol-6-yl]-1H-pyrazole-4-carboxamide | 1-[(2-{6,6-Difluoro-3-azabicyclo[3.1.0]-hexan-3-yl}-4-methylpyrimidin-5-yl)methyl]-3-methyl-1H-pyrazole-4-carboxylic acid |
| 28 | 1-[(2-{3-Azabicyclo[3.1.0]hexan-3-yl}-4-methyl-pyrimidin-5-yl)methyl]-3-(methoxymethyl)-N-[(6R)-3-methyl-1H,4H,5H,6H-cyclopenta[c]pyrazol-6-yl]-1H-pyrazole-4-carboxamide | 1-[(2-{3-Azabicyclo[3.1.0]hexan-3-yl}-4-methylpyrimidin-5-yl)methyl]-3-(methoxy-methyl)-1H-pyrazole-4-carboxylic acid |
| 29 | 1-[(2-{5-Azaspiro[2.3]hexan-5-yl}-4-methyl-pyrimidin-5-yl)methyl]-3-methyl-N-[(6R)-3-methyl-1H,4H,5H,6H-cyclpenta[c]pyrazol-6-yl]-1H-pyrazole-4-carboxamide | 1-[(2-{5-Azaspiro[2.3]hexan-5-yl}-4-methyl-pyrimidin-5-yl)methyl]-3-methyl-1H-pyrazole-4-carboxylic acid |
| 30 | 1-[(2-{5-Azaspiro[2.3]hexan-5-yl}-4-methyl-pyrimidin-5-yl)methyl]-N-[(6R)-3-methyl-1H,4H,5H,6H-cyclopenta[c]pyrazol-6-yl]-1H-pyrazole-4-carboxamide | 1-[(2-{5-Azaspiro[2.3]hexan-5-yl}-4-methyl-pyrimidin-5-yl)methyl]-1H-pyrazole-4-carboxylic acid |
| 31 | 1-[(2-{5-Azaspiro[2.3]hexan-5-yl}-4-methyl-pyrimidin-5-yl)methyl]-3-(methoxymethyl)-N-[(6R)-3-methyl-1H,4H,5H,6H-cyclopenta[c]pyrazol-6-yl]-1H-pyrazole-4-carboxamide | 1-[(2-{5-Azaspiro[2.3]hexan-5-yl}-4-methyl-pyrimidin-5-yl)methyl]-3-(methoxymethyl)-1H-pyrazol-4-carboxylic acid |
| 32 | 1-[(6-{3-Azabicyclo[3.1.0]hexan-3-yl}-2-methyl-pyridin-3-yl)methyl]-1'-methyl-N-[(6R)-3-methyl- | 1-[(6-{3-Azabicyclo[3.1.0]hexan-3-yl}-2-methylpyridin-3-yl)methyl]-3-(1-methyl-1H- |

| Example | Name | Starting Material |
|---|---|---|
|  | 1H,4H,5H,6H-cyclopenta[c]pyrazol-6-yl]-1H,1'H-[3,4'-bipyrazole]-4-carboxamide | pyrazol-4-yl)-1H-pyrazol-4-carboxylic acid |
| 33 | 7-[(2-{5-Azaspiro[2.3]hexan-5-yl}-4-methyl-pyrimidin-5-yl)methyl]-N-[(6R)-3-methyl-1H,4H,5H,6H-cyclopenta[c]pyrazol-6-yl]-7H-pyrrolo[2,3-d]pyrimidine-5-carboxamide | 7-[(2-{5-Azaspiro[2.3]hexan-5-yl}-4-methyl-pyrimidin-5-yl)methyl]-7H-pyrrolo[2,3-d]pyrimidine-5-carboxylic acid |

Example 34

N-[(6R)-3-Methyl-2H,4H,5H,6H-cyclopenta[c]pyrazol-6-yl]-1-{[2-methyl-6-(piperidin-1-yl)pyridin-3-yl]methyl}-1H-pyrazole-4-carboxamide

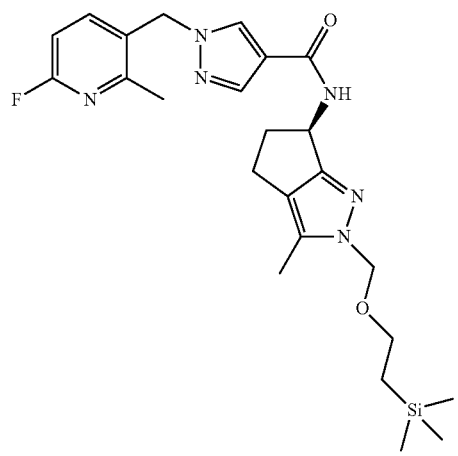

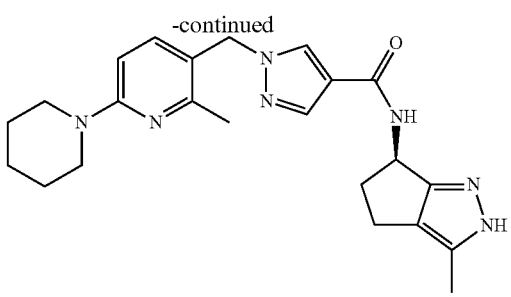

1-[(6-Fluoro-2-methylpyridin-3-yl)methyl]-N-[(6R)-3-methyl-2-{[2-(trimethylsilyl)ethoxy]methyl}-2H,4H,5H,6H-cyclopenta[c]pyrazol-6-yl]-1H-pyrazole-4-carboxamide (24 mg) is dissolved in TFA, stirred at room temperature for 1 h and concentrated in vacuo. The residue is dissolved in DMSO (0.5 mL), piperidine (17 mg) and DIPEA (75 μL) are added and the mixture is stirred for 16 h at 80° C. and additional 3 d at 110° C. After cooling to room temperature, the mixture is purified by HPLC on reversed phase (ACN, water) to give the title compound.

LC (Method 6): $t_R$=0.77 min; Mass spectrum (ESI$^+$): m/z=420 [M+H]$^+$.

Examples 35-53 are prepared analogous to example 34:

| Intermediate | Structure | $t_R$ | Mass spectrum (ESI+): m/z [M + H]$^+$ | LC Method |
|---|---|---|---|---|
| 35 | 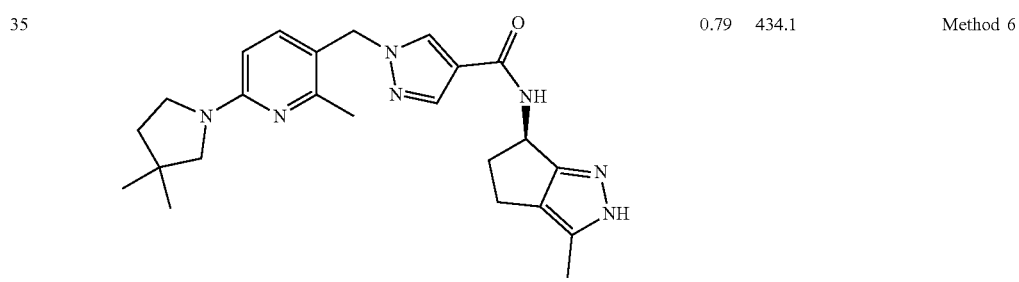 | 0.79 | 434.1 | Method 6 |
| 36 | 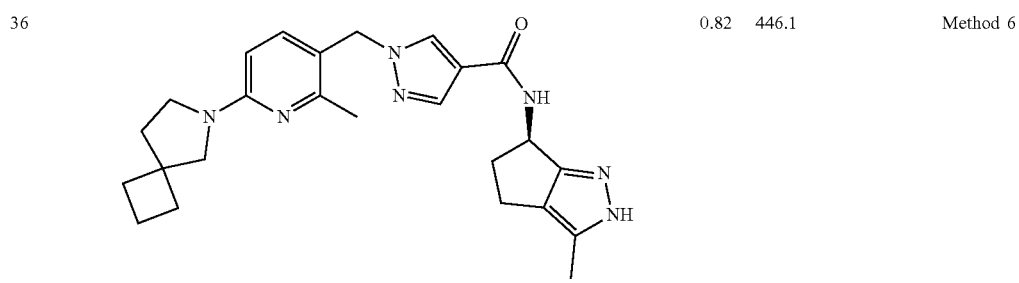 | 0.82 | 446.1 | Method 6 |

-continued

| Intermediate | Structure | $t_R$ | Mass spectrum (ESI+): m/z [M + H]+ | LC Method |
|---|---|---|---|---|
| 37 | 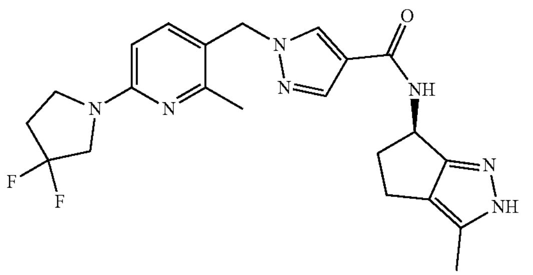 [SMILES: Cc1nc(N2CCC(F)(F)C2)ccc1Cn1cc(C(=O)N[C@@H]2CCc3c2n[nH]c3C)cn1] | 0.68 | 442.0 | Method 6 |
| 38 | 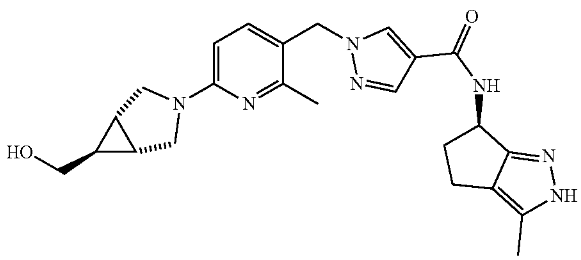 | 0.54 | 448.1 | Method 6 |
| 39 | 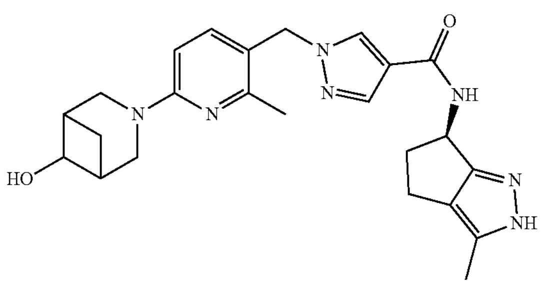 [SMILES: Cc1nc(N2CC3CC(C2)C3O)ccc1Cn1cc(C(=O)N[C@@H]2CCc3c2n[nH]c3C)cn1] | 0.58 | 448.1 | Method 6 |
| 40 | 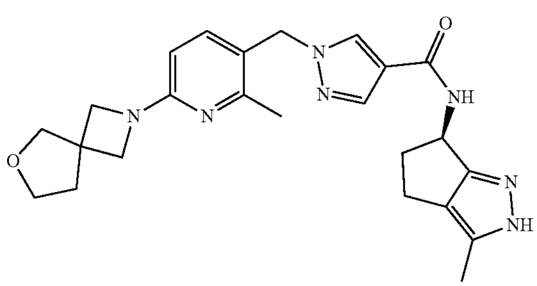 [SMILES: Cc1nc(N2CC3(CCOC3)C2)ccc1Cn1cc(C(=O)N[C@@H]2CCc3c2n[nH]c3C)cn1] | 0.54 | 448.1 | Method 6 |
| 41 | 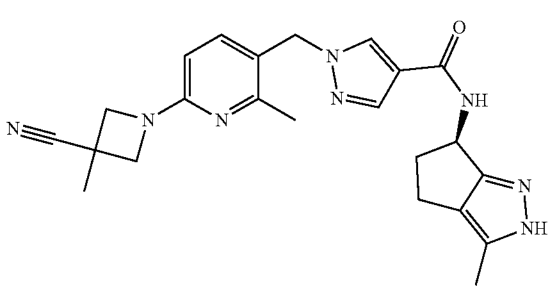 [SMILES: Cc1nc(N2CC(C)(C#N)C2)ccc1Cn1cc(C(=O)N[C@@H]2CCc3c2n[nH]c3C)cn1] | 0.57 | 431.1 | Method 6 |

-continued

| Intermediate | Structure | $t_R$ | Mass spectrum (ESI+): m/z [M + H]+ | LC Method |
|---|---|---|---|---|
| 42 | 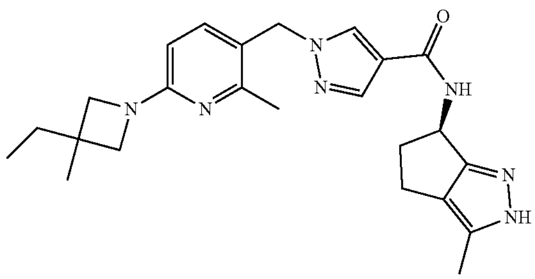 [SMILES: CCC1(C)CN(c2ccc(Cn3cc(C(=O)N[C@@H]4CCc5c4n[nH]c5C)cn3)c(C)n2)C1] | 0.75 | 434.1 | Method 6 |
| 43 | 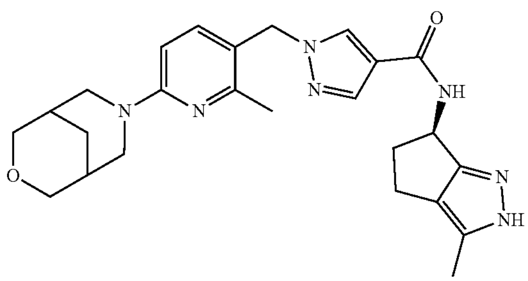 [SMILES: Cc1nc(N2CC3COCC(C3)C2)ccc1Cn1cc(C(=O)N[C@@H]2CCc3c2n[nH]c3C)cn1] | 0.65 | 462.1 | Method 6 |
| 44 | 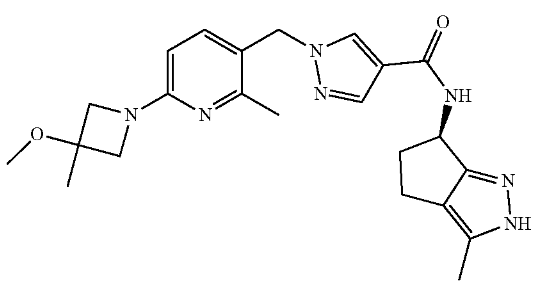 | 0.58 | 436.1 | Method 6 |
| 45 | 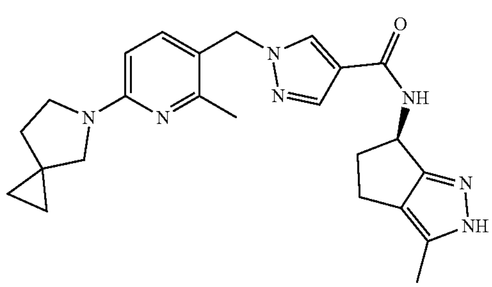 [SMILES: Cc1nc(N2CCC3(CC3)C2)ccc1Cn1cc(C(=O)N[C@@H]2CCc3c2n[nH]c3C)cn1] | 0.75 | 432.1 | Method 6 |
| 46 | 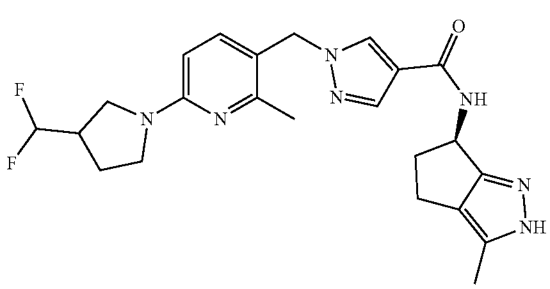 [SMILES: Cc1nc(N2CCC(C(F)F)C2)ccc1Cn1cc(C(=O)N[C@@H]2CCc3c2n[nH]c3C)cn1] | 0.68 | 456.0 | Method 6 |

-continued

| Intermediate | Structure | $t_R$ | Mass spectrum (ESI+): m/z [M + H]$^+$ | LC Method |
|---|---|---|---|---|
| 47 | 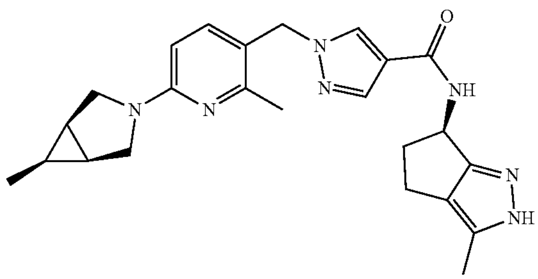 [SMILES: Cc1nc(N2C[C@@H]3[C@H](C)[C@@H]3C2)ccc1Cn1cc(C(=O)N[C@@H]2CCc3c2n[nH]c3C)cn1] | 0.75 | 432.1 | Method 6 |
| 48 | 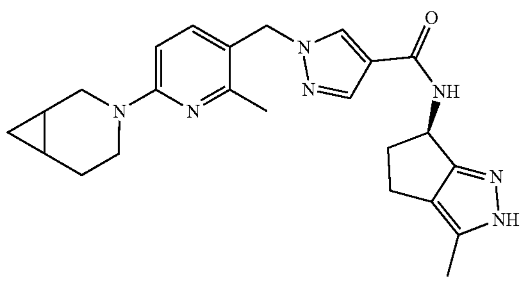 [SMILES: Cc1nc(N2CCC3CC3C2)ccc1Cn1cc(C(=O)N[C@@H]2CCc3c2n[nH]c3C)cn1] | 0.77 | 432.1 | Method 6 |
| 49 | 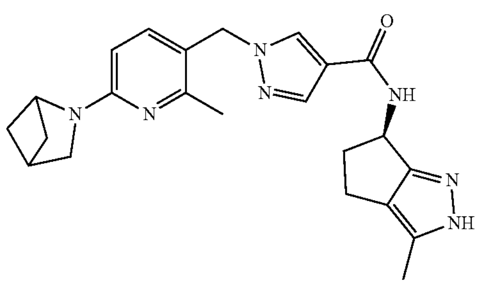 [SMILES: Cc1nc(N2CC3CC2C3)ccc1Cn1cc(C(=O)N[C@@H]2CCc3c2n[nH]c3C)cn1] | 0.65 | 418.1 | Method 6 |
| 50 | 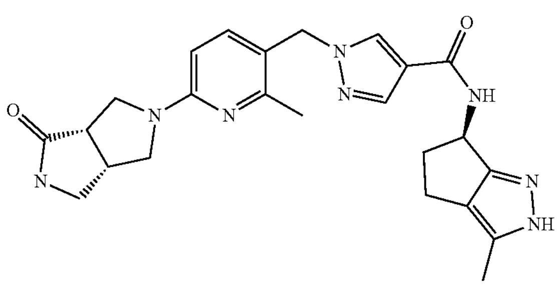 [SMILES: Cc1nc(N2C[C@@H]3CNC(=O)[C@@H]3C2)ccc1Cn1cc(C(=O)N[C@@H]2CCc3c2n[nH]c3C)cn1] | 0.47 | 461.1 | Method 6 |
| 51 | 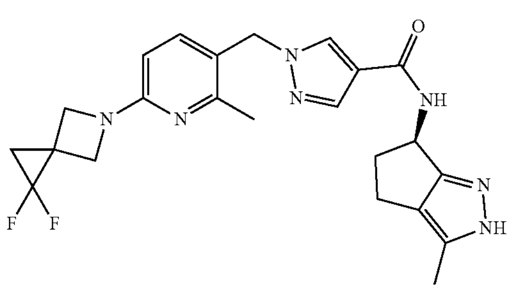 [SMILES: Cc1nc(N2CC3(C2)CC3(F)F)ccc1Cn1cc(C(=O)N[C@@H]2CCc3c2n[nH]c3C)cn1] | 0.66 | 454.0 | Method 6 |

| Intermediate | Structure | $t_R$ | Mass spectrum (ESI+): m/z [M + H]+ | LC Method |
|---|---|---|---|---|
| 52 | 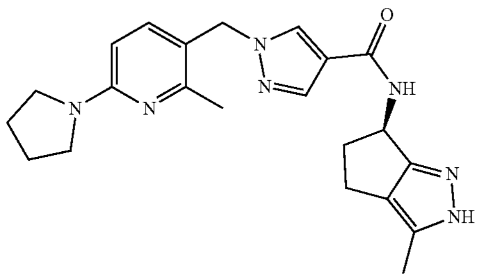 [SMILES: Cc1nc(N2CCCC2)ccc1Cn1cc(C(=O)N[C@@H]2CCc3c2n[nH]c3C)cn1] | 0.66 | 406.1 | Method 6 |
| 53 | 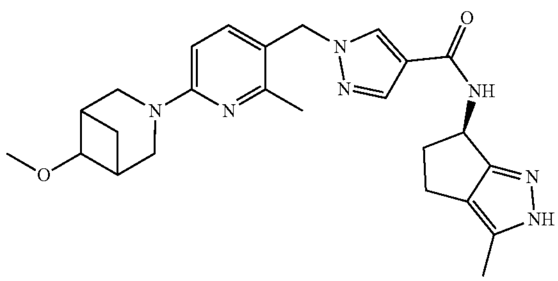 [SMILES: COC1C2CC1CN(c1ccc(Cn3cc(C(=O)N[C@@H]4CCc5c4n[nH]c5C)cn3)c(C)n1)C2] | 0.71 | 462.1 | Method 6 |

| Example | Name |
|---|---|
| 35 | 1{[6-(3,3-Dimethylpyrrolidin-1-yl)-2-methylpyridin-3-yl]methyl}-N-[(6R)-3-methyl-2H,4H,5H,6H-cyclopenta[c]pyrazol-6-yl]-1H-pyrazole-4-carboxamide |
| 36 | 1-[(6-{6-Azaspiro[3.4]octan-6-yl}-2-methylpyridin-3-yl)methyl]-N-[(6R)-3-methyl-2H,4H,5H,6H-cyclopenta[c]pyrazol-6-yl]-1H-pyrazole-4-carboxamide |
| 37 | 1-{[6-(3,3-Difluoropyrrolidin-1-yl)-2-methylpyridin-3-yl]methyl}-N-[(6R)-3-methyl-2H,4H,5H,6H-cyclopenta[c]pyrazol-6-yl]-1H-pyrazole-4-carboxamide |
| 38 | 1-({6-[(1R,5S,6R)-6-(Hydroxymethyl)-3-azabicyclo[3.1.0]hexan-3-yl]-2-methylpyridin-3-yl}methyl)-N-[(6R)-3-methyl-2H,4H,5H,6H-cyclopenta[c]pyrazol-6-yl]-1H-pyrazole-4-carboxamide |
| 39 | 1-[(6-{6-Hydroxy-3-azabicyclo[3.1.1]heptan-3-yl}-2-methylpyridin-3-yl)methyl]-N-[(6R)-3-methyl-2H,4H,5H,6H-cyclopenta[c]pyrazol-6-yl]-1H-pyrazole-4-carboxamide |
| 40 | N-[(6R)-3-Methyl-2H,4H,5H,6H-cyclopenta[c]pyrazol-6-yl]-1-[(2-methyl-6-{6-oxa-2-azaspiro[3.4]octan-2-yl}pyridin-3-yl)methyl]-1H-pyrazole-4-carboxamide |
| 41 | 1-{[6-(3-Cyano-3-methylazetidin-1-yl)-2-methylpyridin-3-yl]methyl}-N-[(6R)-3-methyl-2H,4H,5H,6H-cyclopenta[c]pyrazol-6-yl]-1H-pyrazole-4-carboxamide |
| 42 | 1-{[6-(3-Ethyl-3-methylazetidin-1-yl)-2-methylpyridin-3-yl]methyl}-N-[(6R)-3-methyl-2H,4H,5H,6H-cyclopenta[c]pyrazol-6-yl]-1H-pyrazole-4-carboxamide |
| 43 | N-[(6R)-3-Methyl-2H,4H,5H,6H-cyclopenta[c]pyrazol-6-yl]-1-[(2-methyl-6-{3-oxa-7-azabicyclo[3.3.1]nonan-7-yl}pyridin-3-yl)methyl]-1H-pyrazole-4-carboxamide |
| 44 | 1-{[6-(3-Methoxy-3-methylazetidin-1-yl)-2-methylpyridin-3-yl]methyl}-N-[(6R)-3-methyl-2H,4H,5H,6H-cyclopenta[c]pyrazol-6-yl]-1H-pyrazole-4-carboxamide |
| 45 | 1-[(6-{5-Azaspiro[2.4]heptan-5-yl}-2-methylpyridin-3-yl)methyl]-N-[(6R)-3-methyl-2H,4H,5H,6H-cyclopenta[c]pyrazol-6-yl]-1H-pyrazole-4-carboxamide |
| 46 | 1-({6-[3-(Difluoromethyl)pyrrolidin-1-yl]-2-methylpyridin-3-yl}methyl)-N-[(6R)-3-methyl-2H,4H,5H,6H-cyclopenta[c]pyrazol-6-yl]-1H-pyrazole-4-carboxamide |
| 47 | N-[(6R)-3-Methyl-2H,4H,5H,6H-cyclopenta[c]pyrazol-6-yl]-1-({2-methyl-6-[(1R,5S,6S)-6-methyl-3-azabicyclo[3.1.0]hexan-3-yl]pyridin-3-yl}methyl)-1H-pyrazole-4-carboxamide |
| 48 | 1-[(6-{3-Azabicyclo[4.1.0]heptan-3-yl}-2-methylpyridin-3-yl)methyl]-N-[(6R)-3-methyl-2H,4H,5H,6H-cyclopenta[c]pyrazol-6-yl]-1H-pyrazole-4-carboxamide |
| 49 | 1-[(6-{2-Azabicyclo[2.1.1]hexan-2-yl}-2-methylpyridin-3-yl)methyl]-N-[(6R)-3-methyl-2H,4H,5H,6H-cyclopenta[c]pyrazol-6-yl]-1H-pyrazole-4-carboxamide |
| 50 | 1-({6-[(3aS,6aS)-4-Oxo-octahydropyrrolo[3,4-c]pyrrol-2-yl]-2-methylpyridin-3-yl}methyl)-N-[(6R)-3-methyl-2H,4H,5H,6H-cyclopenta[c]pyrazol-6-yl]-1H-pyrazole-4-carboxamide |
| 51 | 1-[(6-{1,1-Difluoro-5-azaspiro[2.3]hexan-5-yl}-2-methylpyridin-3-yl)methyl]-N-[(6R)-3-methyl-2H,4H,5H,6H-cyclopenta[c]pyrazol-6-yl]-1H-pyrazole-4-carboxamide |
| 52 | N-[(6R)-3-Methyl-2H,4H,5H,6H-cyclopenta[c]pyrazol-6-yl]-1-{[2-methyl-6-(pyrrolidin-1-yl)pyridin-3-yl]methyl}-1H-pyrazole-4-carboxamide |
| 53 | 1-[(6-{6-methoxy-3-azabicyclo[3.1.1]heptan-3-yl}-2-methylpyridin-3-yl)methyl]-N-[(6R)-3-methyl-2H,4H,5H,6H-cyclopenta[c]pyrazol-6-yl]-1H-pyrazole-4-carboxamide |

Example 54

1-[(6-{2-Azaspiro[3.3]heptan-2-yl}-2-methylpyridin-3-yl)methyl]-N-[(6R)-3-methyl-2H,4H,5H,6H-cyclopenta[c]pyrazol-6-yl]-1H-pyrazole-4-

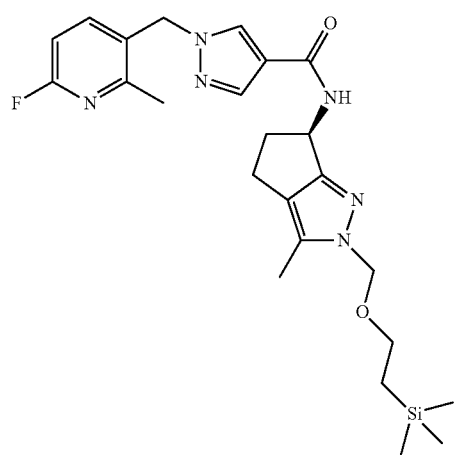

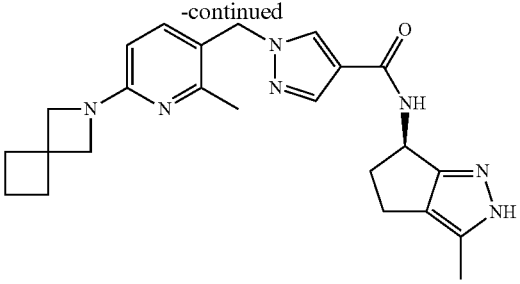

1-[(6-Fluoro-2-methylpyridin-3-yl)methyl]-N-[(6R)-3-methyl-2-{[2-(trimethylsilyl)ethoxy]methyl}-2H,4H,5H,6H-cyclopenta[c]pyrazol-6-yl]-1H-pyrazole-4-carboxamide (24 mg) is dissolved in DMSO (0.5 mL). 2-Azaspiro[3.3]heptane hemioxalate (30 mg) and DIPEA (75 µL) are added and the mixture is stirred for 16 h at 85° C., 8 h at 95° C. and additional 16 h at 105° C. and then concentrated in vacuo. The residue is dissolved in TFA, stirred at room temperature for 16 h and the mixture is purified by HPLC on reversed phase (ACN, water) to give the title compound.

LC (Method 7): $t_R$=0.73 min; Mass spectrum (ESI$^+$): m/z=432 [M+H]$^+$.

Examples 55-83 are prepared analogous to example 54:

| Intermediate | Structure | $t_R$ | Mass spectrum (ESI+): m/z [M + H]$^+$ | LC Method |
|---|---|---|---|---|
| 55 | 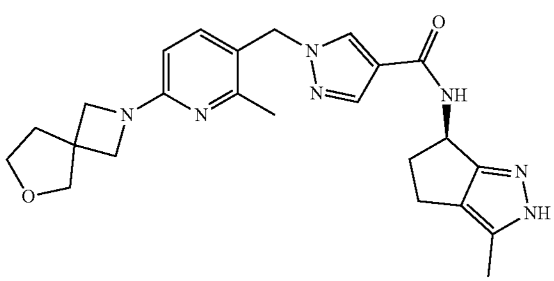 [SMILES: Cc1nc(N2CC3(CCOC3)C2)ccc1Cn1cc(C(=O)N[C@@H]2CCc3c2n[nH]c3C)cn1] | 0.59 | 448 | Method 6 |
| 56 | 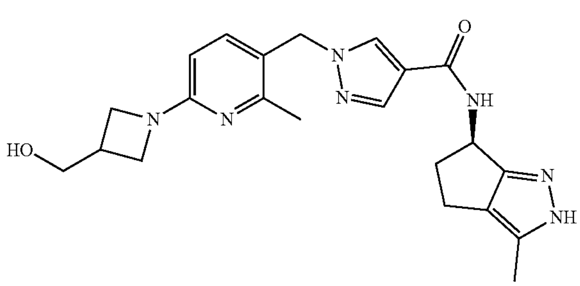 [SMILES: Cc1nc(N2CC(CO)C2)ccc1Cn1cc(C(=O)N[C@@H]2CCc3c2n[nH]c3C)cn1] | 0.65 | 422 | Method 1 |
| 57 | 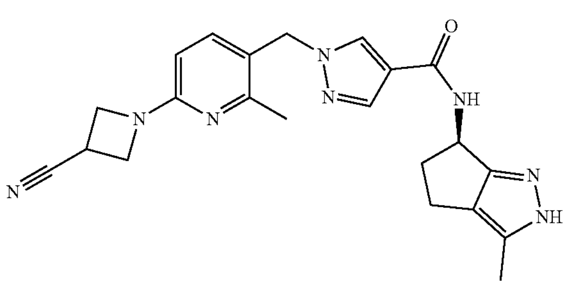 [SMILES: Cc1nc(N2CC(C#N)C2)ccc1Cn1cc(C(=O)N[C@@H]2CCc3c2n[nH]c3C)cn1] | 0.66 | 417 | Method 1 |

-continued

| Intermediate | Structure | $t_R$ | Mass spectrum (ESI+): m/z [M + H]+ | LC Method |
|---|---|---|---|---|
| 58 | 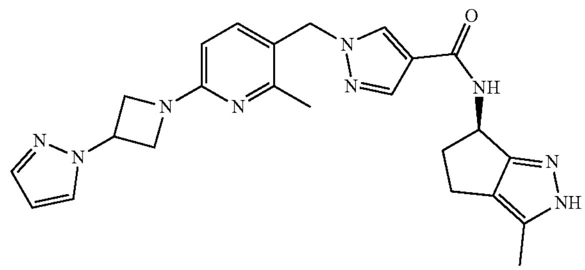 [SMILES: Cc1nc(N2CC(n3cccn3)C2)ccc1Cn1cc(C(=O)N[C@@H]2CCc3c2n[nH]c3C)cn1] | 0.69 | 458 | Method 1 |
| 59 | 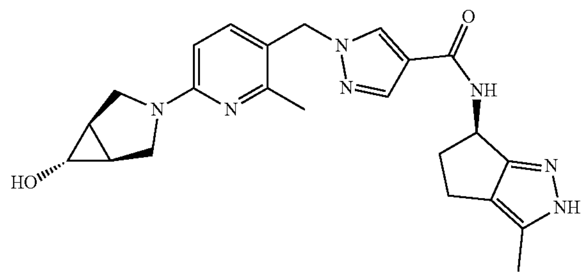 [SMILES: Cc1nc(N2C[C@@H]3[C@@H](O)[C@@H]3C2)ccc1Cn1cc(C(=O)N[C@@H]2CCc3c2n[nH]c3C)cn1] | 0.65 | 434 | Method 1 |
| 60 | 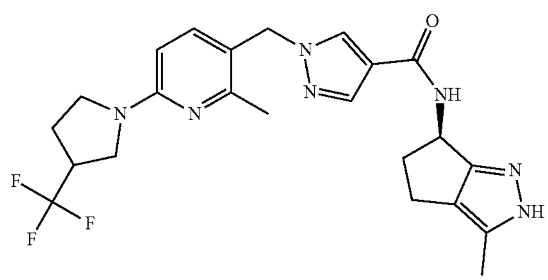 [SMILES: Cc1nc(N2CCC(C(F)(F)F)C2)ccc1Cn1cc(C(=O)N[C@@H]2CCc3c2n[nH]c3C)cn1] | 0.97 | 474 | Method 2 |
| 61 | 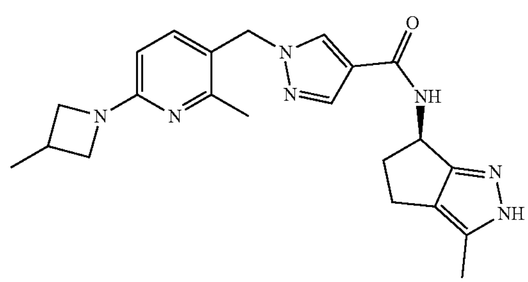 [SMILES: Cc1nc(N2CC(C)C2)ccc1Cn1cc(C(=O)N[C@@H]2CCc3c2n[nH]c3C)cn1] | 0.88 | 406 | Method 2 |
| 62 | 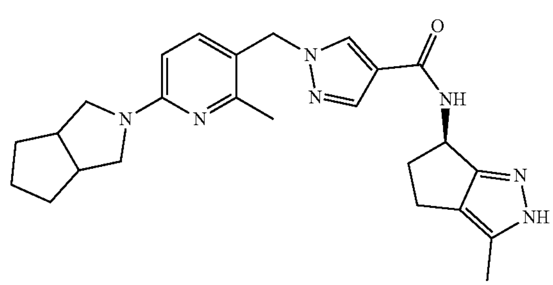 [SMILES: Cc1nc(N2CC3CCCC3C2)ccc1Cn1cc(C(=O)N[C@@H]2CCc3c2n[nH]c3C)cn1] | 1.01 | 446 | Method 2 |

-continued

| Intermediate | Structure | $t_R$ | Mass spectrum (ESI+): m/z [M + H]$^+$ | LC Method |
|---|---|---|---|---|
| 63 | 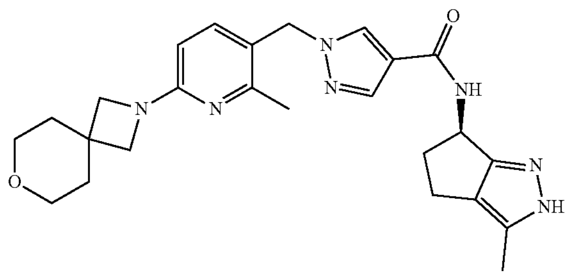 [SMILES: Cc1nc(N2CC3(CCOCC3)C2)ccc1Cn1cc(C(=O)N[C@@H]2CCc3c2n[nH]c3C)cn1] | 0.83 | 462 | Method 2 |
| 64 | 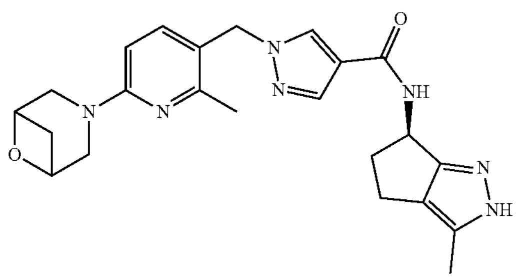 [SMILES: Cc1nc(N2CC3CC(C2)O3)ccc1Cn1cc(C(=O)N[C@@H]2CCc3c2n[nH]c3C)cn1] | 0.81 | 434 | Method 2 |
| 65 | 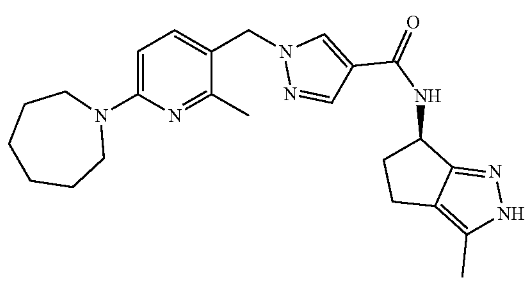 [SMILES: Cc1nc(N2CCCCCC2)ccc1Cn1cc(C(=O)N[C@@H]2CCc3c2n[nH]c3C)cn1] | 0.83 | 434 | Method 6 |
| 66 | 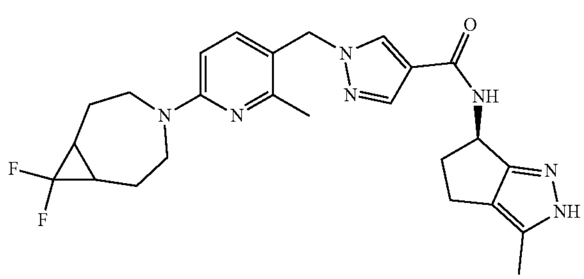 [SMILES: Cc1nc(N2CCC3C(CC2)C3(F)F)ccc1Cn1cc(C(=O)N[C@@H]2CCc3c2n[nH]c3C)cn1] | 0.78 | 482 | Method 6 |
| 67 | 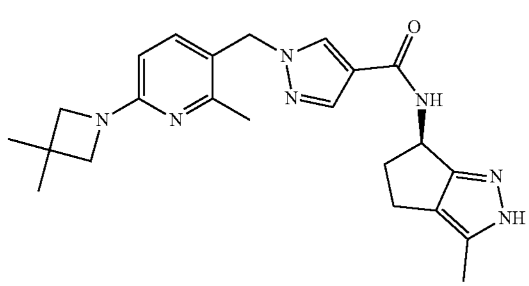 [SMILES: Cc1nc(N2CC(C)(C)C2)ccc1Cn1cc(C(=O)N[C@@H]2CCc3c2n[nH]c3C)cn1] | 0.70 | 420 | Method 6 |

-continued

| Intermediate | Structure | $t_R$ | Mass spectrum (ESI+): m/z [M + H]+ | LC Method |
|---|---|---|---|---|
| 68 | 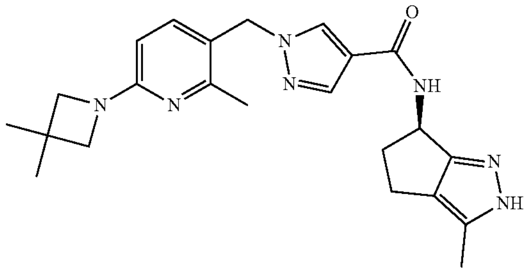 [SMILES: Cc1nc(N2CC(C)(C)C2)ccc1Cn1cc(C(=O)N[C@@H]2CCc3c2n[nH]c3C)cn1] | 0.78 | 432 | Method 6 |
| 69 | 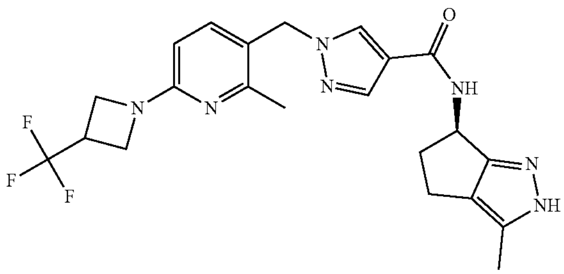 [SMILES: Cc1nc(N2CC(C(F)(F)F)C2)ccc1Cn1cc(C(=O)N[C@@H]2CCc3c2n[nH]c3C)cn1] | 0.68 | 460 | Method 6 |
| 70 | 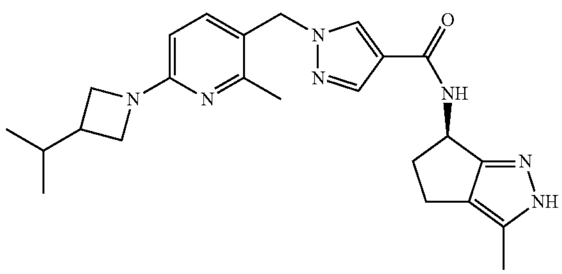 [SMILES: Cc1nc(N2CC(C(C)C)C2)ccc1Cn1cc(C(=O)N[C@@H]2CCc3c2n[nH]c3C)cn1] | 0.76 | 434 | Method 6 |
| 71 | 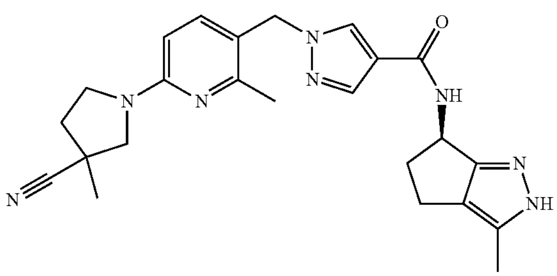 [SMILES: Cc1nc(N2CCC(C)(C#N)C2)ccc1Cn1cc(C(=O)N[C@@H]2CCc3c2n[nH]c3C)cn1] | 0.63 | 445 | Method 6 |
| 72 | 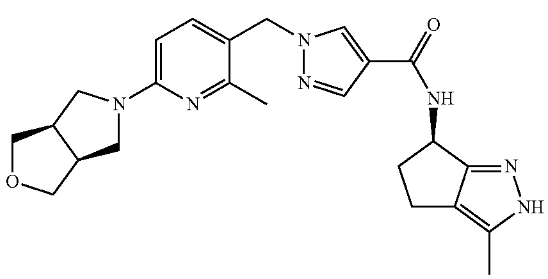 [SMILES: Cc1nc(N2C[C@H]3COC[C@H]3C2)ccc1Cn1cc(C(=O)N[C@@H]2CCc3c2n[nH]c3C)cn1] | 0.58 | 448 | Method 6 |

-continued

| Intermediate | Structure | $t_R$ | Mass spectrum (ESI+): m/z [M + H]+ | LC Method |
|---|---|---|---|---|
| 73 | 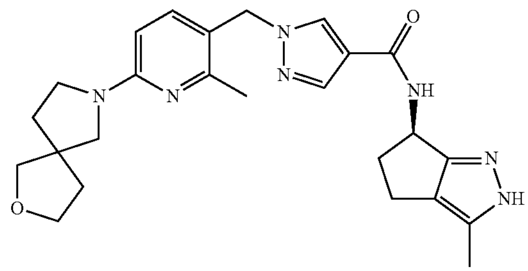 [SMILES: Cc1nc(N2CCC3(CCOC3)C2)ccc1Cn1cc(C(=O)N[C@@H]2CCc3c2n[nH]c3C)cn1] | 0.62 | 462 | Method 6 |
| 74 | 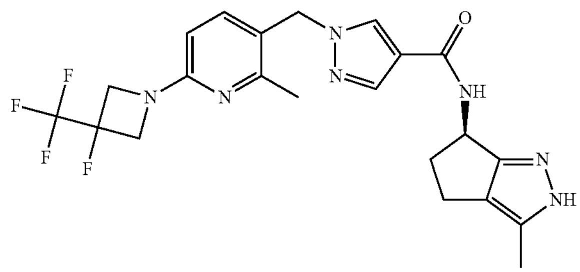 [SMILES: Cc1nc(N2CC(F)(C(F)(F)F)C2)ccc1Cn1cc(C(=O)N[C@@H]2CCc3c2n[nH]c3C)cn1] | 0.72 | 478 | Method 6 |
| 75 | 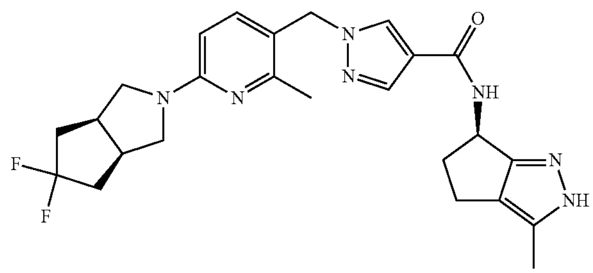 [SMILES: Cc1nc(N2C[C@@H]3CC(F)(F)C[C@@H]3C2)ccc1Cn1cc(C(=O)N[C@@H]2CCc3c2n[nH]c3C)cn1] | 0.74 | 482 | Method 6 |
| 76 | 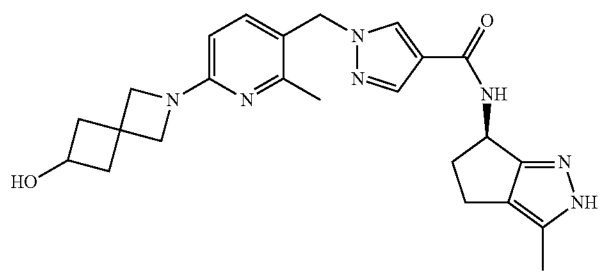 [SMILES: Cc1nc(N2CC3(CC(O)C3)C2)ccc1Cn1cc(C(=O)N[C@@H]2CCc3c2n[nH]c3C)cn1] | 0.50 | 448 | Method 6 |
| 77 | 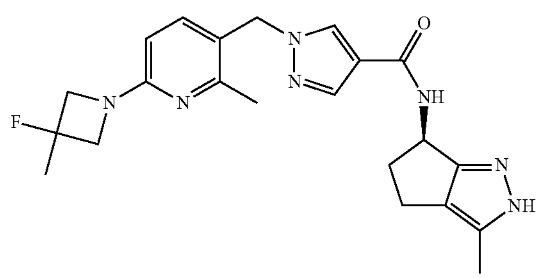 [SMILES: Cc1nc(N2CC(C)(F)C2)ccc1Cn1cc(C(=O)N[C@@H]2CCc3c2n[nH]c3C)cn1] | 0.62 | 424 | Method 6 |

-continued

| Intermediate | Structure | $t_R$ | Mass spectrum (ESI+): m/z [M + H]+ | LC Method |
|---|---|---|---|---|
| 78 | 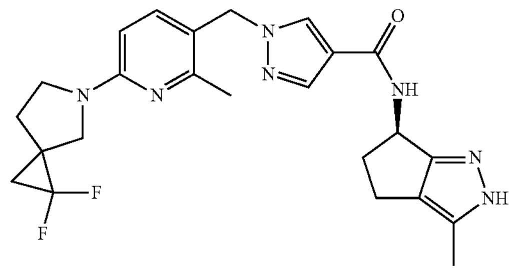 [SMILES: Cc1nc(N2CCC3(C2)CC3(F)F)ccc1Cn1cc(C(=O)N[C@@H]2CCc3c2n[nH]c3C)cn1] | 0.74 | 468 | Method 6 |
| 79 | 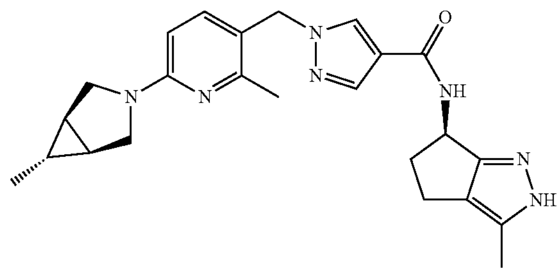 [SMILES: Cc1nc(N2C[C@@H]3[C@@H](C)[C@@H]3C2)ccc1Cn1cc(C(=O)N[C@@H]2CCc3c2n[nH]c3C)cn1] | 0.78 | 432 | Method 6 |
| 80 | 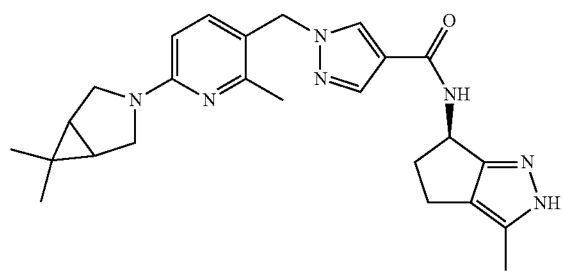 [SMILES: Cc1nc(N2CC3C(C2)C3(C)C)ccc1Cn1cc(C(=O)N[C@@H]2CCc3c2n[nH]c3C)cn1] | 0.83 | 446 | Method 6 |
| 81 | 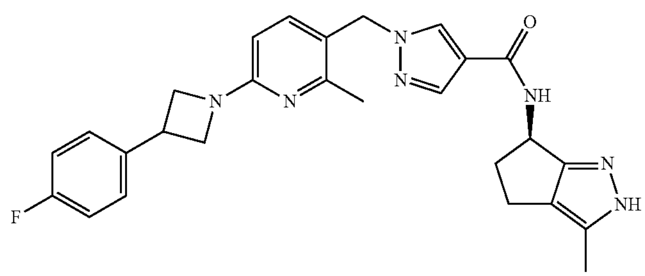 [SMILES: Cc1nc(N2CC(c3ccc(F)cc3)C2)ccc1Cn1cc(C(=O)N[C@@H]2CCc3c2n[nH]c3C)cn1] | 0.77 | 486 | Method 6 |
| 82 | 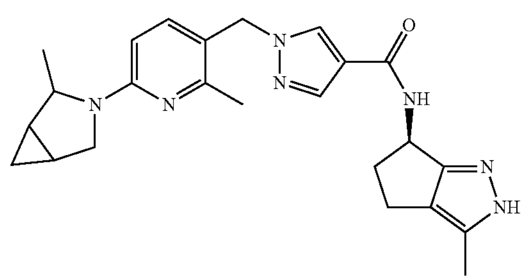 [SMILES: Cc1nc(N2CC3CC3C2C)ccc1Cn1cc(C(=O)N[C@@H]2CCc3c2n[nH]c3C)cn1] | 0.79 | 432 | Method 6 |

-continued

| Intermediate | Structure | $t_R$ | Mass spectrum (ESI+): m/z [M + H]+ | LC Method |
|---|---|---|---|---|
| 83 | 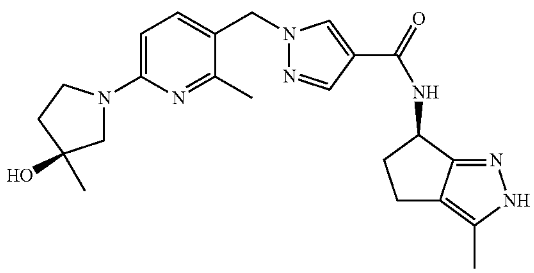 [SMILES: Cc1nc(N2CC[C@](C)(O)C2)ccc1Cn1cc(C(=O)N[C@@H]2CCc3c2n[nH]c3C)cn1] | 0.53 | 436 | Method 6 |

| Example | Name |
|---|---|
| 55 | N-[(6R)-3-Methyl-2H,4H,5H,6H-cyclopenta[c]pyrazol-6-yl]-1-[(2-methyl-6-{5-oxa-2-azaspiro[3.4]octan-2-yl}pyridin-3-yl)methyl]-1H-pyrazole-4-carboxamide |
| 56 | 1-({6-[3-(Hydroxymethyl)azetidin-1-yl]-2-methylpyridin-3-yl}methyl)-N-[(6R)-3-methyl-2H,4H,5H,6H-cyclopenta[c]pyrazol-6-yl]-1H-pyrazole-4-carboxamide |
| 57 | 1-{[6-(3-Cyanoazetidin-1-yl)-2-methylpyridin-3-yl]methyl}-N-[(6R)-3-methyl-2H,4H,5H,6H-cyclopenta[c]pyrazol-6-yl]-1H-pyrazole-4-carboxamide |
| 58 | N-[(6R)-3-Methyl-2H,4H,5H,6H-cyclopenta[c]pyrazol-6-yl]-1-({2-methyl-6[3-(1H-pyrazol-1-yl)azetidin-1-yl]pyridin-3-yl}methyl)-1H-pyrazole-4-carboxamide |
| 59 | 1-({6-[(1R,5S,6R)-6-Hydroxy-3-azabicyclo[3.1.0]hexan-3-yl]-2-methylpyridin-3-yl}methyl)-N-[(6R)-3-methyl-2H,4H,5H,6H-cyclopenta[c]pyrazol-6-yl]-1H-pyrazole-4-carboxamide |
| 60 | N-[(6R)-3-Methyl-2H,4H,5H,6H-cyclopenta[c]pyrazol-6-yl]-1-({2-methyl-6-[3-(trifluoromethyl)pyrrolidin-1-yl]pyridin-3-yl}methyl)-1H-pyrazole-4-carboxamide |
| 61 | N-[(6R)-3-Methyl-2H,4H,5H,6H-cyclopenta[c]pyrazol-6-yl]-1-{[2-methyl-6-(3-methylazetidin-1-yl)pyridin-3-yl]methyl}-1H-pyrazole-4-carboxamide |
| 62 | N-[(6R)-3-Methyl-2H,4H,5H,6H-cyclopenta[c]pyrazol-6-yl]-1-[(2-methyl-6-{octahydrocyclopenta[c]pyrrol-2-yl}pyridin-3-yl)methyl]-1H-pyrazole-4-carboxamide |
| 63 | N-[(6R)-3-Methyl-2H,4H,5H,6H-cyclopenta[c]pyrazol-6-yl]-1-[(2-methyl-6-{7-oxa-2-azaspiro[3.5]nonan-2-yl}pyridin-3-yl)methyl]-1H-pyrazole-4-carboxamide |
| 64 | N-[(6R)-3-Methyl-2H,4H,5H,6H-cyclopenta[c]pyrazol-6-yl]-1-[(2-methyl-6-{6-oxa-3-azabicyclo[3.1.1]heptan-3-yl}pyridin-3-yl)methyl]-1H-pyrazole-4-carboxamide |
| 65 | 1-{[6-(Azepan-1-yl)-2-methylpyridin-3-yl]methyl}-N-[(6R)-3-methyl-2H,4H,5H,6H-cyclopenta[c]pyrazol-6-yl]-1H-pyrazole-4-carboxamide |
| 66 | 1-[(6-{8,8-Difluoro-4-azabicyclo[5.1.0]octan-4-yl}-2-methylpyridin-3-yl)methyl]-N-[(6R)-3-methyl-2H,4H,5H,6H-cyclopenta[c]pyrazol-6-yl]-1H-pyrazole-4-carboxamide |
| 67 | 1-{[6-(3,3-Dimethylazetidin-1-yl)-2-methylpyridin-3-yl]methyl}-N-[(6R)-3-methyl-2H,4H,5H,6H-cyclopenta[c]pyrazol-6-yl]-1H-pyrazole-4-carboxamide |
| 68 | 1-[(6-{3-Azabicyclo[3.2.0]heptan-3-yl}-2-methylpyridin-3-yl)methyl]-N-[(6R)-3-methyl-2H,4H,5H,6H-cyclopenta[c]pyrazol-6-yl]-1H-pyrazole-4-carboxamide |
| 69 | N-[(6R)-3-Methyl-2H,4H,5H,6H-cyclopenta[c]pyrazol-6-yl]-1-({2-methyl-6-[3-(trifluoromethyl)azetidin-1-yl]pyridin-3-yl}methyl)-1H-pyrazole-4-carboxamide |
| 70 | N-[(6R)-3-Methyl-2H,4H,5H,6H-cyclopenta[c]pyrazol-6-yl]-1-({2-methyl-6-[3-(propan-2-yl)azetidin-1-yl]pyridin-3-yl}lmethyl)-1H-pyrazole-4-carboxamide |
| 71 | 1-{[6-(3-Cyano-3-methylpyrrolidin-1-yl)-2-methylpyridin-3-yl]methyl}-N-[(6R)-3-methyl-2H,4H,5H,6H-cyclopenta[c]pyrazol-6-yl]-1H-pyrazole-4-carboxamide |
| 72 | 1-({6-[(3aR,6aS)-Hexahydro-1H-furo[3,4-c]pyrrol-5-yl]-2-methylpyridin-3-yl}methyl)-N-[(6R)-3-methyl-2H,4H,5H,6H-cyclopenta[c]pyrazol-6-yl]-1H-pyrazole-4-carboxamide |
| 73 | N-[(6R)-3-Methyl-2H,4H,5H,6H-cyclopenta[c]pyrazol-6-yl]-1-[(2-methyl-6-{2-oxa-7-azaspiro[4.4]nonan-7-yl}pyridin-3-yl)methyl]-1H-pyrazole-4-carboxamide |
| 74 | 1-({6-[3-Fluoro-3-(trifluoromethyl)azetidin-1-yl]-2-methylpyridin-3-yl}methyl)-N-[(6R)-3-methyl-2H,4H,5H,6H-cyclopenta[c]pyrazol-6-yl]-1H-pyrazole-4-carboxamide |
| 75 | 1-({6-[(3aR,6aS)-5,5-Difluoro-octahydrocyclopenta[c]pyrrol-2-yl]-2-methylpyridin-3-yl}-methyl)-N-[(6R)-3-methyl-2H,4H,5H,6H-cyclopenta[c]pyrazol-6-yl]-1H-pyrazole-4-carboxamide |
| 76 | 1-[(6-{6-Hydroxy-2-azaspiro[3.3]heptan-2-yl}-2-methylpyridin-3-yl)methyl]-N-[(6R)-3-methyl-2H,4H,5H,6H-cyclopenta[c]pyrazol-6-yl]-1H-pyrazole-4-carboxamide |
| 77 | 1-{[6-(3-Fluoro-3-methylazetidin-1-yl)-2-methylpyridin-3-yl]methyl}-N-[(6R)-3-methyl-2H,4H,5H,6H-cyclopenta[c]pyrazol-6-yl]-1H-pyrazole-4-carboxamide |
| 78 | 1-[(6-{1,1-Difluoro-5-azaspiro[2.4]heptan-5-yl}-2-methylpyridin-3-yl)methyl]-N-[(6R)-3-methyl-2H,4H,5H,6H-cyclopenta[c]pyrazol-6-yl]-1H-pyrazole-4-carboxamide |

-continued

| Example | Name |
|---|---|
| 79 | N-[(6R)-3-Methyl-2H,4H,5H,6H-cyclopenta[c]pyrazol-6-yl]-1-({2-methyl-6-[(1R,5S,6R)-6-methyl-3-azabicyclo[3.1.0]hexan-3-yl]pyridin-3-yl}methyl)-1H-pyrazole-4-carboxamide |
| 80 | 1-[(6-{6,6-Dimethyl-3-azabicyclo[3.1.0]hexan-3-yl}-2-methylpyridin-3-yl)methyl]-N-[(6R)-3-methyl-2H,4H,5H,6H-cyclopenta[c]pyrazol-6-yl]-1H-pyrazole-4-carboxamide |
| 81 | 1-({6-[3-(4-Fluorophenyl)azetidin-1-yl]-2-methylpyridin-3-yl}methyl)-N-[(6R)-3-methyl-2H,4H,5H,6H-cyclopenta[c]pyrazol-6-yl]-1H-pyrazole-4-carboxamide |
| 82 | N-[(6R)-3-Methyl-2H,4H,5H,6H-cyclopenta[c]pyrazol-6-yl]-1-[(2-methyl-6-{2-methyl-3-azabicyclo[3.1.0]hexan-3-yl}pyridin-3-yl)methyl]-1H-pyrazole-4-carboxamide |
| 83 | 1-({6-[(3S)-3-Hydroxy-3-methylpyrrolidin-1-yl]-2-methylpyridin-3-yl}methyl)-N-[(6R)-3-methyl-2H,4H,5H,6H-cyclopenta[c]pyrazol-6-yl]-1H-pyrazole-4-carboxamide |

Example 84

1-[(2-{6,6-Difluoro-3-azabicyclo[3.1.0]hexan-3-yl}-4-methylpyrimidin-5-yl)methyl]-N-[(6R)-3-methyl-2H,4H,5H,6H-cyclopenta[c]pyrazol-6-yl]-1H-pyrazole-4-carboxamide, TFA salt Example 85

1-[(2-{6,6-Difluoro-3-azabicyclo[3.1.0]hexan-3-yl}-4-methylpyrimidin-5-yl)methyl]-N-[(6R)-3-methyl-1H,4H,5H,6H-cyclopenta[c]pyrazol-6-yl]-1H-1,2,3-triazole-4-carboxamide

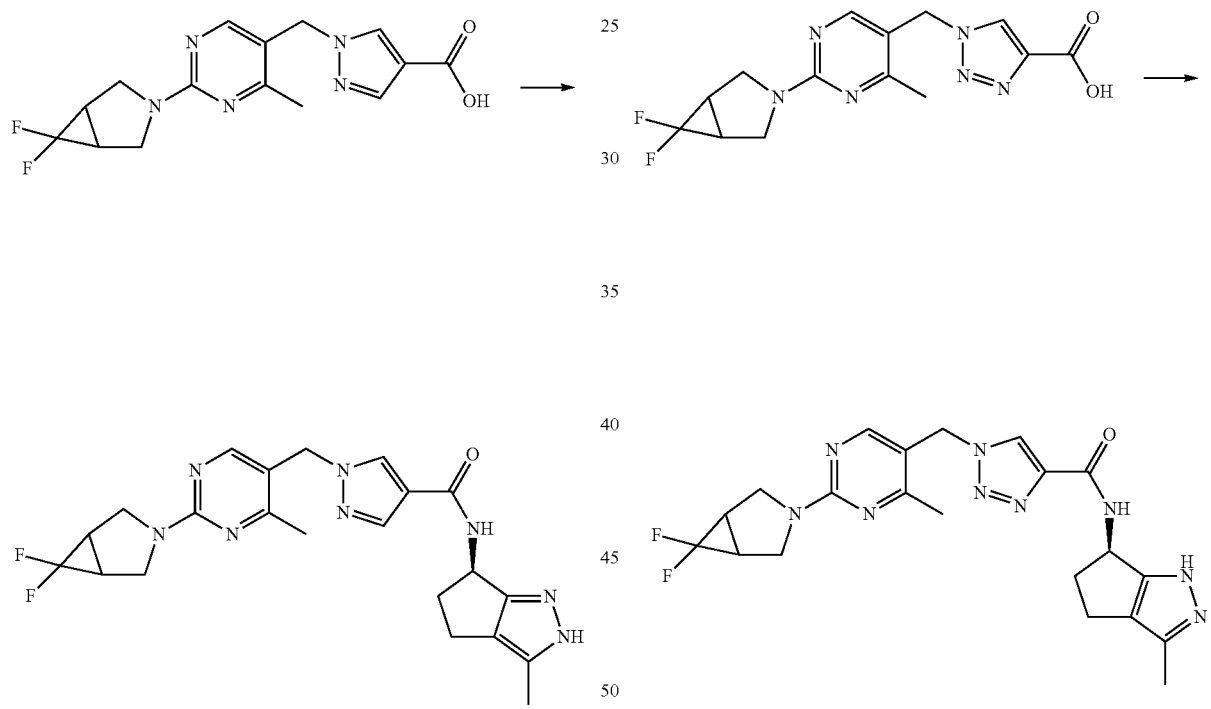

To a solution of 1-[(2-{6,6-difluoro-3-azabicyclo[3.1.0]hexan-3-yl}-4-methylpyrimidin-5-yl)methyl]-1H-pyrazole-4-carboxylic acid, lithium salt (8.8 mg) and (6R)-3-methyl-2-{[2-(trimethylsilyl)ethoxy]methyl}-2H,4H,5H,6H-cyclopenta[c]pyrazol-6-amine (7.4 mg) in DMF (2 mL) are added DIPEA (13.4 µL) and O-(7-azabenzotriazol-1-yl)-N,N,N',N'-tetramethyluronium-hexafluorophosphat (HATU, 10.5 mg) and the mixture is stirred for 2 h. The solvents are evaporated in vacuo, the residue is treated with TFA (0.5 mL) and stirred for 1 h. The mixture is purified by HPLC on reversed phase (ACN, water) to give the title compound.

LC (Method 8): $t_R$=0.51 min; Mass spectrum (ESI$^+$): m/z=455 [M+H]$^+$.

A solution of 1-[(2-{6,6-difluoro-3-azabicyclo[3.1.0]hexan-3-yl}-4-methylpyrimidin-5-yl)methyl]-1H-1,2,3-triazole-4-carboxylic acid (10 mg) and O-(7-azabenzotriazol-1-yl)-N,N,N',N'-tetramethyluronium-hexafluorophosphat (HATU, 11 mg) in DMF (1 mL) is stirred for 10 min. DIPEA (20 µL) and (6R)-3-methyl-1H,4H,5H,6H-cyclopenta[c]pyrazol-6-amine (4.1 mg) are added and the mixture is stirred for 12 h. Then the mixture is purified by HPLC on reversed phase (ACN, water) to give the title compound.

LC (Method 2): $t_R$=0.90 min; Mass spectrum (ESI$^+$): m/z=456 [M+H]$^+$.

Example 86

1-[(6-{3-Azabicyclo[3.1.0]hexan-3-yl}-2-methyl-pyridin-3-yl)methyl]-N-[(6R)-3-methyl-1H,4H,5H,6H-cyclopenta[c]pyrazol-6-yl]-1H-1,2,3-triazole-4-carboxamide

Example 87

1-[(2-{3-Azabicyclo[3.1.0]hexan-3-yl}-4-methylpyrimidin-5-yl)methyl]-N-[(6R)-3-methyl-1H,4H,5H,6H-cyclopenta[c]pyrazol-6-yl]-1H-1,2,3-triazole-4-carboxamide

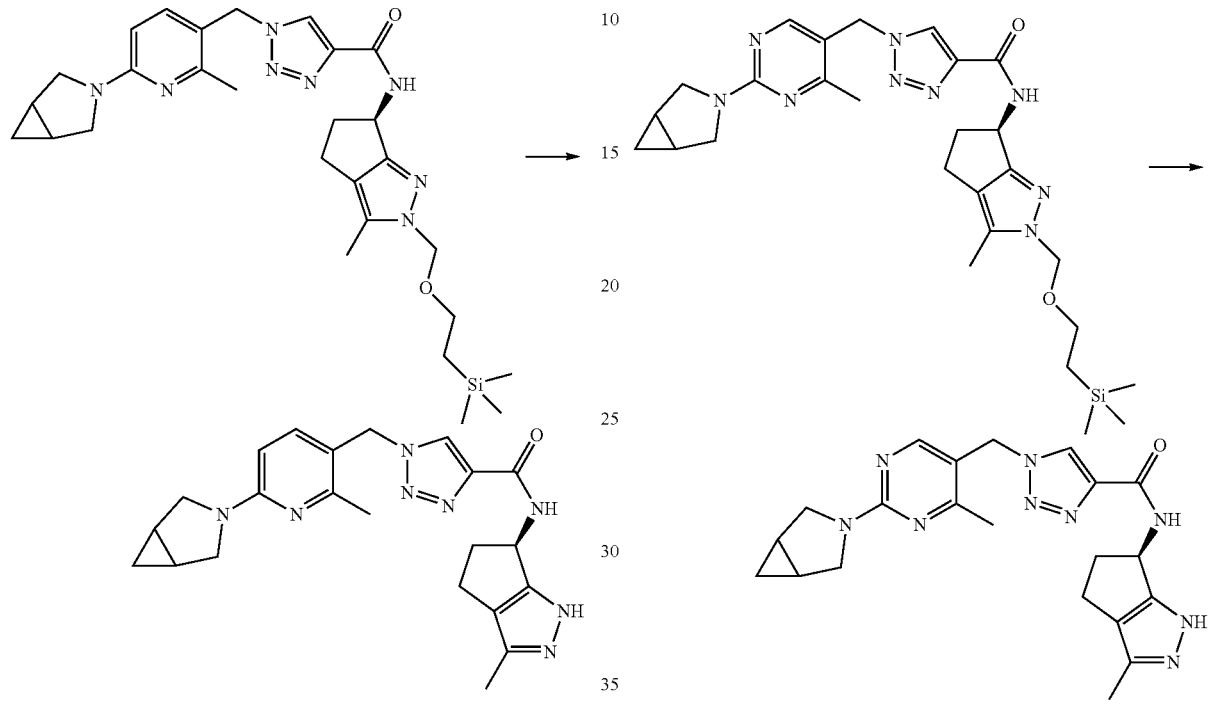

To a mixture of 1-[(6-{3-azabicyclo[3.1.0]hexan-3-yl}-2-methylpyridin-3-yl)methyl]-N-[(6R)-3-methyl-2-{[2-(trimethylsilyl)ethoxy]methyl}-2H,4H,5H,6H-cyclopenta[c]pyrazol-6-yl]-1H-1,2,3-triazole-4-carboxamide (140 mg) in water (300 μL) is added concentrated aqueous HCl (300 μL) and the mixture is stirred for 12 h at room temperature. The solvents are evaporated and the residue is dissolved in water. 1 M aqueous NaOH is added until pH of 14 is reached. The precipitate is collected by filtration and dried in vacuo. The crude product is recrystallized from ACN to give the title compound.

LC (Method 1): $t_R$=0.68 min; Mass spectrum (ESI+): m/z=419 [M+H]+.

To a solution of 1-[(2-{3-azabicyclo[3.1.0]hexan-3-yl}-4-methylpyrimidin-5-yl)methyl]-N-[(6R)-3-methyl-2-{[2-(trimethylsilyl)ethoxy]methyl}-2H,4H,5H,6H-cyclopenta[c]pyrazol-6-yl]-1H-1,2,3-triazole-4-carboxamide (81 mg) in DCM (2 mL) is added TFA (300 μL) and the mixture is stirred for 48 h at room temperature. The mixture is diluted with MeOH, treated with 7 M NH3 in MeOH until pH of 8 is reached and then purified by HPLC on reversed phase (ACN, water) to give the title compound.

LC (Method 7): $t_R$=0.67 min; Mass spectrum (ESI+): m/z=420 [M+H]+.

Examples 88-93 are prepared analogous to example 12:

| Intermediate | Structure | $t_R$ | Mass spectrum (ESI+): m/z [M + H]+ | LC Method |
|---|---|---|---|---|
| 88 | 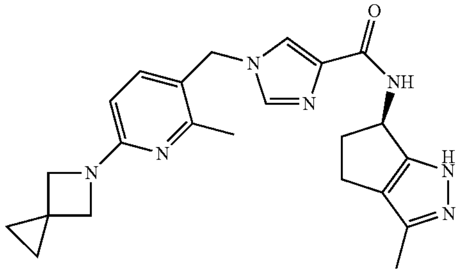 [SMILES: Cc1nc(N2CC3(CC3)C2)ccc1Cn1cnc(C(=O)N[C@@H]2CCc3c(C)n[nH]c32)c1] | 0.38 | 418 | Method 8 |

-continued

| Intermediate | Structure | $t_R$ | Mass spectrum (ESI+): m/z [M + H]+ | LC Method |
|---|---|---|---|---|
| 89 | 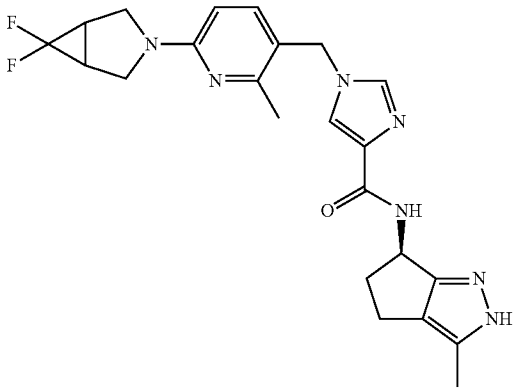 [SMILES: Cc1nc(N2CC3C(C2)C3(F)F)ccc1Cn1cnc(C(=O)N[C@@H]2CCc3c2n[nH]c3C)c1] | 0.69 | 454 | Method 6 |
| 90 | 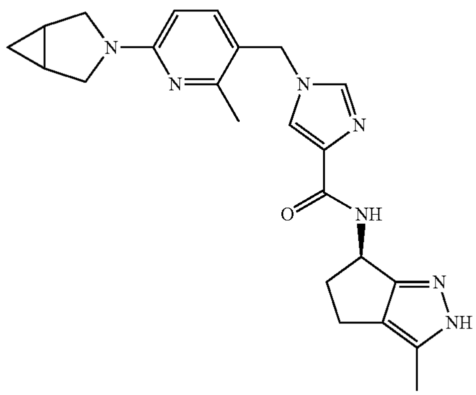 [SMILES: Cc1nc(N2CC3CC3C2)ccc1Cn1cnc(C(=O)N[C@@H]2CCc3c2n[nH]c3C)c1] | 0.72 | 418 | Method 6 |
| 91 | 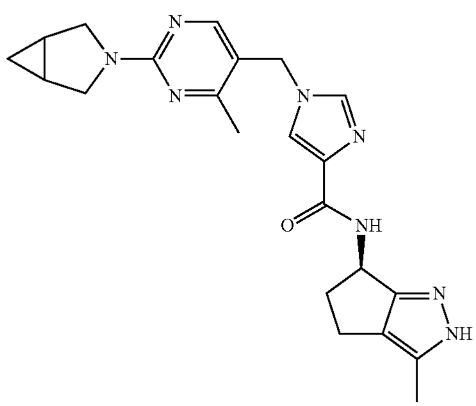 [SMILES: Cc1nc(N2CC3CC3C2)ncc1Cn1cnc(C(=O)N[C@@H]2CCc3c2n[nH]c3C)c1] | 0.63 | 419 | Method 7 |
| 92 | 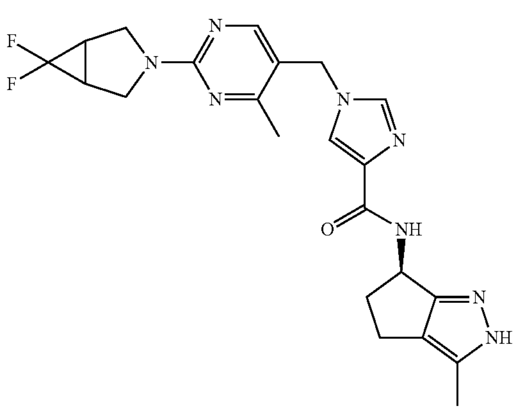 [SMILES: Cc1nc(N2CC3C(C2)C3(F)F)ncc1Cn1cnc(C(=O)N[C@@H]2CCc3c2n[nH]c3C)c1] | 0.62 | 455 | Method 7 |

| Intermediate | Structure | $t_R$ | Mass spectrum (ESI+):<br>m/z [M + H]+ | LC Method |
|---|---|---|---|---|
| 93 | 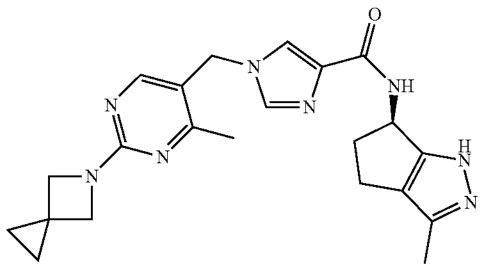 [SMILES: Cc1nc(N2CC3(CC3)C2)ncc1Cn1cnc(C(=O)N[C@@H]2CCc3c(C)n[nH]c32)c1] | 0.58 | 419 | Method 7 |

| Example | Name | Starting Material |
|---|---|---|
| 88 | 1-[(6-{5-Azaspiro[2.3]hexan-5-yl}-2-methylpyridin-3-yl)methyl]-N-[(6R)-3-methyl-2H,4H,5H,6H-cyclopenta[c]pyrazol-6-yl]-1H-imidazole-4-carboxamide | 1-[(6-{5-Azaspiro[2.3]hexan-5-yl}-2-methyl-pyridin-3-yl)methyl]-1H-imidazole-4-carboxylic acid |
| 89 | 1-[(6-{6,6-Difluoro-3-azabicyclo[3.1.0]hexan-3-yl}-2-methylpyridin-3-yl)methyl]-N-[(6R)-3-methyl-2H,4H,5H,6H-cyclopenta[c]pyrazol-6-yl]-1H-imidazole-4-carboxamide | 1-[(6-{6,6-Difluoro-3-azabicyclo[3.1.0]-hexan-3-yl}-2-methylpyridin-3-yl)methyl]-1H-imidazole-4-carboxylic acid |
| 90 | 1-[(6-{3-Azabicyclo[3.1.0]hexan-3-yl}-2-methyl-pyridin-3-yl)methyl]-N-[(6R)-3-methyl-2H,4H,5H,6H-cyclopenta[c]pyrazol-6-yl]-1H-imidazole-4-carboxamide | 1-[(6-{3-Azabicyclo[3.1.0]hexan-3-yl}-2-methylpyridin-3-yl)methyl]-1H-imidazole-4-carboxylic acid |
| 91 | 1-[(2-{3-Azabicyclo[3.1.0]hexan-3-yl}-4-methyl-pyrimidin-5-yl)methyl]-N-[(6R)-3-methyl-2H,4H,5H,6H-cyclopenta[c]pyrazol-6-yl]-1H-imidazole-4-carboxamide | 1-[(6-{3-Azabicyclo[3.1.0]hexan-3-yl}-2-methylpyrimidin-3-yl)methyl]-1H-imidazole-4-carboxylic acid |
| 92 | 1-[(2-{6,6-Difluoro-3-azabicyclo[3.1.0]hexan-3-yl}-4-methylpyrimidin-5-yl)methyl]-N-[(6R)-3-methyl-2H,4H,5H,6H-cyclopenta[c]pyrazol-6-yl]-1H-imidazole-4-carboxamide | 1-[(6-{6,6-Difluoro-3-azabicyclo[3.1.0]-hexan-3-yl}-2-methylpyrimidin-3-yl)methyl]-1H-imidazole-4-carboxylic acid |
| 93 | 1-[(2-{5-Azaspiro[2.3]hexan-5-yl}-4-methyl-pyrimidin-5-yl)methyl]-N-[(6R)-3-methyl-2H,4H,5H,6H-cyclopenta[c]pyrazol-6-yl]-1H-imidazole-4-carboxamide | 1-[(6-{5-Azaspiro[2.3]hexan-5-yl}-2-methyl-pyrimidin-3-yl)methyl]-1H-imidazole-4-carboxylic acid |

Example 94

1-({6-[(1R,5S,6R)-6-(hydroxymethyl)-3-azabicyclo[3.1.0]hexan-3-yl]-2-methylpyridin-3-yl}methyl)-N-[(6R)- 3-methyl-1H,4H,5H,6H-cyclopenta[c]pyrazol-6-yl]-1H-pyrazole-4-carboxamide

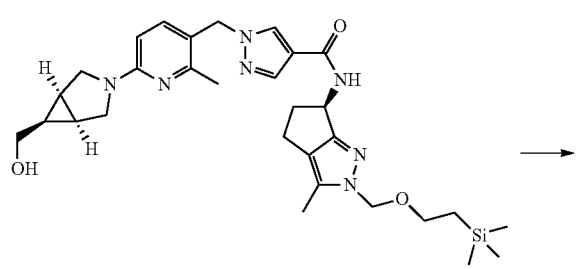

→

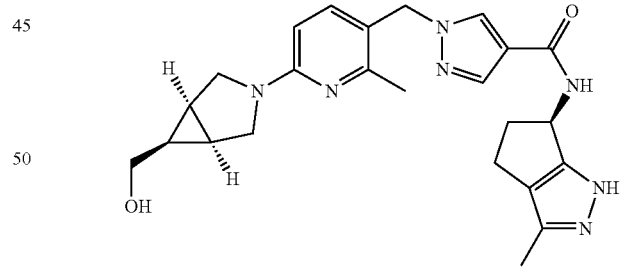

To a solution of 1-({6-[(1R,5S,6R)-6-(hydroxymethyl)-3-azabicyclo[3.1.0]hexan-3-yl]-2-methylpyridin-3-yl}methyl)- N-[(6R)-3-methyl-2-{[2-(trimethylsilyl)ethoxy]methyl}-2H,4H,5H,6H-cyclopenta[c]pyrazol-6-yl]-1H-pyrazole-4-carboxamide (24 mg) in DCM (2 mL) is added TFA (1 mL) and the mixture is stirred for 12 h at room temperature. The solvents are evaporated and the residue is dissolved in MeOH. 1 M KOH in EtOH (55 μL) is added and the mixture is stirred for 30 min. The solvents are evaporated in vacuo and the residue is purified by HPLC on reversed phase (ACN, water) to give the title compound.

LC (Method 2): $t_R$=0.80 min; Mass spectrum (ESI$^+$): m/z=448 [M+H]$^+$.

Example 95

1-({6-[(1R,5S,6R)-6-(Fluoromethyl)-3-azabicyclo[3.1.0]hexan-3-yl]-2-methylpyridin-3-yl}methyl)-N-[(6R)- 3-methyl-2H,4H,5H,6H-cyclopenta[c]pyrazol-6-yl]-1H-pyrazole-4-carboxamide

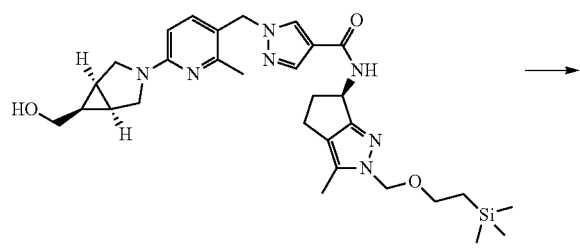

→

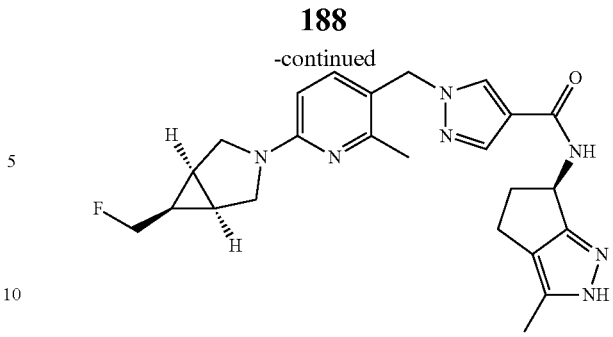

A solution of 1-({6-[(1R,5S,6R)-6-(hydroxymethyl)-3-azabicyclo[3.1.0]hexan-3-yl]-2-methylpyridin-3-yl}methyl)-N- [(6R)-3-methyl-2-{[2-(trimethylsilyl)ethoxy]methyl}-2H,4H,5H,6H-cyclopenta[c]pyrazol-6-yl]-1H-pyrazole-4-carboxamide (10 mg) in DCM (1 mL) is cooled to 0° C. and treated with diethylamino-sulphur-trifluoride (DAST, 4 µL). The mixture is stirred for 12 h while warming to room temperature. The solvent is evaporated in vacuo and the residue is dissolved in DCM (1 mL) and TFA (0.5 mL). The mixture is stirred for 12 h at room temperature and then concentrated in vacuo. The residue is treated for 15 min with 4 M aqueous NaOH and then purified by HPLC on reversed phase (ACN, water) to give the title compound.

LC (Method 2): $t_R$=0.91 min; Mass spectrum (ESI$^+$): m/z=450 [M+H]$^+$.

Examples 96-105 are prepared analogous to example 12:

| Intermediate | Structure | $t_R$ | Mass spectrum (ESI+): m/z [M + H]$^+$ | LC Method |
|---|---|---|---|---|
| 96 | 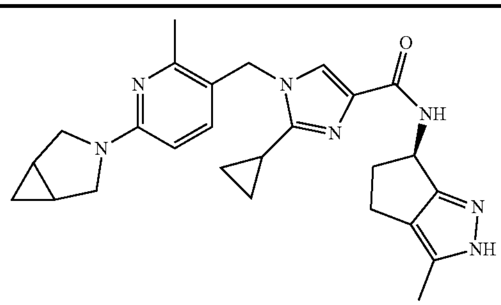 | 1.02 | 458 | Method 2 |
| 97 | 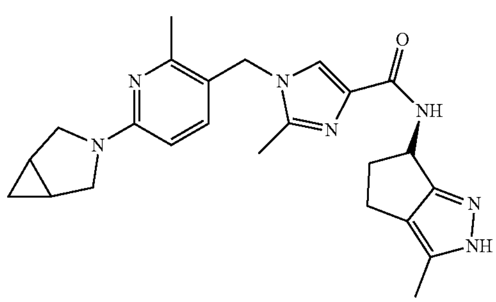 | 0.97 | 432 | Method 2 |
| 98 | 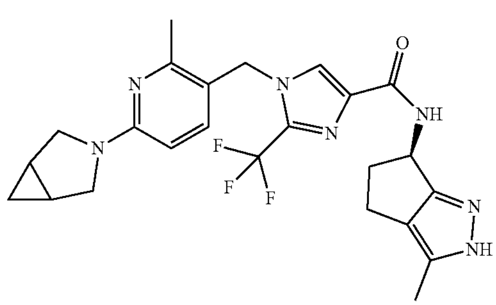 [SMILES: Cc1nc(N2CC3CC3C2)ccc1Cn1cc(C(=O)N[C@@H]2CCc3c2n[nH]c3C)nc1C(F)(F)F] | 1.07 | 486 | Method 2 |

| Intermediate | Structure | $t_R$ | Mass spectrum (ESI+): m/z [M + H]+ | LC Method |
|---|---|---|---|---|
| 99 | 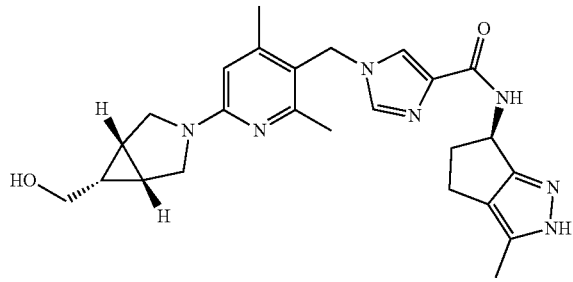 [SMILES: Cc1cc(N2C[C@@H]3[C@H](CO)[C@@H]3C2)nc(C)c1Cn1cnc(C(=O)N[C@@H]2CCc3c2n[nH]c3C)c1] | 0.54 | 448 | Method 7 |
| 100 | 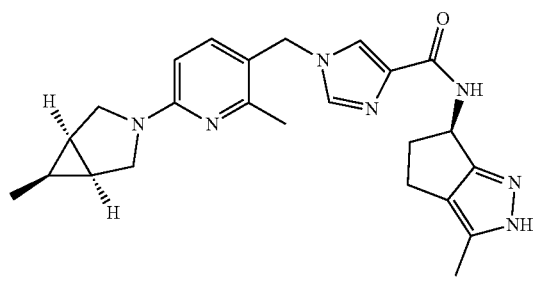 [SMILES: Cc1nc(N2C[C@@H]3[C@H](C)[C@@H]3C2)ccc1Cn1cnc(C(=O)N[C@@H]2CCc3c2n[nH]c3C)c1] | 0.76 | 432.2 | Method 6 |
| 101 | 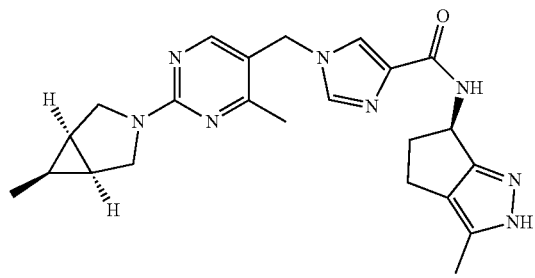 | 0.67 | 433.2 | Method 6 |
| 102 | 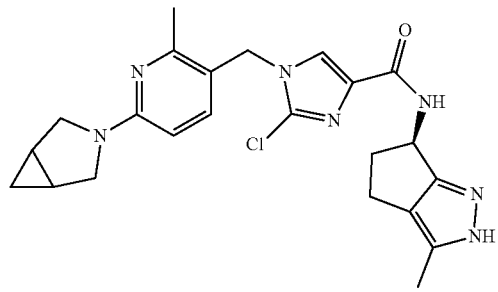 [SMILES: Cc1nc(N2CC3CC3C2)ccc1Cn1cc(C(=O)N[C@@H]2CCc3c2n[nH]c3C)nc1Cl] | 0.82 | 452/454 (Cl) | Method 6 |
| 103 | 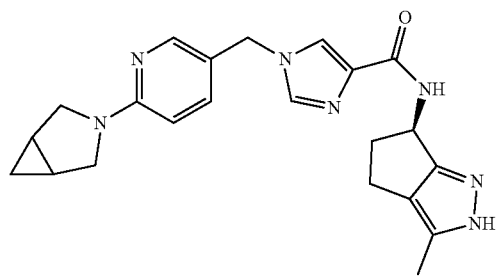 [SMILES: Cc1[nH]nc2c1CC[C@H]2NC(=O)c1cn(Cc2ccc(N3CC4CC4C3)nc2)cn1] | 0.66 | 404 | Method 1 |

-continued

| Intermediate | Structure | $t_R$ | Mass spectrum (ESI+): m/z [M + H]+ | LC Method |
|---|---|---|---|---|
| 104 | 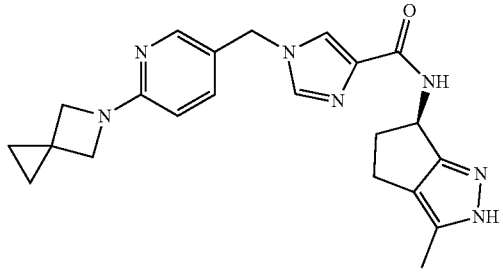 [SMILES: Cc1[nH]nc2c1CC[C@H]2NC(=O)c1cn(Cc2ccc(N3CC4(CC4)C3)nc2)cn1] | 0.87 | 404 | Method 2 |
| 105 | 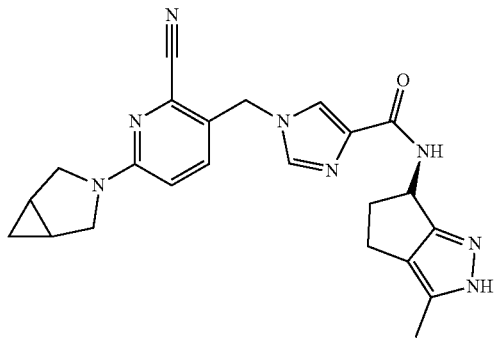 | 0.62 | 429 | Method 5 |

| Example | Name | Starting Material |
|---|---|---|
| 96 | 1-[(6-{3-Azabicyclo[3.1.0]hexan-3-yl}-2-methyl-pyridin-3-yl)methyl]-2-cyclopropyl-N-[(6R)-3-methyl-2H,4H,5H,6H-cyclopenta[c]pyrazol-6-yl]-1H-imidazole-4-carboxamide | 1-[(6-{3-Azabicyclo[3.1.0]hexan-3-yl}-2-methylpyridin-3-yl)methyl]-2-cyclopropyl-1H-imidazole-4-carboxylic acid |
| 97 | 1-[(6-(3-Azabicyclo[3.1.0]hexan-3-yl}-2-methyl-pyridin-3-yl)methyl]-2-methyl-N-[(6R)-3-methyl-2H,4H,5H,6H-cyclopenta[c]pyrazol-6-yl]-1H-imidazole-4-carboxamide | 1-[(6-{3-Azabicyclo[3.1.0]hexan-3-yl}-2-methylpyridin-3-yl)methyl]-2-methyl-1H-imidazole-4-carboxylic acid |
| 98 | 1-[(6-{3-Azabicyclo[3.1.0]hexan-3-yl}-2-methyl-pyridin-3-yl)methyl]-N-[(6R)-3-methyl-2H,4H,5H,6H-cyclopenta[c]pyrazol-6-yl]-2-(trifluoromethyl)-1H-imidazole-4-carboxamide | 1-[(6-{3-Azabicyclo[3.1.0]hexan-3-yl}-2-methylpyridin-3-yl)methyl]-2-(trifluoromethyl)-1H-imidazole-4-carboxylic acid |
| 99 | 1-({6-[(1R,5S,6S)-6-(Hydroxymethyl)-3-azabicyclo[3.1.0]hexan-3-yl]-2-methylpyridin-3-yl}-methyl)-N-[(6R)-3-methyl-2H,4H,5H,6H-cyclopenta[c]pyrazol-6-yl]-1H-imidazole-4-carboxamide | 1-({6-[(1R,5S,6S)-6-(Hydroxymethyl)-3-azabicyclo[3.1.0]hexan-3-yl]-2-methyl-pyridin-3-yl}methyl)-1H-imidazole-4-carboxylic acid |
| 100 | N-[(6R)-3-Methyl-2H,4H,5H,6H-cyclopenta[c]-pyrazol-6-yl]-1-({2-methyl-6-[(1R,5S,6R)-6-methyl-3-azabicyclo[3.1.0]hexan-3-yl]pyridin-3-yl}methyl)-1H-imidazole-4-carboxamide | 1-({4-Methyl-2-[(1R,5S,6R)-6-methyl-3-azabicyclo[3.1.0]hexan-3-yl]pyridin-5-yl}methyl)-1H-imidazole-4-carboxylic acid |
| 101 | 1-({4-Methyl-2-[(1R,5S,6R)-6-methyl-3-azabicyclo[3.1.0]hexan-3-yl]pyrimidin-5-yl}methyl)-N-[(6R)-3-methyl-2H,4H,5H,6H-cyclopenta[c]-pyrazol-6-yl]-1H-imidazole-4-carboxamide | 1-({4-Methyl-2-[(1R,5S,6R)-6-methyl-3-azabicyclo[3.1.0]hexan-3-yl]pyrimidin-5-yl}-methyl)-1H-imidazole-4-carboxylic acid |
| 102 | 1-[(6-{3-Azabicyclo[3.1.0]hexan-3-yl}-2-methyl-pyridin-3-yl)methyl]-2-chloro-N-[(6R)-3-methyl-2H,4H,5H,6H-cyclopenta[c]pyrazol-6-yl]-1H-imidazole-4-carboxamide | 1-[(6-{3-Azabicyclo[3.1.0]hexan-3-yl}-2-methylpyridin-3-yl)methyl]-2-chloro-1H-imidazole-4-carboxylic acid |
| 103 | 1-[(6-{3-Azabicyclo[3.1.0]hexan-3-yl}pyridin-3-yl)-methyl]-N-[(6R)-3-methyl-2H,4H,5H,6H-cyclopenta[c]pyrazol-6-yl]-1H-imidazole-4-carboxamide | 1-[(6-{3-Azabicyclo[3.1.0]hexan-3-yl}pyridin-3-yl)methyl]-1H-imidazole-4-carboxylic acid |
| 104 | 1-[(6-{5-Azaspiro[2.3]hexan-5-yl}pyridin-3-yl)-methyl]-N-[(6R)-3-methyl-2H,4H,5H,6H-cyclopenta[c]pyrazol-6-yl]-1H-imidazole-4-carboxamide | 1-[(6-{5-Azaspiro[2.3]hexan-5-yl}pyridin-3-yl)methyl]-1H-imidazole-4-carboxylic acid |
| 105 | 1-[(6-{3-Azabicyclo[3.1.0]hexan-3-yl}-2-cyano-pyridin-3-yl)methyl]-N-[(6R)-3-methyl-2H,4H,5H,6H-cyclopenta[c]pyrazol-6-yl]-1H-pyrazole-4-carboxamide | 1-[(6-{3-Azabicyclo[3.1.0]hexan-3-yl}-2-cyanopyridin-3-yl)methyl]-1H-pyrazole-4-carboxylic acid |

Example 106

1-[(6-{3-Azabicyclo[3.1.0]hexan-3-yl}-2-methyl-pyridin-3-yl)methyl]-3-(2-hydroxypropan-2-yl)-N-[(6R)-3-methy-2H,4H,5H,6H-cyclopenta[c]pyrazol-6-yl]-1H-pyrazole-4-carboxamide

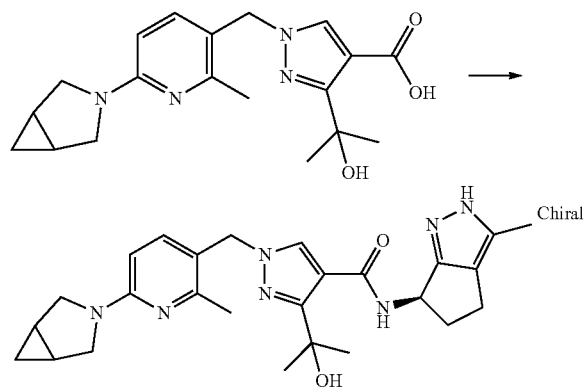

To a solution of 1-[(6-{3-azabicyclo[3.1.0]hexan-3-yl}-2-methylpyridin-3-yl)methyl]-3-(2-hydroxypropan-2-yl)-1H-pyrazole-4-carboxylic acid; TFA (24 mg) and (6R)-3-methyl-2-{[2-(trimethylsilyl)ethoxy]methyl}-2H,4H,5H,6H-cyclopenta[c]pyrazol-6-amine (13 mg) in DMF (1 mL) are added DIPEA (40 µL) and O-(7-azabenzotriazol-1-yl)-N,N,N',N'-tetramethyluronium-hexafluorophosphat (HATU, 19 mg) and the mixture is stirred for 15 min. The solvents are evaporated in vacuo, the residue is treated with TFA (0.25 mL) and stirred for 1 h. Hydrochloric acid (1 mL; 32% in water) is added, the mixture stirred for 16 h at room temperature and then concentrated in vacuo. The residue is purified by HPLC on reversed phase (ACN, water) to give the title compound.

LC (Method 2): $t_R$=1.01 min; Mass spectrum (ESI$^+$): m/z=476 [M+H]$^+$.

Example 107

1-[(6-{3-Azabicyclo[3.1.0]hexan-3-yl}-2-methyl-pyridin-3-yl)methyl]-N-[(6R)-3-methyl-2H,4H,5H,6H-cyclopenta[c]pyrazol-6-yl]-1H-1,2,4-triazole-3-carboxamide

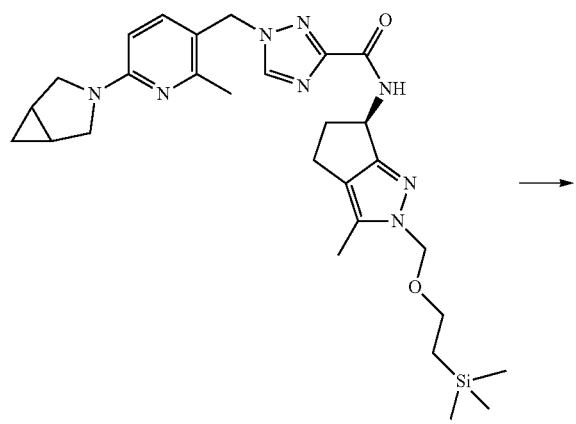

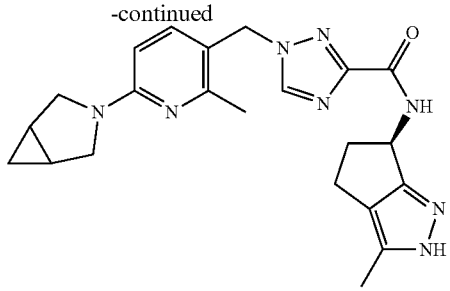

To a solution of 1-[(6-{3-azabicyclo[3.1.0]hexan-3-yl}-2-methylpyridin-3-yl)methyl]-N-[(6R)-3-methyl-2-{[2-(trimethylsilyl)ethoxy]methyl}-2H,4H,5H,6H-cyclopenta[c]pyrazol-6-yl]-1H-1,2,4-triazole-3-carboxamide (94 mg) in DCM (2 mL) is added TFA (1 mL) and the mixture is stirred for 12 h at room temperature. The solvents are evaporated in vacuo and the residue is purified by HPLC on reversed phase (ACN, water) to give the title compound.

LC (Method 6): $t_R$=0.70 min; Mass spectrum (ESI$^+$): m/z=419 [M+H]$^+$.

Example 108

1-[(6-{3-Azabicyclo[3.1.0]hexan-3-yl}-2-methyl-pyridin-3-yl)methyl]-3-{[(6R)-3-methyl-2H,4H,5H,6H-cyclopenta[c]pyrazol-6-yl]carbamoyl}-1H-indole-5-carboxylic acid

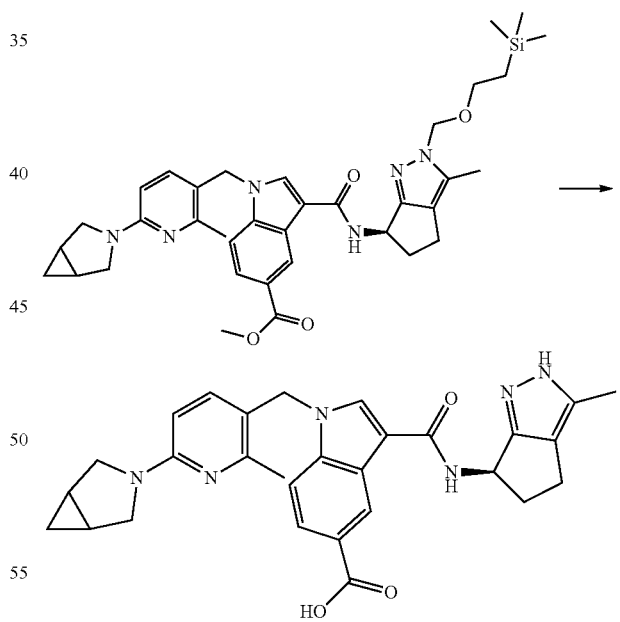

To a solution of methyl 1-[(6-{3-azabicyclo[3.1.0]hexan-3-yl}-2-methylpyridin-3-yl)methyl]-3-{[(6R)-3-methyl-2-{[2-(trimethylsilyl)ethoxy]methyl}-2H,4H,5H,6H-cyclopenta[c]pyrazol-6-yl]carbamoyl}-1H-indole-5-carboxylate (12 mg) in DCM (2 mL) is added TFA (1 mL) and the mixture is stirred for 12 h at room temperature. The solvents are evaporated in vacuo, the residue is dissolved in THF (2 mL) and treated with 1 M solution of KOH in EtOH (100 µL). The mixture is stirred for 12 h at 50° C. Then the mixture is diluted with THF and purified by HPLC on reversed phase (ACN, water) to give the title compound.

LC (Method 1): $t_R$=0.70 min; Mass spectrum (ESI$^+$): m/z=511 [M+H]$^+$.

Example 109

5-[(6-{3-Azabicyclo[3.1.0]hexan-3-yl}-2-methyl-pyridin-3-yl)methyl]-N-[(6R)-3-methyl-1H,4H,5H, 6H- cyclopenta[c]pyrazol-6-yl]-1H-pyrrole-2-carboxamide

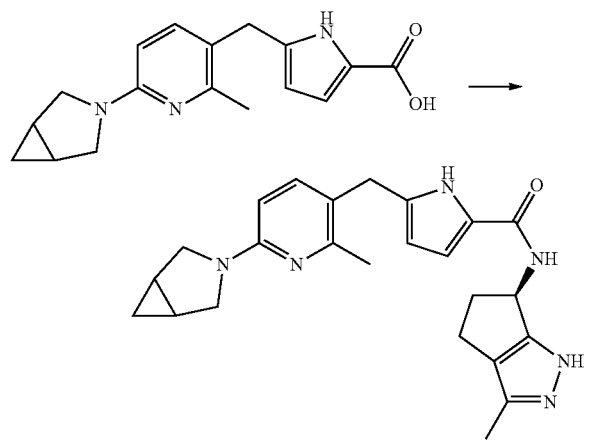

A solution of 5-[(6-{3-azabicyclo[3.1.0]hexan-3-yl}-2-methylpyridin-3-yl)methyl]-1H-pyrrole-2-carboxylic acid (30 mg), DIPEA (84 μL) and O-(7-azabenzotriazol-1-yl)-N,N,N',N'-tetramethyluronium-hexafluorophosphat (HATU, 43 mg) in DMF (1 mL) is stirred for 20 min. (6R)-3-Methyl-1H,4H,5H,6H-cyclopenta[c]pyrazol-6-amine dihydrochloride (22 mg) is added and the mixture is stirred for 1 h at room temperature and for 1.5 h at 40° C. (6R)-3-Methyl-1H,4H,5H,6H-cyclopenta[c]pyrazol-6-amine dihydrochloride (25 mg), DIPEA (34 μL) and O-(7-azabenzo-triazol-1-yl)-N,N,N',N'-tetramethyluronium-hexafluorophosphat (HATU, 30 mg) are added and the mixture is stirred for 12 h at room temperature. The mixture is diluted with DMF and MeOH. 4 M aqueous HCl is added until a solution is obtained. Then the mixture is purified by HPLC on reversed phase (ACN, water) to give the title compound.

LC (Method 1): $t_R$=0.71 min; Mass spectrum (ESI$^+$): m/z=417 [M+H]$^+$.

The invention claimed is:
1. A compound of formula (I)

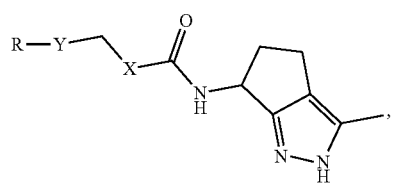

wherein
Y is selected from the group consisting of

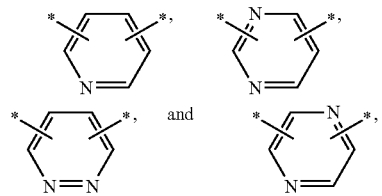

each of which is substituted with 1 or 2 independent substituents $R^1$;
R is selected from the group consisting of
saturated 4- to 7-membered monocyclic and saturated 6- to 12-membered bicyclic ring systems containing 1 to 3 N atoms as ring members and optionally 1 to 2 ring members selected from the group consisting of C=O, O, S, S=O, and SO$_2$,
provided that the ring systems do not contain any heteroatom-heteroatom bonds between ring members,
wherein said ring systems are attached to Y in formula (I) via an N atom, and
wherein said ring systems are optionally substituted with 1 to 6 F, optionally substituted with 1 substituent $R^2$, and optionally substituted with 1 or 2 CH$_3$ groups;
X is selected from the group consisting of
5-membered heteroaryls, containing 1 to 4 N atoms or containing 1 O or S atom or containing 1 to 3 N atoms and 1 O or S atom, and 9-membered heteroaryls, consisting of a 5-membered ring fused to a 6-membered ring and containing 1 to 5 N atoms,
wherein said heteroaryls are attached to the carbonyl group in formula (I) via a C atom of the 5-membered ring and to the CH$_2$ group in formula (I) via a non-adjacent C or N atom of the 5-membered ring, and
wherein said heteroaryls are optionally substituted with 1 substituent $R^3$;
$R^1$ is selected from the group consisting of
H, C$_{1-4}$-alkyl optionally substituted with 1 to 5 F, cyclopropyl optionally substituted with 1 F or 1 CH$_3$ group, CN, OH, O—C$_{1-3}$-alkyl optionally substituted with 1 to 5 F, C$_{1-3}$-alkyl optionally substituted with 1 substituent selected from the group consisting of CN, OH, and O—CH$_3$;
$R^2$ is selected from the group consisting of
Cl, C$_{1-4}$-alkyl optionally substituted with 1 to 5 F, C$_{3-4}$-cycloalkyl, C$_{1-3}$-alkylene-OH, C$_{1-3}$-alkylene-O—C$_{1-4}$-alkyl, CN, COOH, NH$_2$, NH—C$_{1-3}$-alkyl, N(C$_{1-3}$-alkyl)$_2$, OH, O—C$_{1-4}$-alkyl optionally substituted with 1 to 5 F, phenyl, 5-membered heteroaryls containing 1 —NH—, —N<, —O— or —S— ring member and optionally additionally 1 or 2 =N— ring members, and 6-membered heteroaryls containing 1 or 2 =N— ring members;
wherein said phenyl and 5- and 6-membered heteroaryls are optionally substituted at 1 or 2 carbon atoms independently of each other with F, Cl, CH$_3$, CF$_3$, CN, OH, and/or O—CH$_3$, and
wherein N—H groups present within these rings are optionally replaced by N—C$_{1-3}$-alkyl;
$R^3$ is selected from the group consisting of
F, Cl, Br, CN, COOH, C$_{1-3}$-alkyl optionally substituted with 1 to 5 F, C$_{3-5}$-cycloalkyl, C$_{1-3}$-alkylene-OH, C$_{1-3}$-alkylene-O—C$_{1-4}$-alkyl, O—C$_{1-4}$-alkyl optionally substituted with 1 to 5 F, 5-membered heteroaryls containing 1 —NH—, —O— or —S— ring member and optionally additionally 1 or 2 =N— ring members, and 6-membered heteroaryls containing 1 or 2 =N— ring members;
wherein said 5- and 6-membered heteroaryls are optionally substituted at 1 or 2 carbon atoms independently of each other with F, Cl, $CH_3$, $CF_3$, CN, OH, and/or O—$CH_3$, and
wherein N—H groups present within these rings are optionally replaced by N—$C_{1-3}$-alkyl;
and/or the tautomers thereof,
or a salt thereof.

2. The compound according to claim 1,
wherein Y is selected from the group consisting of

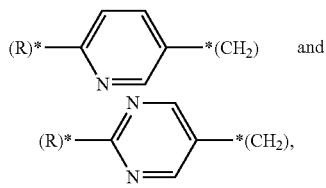

each of which is substituted with 1 substituent $R^1$ and
wherein the bonds with asterisk and brackets indicate the sites of attachment of R and the $CH_2$ group of formula (I), and/or the tautomers thereof,
or a salt thereof.

3. The compound according to claim 1,
wherein R is selected from the group consisting of azetidin-1-yl, 5-aza-spiro[2.3]hexan-5-yl, 2-aza-spiro[3.3]heptan-2-yl, pyrrolidin-1-yl, 3-aza-bicyclo[3.1.0]hexan-3-yl, 5-aza-spiro[2.4]heptan-5-yl, 6-aza-spiro[3.4]octan-6-yl, 3-aza-bicyclo[3.2.0]heptan-3-yl, octahydro-cyclopenta[c]pyrrol-1-yl, 3-aza-bicyclo[4.1.0]heptan-3-yl, 3-aza-bicyclo[3.1.1]heptan-3-yl, and azepan-1-yl,
each of which is optionally substituted with 1 or 2 F, optionally substituted with 1 substituent $R^2$, and optionally substituted with 1 or 2 $CH_3$ groups,
and/or the tautomers thereof,
or a salt thereof.

4. The compound according to claim 1,
wherein X is selected from the group consisting of

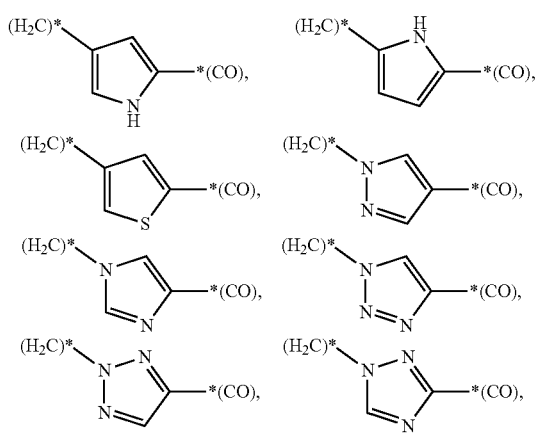

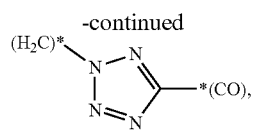

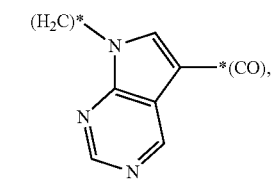

each of which is optionally substituted with 1 substituent $R^3$ and
wherein the bonds with asterisk and brackets indicate the sites of attachment of the groups C=O and $CH_2$ of formula (I), and/or the tautomers thereof,
or a salt thereof.

5. The compound according to claim 1, wherein $R^1$ is selected from the group consisting of H, $CH_3$, CN, $CF_3$, and $CH_2CH_3$,
and/or the tautomers thereof,
or a salt thereof.

6. The compound according to claim 1, wherein $R^2$ is selected from the group consisting of $CH_3$, $CH_2CH_3$, $CH(CH_3)_2$, $CH_2F$, $CHF_2$, $CF_3$, $CH_2OH$, CN, OH, O—$CH_3$, 4-fluorophenyl and pyrazolyl,
and/or the tautomers thereof,
or a salt thereof.

7. The compound according to claim 1, wherein $R^3$ is selected from the group consisting of Cl, CN, COOH, CH optionally substituted with 1 to 3 F, cyclopropyl, $C(CH_3)_2OH$, $CH_2OCH_3$, $OCH_3$, and N-methyl-pyrazolyl,
and/or the tautomers thereof,
or a salt thereof.

8. The compound according to claim 1, wherein the stereochemistry of the compound of formula (I) is according to formula (I.1)

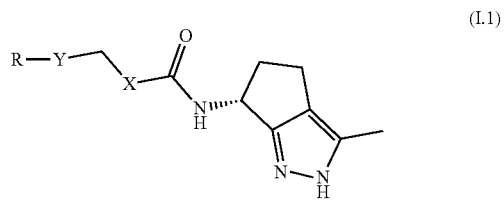

and/or the tautomers thereof,
or a salt thereof.

9. A pharmaceutically acceptable salt of the compound according to claim 1 and/or the tautomers thereof.

10. A pharmaceutical composition comprising one or more compounds according to claim 1, and/or the tautomers thereof, or pharmaceutically acceptable salts thereof, optionally together with one or more inert carriers and/or diluents.

11. A pharmaceutical composition comprising one or more compounds according to claim 1, and/or the tautomers thereof, or pharmaceutically acceptable salts thereof, and one or more additional therapeutic agents, optionally together with one or more inert carriers and/or diluents.

12. The pharmaceutical composition according to claim 11, wherein the one or more additional therapeutic agents is selected from the group consisting of antidiabetic agents, agents for the treatment of overweight and/or obesity, agents for the treatment of high blood pressure, heart failure and/or atherosclerosis, and agents for the treatment of ocular diseases.

13. A method for the treatment of an ocular disease, comprising administering to a patient in need thereof a pharmaceutically effective amount of one or more compounds according to claim 1, and/or the tautomers thereof, or pharmaceutically acceptable salts thereof.

14. The method according to claim 13, wherein the ocular disease is selected from the group consisting of diabetic macular edema, age-related macular degeneration and choroidal neovascularizationt.

15. A compound selected from the group consisting of

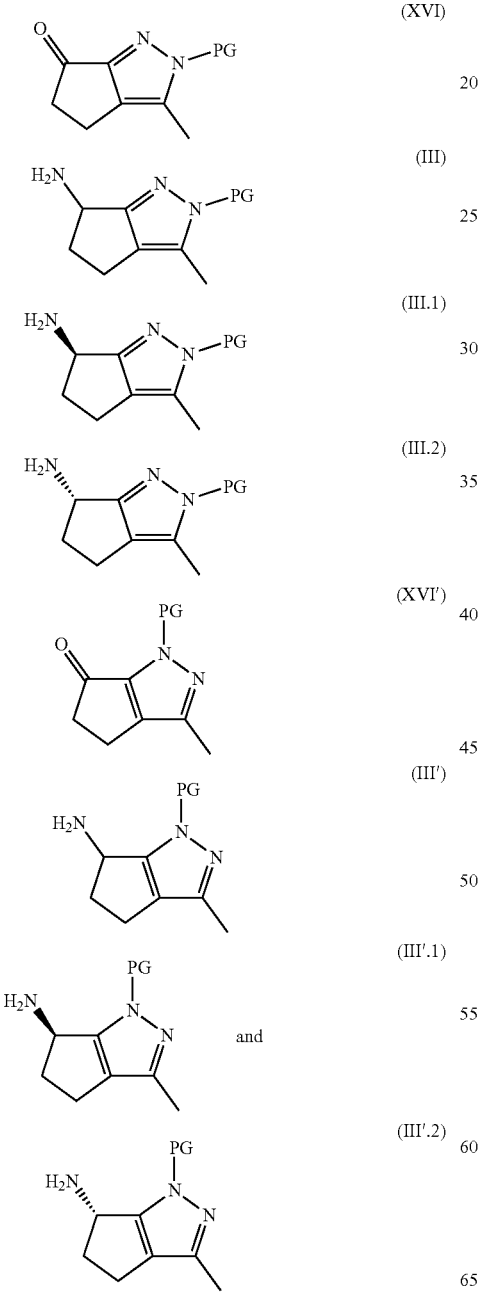

and

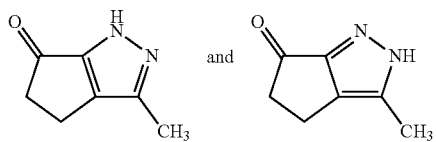

wherein PG is a protective group selected from the group consisting of $C_{1-4}$-alkyl optionally substituted with 1 to 5 F or Cl and optionally substituted with 1 group selected from $Si(CH_3)_3$, CN, $SO_2$—$C_{1-4}$-alkyl, or $SO_2$-phenyl;

$CH_2$-phenyl optionally substituted with 1 or 2 $OCH_3$;

$CH_2$—$N(C_{1-4}$-alkyl$)_2$, $CH_2$-pyrrolidin-1-yl, $CH_2$—NHCO—$C_{1-4}$-alkyl, $CH_2$—$N(CH_3)CO$—$C_{1-4}$-alkyl;

$CH_2$—O—$C_{1-4}$-alkyl optionally substituted with 1 $CH_3$, 1 $Si(CH_3)_3$, or 3 Cl;

$CH_2$—O—$CH_2$-phenyl optionally substituted with 1 or 2 $OCH_3$; tetrahydropyran-2-yl, tetrahydrofuran-2-yl;

CO—$C_{1-4}$-alkyl optionally substituted with 1 to 5 F or Cl;

CO—$N(C_{1-4}$-alkyl$)_2$, CO-pyrrolidin-1-yl;

CO—O—$C_{1-4}$-alkyl optionally substituted with 1 $Si(CH_3)_3$ or 3 Cl;

CO—O—$CH_2$-phenyl optionally substituted with 1 or 2 $OCH_3$;

$SO_2(C_{1-4}$-alkyl) optionally substituted with 1 to 5 F or 1 to 3 Cl;

$SO_2$-phenyl optionally substituted with 1 or 2 groups selected from Cl, Br, $CH_3$, $NO_2$, and $OC_{1-4}$-alkyl;

$SO_2$—$N(C_{1-4}$-alkyl$)_2$, $SO_2$-pyrrolidin-1-yl; and phenyl substituted with 1 or 2 groups selected from Cl, Br, $NO_2$, $OC_{1-4}$-alkyl, and $SO_2C_{1-4}$-alkyl;

or a salt thereof.

16. The compound according to claim 1, selected from the group consisting of:

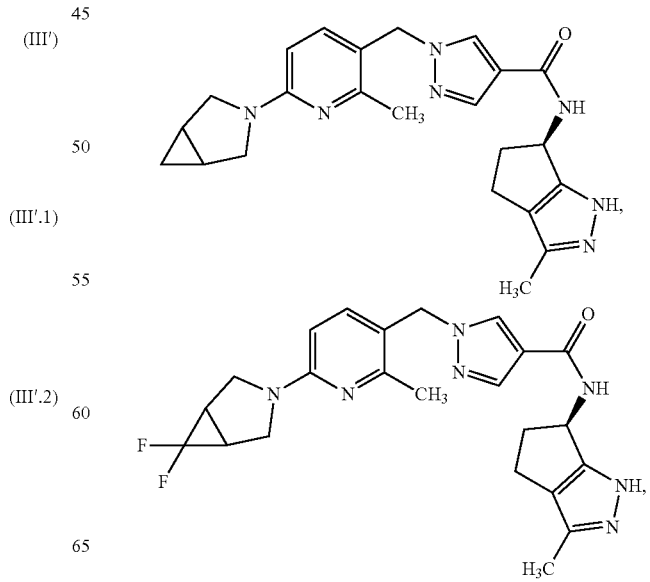

201 202
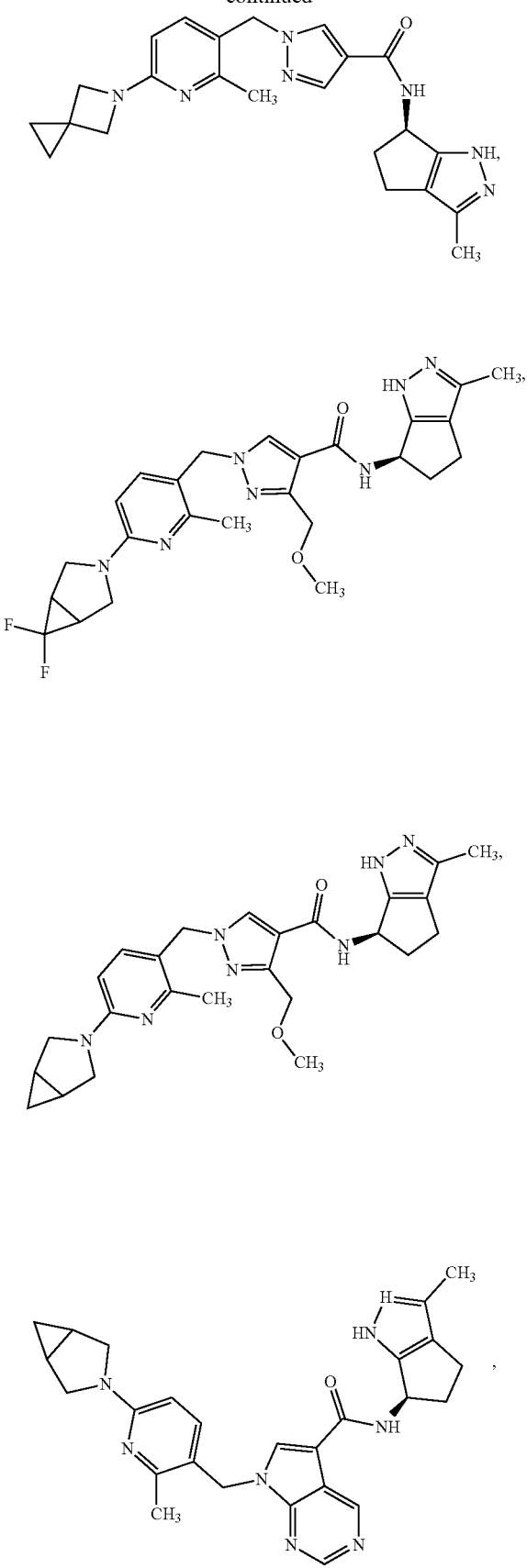
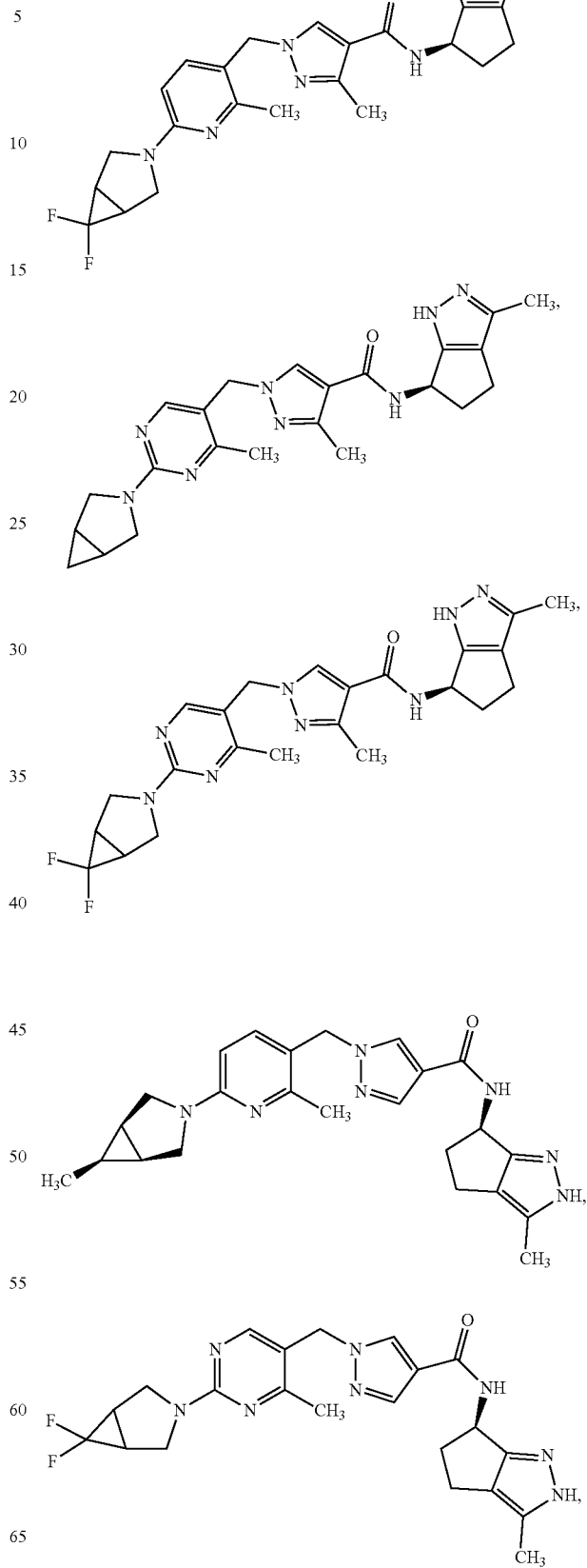

203
-continued
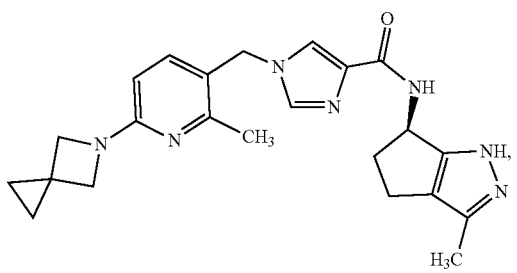
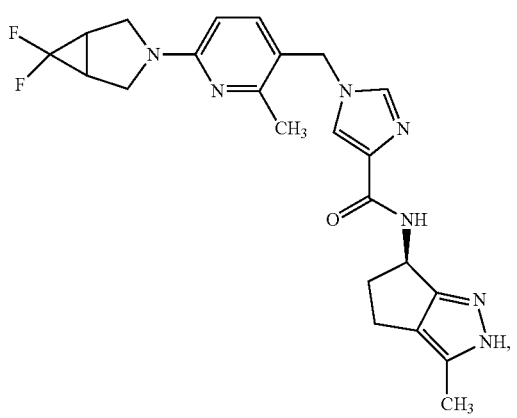
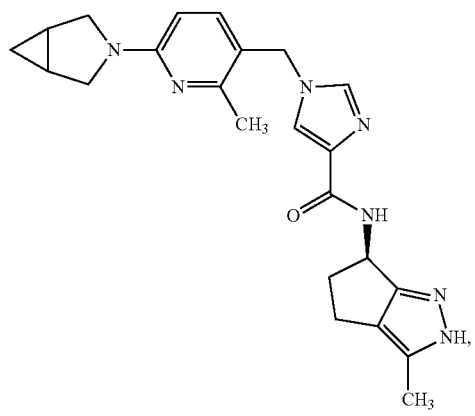
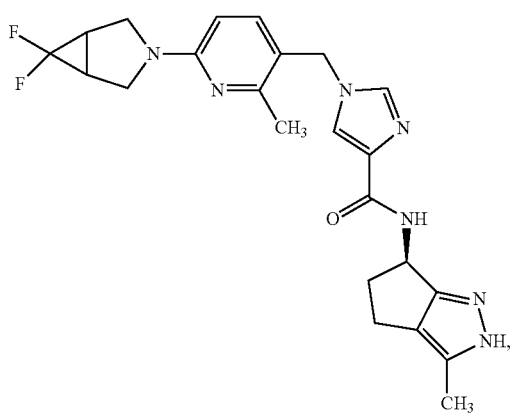
204
-continued
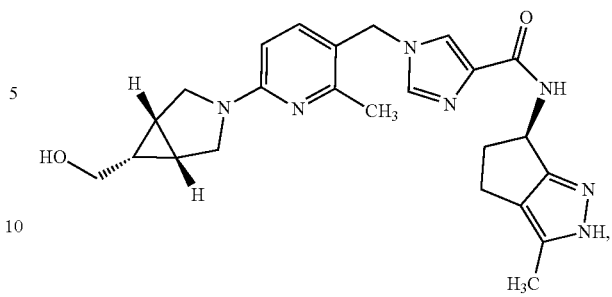
and
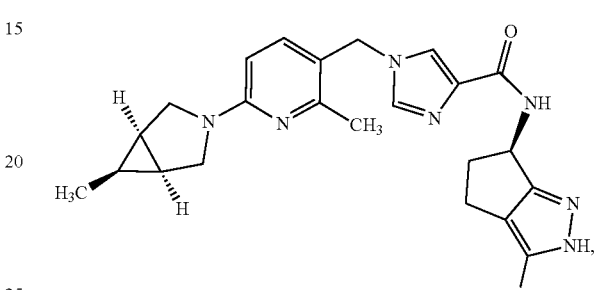
and/or the tautomers thereof,
or a salt thereof.
17. The compound according to claim 1, selected from the group consisting of:
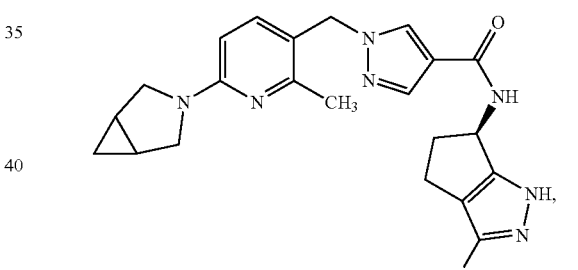
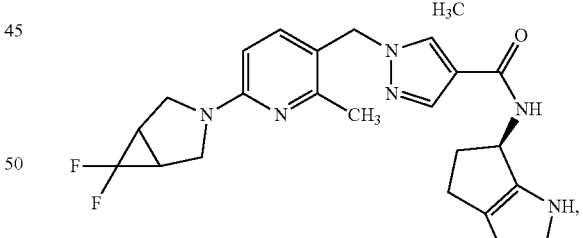
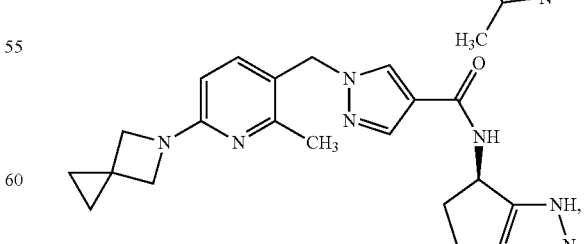

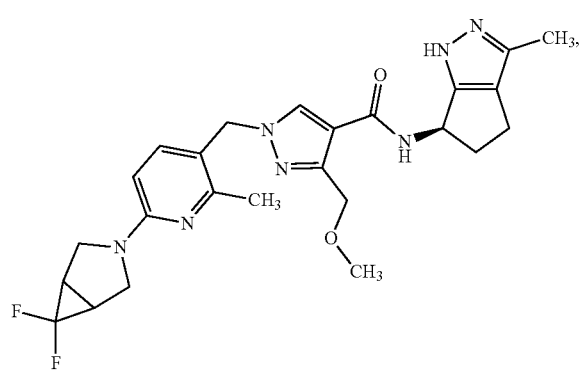
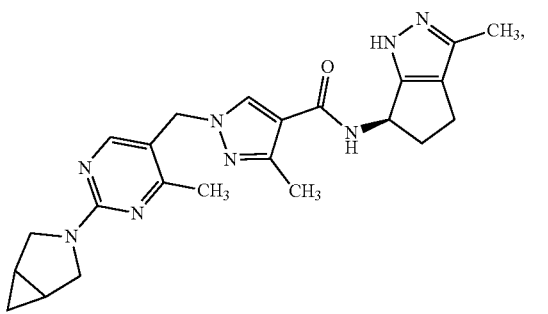
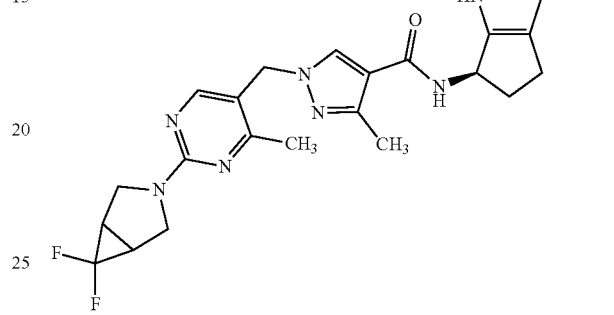
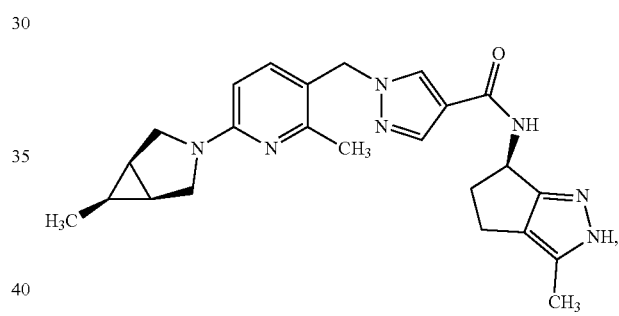
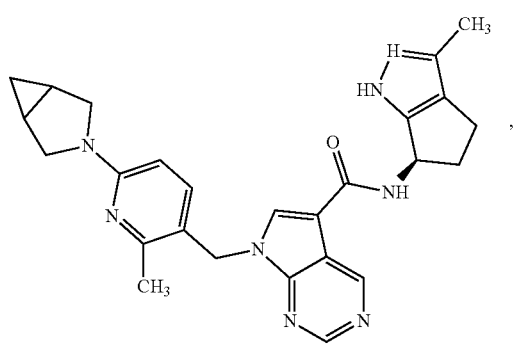
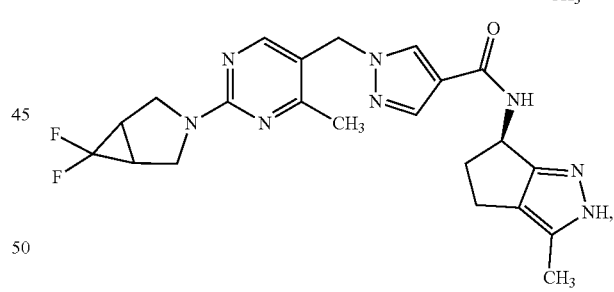
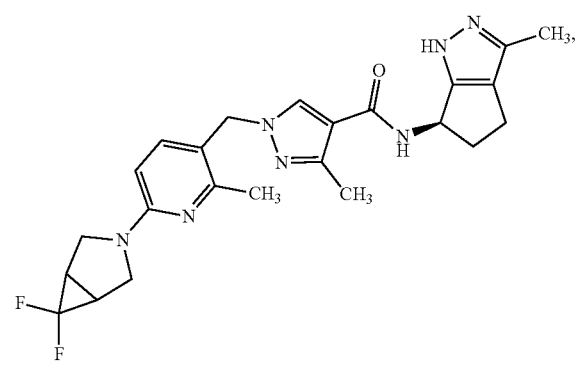

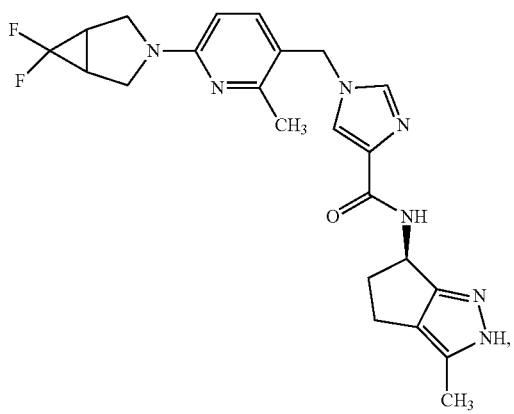
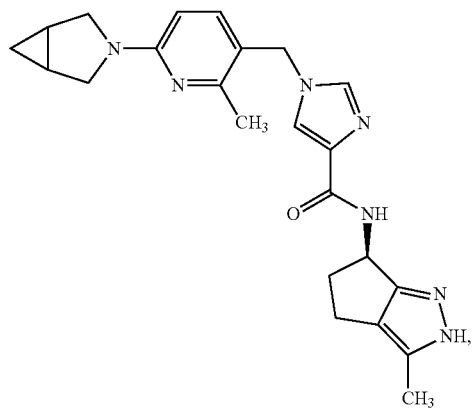
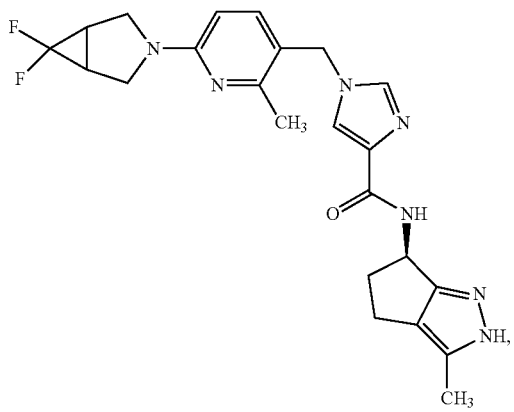
and
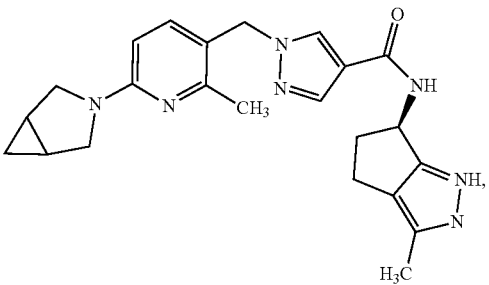
and/or the tautomers thereof.
18. A compound having the structure
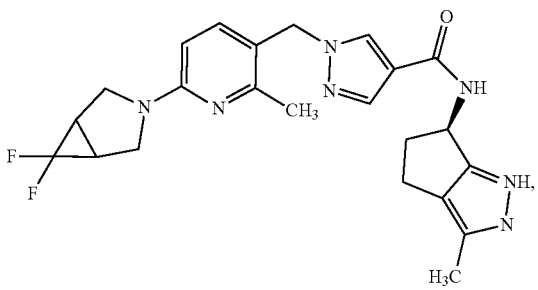
and/or tautomers thereof.
19. A compound having the structure
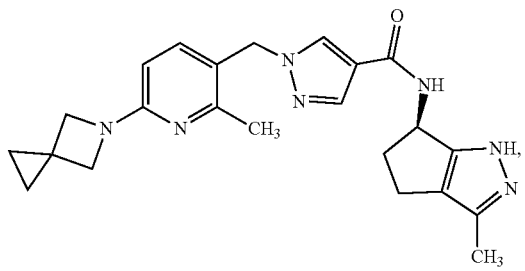 [SMILES: Cc1nc(N2CC3(CC3)C2)ccc1Cn1cc(C(=O)N[C@@H]2CCc3c(C)n[nH]c32)cn1]
and/or tautomers thereof.
20. A compound having the structure 21. A compound having the structure
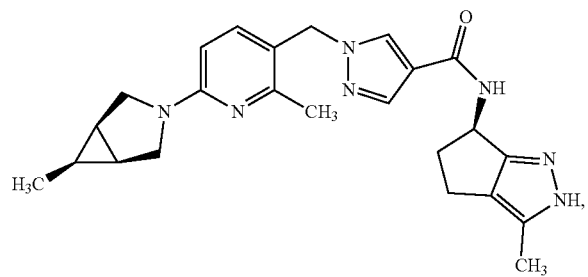 [SMILES: Cc1nc(N2C[C@@H]3[C@H](C)[C@@H]3C2)ccc1Cn1cc(C(=O)N[C@@H]2CCc3c2n[nH]c3C)cn1]
and/or tautomers thereof.
22. A compound having the structure
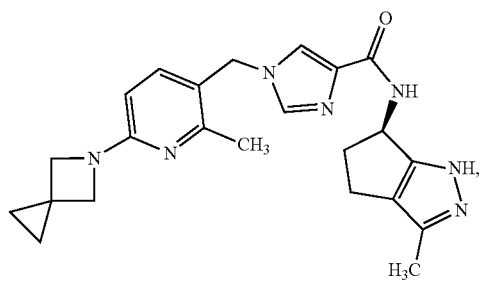 [SMILES: Cc1nc(N2CC3(CC3)C2)ccc1Cn1cnc(C(=O)N[C@@H]2CCc3c(C)n[nH]c32)c1]
and/or tautomers thereof.
23. A compound having the structure
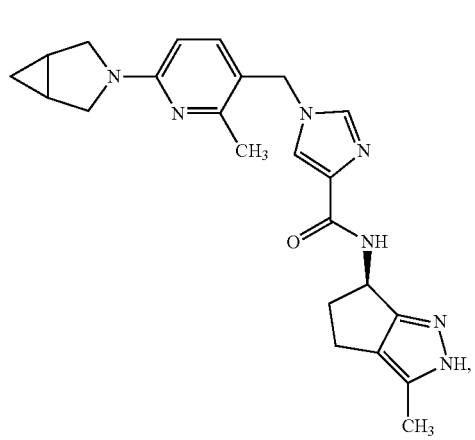 [SMILES: Cc1nc(N2CC3CC3C2)ccc1Cn1cnc(C(=O)N[C@@H]2CCc3c2n[nH]c3C)c1]
and/or tautomers thereof.
24. A compound having the structure
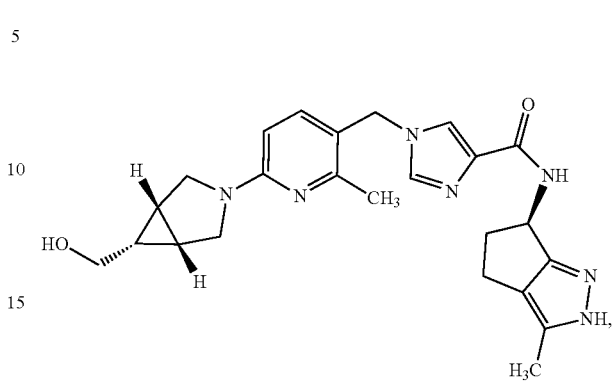
and/or tautomers thereof.
25. A compound having the structure
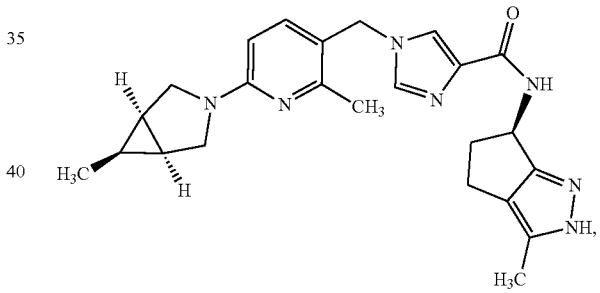
and/or tautomers thereof.
* * * * *

UNITED STATES PATENT AND TRADEMARK OFFICE
CERTIFICATE OF CORRECTION

PATENT NO.        : 10,695,334 B2
APPLICATION NO.   : 16/540091
DATED             : June 30, 2020
INVENTOR(S)       : Matthias Eckhardt et al.

Page 1 of 1

It is certified that error appears in the above-identified patent and that said Letters Patent is hereby corrected as shown below:

On the Title Page

Item (75), replace the term "Bieberach an der Riss" with the term -- Biberach an der Riss --

In the Claims

In Column 198, Lines 33-34, replace the group "$C(CH_3)_{20}H$" with the group -- $C(CH_3)_2OH$ --

Signed and Sealed this
Twelfth Day of January, 2021

Andrei Iancu
*Director of the United States Patent and Trademark Office*